US 8,569,579 B2

(12) United States Patent
Hill et al.

(10) Patent No.: US 8,569,579 B2
(45) Date of Patent: Oct. 29, 2013

(54) BPMV-BASED VIRAL CONSTRUCTS USEFUL FOR VIGS AND EXPRESSION OF HETEROLOGOUS PROTEINS IN LEGUMES

(75) Inventors: John H. Hill, Ames, IA (US);
Chunquan Zhang, Ames, IA (US);
Steve Whitham, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 12/927,579

(22) Filed: Nov. 18, 2010

(65) Prior Publication Data

US 2011/0173717 A1     Jul. 14, 2011

Related U.S. Application Data

(60) Provisional application No. 61/281,469, filed on Nov. 18, 2009.

(51) Int. Cl.
*C12N 15/83* (2006.01)
*C12N 15/33* (2006.01)
*C12N 5/10* (2006.01)

(52) U.S. Cl.
USPC ...... 800/280; 435/320.1; 800/312; 536/23.72

(58) Field of Classification Search
None
See application file for complete search history.

(56) References Cited

U.S. PATENT DOCUMENTS

| 7,005,559 | B1 | 2/2006 | Sela |
| 7,618,815 | B2 | 11/2009 | Ghabrial |
| 2007/0214518 | A1 | 9/2007 | Ghabrial |

FOREIGN PATENT DOCUMENTS

| CA | 2359356 | 7/2000 |
| WO | WO00/42206 | 7/2000 |

OTHER PUBLICATIONS

Gu et al. (2005) Virology 333: 271-283.*
Zhang, Development and Use of an Efficient DNA-Based Viral Gene Silencing Vector for Soybean, The American Phytopathological Society, vol. 22, No. 2, 2009, pp. 123-141.
Zhang, Development of Bean Pod Mottle Virus-Based Vectors for Stable Protein Expression and Sequence-Specific Virus-Induced Gene Silencing in Soybean, Virology 344 (2006), pp. 401-411.
Zhang, The Development of an Efficient Multipurpose Bean Pod Mottle Virus Viral Vector Set for Foreign Gene Expression and RNA Silencing, Plant Physiology, May 2010, vol. 153, pp. 52-65.
Zhang, Development of a high throughput Bean pod mottle virus (BPMV) based gene expression and VIGS vector for soybean host pathogen interaction study. Poster. American Phytopathological Society (APS) annual meeting, 2007, San Diego, CA, Jul. 28-Aug. 1, 2007.
Zhang, Development of a high throughput Bean pod mottle virus (BPMV) based gene expression and VIGS vector for soybean host pathogen interaction study, Phytopathology, vol. 97 No. 7 (Supplement), S129, 2007 Abstract.

* cited by examiner

*Primary Examiner* — David T Fox
*Assistant Examiner* — Steven Bernacki
(74) *Attorney, Agent, or Firm* — McKee, Voorhees & Sease, P.L.C.

(57) ABSTRACT

The invention provides Bean pod mottle virus (BPMV) vectors useful for expression of heterologous proteins in plants such as soybean. The BPMV vectors are also useful for virus-induced gene silencing. The vectors of the invention include modifications of BPMV RNA1 sequences so that infection with the vectors produces only moderate symptoms. The vectors also comprise novel RNA2 vectors which specifically provide for non-translated VIGS constructs and further which do not require in frame insertion of heterologous sequences to be expressed.

4 Claims, 44 Drawing Sheets
(38 of 44 Drawing Sheet(s) Filed in Color)

Figure 1. Schematic representation of the CaMV 35S promoter driven Bean pod mottle virus (BPMV) gene expression and virus-induced gene silencing (VIGS) vector.

```
                                                                                                              Section 1
              (1)    1         10        20        30        40        50        60        70        81
  IL-Cb1 (II) (1)   MKFYPGQNVSEIVYHFQSNETANRLDAYFACGCEEDTEVLARLKQCNPRLLHLSYAAFCLEMGSHSVEEIEYDDGELVFLY
  IIL-Cb1 (I) (1)   MKFYPGQNISEIVYHFQSNETANRLDAYFACGCEEDTEVLARLKQCNPRLLHLSYAAFCLEMGSHSIEEMEYDDGELIFSY
   pBPMV-R1A  (1)   MKFYPGQNISEIVYHFQSNETANRLDAYFACGCEEDTEVLARLKQCNPRLLHLSYAAFCLEMGSHSIEEMEYDDGELIFSY
   pBPMV-R1B  (1)   MKFYPGQNISEIVYHFQSNETANRLDAYFACGCEEDTEVLARLKQCNPRLLHLSYAAFCLEMGSHSIEEMEYDDGELIFSY
         K-G7 (1)   MKFYPGQNISEIVYHFQSNETANRLDAYFACGCEEDTEVLARLKQCNPRLLHLSYAAFCLEMGSHSIEEMEYDDGELIFSY
    Consensus (1)   MKFYPGQNISEIVYHFQSNETANRLDAYFACGCEEDTEVLARLKQCNPRLLHLSYAAFCLEMGSHSIEEMEYDDGELIFSY
                                                                                                              Section 2
              (82)  82        90        100       110       120       130       140       150       162
  IL-Cb1 (II) (82)  FQNFLLSIVSNSSKTANLRAYIRSAFAYHFQHFVEFDQYTNDSLNVMDTSVSAQGIADLALSMVRWIPTQIKKVVNFGVGS
  IIL-Cb1 (I) (82)  FQNFLLSIVSNSSKTTKLRAYIRSTFAYHFQHFVEFDQYTNDSLNTVDTSVSAQGIADLALSMVRWIPTQIKKVVNFGVGS
   pBPMV-R1A  (82)  FQNFLLSIVSNSSKTTKLRAYIRSAFAYHFQHFVEFDQYTNDSLNTVDTSVSAQGIADLALSMVRWIPTQIKKVVNFGVGS
   pBPMV-R1B  (82)  FQNFLLSIVSNSSKTTKLRAYIRSAFAYHFQHFVEFDQYTNDSLNTVDTSVSAQGIADLALSMVRWIPTQIKKVVNFGVGS
         K-G7 (82)  FQNFLLSIVSNSSKTTKLRAYIRSAFAYHFQHFVEFDQYTNDSLNTADTSVSAQGIADLALSMVRWIPTQIKKVVNFGVGS
    Consensus (82)  FQNFLLSIVSNSSKTTKLRAYIRSAFAYHFQHFVEFDQYTNDSLNTVDTSVSAQGIADLALSMVRWIPTQIKKVVNFGVGS
                                                                                                              Section 3
              (163) 163       170       180       190       200       210       220       230       243
  IL-Cb1 (II) (163) VIESFSEHFNKLIMQYCPIVFQAFSWVNNIWTMVKEWIEEAAKEISWFLQGCKELLAWGMCILASSCALGLVEKCLISLGM
  IIL-Cb1 (I) (163) VIESFSEHFNKLLMQYCPIVFQAFSWVNNIWTMVKEWIEEAAKEISWFLQGCKELLAWGMCILASSCALGLVEKCLISLGM
   pBPMV-R1A  (163) VIESFSEHFNKLLMQYCPIVFQAFSWVNNIWTMVKEWIEEAAKEISWFLQGCKELLAWGMCILASSCALGLVEKCLISLGM
   pBPMV-R1B  (163) VIESFSEHFNKLLMQYCPIVFQAFSWVNNIWTMVKEWIEEAAKEISWFLQGCKELLAWGMCILASSCALGLVEKCLISLGM
         K-G7 (163) VIESFSEHFNKLLMQYCPIVFQAFSWVNNIWTMVKEWIEEATKEISWFLQGCKELLAWGMCILASSCALGLVEKCLISLGM
    Consensus (163) VIESFSEHFNKLLMQYCPIVFQAFSWVNNIWTMVKEWIEEAAKEISWFLQGCKELLAWGMCILASSCALGLVEKCLISLGM
                                                                                                              Section 4
              (244) 244       250       260       270       280       290       300       310       324
  IL-Cb1 (II) (244) ISESFDLVGLFVRSAIVGAFCVSIKTGKFVSNSELITCATIAVSTIATVMSQAFKPSEEIKGQFQALSVLEGLATQLTSFC
  IIL-Cb1 (I) (244) ISESFDLVGLFVRSAIVGAFCVSIKTGKFITNSELVTCATIAVSTIATVMSQAFKPSEEIKGQFQALSVLEGLATQLTSFC
   pBPMV-R1A  (244) ISESFDLVGLFVRSAIVGAFCVSIKTGKFITNSELVTCATIAVSTIATVMSQAFKPSEEIKGQFQALSVLEGLATQLTSFC
   pBPMV-R1B  (244) ISESFDLVGLFVRSAIVGAFCVSIKTGKFITNSELVTCATIAVSTIATVMSQAFKPSEEIKGQFQALSVLEGLATQLTSFC
         K-G7 (244) ISESFDLVGLFVRSAIVGAFCVSIKTGKFVTNSELITCATIAVSTIATVMSQAFKPSEEIKGQFQALSVLEGLATQLTSFC
    Consensus (244) ISESFDLVGLFVRSAIVGAFCVSIKTGKFITNSELITCATIAVSTIATVMSQAFKPSEEIKGQFQALSVLEGLATQLTSFC
                                                                                                              Section 5
              (325) 325       330       340       350       360       370       380       390       405
  IL-Cb1 (II) (325) DTSLIAMGKTCTAFNQICTAGKNVKVIAGRLLDVVSNFVRKLLGLDSAFLRDAALIFSQDVDGWLRNISWCQEQFLLKAYM
  IIL-Cb1 (I) (325) DTSLVAMGKTCTAFNQICTAGKNVKVIAGRLLEVVSNFVRKLLGLDSVFLRDAALIFSQDVDGWLRNISWCQEQFLLKAYM
   pBPMV-R1A  (325) DTSLVAMGKTCTAFNQICTAGKNVKVIAGRLLEVVSNFVRKLLGLDSAFLRDAALIFSQDVDGWLRNISWCQEQFLLKAYM
   pBPMV-R1B  (325) DTSLVAMGKTCTAFNQICTAGKNVKVIAGRLLEVVSNFVRKLLGLDSAFLRDAALIFSQDVDGWLRNISWCQEQFLLKAYM
         K-G7 (325) DTSLVAMGKTCTAFNQICTAGKNVKVIAGRLLEVVSNFVRKLLGLDSAFLRDAALIFSQDVDGWLRNISWCQEQFLLKAYM
    Consensus (325) DTSLVAMGKTCTAFNQICTAGKNVKVIAGRLLEVVSNFVRKLLGLDSAFLRDAALIFSQDVDGWLRNISWCQEQFLLKAYM
                                                                                                              Section 6
              (406) 406       420       430       440       450       460       470       486
  IL-Cb1 (II) (406) SQDDLIVLRSLVVKGERMREQMLEGEVKVSPSVCNLIVKGCEEASKLMRESVLHCSKTVRKIPFVIFAHGDSRVGKSLLVD
  IIL-Cb1 (I) (406) SQDDLIVLRSLVVKGERMREQMLEGEVKVSPSVCNLIVKGCEEANKLMRESALHCSKTIRKIPFVIFAHGESRVGKSLLVD
   pBPMV-R1A  (406) SQDDLIVLRSLVVKGERMREQMLEGEVKVSPSVCNLIVKGCEEANKLMRESALHCSKTIRKIPFVIFAHGESRVGKSLLVD
   pBPMV-R1B  (406) SQDDLIVLRSLVVKGERMREQMLEGEVKVSPSVCNLIVKGCEEANKLMRESALHCSKTIRKIPFVIFAHGESRVGKSLLVD
         K-G7 (406) SQDDLIVLRSLVVKGERMREQMLEGEVKVSPSVCNLIVKGCEEANKLMRESALHCSKTIRKIPFVIFAHGESRVGKSLLVD
    Consensus (406) SQDDLIVLRSLVVKGERMREQMLEGEVKVSPSVCNLIVKGCEEANKLMRESALHCSKTIRKIPFVIFAHGESRVGKSLLVD
                                                                                                              Section 7
              (487) 487       500       510       520       530       540       550       567
  IL-Cb1 (II) (487) RLITDFCDHLEIGEDAVYSRNPSDPFWSGYRRQPIVTIDDFAAVASEPSAEAQLIPLISSAPYPLNMASLEEKGMHFDSQY
  IIL-Cb1 (I) (487) KLITDFCDHLEIGEDAVYSRNPSDPFWSGYRRQPIVTIDDFAAVVSEPSASAQLIPLVSSAFYPLNMAGLEEKGMHFDSQI
   pBPMV-R1A  (487) KLITDFCDHLEIGEDAVYSRNPSDPFWSGYRRQPIVTIDDFAAVVSEPSAEAQLIPLVSSAPYPLNMAGLEEKGMHFDSQI
   pBPMV-R1B  (487) KLITDFCDHLEIGEDAVYSRNPSDPFWSGYRRQPIVTIDDFAAVVSEPSAEAQLIPLVSSAPYPLNMAGLEEKGMHFDSQI
         K-G7 (487) RLITDFCDHLEIGEDAVYSRNPSDPFWSGYRRQPIVTIDDFAAVVSEPSAEAQLIPLVSSAPYPLNMAGLEEKGMHFDSQI
    Consensus (487) RLITDFCDHLEIGEDAVYSRNPSDPFWSGYRRQPIVTIDDFAAVVSEPSAEAQLIPLVSSAPYPLNMAGLEEKGMHFDSQI
                                                                                                              Section 8
              (568) 568       580       590       600       610       620       630       648
  IL-Cb1 (II) (568) MMCSSNFLEPSPEAKIRDDMAFRNRRHVLITVELKPGVEYDESDFTKNQRYLLKTWFHDYVVDQTFESYADLLAYCFTKW
  IIL-Cb1 (I) (568) MMCSSNFLEPSPEAKIRDDMAFRNRRHVLITVELKPGVEYDESDFTKNQRYLLKTWFHDHYVVDQTFESYADLLAHCFTKW
   pBPMV-R1A  (568) MMCSSNFLEPSPEAKIRDDMAFRNRRHVLITVELKPGVEYDESDFTKNQRYLLKTWFHDHYVVDQTFESYADLLAHCFTKW
   pBPMV-R1B  (568) MMCSSNFLEPSPEAKIRDDMAFRNRRHVLITVELKPGVEYDESDFTKNQRYLLKTWFHDHYVVDQTFESYADLLAHCFTKW
         K-G7 (568) MMCSSNFLEPSPEAKIRDDMAFRNRRHVLITVELKPGVEYDESDFTKNQRYLLKTWFHDHYVVDQTFESYADLLAHCFTKW
    Consensus (568) MMCSSNFLEPSPEAKIRDDMAFRNRRHVLITVELKPGVEYDESDFTKNQRYLLKTWFHDHYVVDQTFESYADLLAHCFTKW
```

*FIG. 8A*

```
                                                                                              Section 9
              (649)  649       660       670       680       690       700       710        729
   IL-Cb1 (II) (649) ERHVKEQESNLSQIKGKKSESGHFHNFQQLMDLAVSWNLSANIMKERIKADKSDMVYVFSAGRKDKIVHCFLNKEGECSIR
   IL-Cb1 (I)  (649) ERHVKEQESNLSQIKGKKNESGHFNNFQQLMDLAVSWNLSADIMKNRIKAERHDMVYVFSAGRKDKIFHCFLNKEGECTVR
   pBPMV-R1A   (649) ERHVKEQESNLSQIKGKKSESGHFNNFQQLMDLAVSWNLNADIMKNRIKAERSDMVYVFSAGRKDKILHCFLNKEGECTVR
   pBPMV-R1B   (649) ERHVKEQESNLSQIKGKKNESGHFNNFQQLMDLAVSWNLNADIMKNRIKAERSDMVYVFSAGRKDKILHCFLNKEGECTVR
   K-G7        (649) ERHVKEQESNLSQIKGKKNESGHFYNFQQLMDLAVSWNLNADIMKNRIKAERNDMVYVFSAGRKDKILHCFLNKEGECTVR
   Consensus   (649) ERHVKEQESNLSQIKGKKNESGHFNNFQQLMDLAVSWNLNADIMKNRIKAERSDMVYVFSAGRKDKILHCFLNKEGECTVR
                                                                                              Section 10
              (730)  730       740       750       760       770       780       790       800       810
   IL-Cb1 (II) (730) PDSIEDPEAQLLLKASETMLMKAYAFLKYNNATNLIVRTHLAELVNEDFYDEKFNFIGTIGTPAFHRQIAAHLEKMPLWQK
   IL-Cb1 (I)  (730) PDSIDDPEAQALLKASETMLMKAYAFLKYNNATNLIVRTHLAELVNEDFYDEKFNFIGTIGTPAFHRQIAAHLEKMPLWQK
   pBPMV-R1A   (730) PDSIDDPEAQALLKASETMLMKAYAFLKYNNATNLIVRTHLAELVNEDFYDEKFNFIGTIGTPAFHRQIAAHLEKMPLWQK
   pBPMV-R1B   (730) PDSIDDPEAQALLKASETMLMKAYAFLKYNNATNLIVRTHLAELVNEDFYDEKFNFIGTIGTPAFHRQIAAHLEKMPLWQK
   K-G7        (730) PDSIDDPEAQALLKASETMLMKAYAFLKYNNATNLIVRTHLAELVNEDFYDEKFNFIGTIGTPAFHRQIAAHLEKMPLWQK
   Consensus   (730) PDSIDDPEAQALLKASETMLMKAYAFLKYNNATNLIVRTHLAELVNEDFYDEKFNFIGTIGTPAFHRQIAAHLEKMPLWQK
                                                                                              Section 11
              (811)  811       820       830       840       850       860       870       880       891
   IL-Cb1 (II) (811) AILCGMGHCLSRKSKETWYSGMKEKFVQMMKSIYETEVTDWPVPLKIISGTILATILGTTFWKLFSFLRDAGNGGVFVGNV
   IL-Cb1 (I)  (811) AILCGMGHCLSRKSKETWYTGMKEKFVQMMKSIYETEVTDWPVPLKIISGTILATILGTTFWKLFSFLRDAGNGGVFVGNV
   pBPMV-R1A   (811) AILCGMGHCLSRKSKETWYTGMKEKFVQMMKSIYETEVTDWPVPLKIISGTILATILGTTFWKLFSFLRDAGNGGVFVGNV
   pBPMV-R1B   (811) AILCGMGHCLSRKSKETWYTGMKEKFVQMMKSIYETEVTDWPVPLKIISGTILATILGTTFWKLFSFLRDAGNGGVFVGNV
   K-G7        (811) AILCGMGHCLSRKSKETWYTGMKEKFVQMMKSIYETEVTDWPVPLKIISGTILATILGTTFWKLFSFLRDAGNGGVFVGNV
   Consensus   (811) AILCGMGHCLSRKSKETWYTGMKEKFVQMMKSIYETEVTDWPVPLKIISGTILATILGTTFWKLFSFLRDAGNGGVFVGNV
                                                                                              Section 12
              (892)  892       900       910       920       930       940       950       960       972
   IL-Cb1 (II) (892) ASAFTTSSVLEAQSRKPNRYEVSQYRYRNVPIKRRAWVEGQMSFDQSVVAIMSKCKASMRMGNTDAQILMVPGRRFIAHGH
   IL-Cb1 (I)  (892) ASAFTTSSVLEAQSRKPNRYEVSQYRYRNVPIKRRAWVEGQMSFDQSVVAIMSKCKASMRMGNTDAQILMVPGRRFIAHGH
   pBPMV-R1A   (892) ASAFTTSSVLEAQSRKPNRYEVSQYRYRNVPIKRRAWVEGQMSFDQSVVAIMSKCKASMRMGNTDAQILMVPGRRFIAHGH
   pBPMV-R1B   (892) ASAFTTSSVLEAQSRKPNRYEVSQYRYRNVPIKRRAWVEGQMSFDQSVVAIMSKCKASMRMGNTDAQILMVPGRRFIAHGH
   K-G7        (892) ASAFTTSSVLEAQSRKPNRYEVSQYRYRNVPIKRRAWVEGQMSFDQSVVAIMSKCKASMRMGNTDAQILMVPGRRFIAHGH
   Consensus   (892) ASAFTTSSVLEAQSRKPNRYEVSQYRYRNVPIKRRAWVEGQMSFDQSVVAIMSKCKASMRMGNTDAQILMVPGRRFIAHGH
                                                                                              Section 13
              (973)  973       980       990       1000      1010      1020      1030      1040      1053
   IL-Cb1 (II) (973) FFKNLTQKVRVQIVTSEKSYWHVYDPDKFQMFDNSEIGLYYNPTLEDIPHSAWDLFCWDSEKTLPNNFSAELLSCKLDTVT
   IL-Cb1 (I)  (973) FFKNLTQKVRVQIVTSEKSYWHVYDPDKFQMFDNSEIGLYTNPTLEDIPHSAWDLFCWDSEKTLPNNFSAELLSCKLDTVT
   pBPMV-R1A   (973) FFKNLTQKVRVQIVTSEKSYWHVYDPDKFQMFDNSEIGLYTNPTLEDIPHSAWDLFCWDSEKTLPNNFSAELLSCKLDTVT
   pBPMV-R1B   (973) FFKNLTQKVRVQIVTSEKSYWHVYDPDKFQMFDNSEIGLYTNPTLEDIPHSAWDLFCWDSEKTLPNNFSAELLSCKLDTVT
   K-G7        (973) FFKNLTQKVRVQIVTSEKSYWHVYDPDKFQMFDNSEIGLYTNPTLEDIPHSAWDLFCWDSEKTLPNNFSAELLSCKLDTVT
   Consensus   (973) FFKNLTQKVRVQIVTSEKSYWHVYDPDKFQMFDNSEIGLYTNPTLEDIPHSAWDLFCWDSEKTLPNNFSAELLSCKLDTVT
                                                                                              Section 14
             (1054)  1054      1060      1070      1080      1090      1100      1110      1120      1134
   IL-Cb1 (II)(1054) GQYYPEWAPINCRVHRQPIHITEGNYVRKQDVSIEYDACTIPNDCGSLVVAKVGNHKQIVGFHVAGSKGRLGYASLIPYVE
   IL-Cb1 (I) (1054) GQYYPEWAPINCRVHRQPIHITEGNYVRKQDVSIEYDACTIPNDCGSLVVAKVGNHKQVVGFHVAGSKGRLGYASLIPYVE
   pBPMV-R1A  (1054) GQYYPEWAPINCRVHRQPIHITEGNYVRKQDVSIEYDACTIPNDCGSLVVAKVGNHKQIVGFHVAGSKGRLGYASLIPYVE
   pBPMV-R1B  (1054) GQYYPEWAPINCRVHRQPIHITEGNYVRKQDVSIEYDACTIPNDCGSLVVAKVGNHKQIVGFHVAGSKGRLGYASLIPYVE
   K-G7       (1054) GQYYPRMAPINCRVHRQPIHITEGNYVRKQDVSIEYDACTIPNDCGSLVVAKVGNHKQIVGFHVAGSKGRLGYASLIPYVE
   Consensus  (1054) GQYYPEWAPINCRVHRQPIHITEGNYVRKQDVSIEYDACTIPNDCGSLVVAKVGNHKQIVGFHVAGSKGRLGYASLIPYVE
                                                                                              Section 15
             (1135)  1135      1140      1150      1160      1170      1180      1190      1200      1215
   IL-Cb1 (II)(1135) PVVQAQSAEVYFDFFPVEVDSQEGVAHIGELKSGVYYPLFTKTNLVETPKEWQLDLPCDKIPSVLTTTDERLVGTEHEGYD
   IL-Cb1 (I) (1135) PVVQAQSAEVYFDFFPVEVDSQEGVAHIGELKSGVYVPLPTKTNLVETPKEWQLDLPCDKIPSVLTTTDERLVGTEHEGYD
   pBPMV-R1A  (1135) PVVQAQSAEVYFDFFPVEVDSQEGVAHIGELKSGVYVPLPTKTNLVETPKEWQLDLPCDKIPSVLTTTDERLVGTEHEGYD
   pBPMV-R1B  (1135) PVVQAQSAEVYFDFFPVEVDSQEGVAHIGELKSGVYVPLPTKTNLVETPKEWQLDLPCDKIPSVLTTTDERLVGTEHEGYD
   K-G7       (1135) PVVQAQSAEVYFDFFPVEVDSQEGVAHIGELKSGVYVPLPTKTNLVETPKEWQLDLPCDKIPSVLTTTDERLVGTEHDMT
   Consensus  (1135) PVVQAQSAEVYFDFFPVEVDSQEGVAHIGELKSGVYVPLPTKTNLVETPKEWQLDLPCDKIPSVLTTTDERLVGTEHEGYD
                                                                                              Section 16
             (1216)  1216      1230      1240      1250      1260      1270      1280      1296
   IL-Cb1 (II)(1216) PFLGGIQKYATPMMPLDEEILSKVAQDMVEEWFDCVDEEDSFEEVSLSAALNGVEGLDYMERIPLATSEGFPHVLSRKNGE
   IL-Cb1 (I) (1216) PFLGGIQKYATPMMPLDEEILSKVAQDMVEEWFDCVDEEDTFEEVSLSAALNGVEGLDYMERIPLATSEGFPHVLSRKNGE
   pBPMV-R1A  (1216) PFLGGIQKYATPMMPLDEEILSKVAQDMVEEWFDCVDEEDTFEEVSLSAALNGVEGLDYMERIPLATSEGFPHVLSRKNGE
   pBPMV-R1B  (1216) PFLGGIQKYATPMMPLDEEILSKVAQDMVEEWFDCVDEEDTFEEVSLSAALNGVEGLDYMERIPLATSEGFPHVLSRKNGE
   K-G7       (1216) -HSWYSKYATPMMPLDEEILSKVAQDMVEEWFDCVDEEDTFEEVSLSAALNGVEGLDYMERIPLATSEGFPHVLSRKNGE
   Consensus  (1216) PFLGGIQKYATPMMPLDEEILSKVAQDMVEEWFDCVDEEDTFEEVSLSAALNGVEGLDYMERIPLATSEGFPHVLSRKNGE
```

*FIG. 8B*

```
                                                                                              Section 17
             (1297) 1297      1310      1320      1330      1340      1350      1360      1377
   IL-Cb1 (II) (1297) KGKRRFVSGDGEEMTLIPGTSVEEAYNKLIVELEKSVPTLVGIECPKDEKLPRRKIFDKPKTRCFTILPMEFNLVVRQKFL
   IIL-Cb1 (I) (1297) KGKRRFVTGDGEEMSLIPGTSVEEAYNKLTVELEKCVPTLVGIECPKDEKLPRRKIFDKPKTRCFTILSMEFNLVVRQKFL
   pBPMV-R1A (1297) KGKRRFVTGDGEEMSLIPGTSVEEAYNKLTVELEKCVPTLVGIECPKDEKLPRRKIFDKPKTRCFTILPMEFNLVVRQKFL
   pBPMV-R1B (1297) KGKRRFVTGDGEEMSLIPGTSVEEAYNKLTVELEKCVPTLVGIECPKDEKLPRRKIFDKPKTRCFTILPMEFNLVVRQKFL
          K-G7 (1296) KGKRRFVTGDGEEMSLIPGTSVEEAYNKLTVELEKCVPTLVGIECPKDEKLPRRKIFDKPKTRCFTILPMEFNLVVRQKFL
     Consensus (1297) KGKRRFVTGDGEEMSLIPGTSVEEAYNKLTVELEKCVPTLVGIECPKDEKLPRRKIFDKPKTRCFTILPMEFNLVVRQKFL
                                                                                              Section 18
             (1378) 1378      1390      1400      1410      1420      1430      1440      1458
   IL-Cb1 (II) (1378) NFVRFIMKKRDKLSCQVGINPYSMEWTGLANRLLSKGNDILCCDYASFDGLITKQVMSKMAEMINSLCGGDEKLMRERTHL
   IIL-Cb1 (I) (1378) NFVRFIMKKRDKLSCQVGINPYSMEWTGLANRLLSKGNDILCCDYASFDGLITKQVMSKMAEMINSLCGGDEKLMRERTHL
   pBPMV-R1A (1378) NFVRFIMKKRDKLSCQVGINPYSMEWTGLANRLLSKGNDILCCDYASFDGLITKQVMSKMAEMINSLCGGDEKLMRERTHL
   pBPMV-R1B (1378) NFVRFIMKKRDKLSCQVGINPYSMEWTGLANRLLSKGNDILCCDYASFDGLITKQVMSKMAEMINSLCGGDEKLMRERTHL
          K-G7 (1377) NFVRFIMKKRDKLSCQVGINPYSMEWTGLANRLLSKGNDILCCDYASFSGLITKQVMSKMAEMINSLCGGDEKLMRERTHL
     Consensus (1378) NFVRFIMKKRDKLSCQVGINPYSMEWTGLANRLLSKGNDILCCDYASFDGLITKQVMSKMAEMINSLCGGDEKLMRERTHL
                                                                                              Section 19
             (1459) 1459      1470      1480      1490      1500      1510      1520      1539
   IL-Cb1 (II) (1459) LLACCSRMAICKKDVWRVECGIPSGFPLTVICNSIFNEMLIRYSYEKLLRQAKAPSMFLQSFKNFVSLCVYGDDNFISVHE
   IIL-Cb1 (I) (1459) LLACCSRMAICKKNVWRVECGIPSGFPLTVICNSIFNEMLIRYSYEKLLRQAKAPSMFLQSFKNFISLCVYGDDNLISVHE
   pBPMV-R1A (1459) LLACCSRMAICKKDVWRVECGIPSGFPLTVICNSIFNEMLIRYSYEKLLRQAKAPSMFLQSFKNFISLCVYGDDNLISVHE
   pBPMV-R1B (1459) LLACCSRMAICKKDVWRVECGIPSGFPLTVICNSIFNEMLIRYSYEKLLRQAKAPSMFLQSFKNFISLCVYGDDNLISVHE
          K-G7 (1458) LLACCSRMAICKKDIWRVECGIPSGFPLTVICNSIFNEMLIRYSYEKLLRQAKAPSMFLQSFRNFISLCVYGDDNLISVHE
     Consensus (1459) LLACCSRMAICKKDVWRVECGIPSGFPLTVICNSIFNEMLIRYSYEKLLRQAKAPSMFLQSFKNFISLCVYGDDNLISVHE
                                                                                              Section 20
             (1540) 1540      1550      1560      1570      1580      1590      1600      1610      1620
   IL-Cb1 (II) (1540) YVKPYFSGSKLKSFLAGHNITITDGIDKTSATLQFRKLADCDFLKRNFKQMSNVLWVAPEDKASLWSQLHYVSCNRLEMQE
   IIL-Cb1 (I) (1540) YVKPYFSGSKLKSFLASHNITITDGIDKTSATLQFRKLSECDFLKRNFKQMSNVLWVAPEDKASLWSQLHYVSCNRLEMQE
   pBPMV-R1A (1540) YVKPYFSGSKLKSFLASHNITITDGIDKTSATLQFRKLSECDFLKRNFKQMSNVLWVAPEDKASLWSQLHYVSCNRLEMQE
   pBPMV-R1B (1540) YVKPYFSGSKLKSFLASHNITITDGIDKTSATLQFRKLSECDFLKRNFKQMSNVLWVAPEDKASLWSQLHYVSCNRLEMQE
          K-G7 (1539) YVKPYFSGSKLKSFLASHNITITDGIDKTSATLQFRKLSECDFLKRNFKQMSNVLWVAPEDKASLWSQLHYVSCNRLEMQE
     Consensus (1540) YVKPYFSGSKLKSFLASHNITITDGIDKTSATLQFRKLSECDFLKRNFKQMSNVLWVAPEDKASLWSQLHYVSCNRLEMQE
                                                                                              Section 21
             (1621) 1621      1630      1640      1650      1660      1670      1680      1690      1701
   IL-Cb1 (II) (1621) AYLVNLVNVLRELYLHSPEEARQLRRKALSRIEWLQKADVFTIAQIEEFHSMQRMMNAPDSNDNIDLLLSIDLLGLQGAGK
   IIL-Cb1 (I) (1621) AYLVNLVNVLRELYLHSPEEARQLRRKALSRIEWLQKADVPTIAQIEEFHSMQRIMNAPDSNDNIDLLLSIDLLGLQGAGK
   pBPMV-R1A (1621) AYLVNLVNVLRELYLHSPEEARQLRRKALSRIEWLQKADVPTIAQIEEFHSMQRIMNAPDSNDNIDLLLSIDLLGLQGAGK
   pBPMV-R1B (1621) AYLVNLVNVLRELYLHSPEEARQLRRKALSRIEWLQKADVPTIAQIEEFHSMQRIMNAPDSNDNIDLLLSIDLLGLQGAGK
          K-G7 (1620) AYLVNLVNVLRELYLHSPEEARRLRRKALSCIEWLQKADVPTIAQIEEFHSMQRIMNAPDSNDNIDLLLSIDLLGLQGAAR
     Consensus (1621) AYLVNLVNVLRELYLHSPEEARQLRRKALSRIEWLQKADVPTIAQIEEFHSMQRIMNAPDSNDNIDLLLSIDLLGLQGAGK
                                                                                              Section 22
             (1702) 1702      1710      1720      1730      1740      1750      1760      1770      1782
   IL-Cb1 (II) (1702) AFPNKIVFDDKLVLANTQEFFDGNFPVDSWLPIFVNCLYPVSQLPPEAVVNVTCGSGRGGLPTTAWISSAVNNRSSDINK
   IIL-Cb1 (I) (1702) AFPNKIVFDDKLVLANTQEFFDGNFPTDSWLPIFVNCLYPVSQLPAEAVIVNVCGSGRGGLPTTAWISSAVNNRSSDINK
   pBPMV-R1A (1702) AFPNKIVFDDKLVLANTQEFFDGNFPTDSWLPIFVNCLYPVSQLPAEAVTVNVVCGSGRGGLPTTAWISSAVNNRSSDINK
   pBPMV-R1B (1702) AFPNKIVFDDKLVLANTQEFFDGNFPTDSWLPIFVNCLYPVSQLPAEAVTVNVVCGSGRGGLPTTAWISSAVNNRSSDINK
          K-G7 (1701) FSQIRLWFDDKLVLANTQEFFDGNFPADSWLPIFVNCLYPVSQLPAEAVIVNVVCGSGRGGLPTTAWISSAVNNRSSDINK
     Consensus (1702) AFPNKIVFDDKLVLANTQEFFDGNFPTDSWLPIFVNCLYPVSQLPAEAVIVNVVCGSGRGGLPTTAWISSAVNNRSSDINK
                                                                                              Section 23
             (1783) 1783      1790      1800      1810      1820      1830      1840      1851
   IL-Cb1 (II) (1783) KIRTALGKGKKIVFLTRVDPFPVALLAVLFGVKNEILSSNATNPMLTRLLENCKSLKYLVDECPFAFVN
   IIL-Cb1 (I) (1783) KIRTALGKGKKIVFLTRVDPFPVALLAVLFGVKNEILSSNATNPMLTRLLENCKSLKYLVDECPFAFVN
   pBPMV-R1A (1783) KIRTALGKGKKIVFLTRVDPFPVALLAVLFGVKNEILSSNATNPMLTRLLENCKSLKYLVDECPFAFVN
   pBPMV-R1B (1783) KIRTALGKGKKIVFLTRVDPFPVALLAVLFGVKNEILSSNATNPMLTRLLENCKSLKYLVDECPFAFVN
          K-G7 (1782) KIRTALGKGKKIVFLTRVDPFPVALLAVLFGVKNEILSSNATNPMLTRLLENCKSLKYLVDECPFAFVN
     Consensus (1783) KIRTALGKGKKIVFLTRVDPFPVALLAVLFGVKNEILSSNATNPMLTRLLENCKSLKYLVDECPFAFVN
```

*FIG. 8C*

```
                                                                                                      Section 1
              (1)  1         10        20        30        40        50        60        70        80
     K-G7     (1)  ----------------------------------------------------------------------------------
pBPMV-R1A    (1)  TATAGTGAGTCGTATTACAATTCACTGGCCGTCGTTTTACAACGTCGTGACTGGGAAAACCCTGGCGTTACCCAACTTAA
 Consensus   (1)
                                                                                                      Section 2
              (81) 81        90        100       110       120       130       140       150       160
     K-G7     (1)  ----------------------------------------------------------------------------------
pBPMV-R1A    (81) TCGCCTTGCAGCACATCCCCCTTTCGCCAGCTGGCGTAATAGCGAAGAGGCCCGCACCGATCGCCCTTCCCAACAGTTGC
 Consensus   (81)
                                                                                                      Section 3
              (161) 161      170       180       190       200       210       220       230       240
     K-G7     (1)  ----------------------------------------------------------------------------------
pBPMV-R1A    (161) GCAGCCTGAATGGCGAATGGACGCGCCCTGTAGCGGCGCATTAAGCGCGGCGGGTGTGGTGGTTACGCGCAGCGTGACCG
 Consensus   (161)
                                                                                                      Section 4
              (241) 241      250       260       270       280       290       300       310       320
     K-G7     (1)  ----------------------------------------------------------------------------------
pBPMV-R1A    (241) CTACACTTGCCAGCGCCCTAGCGCCCGCTCCTTTCGCTTTCTTCCCTTCCTTTCTCGCCACGTTCGCCGGCTTTCCCCGT
 Consensus   (241)
                                                                                                      Section 5
              (321) 321      330       340       350       360       370       380       390       400
     K-G7     (1)  ----------------------------------------------------------------------------------
pBPMV-R1A    (321) CAAGCTCTAAATCGGGGGCTCCCTTTAGGGTTCCGATTTAGTGCTTTACGGCACCTCGACCCCAAAAAACTTGATTAGGG
 Consensus   (321)
                                                                                                      Section 6
              (401) 401      410       420       430       440       450       460       470       480
     K-G7     (1)  ----------------------------------------------------------------------------------
pBPMV-R1A    (401) TGATGGTTCACGTAGTGGGCCATCGCCCTGATAGACGGTTTTTCGCCCTTTGACGTTGGAGTCCACGTTCTTTAATAGTG
 Consensus   (401)
                                                                                                      Section 7
              (481) 481      490       500       510       520       530       540       550       560
     K-G7     (1)  ----------------------------------------------------------------------------------
pBPMV-R1A    (481) GACTCTTGTTCCAAACTGGAACAACACTCAACCCTATCTCGGTCTATTCTTTTGATTTATAAGGGATTTTGCCGATTTCG
 Consensus   (481)
                                                                                                      Section 8
              (561) 561      570       580       590       600       610       620       630       640
     K-G7     (1)  ----------------------------------------------------------------------------------
pBPMV-R1A    (561) GCCTATTGGTTAAAAAATGAGCTGATTTAACAAAAATTTAACGCGAATTTTAACAAAATATTAACGCTTACAATTTCCTG
 Consensus   (561)
                                                                                                      Section 9
              (641) 641      650       660       670       680       690       700       710       720
     K-G7     (1)  ----------------------------------------------------------------------------------
pBPMV-R1A    (641) ATGCGGTATTTTCTCCTTACGCATCTGTGCGGTATTTCACACCGCATATGGTGCACTCTCAGTACAATCTGCTCTGATGC
 Consensus   (641)
                                                                                                      Section 10
              (721) 721      730       740       750       760       770       780       790       800
     K-G7     (1)  ----------------------------------------------------------------------------------
pBPMV-R1A    (721) CGCATAGTTAAGCCAGCCCCGACACCCGCCAACACCCGCTGACGCGCCCTGACGGGCTTGTCTGCTCCCGGCATCCGCTT
 Consensus   (721)
                                                                                                      Section 11
              (801) 801      810       820       830       840       850       860       870       880
     K-G7     (1)  ----------------------------------------------------------------------------------
pBPMV-R1A    (801) ACAGACAAGCTGTGACCGTCTCCGGGAGCTGCATGTGTCAGAGGTTTTCACCGTCATCACCGAAACGCGCGAGACGAAAG
 Consensus   (801)
```

*FIG. 9A*

```
                                                                                              Section 12
              (881) 881      890       900       910       920       930       940       950       960
       K-G7    (1) ----------------------------------------------------------------------------------
   pBPMV-R1A (881) GGCCTCGTGATACGCCTATTTTTATAGGTTAATGTCATGATAATAATGGTTTCTTAGACGTCAGGTGGCACTTTTCGGGG
   Consensus (881)
                                                                                              Section 13
              (961) 961      970       980       990      1000      1010      1020      1030      1040
       K-G7    (1) ----------------------------------------------------------------------------------
   pBPMV-R1A (961) AAATGTGCGCGGAACCCCTATTTGTTTATTTTTCTAAATACATTCAAATATGTATCCGCTCATGAGACAATAACCCTGAT
   Consensus (961)
                                                                                              Section 14
             (1041) 1041     1050      1060      1070      1080      1090      1100      1110      1120
       K-G7    (1) ----------------------------------------------------------------------------------
   pBPMV-R1A (1041) AAATGCTTCAATAATATTGAAAAAGGAAGAGTATGAGTATTCAACATTTCCGTGTCGCCCTTATTCCCTTTTTTGCGGCA
   Consensus (1041)
                                                                                              Section 15
             (1121) 1121     1130      1140      1150      1160      1170      1180      1190      1200
       K-G7    (1) ----------------------------------------------------------------------------------
   pBPMV-R1A (1121) TTTTGCCTTCCTGTTTTTGCTCACCCAGAAACGCTGGTGAAAGTAAAAGATGCTGAAGATCAGTTGGGTGCACGAGTGGG
   Consensus (1121)
                                                                                              Section 16
             (1201) 1201     1210      1220      1230      1240      1250      1260      1270      1280
       K-G7    (1) ----------------------------------------------------------------------------------
   pBPMV-R1A (1201) TTACATCGAACTGGATCTCAACAGCGGTAAGATCCTTGAGAGTTTTCGCCCCGAAGAACGTTTTCCAATGATGAGCACTT
   Consensus (1201)
                                                                                              Section 17
             (1281) 1281     1290      1300      1310      1320      1330      1340      1350      1360
       K-G7    (1) ----------------------------------------------------------------------------------
   pBPMV-R1A (1281) TTAAAGTTCTGCTATGTGGCGCGGTATTATCCCGTATTGACGCCGGGCAAGAGCAACTCGGTCGCCGCATACACTATTCT
   Consensus (1281)
                                                                                              Section 18
             (1361) 1361     1370      1380      1390      1400      1410      1420      1430      1440
       K-G7    (1) ----------------------------------------------------------------------------------
   pBPMV-R1A (1361) CAGAATGACTTGGTTGAGTACTCACCAGTCACAGAAAAGCATCTTACGGATGGCATGACAGTAAGAGAATTATGCAGTGC
   Consensus (1361)
                                                                                              Section 19
             (1441) 1441     1450      1460      1470      1480      1490      1500      1510      1520
       K-G7    (1) ----------------------------------------------------------------------------------
   pBPMV-R1A (1441) TGCCATAACCATGAGTGATAACACTGCGGCCAACTTACTTCTGACAACGATCGGAGGACCGAAGGAGCTAACCGCTTTTT
   Consensus (1441)
                                                                                              Section 20
             (1521) 1521     1530      1540      1550      1560      1570      1580      1590      1600
       K-G7    (1) ----------------------------------------------------------------------------------
   pBPMV-R1A (1521) TGCACAACATGGGGGATCATGTAACTCGCCTTGATCGTTGGGAACCGGAGCTGAATGAAGCCATACCAAACGACGAGCGT
   Consensus (1521)
                                                                                              Section 21
             (1601) 1601     1610      1620      1630      1640      1650      1660      1670      1680
       K-G7    (1) ----------------------------------------------------------------------------------
   pBPMV-R1A (1601) GACACCACGATGCCTGTAGCAATGGCAACAACGTTGCGCAAACTATTAACTGGCGAACTACTTACTCTAGCTTCCCGGCA
   Consensus (1601)
                                                                                              Section 22
             (1681) 1681     1690      1700      1710      1720      1730      1740      1750      1760
       K-G7    (1) ----------------------------------------------------------------------------------
   pBPMV-R1A (1681) ACAATTAATAGACTGGATGGAGGCGGATAAAGTTGCAGGACCACTTCTGCGCTCGGCCCTTCCGGCTGGCTGGTTTATTG
   Consensus (1681)
```

*FIG. 9B*

```
                                                                                                    Section 23
              (1761) 1761      1770      1780      1790      1800      1810      1820      1830      1840
      K-G7      (1)  -----------------------------------------------------------------------------------
 pBPMV-R1A   (1761)  CTGATAAATCTGGAGCCGGTGAGCGTGGGTCTCGCGGTATCATTGCAGCACTGGGGCCAGATGGTAAGCCCTCCCGTATC
 Consensus   (1761)
                                                                                                    Section 24
              (1841) 1841      1850      1860      1870      1880      1890      1900      1910      1920
      K-G7      (1)  -----------------------------------------------------------------------------------
 pBPMV-R1A   (1841)  GTAGTTATCTACACGACGGGGAGTCAGGCAACTATGGATGAACGAAATAGACAGATCGCTGAGATAGGTGCCTCACTGAT
 Consensus   (1841)
                                                                                                    Section 25
              (1921) 1921      1930      1940      1950      1960      1970      1980      1990      2000
      K-G7      (1)  -----------------------------------------------------------------------------------
 pBPMV-R1A   (1921)  TAAGCATTGGTAACTGTCAGACCAAGTTTACTCATATATACTTTAGATTGATTTAAAACTTCATTTTTAATTTAAAAGGA
 Consensus   (1921)
                                                                                                    Section 26
              (2001) 2001      2010      2020      2030      2040      2050      2060      2070      2080
      K-G7      (1)  -----------------------------------------------------------------------------------
 pBPMV-R1A   (2001)  TCTAGGTGAAGATCCTTTTTGATAATCTCATGACCAAAATCCCTTAACGTGAGTTTTCGTTCCACTGAGCGTCAGACCCC
 Consensus   (2001)
                                                                                                    Section 27
              (2081) 2081      2090      2100      2110      2120      2130      2140      2150      2160
      K-G7      (1)  -----------------------------------------------------------------------------------
 pBPMV-R1A   (2081)  GTAGAAAAGATCAAAGGATCTTCTTGAGATCCTTTTTTTCTGCGCGTAATCTGCTGCTTGCAAACAAAAAAACCACCGCT
 Consensus   (2081)
                                                                                                    Section 28
              (2161) 2161      2170      2180      2190      2200      2210      2220      2230      2240
      K-G7      (1)  -----------------------------------------------------------------------------------
 pBPMV-R1A   (2161)  ACCAGCGGTGGTTTGTTTGCCGGATCAAGAGCTACCAACTCTTTTTCCGAAGGTAACTGGCTTCAGCAGAGCGCAGATAC
 Consensus   (2161)
                                                                                                    Section 29
              (2241) 2241      2250      2260      2270      2280      2290      2300      2310      2320
      K-G7      (1)  -----------------------------------------------------------------------------------
 pBPMV-R1A   (2241)  CAAATACTGTTCTTCTAGTGTAGCCGTAGTTAGGCCACCACTTCAAGAACTCTGTAGCACCGCCTACATACCTCGCTCTG
 Consensus   (2241)
                                                                                                    Section 30
              (2321) 2321      2330      2340      2350      2360      2370      2380      2390      2400
      K-G7      (1)  -----------------------------------------------------------------------------------
 pBPMV-R1A   (2321)  CTAATCCTGTTACCAGTGGCTGCTGCCAGTGGCGATAAGTCGTGTCTTACCGGGTTGGACTCAAGACGATAGTTACCGGA
 Consensus   (2321)
                                                                                                    Section 31
              (2401) 2401      2410      2420      2430      2440      2450      2460      2470      2480
      K-G7      (1)  -----------------------------------------------------------------------------------
 pBPMV-R1A   (2401)  TAAGGCGCAGCGGTCGGGCTGAACGGGGGGTTCGTGCACACAGCCCAGCTTGGAGCGAACGACCTACACCGAACTGAGAT
 Consensus   (2401)
                                                                                                    Section 32
              (2481) 2481      2490      2500      2510      2520      2530      2540      2550      2560
      K-G7      (1)  -----------------------------------------------------------------------------------
 pBPMV-R1A   (2481)  ACCTACAGCGTGAGCTATGAGAAAGCGCCACGCTTCCCGAAGGGAGAAAGGCGGACAGGTATCCGGTAAGCGGCAGGGTC
 Consensus   (2481)
                                                                                                    Section 33
              (2561) 2561      2570      2580      2590      2600      2610      2620      2630      2640
      K-G7      (1)  -----------------------------------------------------------------------------------
 pBPMV-R1A   (2561)  GGAACAGGAGAGCGCACGAGGGAGCTTCCAGGGGGAAACGCCTGGTATCTTTATAGTCCTGTCGGGTTTCGCCACCTCTG
 Consensus   (2561)
```

*FIG. 9C*

```
                                                                                                                          Section 34
              (2641) 2641      2650      2660      2670      2680      2690      2700      2710      2720
        K-G7    (1)  ---------------------------------------------------------------------------------------
   pBPMV-R1A  (2641) ACTTGAGCGTCGATTTTTGTGATGCTCGTCAGGGGGCGGAGCCTATGGAAAAACGCCAGCAACGCGGCCTTTTTACGGT
   Consensus  (2641)
                                                                                                                          Section 35
              (2721) 2721      2730      2740      2750      2760      2770      2780      2790      2800
        K-G7    (1)  ---------------------------------------------------------------------------------------
   pBPMV-R1A  (2721) TCCTGGCCTTTTGCTGGCCTTTTGCTCACATGTTCTTTCCTGCGTTATCCCCTGATTCTGTGGATAACCGTATTACCGCC
   Consensus  (2721)
                                                                                                                          Section 36
              (2801) 2801      2810      2820      2830      2840      2850      2860      2870      2880
        K-G7    (1)  ---------------------------------------------------------------------------------------
   pBPMV-R1A  (2801) TTTGAGTGAGCTGATACCGCTCGCCGCAGCCGAACGACCGAGCGCAGCGAGTCAGTGAGCGAGGAAGCGGAAGAGCGCCC
   Consensus  (2801)
                                                                                                                          Section 37
              (2881) 2881      2890      2900      2910      2920      2930      2940      2950      2960
        K-G7    (1)  ---------------------------------------------------------------------------------------
   pBPMV-R1A  (2881) AATACGCAAACCGCCTCTCCCCGCGCGTTGGCCGATTCATTAATGCAGCTGGCACGACAGGTTTCCCGACTGGAAAGCGG
   Consensus  (2881)
                                                                                                                          Section 38
              (2961) 2961      2970      2980      2990      3000      3010      3020      3030      3040
        K-G7    (1)  ---------------------------------------------------------------------------------------
   pBPMV-R1A  (2961) GCAGTGAGCGCAACGCAATTAATGTGAGTTAGCTCACTCATTAGGCACCCCAGGCTTTACACTTTATGCTTCCGGCTCGT
   Consensus  (2961)
                                                                                                                          Section 39
              (3041) 3041      3050      3060      3070      3080      3090      3100      3110      3120
        K-G7    (1)  ---------------------------------------------------------------------------------------
   pBPMV-R1A  (3041) ATGTTGTGTGGAATTGTGAGCGGATAACAATTTCACACAGGAAACAGCTATGACCATGATTACGCCAAGCTATTTAGGTG
   Consensus  (3041)
                                                                                                                          Section 40
              (3121) 3121      3130      3140      3150      3160      3170      3180      3190      3200
        K-G7    (1)  ---------------------------------------------------------------------------------------
   pBPMV-R1A  (3121) ACACTATAGAATACTCAAGCGGCCGCCTACTCCAAGAATATCAAAGATACAGTCTCAGAAGACCAAAGGGCTATTGAGAC
   Consensus  (3121)
                                                                                                                          Section 41
              (3201) 3201      3210      3220      3230      3240      3250      3260      3270      3280
        K-G7    (1)  ---------------------------------------------------------------------------------------
   pBPMV-R1A  (3201) TTTTCAACAAAGGGTAATATCGGGAAACCTCCTCGGATTCCATTGCCCAGCTATCTGTCACTTCATCAAAAGGACAGTAG
   Consensus  (3201)
                                                                                                                          Section 42
              (3281) 3281      3290      3300      3310      3320      3330      3340      3350      3360
        K-G7    (1)  ---------------------------------------------------------------------------------------
   pBPMV-R1A  (3281) AAAAGGAAGGTGGCACCTACAAATGCCATCATTGCGATAAAGGAAAGGCTATCGTTCAAGATGCCTCTGCCGACAGTGGT
   Consensus  (3281)
                                                                                                                          Section 43
              (3361) 3361      3370      3380      3390      3400      3410      3420      3430      3440
        K-G7    (1)  ---------------------------------------------------------------------------------------
   pBPMV-R1A  (3361) CCCAAAGATGGACCCCCACCCACGAGGAGCATCGTGGAAAAAGAAGACGTTCCAACCACGTCTTCAAAGCAAGTGGATTG
   Consensus  (3361)
                                                                                                                          Section 44
              (3441) 3441      3450      3460      3470      3480      3490      3500      3510      3520
        K-G7    (1)  ---------------------------------------------------------------------------------------
   pBPMV-R1A  (3441) ATGTGATCTACTCCAAGAATATCAAAGATACAGTCTCAGAAGACCAAAGGGCTATTGAGACTTTTCAACAAAGGGTAATA
   Consensus  (3441)
```

*FIG. 9D*

```
                                                                                                      Section 45
              (3521)  3521      3530      3540      3550      3560      3570      3580      3590      3600
       K-G7     (1)  ------------------------------------------------------------------------------------
   pBPMV-R1A (3521)  TCGGGAAACCTCCTCGGATTCCATTGCCCAGCTATCTGTCACTTCATCAAAAGGACAGTAGAAAAGGAAGGTGGCACCTA
   Consensus (3521)
                                                                                                      Section 46
              (3601)  3601      3610      3620      3630      3640      3650      3660      3670      3680
       K-G7     (1)  ------------------------------------------------------------------------------------
   pBPMV-R1A (3601)  CAAATGCCATCATTGCGATAAAGGAAAGGCTATCGTTCAAGATGCCTCTGCCGACAGTGGTCCCAAAGATGGACCCCCAC
   Consensus (3601)
                                                                                                      Section 47
              (3681)  3681      3690      3700      3710      3720      3730      3740      3750      3760
       K-G7     (1)  ------------------------------------------------------------------------------------
   pBPMV-R1A (3681)  CCACGAGGAGCATCGTGGAAAAAGAAGACGTTCCAACCACGTCTTCAAAGCAAGTGGATTGATGTGATATCTCCACTGAC
   Consensus (3681)
                                                                                                      Section 48
              (3761)  3761      3770      3780      3790      3800      3810      3820      3830      3840
       K-G7     (1)  -------------------------------------------------------------------------------- TA
   pBPMV-R1A (3761)  GTAAGGGATGACGCACAATCCCACTATCCTTCGCAAGACCCTTCCTCTATATAAGGAAGTTCATTTCATTTGGAGAGGTA
   Consensus (3761)                                                                                    TA
                                                                                                      Section 49
              (3841)  3841      3850      3860      3870      3880      3890      3900      3910      3920
       K-G7     (3)  TTAAAATTTTCATAAGATTTGAAATTTTGATAAACCGCGATCATAGGTTGCCGCACCTTAAAACCGGAAACAAAAGCAAT
   pBPMV-R1A (3841)  TTAAAATTTTCATAAGATTTGAAATTTTGATAAACCGCGATCATAGGTTGCCGCACCTTAAAACCGGAAACAAAAGCAAT
   Consensus (3841)  TTAAAATTTTCATAAGATTTGAAATTTTGATAAACCGCGATCATAGGTTGCCGCACCTTAAAACCGGAAACAAAAGCAAT
                                                                                                      Section 50
              (3921)  3921      3930      3940      3950      3960      3970      3980      3990      4000
       K-G7    (83)  CGTTACTTGATTTCAAAGACTTCTCAATTTCTCTCTACATTTCTTGTATACAGCTTTCAAAGTGAAAGAAAATCACTCTC
   pBPMV-R1A (3921)  CGTTACTTGATTTCAAAGACTTCTCAATTTCTTCTACATTTCTTGTATACGGCTTTCAAAGTGAAAGAAAATCACTCTC
   Consensus (3921)  CGTTACTTGATTTCAAAGACTTCTCAATTTCT TCTACATTTCTTGTATAC GCTTTCAAAGTGAAAGAAAATCACTCTC
                                                                                                      Section 51
              (4001)  4001      4010      4020      4030      4040      4050      4060      4070      4080
       K-G7   (163)  TGTGCTGGTCGCAGACTTCGTGAATCATTTCTTTCTGCTCTCAGTTCATTTGCTGAACACTCTCCTATTTGATATAGGA
   pBPMV-R1A (4001)  TGTGCTGGTCACAGACTTCGTGAATCATTTCTTTCTGCTCTCAGTTCATTTGCTGAACACTCTCCTATTTGATATAGGA
   Consensus (4001)  TGTGCTGGTC CAGACTTCGTGAATCATTTCTTTCTGCTCTCAGTTCATTTGCTGAACACTCTCCTATTTGATATAGGA
                                                                                                      Section 52
              (4081)  4081      4090      4100      4110      4120      4130      4140      4150      4160
       K-G7   (243)  CTTCGTGTCAGATTTGAACTTCTCTTACCTCTCTTTCTCGGTTCTTCATTTGATTTCAAATTTCTCTGAAATTTAAATTT
   pBPMV-R1A (4081)  CTTCGTGTCAGATTTGAACTTCTGCTATCTCTTTTCTCGGTTCTTCATTTGATTTCAAACTTTTCTGAAATTTAAATCT
   Consensus (4081)  CTTCGTGTCAGATTTGAACTTCTC TA CTCT TTTCTCGGTTCTTCATTTGATTTCAAA TT TCTGAAATTTAAAT T
                                                                                                      Section 53
              (4161)  4161      4170      4180      4190      4200      4210      4220      4230      4240
       K-G7   (323)  CTTTTGACATTTGAACTTTGTGTTGGCTCCATTTGAAAAACAACATGAAGTTCTATCCTGGTCAGAATATTTCTGAAAT
   pBPMV-R1A (4161)  CTTTTGACATTTGAACTTTGTGTTGGCTCCATTTGAAAAACAACATGAAGTTCTATCCTGGTCAAAATATTTCCGAAAT
   Consensus (4161)  CTTTTGACATTTGAACTTTGTGTTGGCTCCATTTGAAAAACAACATGAAGTTCTATCCTGGTCA AATATTTC GAAAT
                                                                                                      Section 54
              (4241)  4241      4250      4260      4270      4280      4290      4300      4310      4320
       K-G7   (403)  TGTTTACCACTTTCAGAGTAATGAGACAGCCAATAGGTTAGATGCATATTTTGCTTGTGGCTGTGAGGAGGATACTGAAG
   pBPMV-R1A (4241)  TGTTTACCACTTTCAGAGTAATGAGACAGCCAATAGGTTAGATGCATATTTTGCTTGTGGCTGTGAGGAGGATACTGAAG
   Consensus (4241)  TGTTTACCACTTTCAGAGTAATGAGACAGCCAATAGGTTAGATGCATATTTTGCTTGTGGCTGTGAGGAGGATACTGAAG
                                                                                                      Section 55
              (4321)  4321      4330      4340      4350      4360      4370      4380      4390      4400
       K-G7   (483)  TCCTCGCTCGTTTGAAGCAGTGTAATCCTCGTCTGCTTCATCTGTCATATGCTGCCTTTTGTTTGGAAATGGGCAGTCAT
   pBPMV-R1A (4321)  TCCTCGCTCGTTTGAAGCAGTGTAATCCTCGTCTGCTTCATCTGTCATATGCTGCCTTTTGTTTGGAAATGGGCAGTCAT
   Consensus (4321)  TCCTCGCTCGTTTGAAGCAGTGTAATCCTCGTCTGCTTCATCTGTCATATGCTGCCTTTTGTTTGGAAATGGGCAGTCAT
```

```
                                                                                                          Section 67
              (5281) 5281      5290       5300       5310       5320       5330       5340       5350       5360
       K-G7  (1443) TTTCTAATTTTGTTAGAAAATTATTAGGATTGGATAGTGCTTTTCTCAGAGATGCTGCACTCATTTTTTCTCAAGATGTG
   pBPMV-R1A (5281) TTTCTAATTTTGTCAGAAAATTATTAGGATTGGATAGTGCTTTTCTCAGAGATGCTGCACTCATTTTTTCCCAAGATGTG
   Consensus (5281) TTTCTAATTTTGT AGAAAATTATTAGGATTGGATAGTGCTTTTCTCAGAGATGCTGCACTCATTTTTTC  CAAGATGTG
                                                                                                          Section 68
              (5361) 5361      5370       5380       5390       5400       5410       5420       5430       5440
       K-G7  (1523) GATGGATGGTTGCGTAACATTAGTTGGTGCCAAGAACAGTTTTTGTTGAAAGCTTACATGTCGCAAGATGATCTTATTGT
   pBPMV-R1A (5361) GATGGATGGTTGCGTAACATCAGTTGGTGCCAGGAACAGTTTTTGTTGAAAGCTTACATGTCGCAAGATGATCTTATTGT
   Consensus (5361) GATGGATGGTTGCGTAACAT AGTTGGTGCCA GAACAGTTTTTGTTGAAAGCTTACATGTCGCAAGATGATCTTATTGT
                                                                                                          Section 69
              (5441) 5441      5450       5460       5470       5480       5490       5500       5510       5520
       K-G7  (1603) CTTACGCTCTTTAGTTGTCAAAGGTGAAAGAATGAGGGAACAGATGCTTGAAGGAGAAGTTAAGGTGTCTCCAAGTGTTT
   pBPMV-R1A (5441) CCTGCGCTCTTTAGTTGTTAAAGGTGAAAGAATGAGGGAACAGATGCTTGAAGCAGAAGTTAAGGTATCTCCAAGTGTTT
   Consensus (5441) C T CGCTCTTTAGTTGT AAAGGTGAAAGAATGAGGGAACAGATGCTTGAAGGAGAAGTTAAGGT TCTCCAAGTGTTT
                                                                                                          Section 70
              (5521) 5521      5530       5540       5550       5560       5570       5580       5590       5600
       K-G7  (1683) GCAACCTTATTGTCAAAGGCTGTGAAGAAGCAAATAAATTGATGCGTGAGAGCCGACTTCATTGTTCAAAAACAATTAGG
   pBPMV-R1A (5521) GCAACCTTATTGTCAAAGGCTGTGAAGAAGCAAATAAATTGATGCGTGAGAGCCCACTTCATTGTTCAAAAACAATTAGC
   Consensus (5521) GCAACCTTATTGTCAAAGGCTGTGAAGAAGCAAATAAATTGATGCGTGAGAGC  ACTTCATTGTTCAAAAACAATTAGG
                                                                                                          Section 71
              (5601) 5601      5610       5620       5630       5640       5650       5660       5670       5680
       K-G7  (1763) AAAATTCCTTTTGTTATTTTTGCTCACGGTGAATCCCGAGTTGGGAAATCTCTGCTGGTTGATAGGCTAATCACAGATTT
   pBPMV-R1A (5601) AAGATTCCTTTTGTTATTTTTGCTCACGGTGAATCCCGAGTTGGGAAATCTCTGTTGGTTGATAGCTAATCACAGATTT
   Consensus (5601) AA ATTCCTTTTGTTATTTTTGCTCACGGTGAATCCCGAGTTGGGAAATCTCTG TGGTTGATA GCTAATCACAGATTT
                                                                                                          Section 72
              (5681) 5681      5690       5700       5710       5720       5730       5740       5750       5760
       K-G7  (1843) CTGTGATCATTTGGAAATTGGAGAAGATGCTGTGTACTCAAGGAATCCATCAGATCCTTTTTGGAGTGGATATAGAAGGC
   pBPMV-R1A (5681) CTGTGATCATTTGGAAATTGGAGAAGATGCTGTGTACTCAAGGAATCCATCAGATCCTTTCTGGAGTGGATATAGAAGGC
   Consensus (5681) CTGTGATCATTTGGAAATTGGAGAAGATGCTGTGTACTCAAGGAATCCATCAGATCCTTT TGGAGTGGATATAGAAGGC
                                                                                                          Section 73
              (5761) 5761      5770       5780       5790       5800       5810       5820       5830       5840
       K-G7  (1923) AGCCAATTGTTACTATTGATGATTTGCTGCTGTTGTTTCGGAGCCATCTGCTGAAGCTCAATTAATTCCATTAGTTTCA
   pBPMV-R1A (5761) AGCCAATTGTTACTATTGATGATTTGCTGCTGTTGTTTCGGAGCCATCTGCTGAAGCTCAATTAATTCCATTAGTTTCA
   Consensus (5761) AGCCAATTGTTACTATTGATGATTTGCTGCTGTTGTTTCGGAGCCATCTGCTGAAGCTCAATTAATTCCATTAGTTTCA
                                                                                                          Section 74
              (5841) 5841      5850       5860       5870       5880       5890       5900       5910       5920
       K-G7  (2003) AGTGCTCTCCAATAAACATGGCTGGTTTGGAGGAGAAGGGAATGCACTTTGATTCCCAGATCATGATGTGTTCTTC
   pBPMV-R1A (5841) AGTGCTCCTTATCCATTAAACATGGCTGGTTTAGAGGAGAAGGGAATGCACTTTGATTCCCAGATCATGATGTGTTCTTC
   Consensus (5841) AGTGCTCCTTATCCA TAAACATGGCTGGTTT GAGGA AAGGGAATGCACTTTGATTCCCAGATCATGATGTGTTCTTC
                                                                                                          Section 75
              (5921) 5921      5930       5940       5950       5960       5970       5980       5990       6000
       K-G7  (2083) GAATTTTTTAGAGCCGTCTCCTGAAGCTAAAATTAGAGATGATATGGCTTTTAGAAATCGAAGACATGTGCTGATCACAG
   pBPMV-R1A (5921) AAATTTCTTAGAGCCGTCTCCTGAAGCTAAAATTAGAGATGATATGGCTTTTAGAAATCGGAGACATGTGCTGATCACAG
   Consensus (5921)   AATTT TTAGAGCCGTCTCCTGAAGCTAAAATTAGAGATGATATGGCTTTTAGAAATCG AGACATGTGCTGATCACAG
                                                                                                          Section 76
              (6001) 6001      6010       6020       6030       6040       6050       6060       6070       6080
       K-G7  (2163) TTGAACTCAAACCTGGGGTTGAATATGATGAGAGTGATTTTACTAAAAATCAGCGATATTGCTGAAAACTTGGTTTCAT
   pBPMV-R1A (6001) TTGAACTCAAACCTGGGGTTGAATATGATGAGAGTGATTTTACTAAAAATCAGCGATATTTGCTGAAAACTTGGTTTCAT
   Consensus (6001) TTGAACTCAAACCTGGGGTTGAATATGATGAGAGTGATTTTACTAAAAATCAGCGATATTTGCTGAAAACTTGGTTTCAT
                                                                                                          Section 77
              (6081) 6081      6090       6100       6110       6120       6130       6140       6150       6160
       K-G7  (2243) GATCATTATGTTGTAGACCAAACTTTTGAGTCTTATGCTGATCTGCTGGCACATTGTTTTACCAAGTGGGAGAGACATGT
   pBPMV-R1A (6081) GATCATTATGTTGTAGACCAAACTTTTGAGTCCTATGCTGATCTGCTGGCACATTGTTTTACCAAGTGGGAGAGACATGT
   Consensus (6081) GATCATTATGTTGTAGACCAAACTTTTGAGTC TATGCTGATCTGCTGGCACATTGTTTTACCAAGTGGGAGAGACATGT
```

*FIG. 9G*

```
                                                                              Section 78
          (6161) 6161      6170      6180      6190      6200      6210      6220      6230      6240
    K-G7  (2323) TAAGGAGCAAGAGTCAAACCTGTCTCAAATTAAGGGCAAGAAAAATGAAAGTGGTCATTTCTATAACTTTCAACAACTTA
pBPMV-R1A (6161) TAAGGAGCAAGAGTCAAATCTGTCTCAAATTAAGGGCAAGAAAAGTGAAAGTGGTCATTTTTATAATTTTCAACAACTTA
Consensus (6161) TAAGGAGCAAGAGTCAAA CTGTCTCAAATTAAGGGCAAGAAAA TGAAAGTGGTCATTT TATAA TTTCAACAACTTA
                                                                              Section 79
          (6241) 6241      6250      6260      6270      6280      6290      6300      6310      6320
    K-G7  (2403) TGGATTTGGCTGTTTCATGGAATCTTAATGCAGATATCATGAAAAACAGGATCAAGGCTGAGAGAAATGACATGGTTTAT
pBPMV-R1A (6241) TGGATTTGGCTGTTTCTTGGAATCTTAATGCAGATATCATGAAAAACAGGATCAAGGCTGAGAGAAGTGACATGGTTTAT
Consensus (6241) TGGATTTGGCTGTTTC TGGAATCTTAATGCAGATATCATGAAAAACAGGATCAAGGCTGAGAGA TGACATGGTTTAT
                                                                              Section 80
          (6321) 6321      6330      6340      6350      6360      6370      6380      6390      6400
    K-G7  (2483) GTTTTTTCTGCAGGGAGGAAGGATAAAATTTTGCATTGTTTTTTGAACAAGGAAGGCGAGTGCACGGTTCGTCCTGATTC
pBPMV-R1A (6321) GTTTTTTCTGCAGGGAGGAAGGATAAAATTTTGCATTGTTTTCTGAACAAGGAAGGCGAGTGCACGGTTCGTCCTGATTC
Consensus (6321) GTTTTTTCTGCAGGGAGGAAGGATAAAATTTTGCATTGTTTT TGAACAAGGAAGGCGAGTGCACGGTTCGTCCTGATTC
                                                                              Section 81
          (6401) 6401      6410      6420      6430      6440      6450      6460      6470      6480
    K-G7  (2563) AATAGATGATCCTGAAGCGCAAGCTTTGCTCAAAGCTTCAGAGACAATGCTCATGAAAGCCTATGCCTTCCTCAAATACA
pBPMV-R1A (6401) AATAGATGATCCTGAAGCGCAAGCTTGCTCAAAGCTTCAGAGACAATGCTCATGAAAGCCTATGCCTTCCTTAAATACA
Consensus (6401) AATAGATGATCCTGAAGCGCAAGCTTTGCTCAAAGCTTCAGAGACAATGCTCATGAAAGCCTATGCCTTCCT AAATACA
                                                                              Section 82
          (6481) 6481      6490      6500      6510      6520      6530      6540      6550      6560
    K-G7  (2643) ATAATGCAACAAATTTGATTGTCAGGACCCATTTGGCAGAACTGGTGAATGAAGATTTTTATGATGAGAAATTCAATTTC
pBPMV-R1A (6481) ATAATGCAACAAATTTGATTGTCAGAACCCATTTGGCAGAACTAGTGAATGAAGATTTTTATGATGAGAAATTCAATTTC
Consensus (6481) ATAATGCAACAAATTTGATTGTCAG ACCCATTTGGCAGAACT GTGAATGAAGATTTTTATGATGA AAATTCAATTTC
                                                                              Section 83
          (6561) 6561      6570      6580      6590      6600      6610      6620      6630      6640
    K-G7  (2723) ATTGGAACAATTGGAACACCAGCTTTTCATCGCCAAATAGCTGCACATTTGGAAAGATGCCATTGTGGCAAAAAGCAAT
pBPMV-R1A (6561) ATTGGAACAATTGGAACACCGGCTTTTCATCGCCAAATAGCTGCACATTTGGAAAGATGCCATTGTGGCAAAAAGCAAT
Consensus (6561) ATTGGAACAATTGGAACACC GCTTTTCATCGCCAAATAGCTGCACATTTGGAAAGATGCCATTGTGGCAAAAAGCAAT
                                                                              Section 84
          (6641) 6641      6650      6660      6670      6680      6690      6700      6710      6720
    K-G7  (2803) TTTGTGTGGAATGGGACATTGTTTGTCTCGGAAAAGCAAAGAAAACCTGGTATACTGGTATGAAGGAGAAGTTTGTGCAGA
pBPMV-R1A (6641) TTTGTGTGGAATGGGACATTGTTTGTCTCGGAAAAGACAAAGAGACCTGGTATACTGGTATGAAGGAGAAATTTGTGCAGA
Consensus (6641) TTTGTGTGGAATGGGACATTGTTTGTCTCGGAAAAGCAAAG ACCTGGTATACTGGTATGAAGGAGAA TTTGTGCAGA
                                                                              Section 85
          (6721) 6721      6730      6740      6750      6760      6770      6780      6790      6800
    K-G7  (2883) TGATGAAAACATTTATGAAACTGAAGTCACAGATTGGCCAGTGCCATTGAAAATCATTTCTGGTACTATTCTAGCCACC
pBPMV-R1A (6721) TGATGAAAAGCATCTATGAAACTGAAGTCACAGACTGGCCAGTGCCATTGAAAATCATTTCTGGTACTATTCTAGCCACC
Consensus (6721) TGATGAAAAGCAT TATGAAACTGAAGTCACAGA TGGCCAGTGCCATTGAAAATCATTTCTGGTACTATTCTAGCCACC
                                                                              Section 86
          (6801) 6801      6810      6820      6830      6840      6850      6860      6870      6880
    K-G7  (2963) ATTTTGGGAACAACTTTTTGAAGTTATTTTCCTTTTAAGGGATGCTGGTAATGGAGGTGTTTTTGTTGGTAATGTTGC
pBPMV-R1A (6801) ATTTTGGGAACAACTTTTTGGAAGTTATTTTCCTTTTAAGGGATGCTGGCAATGGAGGCGTGTTTTGTTGGTAATGTTGC
Consensus (6801) ATTTTGGGAACAACTTTTTGGAAGTTATTTTCCTTTTAAGGGATGCTGG AATGGAGGTGTTTTTGTTGGTAATGTTGC
                                                                              Section 87
          (6881) 6881      6890      6900      6910      6920      6930      6940      6950      6960
    K-G7  (3043) TTCAGCATTTACTACATCAAGTGTGCTCGAGGCGCAAAGCCGAAAACCCAACAGATATGAGGTCTCTCAATATAGGTATC
pBPMV-R1A (6881) TTCAGCATTTACCACATCAAGTGTGCTTGAGGCGCAAAGCCGAAAACCCAACAGATATGAGGTCTCTCAATATAGGTATC
Consensus (6881) TTCAGCATTTAC ACATCAAGTGTGCT GAGGCGCAAAGCCGAAAACCCAACAGATATGAGGTCTCTCAATATAGGTATC
                                                                              Section 88
          (6961) 6961      6970      6980      6990      7000      7010      7020      7030      7040
    K-G7  (3123) GCAATGTGCCAATAAAGCGCAGAGCGTGGGTTGAGGGCCAAATGTCTTTTGATCAATCAGTGGTAGCAATTATGTCAAAA
pBPMV-R1A (6961) GCAATGTGCCAATAAAGCGCAGAGCGTGGGTTGAGGGTCAAATGTCTTTTGATCAATCAGTGGTGGCAATTATGTCAAAA
Consensus (6961) GCAATGTGCCAATAAAGCGCAGAGCGTGGGTTGAGGG CAAATGTCTTTTGATCAATCAGTGGT GCAATTATGTCAAAA
```

*FIG. 9H*

```
                                                                                                    Section 89
              (7041) 7041      7050      7060      7070      7080      7090      7100      7110      7120
       K-G7  (3203) TGTAAAGCCAGTATGAGAATGGGAAACACTGATGCTCAGATTTTGATGGTTCCAGGGCGTAGATTCATTGCACATGGTCA
   pBPMV-R1A (7041) TGTAAAGCCAGTATGAGAATGGGAAACACTGATGCTCAAATTTTGATGGTTCCAGGGCGTAGATTCATTGCACATGGTCA
   Consensus (7041) TGTAAAGCCAGTATGAGAATGGGAAACACTGATGCTCA ATTTTGATGGTTCCAGGGCGTAGATTCATTGCACATGGTCA
                                                                                                    Section 90
              (7121) 7121      7130      7140      7150      7160      7170      7180      7190      7200
       K-G7  (3283) TTTTTTCAAGAATCTCACCCAAAAAGTTAGAGTCCAAATTGTTACTTCTGAGAAAAGCTATTGGCATGTGTATGATCCTG
   pBPMV-R1A (7121) TTTTTTTAAGAATCTCACCCAAAAAGTTAGAGTCCAAATTGTTACTTCTGAGAAAAGCTATTGGCATGTGTATGATCCTG
   Consensus (7121) TTTTTT AAGAATCTCACCCAAAAAGTTAGAGTCCAAATTGTTACTTCTGAGAAAAGCTATTGGCATGTGTATGATCCTG
                                                                                                    Section 91
              (7201) 7201      7210      7220      7230      7240      7250      7260      7270      7280
       K-G7  (3363) ATAAATTTCAAATGTTTGATAACAGTGAAATTGGGTTGTATACAAATCCAACTTTGGAGGACATCCCACATTCTGCTTGG
   pBPMV-R1A (7201) ATAAATTTCAAATGTTTGATAACAGTGAAAT GGGTTGTATACAAATCCAACTTTGGAGGACATCCCACATTCTGCTTGG
   Consensus (7201) ATAAATTTCAAATGTTTGATAACAGTGAAAT GGGTTGTATACAAATCCAACTTTGGAGGACATCCCACATTCTGCTTGG
                                                                                                    Section 92
              (7281) 7281      7290      7300      7310      7320      7330      7340      7350      7360
       K-G7  (3443) GACCTTTTCTGCTGGGACAGTGAGAAAACTTTGCCAAACAATTTTTCTGCTGAATTGCTTTCCTGTAAATTGGACACTGT
   pBPMV-R1A (7281) GACCTTTTCTGCTGGGACAGTGAGAAAACTTTGCCAAACAATTTTTCTGCTGAACTGCTTTCCTGTAAATTGGACACCGT
   Consensus (7281) GACCTTTTCTGCTGGGACAGTGAGAAAACTTTGCCAAACAATTTTTCTGCTGAA TGCTTTCCTGTAAATTGGACAC GT
                                                                                                    Section 93
              (7361) 7361      7370      7380      7390      7400      7410      7420      7430      7440
       K-G7  (3523) TACGGGACAATATTATCCCAGAATGG-CTCCAATAAATTGTCGAGTACATCGGCAACCAATTCACATAACTGAAGGGAAT
   pBPMV-R1A (7361) TACGGGACAATATTA-CCCAGAATGGGCTCCAATAAATTGTCGAGTACATCGGCAACCAATTCACATAACTGAAGGGAAT
   Consensus (7361) TACGGGACAATATTA CCCAGAATGG CTCCAATAAATTGTCGAGTACATCGGCAACCAATTCACATAACTGAAGGGAAT
                                                                                                    Section 94
              (7441) 7441      7450      7460      7470      7480      7490      7500      7510      7520
       K-G7  (3602) TATGTTAGGAAACAAGATGTAAGCATTGAATATGATGCCTGCACAATTCCCAATGATTGTGGATCTCTGGTGGTTGCTAA
   pBPMV-R1A (7440) TATGTCAGGAAACAAGATGTGAGCATTGAATATGATGCCTGCACAATTCCTAATGATTGTGGATCTCTGGTGGTTGCTAA
   Consensus (7441) TATGT AGGAAACAAGATGT AGCATTGAATATGATGCCTGCACAATTCC AATGATTGTGGATCTCTGGTGGTTGCTAA
                                                                                                    Section 95
              (7521) 7521      7530      7540      7550      7560      7570      7580      7590      7600
       K-G7  (3682) GGTTGGAAATCACAAGCAAATTGTTGGTTTCCATGTTGCTGGAAGCAAGGAAGATTGGGCTATGCTTCATTAATACCAT
   pBPMV-R1A (7520) GGTTGGAAATCACAAGCAAATTGTTGGTTTCCATGTTGCTGGAAGTAAAGGAAGATTGGGCTATGCTTCATTGATACCAT
   Consensus (7521) GGT GGAAATCACAAGCAAATTGTTGGTTTCCATGTTGCTGGAAG AAAGGAAGATTGGGCTATGCTTCATT ATACCAT
                                                                                                    Section 96
              (7601) 7601      7610      7620      7630      7640      7650      7660      7670      7680
       K-G7  (3762) ATGTTGAGCCTGTGGTACAAGCCCAAAGTGCTGAAGTCTATTTTGATTTCTTTCCTGTGAAGTTGATAGTCAAGAGGGA
   pBPMV-R1A (7600) ATGTTGAGCCTGTGGTACAAGCCCAAAGTGCTGAAGTCTATTTTGATTTCTTTCCTGTGAAGTTGATAGTCAAGAGGGA
   Consensus (7601) ATGTTGAGCCTGTGGTACAAGCCCAAAGTGCTGAAGTCTATTTTGATTTCTTTCCTGTGAAGTTGATAGTCAAGAGGGA
                                                                                                    Section 97
              (7681) 7681      7690      7700      7710      7720      7730      7740      7750      7760
       K-G7  (3842) GTAGCTCATATTGGTGAACTCAAATCTGGAGTTTATGTACCACTGCCCACAAAAACTAATCTTGTGGAAACTCCCAAAGA
   pBPMV-R1A (7680) GTGCTCATATTGGTGAACTCAAATCTGGAGTTTATGTACCATTGCCCACAAAAACTAATCTTGTGGAAACTCCCAAAGA
   Consensus (7681) GT GCTCATATTGGTGAACTCAAATCTGGAGTTTATGTACCA TGCCCACAAAAACTAATCTTGTGGAAACTCCCAAAGA
                                                                                                    Section 98
              (7761) 7761      7770      7780      7790      7800      7810      7820      7830      7840
       K-G7  (3922) ATGGCAGTTGGATTTGCCTTGTGATAAGATTCCAAGTGTTAACCACTACTGATGAGAGATTGGTTGGCACAGAGCATG
   pBPMV-R1A (7760) ATGGCAGTTGGATTTGCCTTGTGATAAGATTCCAAGTGTGTTAACCACTACTGATGAGAGATTGGTTGGCACGGAGCATG
   Consensus (7761) ATGGCAGTTGGATTTGCCTTGTGATAAGATTCCAAGTGTGTTAACCACTACTGATGAGAGATTGGTTGGCAC GAGCATG
                                                                                                    Section 99
              (7841) 7841      7850      7860      7870      7880      7890      7900      7910      7920
       K-G7  (4002) AAG-ATATGACCCATT-CTTGGTGGTATTCAAAA-TATGCAACTCCCATGATGCCTCTTGATGAGGAGATTCTTTCCAAA
   pBPMV-R1A (7840) AAGGATATGACCCATTTCTTGGTGGTATTCAAAAATATGCAACTCCCATGATGCCTCTAGATGAGGAGATTCTTTCCAAA
   Consensus (7841) AAG ATATGACCCATT CTTGGTGGTATTCAAAA TATGCAACTCCCATGATGCCTCT GATGAGGAGATTCTTTCCAAA
```

FIG. 9I

```
                                                                                                                                    Section 100
              (7921) 7921      7930      7940      7950      7960      7970      7980      7990      8000
       K-G7  (4079) GTTGCACAAGACATGGTTGAAGAGTGGTTTGATTGTGTTGATGAGGAGGATACATTTGAAGAAGTTTCTTTGAGTGCTGC
   pBPMV-R1A (7920) GTTGCACAAGACATGGTTGAAGAATGGTTTGATTGTGTTGATGAGGAGGATACATTTGAAGAAGTTTCTTTGAGTGCTGC
   Consensus (7921) GTTGCACAAGACATGGTTGAAGA TGGTTTGATTGTGTTGATGAGGAGGATACATTTGAAGAAGTTTCTTTGAGTGCTGC
                                                                                                                                    Section 101
              (8001) 8001      8010      8020      8030      8040      8050      8060      8070      8080
       K-G7  (4159) ACTCAATGGTGTTGAAGGTTTGGATTACATGGAACGCATTCCTCTTGCCACTTCAGAGGGTTTTCCTCATGTTCTGTCCA
   pBPMV-R1A (8000) ACTCAATGGTGTTGAAGGTTTGGATTACATGGAACGCATTCCTCTTGCCACTTCAGAGGGTTTTCCTCATGTTCTGTCCA
   Consensus (8001) ACTCAATGGTGTTGAAGGTTTGGATTACATGGAACGCATTCCTCTTGCCACTTCAGAGGGTTTTCCTCATGTTCTGTCCA
                                                                                                                                    Section 102
              (8081) 8081      8090      8100      8110      8120      8130      8140      8150      8160
       K-G7  (4239) GGAAAATGGTGAAAAAGGCAAGAGAAGATTTGTCACTGGAGATGGTGAAGAAATGTCACTAATTCCTGGTACCAGTGTT
   pBPMV-R1A (8080) GGAAAAATGGTGAAAAAGGCAAGAGAAGATTTGTCACTGGAGATGGTGAAGAAATGTCACTAATTCCTGGTACCAGTGTT
   Consensus (8081) GGAAAAATGGTGAAAAAGGCAAGAGAAGATTTGTCACTGGAGATGGTGAAGAAATGTCACTAATTCCTGGTACCAGTGTT
                                                                                                                                    Section 103
              (8161) 8161      8170      8180      8190      8200      8210      8220      8230      8240
       K-G7  (4319) GAAGAAGCGTACAATAAATTGACTGTTGAATTAGAAAAGTGTGTTCCAACATTGGTTGGTATAGAATGTCCTAAAGATGA
   pBPMV-R1A (8160) GAAGAAGCATACAATAAATTGACTGTTGAACTAGAAAAGTGTGTTCCAACATTGGTTGGCATAGAATGTCCCAAAGATGA
   Consensus (8161) GAAGAAGC TACAATAAATTGACTGTTGAA TAGAAAAGTGTGTTCCAACATTGGTTGG ATAGAATGTCC AAAGATGA
                                                                                                                                    Section 104
              (8241) 8241      8250      8260      8270      8280      8290      8300      8310      8320
       K-G7  (4399) AAAACTTCCTCGTCGCAAAATTTTTGATAAACCCAAGACGCGCTGCTTCACCATACTTCCTATGGAATTTAATTTAGTGG
   pBPMV-R1A (8240) AAAACTTCCCCGTCGCAAAATTTTTGATAAACCCAAGACGCGCTGCTTCACCATACTTCCTATGGAATTTAATCTGGTGG
   Consensus (8241) AAAACTTCC CGTCGCAAAATTTTTGATAAACCCAAGACGCGCTGCTTCACCATACTTCCTATGGAATTTAAT T GTGG
                                                                                                                                    Section 105
              (8321) 8321      8330      8340      8350      8360      8370      8380      8390      8400
       K-G7  (4479) TGCGTCAAAAGTTCTTGAATTTTGTGCGATTCATTATGAAGAAAAGGGACAAATTGAGTTGCCAAGTTGGAATCAATCCA
   pBPMV-R1A (8320) TGCGTCAAAAATTCTTGAATTTTGTGCGATTCATTATGAAGAAAAGGGACAAATTGAGTTGCCAAGTTGGAATCAATCCA
   Consensus (8321) TGCGTCAAAA TTCTTGAATTTTGTGCGATTCATTATGAAGAAAAGGGACAAATTGAGTTGCCAAGTTGGAATCAATCCA
                                                                                                                                    Section 106
              (8401) 8401      8410      8420      8430      8440      8450      8460      8470      8480
       K-G7  (4559) TATTCCATGGAGTGGACTGGTTTGGCAAATAGACTGTTGAGCAAGGGAAATGACATTTTGTGTTGTGACTATGCTAGTTT
   pBPMV-R1A (8400) TATTCTATGGAGTGGACTGGTTTGGCAAATAGACTGTTGAGCAAGGGAAATGACATTTTGTGTTGTGATTATGCTAGTTT
   Consensus (8401) TATTC ATGGAGTGGACTGGTTTGGCAAATAGACTGTTGAGCAAGGGAAATGACATTTTGTGTTGTGA TATGCTAGTTT
                                                                                                                                    Section 107
              (8481) 8481      8490      8500      8510      8520      8530      8540      8550      8560
       K-G7  (4639) TAGTGGTCTGATAACTAAGCAAGTCATGAGCAAGATGGCAGAAATGATAAACAGTCTTTGTGGTGGAGATGAGAAACTGA
   pBPMV-R1A (8480) TGATGGTCTGATAACTAAGCAAGTCATGAGCAAGATGGCAGAAATGATAAACAGTCTTTGTGGTGGAGATGAGAAACTGA
   Consensus (8481) T  TGGTCTGATAACTAAGCAAGTCATGAGCAAGATGGCAGAAATGATAAACAGTCTTTGTGGTGGAGATGAGAAACTGA
                                                                                                                                    Section 108
              (8561) 8561      8570      8580      8590      8600      8610      8620      8630      8640
       K-G7  (4719) TGCGTGAGAGAACTCATCTTCTGTTAGCTTGTTGCTCCAGGATGGCAATCTGTAAAAAGATATTTGGAGAGTTGAGTGT
   pBPMV-R1A (8560) TGCGTGAGAGAACGCATCTTCTGTTAGCTTGTTGCTCCAGGATGGCAATCTGTAAAAAAGATGTTTGGAGAGTTGAGTGT
   Consensus (8561) TGCGTGAGAGAAC CATCTTCTGTTAGCTTGTTGCTCCAGGATGGCAATCTGTAAAAAAGAT TTTGGAGAGTTGAGTGT
                                                                                                                                    Section 109
              (8641) 8641      8650      8660      8670      8680      8690      8700      8710      8720
       K-G7  (4799) GGTATCCCCTCTGGATTTCCACTCACTGTTATCTGCAATAGCATTTTCAATGAGATGCTTATCAGATATAGTTATGAAAA
   pBPMV-R1A (8640) GGTATCCCTTCTGGATTTCCACTCACTGTTATCTGCAATAGCATTTTCAATGAGATGCTTATCAGATATAGTTATGAAAA
   Consensus (8641) GGTATCCC TCTGGATTTCCACTCACTGTTATCTGCAATAGCATTTTCAATGAGATGCTTATCAGATATAGTTATGAAAA
                                                                                                                                    Section 110
              (8721) 8721      8730      8740      8750      8760      8770      8780      8790      8800
       K-G7  (4879) GTTGTTGCGTCAAGCTAAGGCTCCAGTATGTTTCTCCAGTCTTTTAGAAATTTTATTTCTTTGTGTGTTTATGGAGATG
   pBPMV-R1A (8720) GTTGCTGCGTCAAGCTAAGGCTCCAGTATGTTTCTCCAGTCTTTTAAAAATTTTATTTCTTTGTGTGTTTATGGAGATG
   Consensus (8721) GTTG TGCGTCAAGCTAAGGCTCCAGTATGTTTCTCCAGTCTTTTA AAATTTTATTTCTTTGTGTGTTTATGGAGATG
```

*FIG. 9J*

```
                                                                                                Section 111
              (8801) 8601      8610      8820      8830      8840      8650      8860      8870      8880
      K-G7   (4959) ATAATTTAATTAGTGTTCATGAGTATGTCAAGCCATATTTTAGTGGTTCTAAATTGAAAAGTTTCCTAGCTAGTCATAAC
  pBPMV-R1A  (8800) ATAATTTAATTAGTGTTCATGAGTATGTTAAGCCATATTTTAGTGGTTCTAAATTGAAAAGTTTCCTAGCTAGTCATAAC
  Consensus  (8801) ATAATTTAATTAGTGTTCATGAGTATGT AAGCCATATTTTAGTGGTTCTAAATTGAAAAGTTTCCTAGCTAGTCATAAC
                                                                                                Section 112
              (8881) 8881      8890      8900      8910      8920      8930      8940      8950      8960
      K-G7   (5039) ATCACCATCACTGATGGAATTGACAAAACTAGTGCAACTTTACAGTTTAGAAAGTTGTCTGAGTGTGATTTTCTTAAAAG
  pBPMV-R1A  (8880) ATCACCATTACTGATGGAATTGACAAAACTAGTGCAACTTTACAGTTTAGAAAGTTGTCAGAGTGTGATTTTCTTAAAAG
  Consensus  (8881) ATCACCAT ACTGATGGAATTGACAAAACTAGTGCAACTTTACAGTTTAGAAAGTTGTC GAGTGTGATTTTCTTAAAAG
                                                                                                Section 113
              (8961) 8961      8970      8980      8990      9000      9010      9020      9030      9040
      K-G7   (5119) AAATTTTAAGCAAATGTCCAATGTTTTGTGGGTAGCTCCTGAAGACAAAGCTAGTTTGTGGTCACAATTGCACTATGTTT
  pBPMV-R1A  (8960) AAATTTTAAGCAAATGTCCAATGTTTTGTGGGTAGCTCCTGAAGACAAAGCTAGTTTGTGGTCACAATTACACTATGTTT
  Consensus  (8961) AAATTTTAAGCAAATGTCCAATGTTTTGTGGGTAGCTCCTGAAGACAAAGCTAGTTTGTGGTCACAATT CACTATGTTT
                                                                                                Section 114
              (9041) 9041      9050      9060      9070      9080      9090      9100      9110      9120
      K-G7   (5199) CATGTAACAATTTGGAAATGCAAGAAGCTTATCTTGTTAACTTGGTTAATGTGTTGCGTGAGTTGTACCTGCATAGTCCA
  pBPMV-R1A  (9040) CATGTAACAATTTGGAAATGCAAGAAGCTTATCTTGTTAACTTGGTTAATGTGTTGCGTGAGTTGTACCTGCACAGTCCA
  Consensus  (9041) CATGTAACAATTTGGAAATGCAAGAAGCTTATCTTGTTAACTTGGTTAATGTGTTGCGTGAGTTGTACCTGCA AGTCCA
                                                                                                Section 115
              (9121) 9121      9130      9140      9150      9160      9170      9180      9190      9200
      K-G7   (5279) GAAGAAGCTCGTCGATTGAGAAGAAAGGCTCTCTCTGTATTGAGTGGTTGCAAAAAGCTGATGTGCCCACCATAGCACA
  pBPMV-R1A  (9120) GAAGAAGCTCGTCAATTGAGAAGAAAGGCTCTCTCTCGCATTGAGTGGTTGCAAAAAGCTGATGTGCCCACCATAGCACA
  Consensus  (9121) GAAGAAGCTCGTC ATTGAGAAGAAAGGCTCTCTC G ATTGAGTGGTTGCAAAAAGCTGATGTGCCCACCATAGCACA
                                                                                                Section 116
              (9201) 9201      9210      9220      9230      9240      9250      9260      9270      9280
      K-G7   (5359) AATTGAAGAATTTCATTCAATGCAGAGGATTATGAATGCTCCTGATTCAAATGATAATATTGATCTTTTGTTGAGCATTG
  pBPMV-R1A  (9200) AATTGAAGAATTTCATTCAATGCAGAGGATTATGAATGCTCCTGACTCAAATGATAATATTGATCTTTTGTTGAGCATTG
  Consensus  (9201) AATTGAAGAATTTCATTCAATGCAGAGGATTATGAATGCTCCTGA TCAAATGATAATATTGATCTTTTGTTGAGCATTG
                                                                                                Section 117
              (9281) 9281      9290      9300      9310      9320      9330      9340      9350      9360
      K-G7   (5439) ACTTGTTGGGTCTTCAGGGTGCAG-CAAGGCCTTCCCAAATAAGATTGTGGTTTGATGATAAATTGGTATTGGCAAATAC
  pBPMV-R1A  (9280) ACTTGTTGGGTCTTCAGGGTGCAGGCAAGGCCTTCCCAAATAAGATTGTG-TTTGATGATAAATTGGTATTGGCAAATAC
  Consensus  (9281) ACTTGTTGGGTCTTCAGGGTGCAG CAAGGCCTTCCCAAATAAGATTGTG TTTGATGATAAATTGGTATTGGCAAATAC
                                                                                                Section 118
              (9361) 9361      9370      9380      9390      9400      9410      9420      9430      9440
      K-G7   (5518) ACAAGAATTTTTTGATGGAAATTTTCCAGCAGATTCTTGCTTACCAATATTTGTTAATTGTCTTTACCCTGTGAGTCAAT
  pBPMV-R1A  (9359) ACAAGAATTTTTTGATGGAAATTTTCCAACAGATTCTTGGTTACCAATATTTGTCAATTGTCTTTACCCTGTGAGTCAAT
  Consensus  (9361) ACAAGAATTTTTTGATGGAAATTTTCCA CAGATTCTTGGTTACCAATATTTGT AATTGTCTTTACCCTGTGAGTCAAT
                                                                                                Section 119
              (9441) 9441      9450      9460      9470      9480      9490      9500      9510      9520
      K-G7   (5598) TGCCCGCAGAAGCTGTCATTGTTAATGTTGTTTGTGGGAGTGGGCGTGGTGGTTTGCCTACTACTGCTTGGATTAGTTCT
  pBPMV-R1A  (9439) TGCCCGCAGAGGCTGTCACTGTTAATGTTGTTTGTGGGAGTGGGCGTGGTGGTTTGCCTACTACTGCTTGGATTAGTTCT
  Consensus  (9441) TGCCCGCAGA GCTGTCA TGTTAATGTTGTTTGTGGGAGTGGGCGTGGTGGTTTGCCTACTACTGCTTGGATTAGTTCT
                                                                                                Section 120
              (9521) 9521      9530      9540      9550      9560      9570      9580      9590      9600
      K-G7   (5678) GCAGTTAACAATCGCTCCTCAGATATCAATAAGAAAATTCGGACAGCGCCTTGGAAAAGGTAAGAAAATTGTCTTTTTGAC
  pBPMV-R1A  (9519) GCAGTTAACAATCGCTCCTCAGATATCAATAAGAAAATTCGGACAGCCACTTGGGAAAGGTAAGAAAATTGTCTTTTTGAC
  Consensus  (9521) GCAGTTAACAATCGCTCCTCAGATATCAATAAGAAAATTCGGACAGC CTTGG AAAGGTAAGAAAATTGTCTTTTTGAC
                                                                                                Section 121
              (9601) 9601      9610      9620      9630      9640      9650      9660      9670      9680
      K-G7   (5758) TAGAGTTGATCCTTTTCCTGTGGCCTTGTTAGCTGTTCTCTTTGGTGTTAAGAACGAAATTCTGAGTTCTAATGCCACAA
  pBPMV-R1A  (9599) TAGAGTTGATCCTTTTCCTGTGGCCTTGTTAGCTGTTCTTTTTGGTGTTAAGAACGAAATTCTGAGTTCTAATGCCACAA
  Consensus  (9601) TAGAGTTGATCCTTTTCCTGTGGCCTTGTTAGCTGTTCT TTTGGTGTTAAGAACGAAATTCTGAGTTCTAATGCCACAA
```

*FIG. 9K*

```
                                                                                               Section 122
           (9681) 9681      9690      9700      9710      9720      9730      9740      9750      9760
     K-G7  (5838) ATCCAATGTTGACAAGGCTTCTTGAGAACTGCAAGAGTCTTAAATATTTGGTTGATGAGTGTCCTTTTGCATTTGTTAAC
pBPMV-R1A  (9679) ATCCAATGTTGACAAGGCTTCTTGAGAACTGCAAGAGTCTTAAATATTTGGTTGATGAGTGTCCTTTTGCATTTGTTAAC
Consensus  (9681) ATCCAATGTTGACAAGGCTTCTTGAGAACTGCAAGAGTCTTAAATATTTGGTTGATGAGTGTCCTTTTGCATTTGTTAAC
                                                                                               Section 123
           (9761) 9761      9770      9780      9790      9800      9810      9820      9830      9840
     K-G7  (5918) TAGTTTGTAATATTTTGTTCACTTAAATAAAGCGCATTACTATGTGCAATAAGTGTGTCTAAATATAAAAAAAAAAAA--
pBPMV-R1A  (9759) TAGTTTGTAATATTTTGCTCACTTAAATAAAGCGCATTACTATGTGCAATAAGTGTGTTTAAATATAAAAAAAAAAAAAA
Consensus  (9761) TAGTTTGTAATATTTTG TCACTTAAATAAAGCGCATTACTATGTGCAATAAGTGTGT TAAATATAAAAAAAAAAAA
                                                                                               Section 124
           (9841) 9841      9850      9860      9870      9880      9890      9900      9910      9920
     K-G7  (5996) --------------------------------------------------------------------------------
pBPMV-R1A  (9839) AAAAAATCGATGGGCCTGGATCCTAGGTTCACAAAGTGTCATCGATAGCTCGAATTTCCCCGATCGTTCAAACATTTGGC
Consensus  (9841)
                                                                                               Section 125
           (9921) 9921      9930      9940      9950      9960      9970      9980      9990     10000
     K-G7  (5996) --------------------------------------------------------------------------------
pBPMV-R1A  (9919) AATAAAGTTTCTTAAGATTGAATCCTGTTGCCGGTCTTGCGATGATTATCATATAATTTCTGTTGAATTACGTTAAGCAT
Consensus  (9921)
                                                                                               Section 126
          (10001) 10001     10010     10020     10030     10040     10050     10060     10070     10080
     K-G7  (5996) --------------------------------------------------------------------------------
pBPMV-R1A  (9999) GTAATAATTAACATGTAATGCATGACGTTATTTATGAGATGGGTTTTTATGATTAGAGTCCCGCAATTATACATTTAATA
Consensus (10001)
                                                                                               Section 127
          (10081) 10081     10090     10100     10110     10120     10130     10140     10150     10160
     K-G7  (5996) --------------------------------------------------------------------------------
pBPMV-R1A (10079) CGCGATAGAAAACAAAATATAGCGCGCAAACTAGGATAAATTATCGCGCGCGGTGTCATCTATGTTACTAGATCGGGAAT
Consensus (10081)
                                                                                               Section 128
          (10161) 10161 10171
     K-G7  (5996) ----------
pBPMV-R1A (10159) TCCAATTCGCC
Consensus (10161)
```

*FIG. 9L*

```
                                                                                                    Section 1
                    (1)  1         10        20        30        40        50        60        70        80
      IL-Cb1 (I)    (1)  --------------------------------------------------------------------------------
           K-G7     (1)  --------------------------------------------------------------------------------
       pBPMV-R1A    (1)  TATAGTGAGTCGTATTACAATTCACTGGCCGTCGTTTTACAACGTCGTGACTGGGAAAACCCTGGCGTTACCCAACTTAA
       pBPMV-R1B    (1)  TATAGTGAGTCGTATTACAATTCACTGGCCGTCGTTTTACAACGTCGTGACTGGGAAAACCCTGGCGTTACCCAACTTAA
          K-Ho1     (1)  --------------------------------------------------------------------------------
      II-Cb1 (II)   (1)  --------------------------------------------------------------------------------
          K-Ha1     (1)  --------------------------------------------------------------------------------
      Consensus     (1)
                                                                                                    Section 2
                   (81)  81        90       100       110       120       130       140       150      160
      IL-Cb1 (I)    (1)  --------------------------------------------------------------------------------
           K-G7     (1)  --------------------------------------------------------------------------------
       pBPMV-R1A   (81)  TCGCCTTGCAGCACATCCCCCTTTCGCCAGCTGGCGTAATAGCGAAGAGGCCCGCACCGATCGCCCTTCCCAACAGTTGC
       pBPMV-R1B   (81)  TCGCCTTGCAGCACATCCCCCTTTCGCCAGCTGGCGTAATAGCGAAGAGGCCCGCACCGATCGCCCTTCCCAACAGTTGC
          K-Ho1     (1)  --------------------------------------------------------------------------------
      II-Cb1 (II)   (1)  --------------------------------------------------------------------------------
          K-Ha1     (1)  --------------------------------------------------------------------------------
      Consensus    (81)
                                                                                                    Section 3
                  (161)  161       170       180       190       200       210       220       230      240
      IL-Cb1 (I)    (1)  --------------------------------------------------------------------------------
           K-G7     (1)  --------------------------------------------------------------------------------
       pBPMV-R1A  (161)  GCAGCCTGAATGGCGAATGGACGCGCCCTGTAGCGGCGCATTAAGCGCGGCGGGTGTGGTGGTTACGCGCAGCGTGACCG
       pBPMV-R1B  (161)  GCAGCCTGAATGGCGAATGGACGCGCCCTGTAGCGGCGCATTAAGCGCGGCGGGTGTGGTGGTTACGCGCAGCGTGACCG
          K-Ho1     (1)  --------------------------------------------------------------------------------
      II-Cb1 (II)   (1)  --------------------------------------------------------------------------------
          K-Ha1     (1)  --------------------------------------------------------------------------------
      Consensus   (161)
                                                                                                    Section 4
                  (241)  241       250       260       270       280       290       300       310      320
      IL-Cb1 (I)    (1)  --------------------------------------------------------------------------------
           K-G7     (1)  --------------------------------------------------------------------------------
       pBPMV-R1A  (241)  CTACACTTGCCAGCGCCCTAGCGCCCGCTCCTTTCGCTTTCTTCCCTTCCTTTCTCGCCACGTTCGCCGGCTTTCCCCGT
       pBPMV-R1B  (241)  CTACACTTGCCAGCGCCCTAGCGCCCGCTCCTTTCGCTTTCTTCCCTTCCTTTCTCGCCACGTTCGCCGGCTTTCCCCGT
          K-Ho1     (1)  --------------------------------------------------------------------------------
      II-Cb1 (II)   (1)  --------------------------------------------------------------------------------
          K-Ha1     (1)  --------------------------------------------------------------------------------
      Consensus   (241)
                                                                                                    Section 5
                  (321)  321       330       340       350       360       370       380       390      400
      IL-Cb1 (I)    (1)  --------------------------------------------------------------------------------
           K-G7     (1)  --------------------------------------------------------------------------------
       pBPMV-R1A  (321)  CAAGCTCTAAATCGGGGGCTCCCTTTAGGGTTCCGATTTAGTGCTTTACGGCACCTCGACCCCAAAAAACTTGATTAGGG
       pBPMV-R1B  (321)  CAAGCTCTAAATCGGGGGCTCCCTTTAGGGTTCCGATTTAGTGCTTTACGGCACCTCGACCCCAAAAAACTTGATTAGGG
          K-Ho1     (1)  --------------------------------------------------------------------------------
      II-Cb1 (II)   (1)  --------------------------------------------------------------------------------
          K-Ha1     (1)  --------------------------------------------------------------------------------
      Consensus   (321)
                                                                                                    Section 6
                  (401)  401       410       420       430       440       450       460       470      480
      IL-Cb1 (I)    (1)  --------------------------------------------------------------------------------
           K-G7     (1)  --------------------------------------------------------------------------------
       pBPMV-R1A  (401)  TGATGGTTCACGTAGTGGGCCATCGCCCTGATAGACGGTTTTTCGCCCTTTGACGTTGGAGTCCACGTTCTTTAATAGTG
       pBPMV-R1B  (401)  TGATGGTTCACGTAGTGGGCCATCGCCCTGATAGACGGTTTTTCGCCCTTTGACGTTGGAGTCCACGTTCTTTAATAGTG
          K-Ho1     (1)  --------------------------------------------------------------------------------
      II-Cb1 (II)   (1)  --------------------------------------------------------------------------------
          K-Ha1     (1)  --------------------------------------------------------------------------------
      Consensus   (401)
```

*FIG. 10A*

```
                          Section 7
             (481) 481      490       500       510       520       530       540       550       560
IL-Cb1 (I)    (1)  ----------------------------------------------------------------------------------
   K-G7       (1)  ----------------------------------------------------------------------------------
pBPMV-R1A    (481) GACTCTTGTTCCAAACTGGAACAACACTCAACCCTATCTCGGTCTATTCTTTTGATTTATAAGGGATTTTGCCGATTTCG
pBPMV-R1B    (481) GACTCTTGTTCCAAACTGGAACAACACTCAACCCTATCTCGGTCTATTCTTTTGATTTATAAGGGATTTTGCCGATTTCG
   K-Ho1      (1)  ----------------------------------------------------------------------------------
II-Cb1 (II)   (1)  ----------------------------------------------------------------------------------
   K-Ha1      (1)  ----------------------------------------------------------------------------------
Consensus    (481)
                          Section 8
             (561) 561      570       580       590       600       610       620       630       640
IL-Cb1 (I)    (1)  ----------------------------------------------------------------------------------
   K-G7       (1)  ----------------------------------------------------------------------------------
pBPMV-R1A    (561) GCCTATTGGTTAAAAAATGAGCTGATTTAACAAAAATTTAACGCGAATTTTAACAAAATATTAACGCTTACAATTTCCTG
pBPMV-R1B    (561) GCCTATTGGTTAAAAAATGAGCTGATTTAACAAAAATTTAACGCGAATTTTAACAAAATATTAACGCTTACAATTTCCTG
   K-Ho1      (1)  ----------------------------------------------------------------------------------
II-Cb1 (II)   (1)  ----------------------------------------------------------------------------------
   K-Ha1      (1)  ----------------------------------------------------------------------------------
Consensus    (561)
                          Section 9
             (641) 641      650       660       670       680       690       700       710       720
IL-Cb1 (I)    (1)  ----------------------------------------------------------------------------------
   K-G7       (1)  ----------------------------------------------------------------------------------
pBPMV-R1A    (641) ATGCGGTATTTTCTCCTTACGCATCTGTGCGGTATTTCACACCGCATATGGTGCACTCTCAGTACAATCTGCTCTGATGC
pBPMV-R1B    (641) ATGCGGTATTTTCTCCTTACGCATCTGTGCGGTATTTCACACCGCATATGGTGCACTCTCAGTACAATCTGCTCTGATGC
   K-Ho1      (1)  ----------------------------------------------------------------------------------
II-Cb1 (II)   (1)  ----------------------------------------------------------------------------------
   K-Ha1      (1)  ----------------------------------------------------------------------------------
Consensus    (641)
                          Section 10
             (721) 721      730       740       750       760       770       780       790       800
IL-Cb1 (I)    (1)  ----------------------------------------------------------------------------------
   K-G7       (1)  ----------------------------------------------------------------------------------
pBPMV-R1A    (721) CGCATAGTTAAGCCAGCCCCGACACCCGCCAACACCCGCTGACGCGCCCTGACGGGCTTGTCTGCTCCCGGCATCCGCTT
pBPMV-R1B    (721) CGCATAGTTAAGCCAGCCCCGACACCCGCCAACACCCGCTGACGCGCCCTGACGGGCTTGTCTGCTCCCGGCATCCGCTT
   K-Ho1      (1)  ----------------------------------------------------------------------------------
II-Cb1 (II)   (1)  ----------------------------------------------------------------------------------
   K-Ha1      (1)  ----------------------------------------------------------------------------------
Consensus    (721)
                          Section 11
             (801) 801      810       820       830       840       850       860       870       880
IL-Cb1 (I)    (1)  ----------------------------------------------------------------------------------
   K-G7       (1)  ----------------------------------------------------------------------------------
pBPMV-R1A    (801) ACAGACAAGCTGTGACCGTCTCCGGGAGCTGCATGTGTCAGAGGTTTTCACCGTCATCACCGAAACGCGCGAGACGAAAG
pBPMV-R1B    (801) ACAGACAAGCTGTGACCGTCTCCGGGAGCTGCATGTGTCAGAGGTTTTCACCGTCATCACCGAAACGCGCGAGACGAAAG
   K-Ho1      (1)  ----------------------------------------------------------------------------------
II-Cb1 (II)   (1)  ----------------------------------------------------------------------------------
   K-Ha1      (1)  ----------------------------------------------------------------------------------
Consensus    (801)
                          Section 12
             (881) 881      890       900       910       920       930       940       950       960
IL-Cb1 (I)    (1)  ----------------------------------------------------------------------------------
   K-G7       (1)  ----------------------------------------------------------------------------------
pBPMV-R1A    (881) GGCCTCGTGATACGCCTATTTTTATAGGTTAATGTCATGATAATAATGGTTTCTTAGACGTCAGGTGGCACTTTTCGGGG
pBPMV-R1B    (881) GGCCTCGTGATACGCCTATTTTTATAGGTTAATGTCATGATAATAATGGTTTCTTAGACGTCAGGTGGCACTTTTCGGGG
   K-Ho1      (1)  ----------------------------------------------------------------------------------
II-Cb1 (II)   (1)  ----------------------------------------------------------------------------------
   K-Ha1      (1)  ----------------------------------------------------------------------------------
Consensus    (881)
```

*FIG. 10B*

```
                                                                                                                    Section 13
              (961) 961     970       980       990      1000      1010      1020      1030      1040
   IL-Cb1 (I)   (1) ----------------------------------------------------------------------------------
         K-G7   (1) ----------------------------------------------------------------------------------
   pBPMV-R1A  (961) AAATGTGCGCGGAACCCCTATTTGTTTATTTTTCTAAATACATTCAAATATGTATCCGCTCATGAGACAATAACCCTGAT
   pBPMV-R1B  (961) AAATGTGCGCGGAACCCCTATTTGTTTATTTTTCTAAATACATTCAAATATGTATCCGCTCATGAGACAATAACCCTGAT
         K-Ho1  (1) ----------------------------------------------------------------------------------
    II-Cb1 (II)  (1) ----------------------------------------------------------------------------------
         K-Ha1  (1) ----------------------------------------------------------------------------------
   Consensus  (961)
                                                                                                                    Section 14
             (1041) 1041    1050      1060      1070      1080      1090      1100      1110      1120
   IL-Cb1 (I)   (1) ----------------------------------------------------------------------------------
         K-G7   (1) ----------------------------------------------------------------------------------
   pBPMV-R1A (1041) AAATGCTTCAATAATATTGAAAAAGGAAGAGTATGAGTATTCAACATTTCCGTGTCGCCCTTATTCCCTTTTTTGCGGCA
   pBPMV-R1B (1041) AAATGCTTCAATAATATTGAAAAAGGAAGAGTATGAGTATTCAACATTTCCGTGTCGCCCTTATTCCCTTTTTTGCGGCA
         K-Ho1  (1) ----------------------------------------------------------------------------------
    II-Cb1 (II)  (1) ----------------------------------------------------------------------------------
         K-Ha1  (1) ----------------------------------------------------------------------------------
   Consensus (1041)
                                                                                                                    Section 15
             (1121) 1121    1130      1140      1150      1160      1170      1180      1190      1200
   IL-Cb1 (I)   (1) ----------------------------------------------------------------------------------
         K-G7   (1) ----------------------------------------------------------------------------------
   pBPMV-R1A (1121) TTTTGCCTTCCTGTTTTTGCTCACCCAGAAACGCTGGTGAAAGTAAAAGATGCTGAAGATCAGTTGGGTGCACGAGTGGG
   pBPMV-R1B (1121) TTTTGCCTTCCTGTTTTTGCTCACCCAGAAACGCTGGTGAAAGTAAAAGATGCTGAAGATCAGTTGGGTGCACGAGTGGG
         K-Ho1  (1) ----------------------------------------------------------------------------------
    II-Cb1 (II)  (1) ----------------------------------------------------------------------------------
         K-Ha1  (1) ----------------------------------------------------------------------------------
   Consensus (1121)
                                                                                                                    Section 16
             (1201) 1201    1210      1220      1230      1240      1250      1260      1270      1280
   IL-Cb1 (I)   (1) ----------------------------------------------------------------------------------
         K-G7   (1) ----------------------------------------------------------------------------------
   pBPMV-R1A (1201) TTACATCGAACTGGATCTCAACAGCGGTAAGATCCTTGAGAGTTTTCGCCCCGAAGAACGTTTTCCAATGATGAGCACTT
   pBPMV-R1B (1201) TTACATCGAACTGGATCTCAACAGCGGTAAGATCCTTGAGAGTTTTCGCCCCGAAGAACGTTTTCCAATGATGAGCACTT
         K-Ho1  (1) ----------------------------------------------------------------------------------
    II-Cb1 (II)  (1) ----------------------------------------------------------------------------------
         K-Ha1  (1) ----------------------------------------------------------------------------------
   Consensus (1201)
                                                                                                                    Section 17
             (1281) 1281    1290      1300      1310      1320      1330      1340      1350      1360
   IL-Cb1 (I)   (1) ----------------------------------------------------------------------------------
         K-G7   (1) ----------------------------------------------------------------------------------
   pBPMV-R1A (1281) TTAAAGTTCTGCTATGTGGCGCGGTATTATCCCGTATTGACGCCGGGCAAGAGCAACTCGGTCGCCGCATACACTATTCT
   pBPMV-R1B (1281) TTAAAGTTCTGCTATGTGGCGCGGTATTATCCCGTATTGACGCCGGGCAAGAGCAACTCGGTCGCCGCATACACTATTCT
         K-Ho1  (1) ----------------------------------------------------------------------------------
    II-Cb1 (II)  (1) ----------------------------------------------------------------------------------
         K-Ha1  (1) ----------------------------------------------------------------------------------
   Consensus (1281)
                                                                                                                    Section 18
             (1361) 1361    1370      1380      1390      1400      1410      1420      1430      1440
   IL-Cb1 (I)   (1) ----------------------------------------------------------------------------------
         K-G7   (1) ----------------------------------------------------------------------------------
   pBPMV-R1A (1361) CAGAATGACTTGGTTGAGTACTCACCAGTCACAGAAAAGCATCTTACGGATGGCATGACAGTAAGAGAATTATGCAGTGC
   pBPMV-R1B (1361) CAGAATGACTTGGTTGAGTACTCACCAGTCACAGAAAAGCATCTTACGGATGGCATGACAGTAAGAGAATTATGCAGTGC
         K-Ho1  (1) ----------------------------------------------------------------------------------
    II-Cb1 (II)  (1) ----------------------------------------------------------------------------------
         K-Ha1  (1) ----------------------------------------------------------------------------------
   Consensus (1361)
```

*FIG. 10C*

```
                                                                                                                            Section 19
              (1441) 1441      1450      1460      1470      1480      1490      1500      1510      1520
   IL-Cb1 (I)   (1)  ------------------------------------------------------------------------------------
        K-G7    (1)  ------------------------------------------------------------------------------------
   pBPMV-R1A (1441) TGCCATAACCATGAGTGATAACACTGCGGCCAACTTACTTCTGACAACGATCGGAGGACCGAAGGAGCTAACCGCTTTTT
   pBPMV-R1B (1441) TGCCATAACCATGAGTGATAACACTGCGGCCAACTTACTTCTGACAACGATCGGAGGACCGAAGGAGCTAACCGCTTTTT
        K-Ho1   (1)  ------------------------------------------------------------------------------------
   II-Cb1 (II)  (1)  ------------------------------------------------------------------------------------
        K-Ha1   (1)  ------------------------------------------------------------------------------------
   Consensus (1441)
                                                                                                                            Section 20
              (1521) 1521      1530      1540      1550      1560      1570      1580      1590      1600
   IL-Cb1 (I)   (1)  ------------------------------------------------------------------------------------
        K-G7    (1)  ------------------------------------------------------------------------------------
   pBPMV-R1A (1521) TGCACAACATGGGGGATCATGTAACTCGCCTTGATCGTTGGGAACCGGAGCTGAATGAAGCCATACCAAACGACGAGCGT
   pBPMV-R1B (1521) TGCACAACATGGGGGATCATGTAACTCGCCTTGATCGTTGGGAACCGGAGCTGAATGAAGCCATACCAAACGACGAGCGT
        K-Ho1   (1)  ------------------------------------------------------------------------------------
   II-Cb1 (II)  (1)  ------------------------------------------------------------------------------------
        K-Ha1   (1)  ------------------------------------------------------------------------------------
   Consensus (1521)
                                                                                                                            Section 21
              (1601) 1601      1610      1620      1630      1640      1650      1660      1670      1680
   IL-Cb1 (I)   (1)  ------------------------------------------------------------------------------------
        K-G7    (1)  ------------------------------------------------------------------------------------
   pBPMV-R1A (1601) GACACCACGATGCCTGTAGCAATGGCAACAACGTTGCGCAAACTATTAACTGGCGAACTACTTACTCTAGCTTCCCGGCA
   pBPMV-R1B (1601) GACACCACGATGCCTGTAGCAATGGCAACAACGTTGCGCAAACTATTAACTGGCGAACTACTTACTCTAGCTTCCCGGCA
        K-Ho1   (1)  ------------------------------------------------------------------------------------
   II-Cb1 (II)  (1)  ------------------------------------------------------------------------------------
        K-Ha1   (1)  ------------------------------------------------------------------------------------
   Consensus (1601)
                                                                                                                            Section 22
              (1681) 1681      1690      1700      1710      1720      1730      1740      1750      1760
   IL-Cb1 (I)   (1)  ------------------------------------------------------------------------------------
        K-G7    (1)  ------------------------------------------------------------------------------------
   pBPMV-R1A (1681) ACAATTAATAGACTGGATGGAGGCGGATAAAGTTGCAGGACCACTTCTGCGCTCGGCCCTTCCGGCTGGCTGGTTTATTG
   pBPMV-R1B (1681) ACAATTAATAGACTGGATGGAGGCGGATAAAGTTGCAGGACCACTTCTGCGCTCGGCCCTTCCGGCTGGCTGGTTTATTG
        K-Ho1   (1)  ------------------------------------------------------------------------------------
   II-Cb1 (II)  (1)  ------------------------------------------------------------------------------------
        K-Ha1   (1)  ------------------------------------------------------------------------------------
   Consensus (1681)
                                                                                                                            Section 23
              (1761) 1761      1770      1780      1790      1800      1810      1820      1830      1840
   IL-Cb1 (I)   (1)  ------------------------------------------------------------------------------------
        K-G7    (1)  ------------------------------------------------------------------------------------
   pBPMV-R1A (1761) CTGATAAATCTGGAGCCGGTGAGCGTGGGTCTCGCGGTATCATTGCAGCACTGGGGCCAGATGGTAAGCCCTCCCGTATC
   pBPMV-R1B (1761) CTGATAAATCTGGAGCCGGTGAGCGTGGGTCTCGCGGTATCATTGCAGCACTGGGGCCAGATGGTAAGCCCTCCCGTATC
        K-Ho1   (1)  ------------------------------------------------------------------------------------
   II-Cb1 (II)  (1)  ------------------------------------------------------------------------------------
        K-Ha1   (1)  ------------------------------------------------------------------------------------
   Consensus (1761)
                                                                                                                            Section 24
              (1841) 1841      1850      1860      1870      1880      1890      1900      1910      1920
   IL-Cb1 (I)   (1)  ------------------------------------------------------------------------------------
        K-G7    (1)  ------------------------------------------------------------------------------------
   pBPMV-R1A (1841) GTAGTTATCTACACGACGGGGAGTCAGGCAACTATGGATGAACGAAATAGACAGATCGCTGAGATAGGTGCCTCACTGAT
   pBPMV-R1B (1841) GTAGTTATCTACACGACGGGGAGTCAGGCAACTATGGATGAACGAAATAGACAGATCGCTGAGATAGGTGCCTCACTGAT
        K-Ho1   (1)  ------------------------------------------------------------------------------------
   II-Cb1 (II)  (1)  ------------------------------------------------------------------------------------
        K-Ha1   (1)  ------------------------------------------------------------------------------------
   Consensus (1841)
```

*FIG. 10D*

```
                                                                                                    Section 25
              (1921) 1921      1930      1940      1950      1960      1970      1980      1990      2000
   IL-Cb1 (I)   (1) ----------------------------------------------------------------------------------
        K-G7    (1) ----------------------------------------------------------------------------------
   pBPMV-R1A (1921) TAAGCATTGGTAACTGTCAGACCAAGTTTACTCATATATACTTTAGATTGATTTAAAACTTCATTTTTAATTTAAAAGGA
   pBPMV-R1B (1921) TAAGCATTGGTAACTGTCAGACCAAGTTTACTCATATATACTTTAGATTGATTTAAAACTTCATTTTTAATTTAAAAGGA
        K-Ho1   (1) ----------------------------------------------------------------------------------
   II-Cb1 (II)  (1) ----------------------------------------------------------------------------------
        K-Ha1   (1) ----------------------------------------------------------------------------------
   Consensus (1921)
                                                                                                    Section 26
              (2001) 2001      2010      2020      2030      2040      2050      2060      2070      2080
   IL-Cb1 (I)   (1) ----------------------------------------------------------------------------------
        K-G7    (1) ----------------------------------------------------------------------------------
   pBPMV-R1A (2001) TCTAGGTGAAGATCCTTTTTGATAATCTCATGACCAAAATCCCTTAACGTGAGTTTTCGTTCCACTGAGCGTCAGACCCC
   pBPMV-R1B (2001) TCTAGGTGAAGATCCTTTTTGATAATCTCATGACCAAAATCCCTTAACGTGAGTTTTCGTTCCACTGAGCGTCAGACCCC
        K-Ho1   (1) ----------------------------------------------------------------------------------
   II-Cb1 (II)  (1) ----------------------------------------------------------------------------------
        K-Ha1   (1) ----------------------------------------------------------------------------------
   Consensus (2001)
                                                                                                    Section 27
              (2081) 2081      2090      2100      2110      2120      2130      2140      2150      2160
   IL-Cb1 (I)   (1) ----------------------------------------------------------------------------------
        K-G7    (1) ----------------------------------------------------------------------------------
   pBPMV-R1A (2081) GTAGAAAAGATCAAAGGATCTTCTTGAGATCCTTTTTTTCTGCGCGTAATCTGCTGCTTGCAAACAAAAAAACCACCGCT
   pBPMV-R1B (2081) GTAGAAAAGATCAAAGGATCTTCTTGAGATCCTTTTTTTCTGCGCGTAATCTGCTGCTTGCAAACAAAAAAACCACCGCT
        K-Ho1   (1) ----------------------------------------------------------------------------------
   II-Cb1 (II)  (1) ----------------------------------------------------------------------------------
        K-Ha1   (1) ----------------------------------------------------------------------------------
   Consensus (2081)
                                                                                                    Section 28
              (2161) 2161      2170      2180      2190      2200      2210      2220      2230      2240
   IL-Cb1 (I)   (1) ----------------------------------------------------------------------------------
        K-G7    (1) ----------------------------------------------------------------------------------
   pBPMV-R1A (2161) ACCAGCGGTGGTTTGTTTGCCGGATCAAGAGCTACCAACTCTTTTTCCGAAGGTAACTGGCTTCAGCAGAGCGCAGATAC
   pBPMV-R1B (2161) ACCAGCGGTGGTTTGTTTGCCGGATCAAGAGCTACCAACTCTTTTTCCGAAGGTAACTGGCTTCAGCAGAGCGCAGATAC
        K-Ho1   (1) ----------------------------------------------------------------------------------
   II-Cb1 (II)  (1) ----------------------------------------------------------------------------------
        K-Ha1   (1) ----------------------------------------------------------------------------------
   Consensus (2161)
                                                                                                    Section 29
              (2241) 2241      2250      2260      2270      2280      2290      2300      2310      2320
   IL-Cb1 (I)   (1) ----------------------------------------------------------------------------------
        K-G7    (1) ----------------------------------------------------------------------------------
   pBPMV-R1A (2241) CAAATACTGTTCTTCTAGTGTAGCCGTAGTTAGGCCACCACTTCAAGAACTCTGTAGCACCGCCTACATACCTCGCTCTG
   pBPMV-R1B (2241) CAAATACTGTTCTTCTAGTGTAGCCGTAGTTAGGCCACCACTTCAAGAACTCTGTAGCACCGCCTACATACCTCGCTCTG
        K-Ho1   (1) ----------------------------------------------------------------------------------
   II-Cb1 (II)  (1) ----------------------------------------------------------------------------------
        K-Ha1   (1) ----------------------------------------------------------------------------------
   Consensus (2241)
                                                                                                    Section 30
              (2321) 2321      2330      2340      2350      2360      2370      2380      2390      2400
   IL-Cb1 (I)   (1) ----------------------------------------------------------------------------------
        K-G7    (1) ----------------------------------------------------------------------------------
   pBPMV-R1A (2321) CTAATCCTGTTACCAGTGGCTGCTGCCAGTGGCGATAAGTCGTGTCTTACCGGGTTGGACTCAAGACGATAGTTACCGGA
   pBPMV-R1B (2321) CTAATCCTGTTACCAGTGGCTGCTGCCAGTGGCGATAAGTCGTGTCTTACCGGGTTGGACTCAAGACGATAGTTACCGGA
        K-Ho1   (1) ----------------------------------------------------------------------------------
   II-Cb1 (II)  (1) ----------------------------------------------------------------------------------
        K-Ha1   (1) ----------------------------------------------------------------------------------
   Consensus (2321)
```

*FIG. 10E*

```
                                                                                                    Section 31
              (2401) 2401      2410      2420      2430      2440      2450      2460      2470      2480
   IL-Cb1 (I)    (1) ----------------------------------------------------------------------------------
        K-G7     (1) ----------------------------------------------------------------------------------
   pBPMV-R1A (2401) TAAGGCGCAGCGGTCGGGCTGAACGGGGGGTTCGTGCACACAGCCCAGCTTGGAGCGAACGACCTACACCGAACTGAGAT
   pBPMV-R1B (2401) TAAGGCGCAGCGGTCGGGCTGAACGGGGGGTTCGTGCACACAGCCCAGCTTGGAGCGAACGACCTACACCGAACTGAGAT
       K-Ho1     (1) ----------------------------------------------------------------------------------
   II-Cb1 (II)   (1) ----------------------------------------------------------------------------------
        K-Ha1    (1) ----------------------------------------------------------------------------------
   Consensus  (2401)
                                                                                                    Section 32
              (2481) 2481      2490      2500      2510      2520      2530      2540      2550      2560
   IL-Cb1 (I)    (1) ----------------------------------------------------------------------------------
        K-G7     (1) ----------------------------------------------------------------------------------
   pBPMV-R1A (2481) ACCTACAGCGTGAGCTATGAGAAAGCGCCACGCTTCCCGAAGGGAGAAAGGCGGACAGGTATCCGGTAAGCGGCAGGGTC
   pBPMV-R1B (2481) ACCTACAGCGTGAGCTATGAGAAAGCGCCACGCTTCCCGAAGGGAGAAAGGCGGACAGGTATCCGGTAAGCGGCAGGGTC
       K-Ho1     (1) ----------------------------------------------------------------------------------
   II-Cb1 (II)   (1) ----------------------------------------------------------------------------------
        K-Ha1    (1) ----------------------------------------------------------------------------------
   Consensus  (2481)
                                                                                                    Section 33
              (2561) 2561      2570      2580      2590      2600      2610      2620      2630      2640
   IL-Cb1 (I)    (1) ----------------------------------------------------------------------------------
        K-G7     (1) ----------------------------------------------------------------------------------
   pBPMV-R1A (2561) GGAACAGGAGAGCGCACGAGGGAGCTTCCAGGGGGAAACGCCTGGTATCTTTATAGTCCTGTCGGGTTTCGCCACCTCTG
   pBPMV-R1B (2561) GGAACAGGAGAGCGCACGAGGGAGCTTCCAGGGGGAAACGCCTGGTATCTTTATAGTCCTGTCGGGTTTCGCCACCTCTG
       K-Ho1     (1) ----------------------------------------------------------------------------------
   II-Cb1 (II)   (1) ----------------------------------------------------------------------------------
        K-Ha1    (1) ----------------------------------------------------------------------------------
   Consensus  (2561)
                                                                                                    Section 34
              (2641) 2641      2650      2660      2670      2680      2690      2700      2710      2720
   IL-Cb1 (I)    (1) ----------------------------------------------------------------------------------
        K-G7     (1) ----------------------------------------------------------------------------------
   pBPMV-R1A (2641) ACTTGAGCGTCGATTTTTGTGATGCTCGTCAGGGGGGCGGAGCCTATGGAAAAACGCCAGCAACGCGGCCTTTTTACGGT
   pBPMV-R1B (2641) ACTTGAGCGTCGATTTTTGTGATGCTCGTCAGGGGGGCGGAGCCTATGGAAAAACGCCAGCAACGCGGCCTTTTTACGGT
       K-Ho1     (1) ----------------------------------------------------------------------------------
   II-Cb1 (II)   (1) ----------------------------------------------------------------------------------
        K-Ha1    (1) ----------------------------------------------------------------------------------
   Consensus  (2641)
                                                                                                    Section 35
              (2721) 2721      2730      2740      2750      2760      2770      2780      2790      2800
   IL-Cb1 (I)    (1) ----------------------------------------------------------------------------------
        K-G7     (1) ----------------------------------------------------------------------------------
   pBPMV-R1A (2721) TCCTGGCCTTTTGCTGGCCTTTTGCTCACATGTTCTTTCCTGCGTTATCCCCTGATTCTGTGGATAACCGTATTACCGCC
   pBPMV-R1B (2721) TCCTGGCCTTTTGCTGGCCTTTTGCTCACATGTTCTTTCCTGCGTTATCCCCTGATTCTGTGGATAACCGTATTACCGCC
       K-Ho1     (1) ----------------------------------------------------------------------------------
   II-Cb1 (II)   (1) ----------------------------------------------------------------------------------
        K-Ha1    (1) ----------------------------------------------------------------------------------
   Consensus  (2721)
                                                                                                    Section 36
              (2801) 2801      2810      2820      2830      2840      2850      2860      2870      2880
   IL-Cb1 (I)    (1) ----------------------------------------------------------------------------------
        K-G7     (1) ----------------------------------------------------------------------------------
   pBPMV-R1A (2801) TTTGAGTGAGCTGATACCGCTCGCCGCAGCCGAACGACCGAGCGCAGCGAGTCAGTGAGCGAGGAAGCGGAAGAGCGCCC
   pBPMV-R1B (2801) TTTGAGTGAGCTGATACCGCTCGCCGCAGCCGAACGACCGAGCGCAGCGAGTCAGTGAGCGAGGAAGCGGAAGAGCGCCC
       K-Ho1     (1) ----------------------------------------------------------------------------------
   II-Cb1 (II)   (1) ----------------------------------------------------------------------------------
        K-Ha1    (1) ----------------------------------------------------------------------------------
   Consensus  (2801)
```

*FIG. 10F*

```
                                                                                                        Section 37
              (2881) 2881     2890      2900      2910      2920      2930      2940      2950      2960
   IL-Cb1 (I)   (1)  ----------------------------------------------------------------------------------
        K-G7    (1)  ----------------------------------------------------------------------------------
   pBPMV-R1A (2881)  AATACGCAAACCGCCTCTCCCCGCGCGTTGGCCGATTCATTAATGCAGCTGGCACGACAGGTTTCCCGACTGGAAAGCGG
   pBPMV-R1B (2881)  AATACGCAAACCGCCTCTCCCCGCGCGTTGGCCGATTCATTAATGCAGCTGGCACGACAGGTTTCCCGACTGGAAAGCGG
       K-Ho1    (1)  ----------------------------------------------------------------------------------
   II-Cb1 (II)  (1)  ----------------------------------------------------------------------------------
        K-Ha1   (1)  ----------------------------------------------------------------------------------
   Consensus (2881)
                                                                                                        Section 38
              (2961) 2961     2970      2980      2990      3000      3010      3020      3030      3040
   IL-Cb1 (I)   (1)  ----------------------------------------------------------------------------------
        K-G7    (1)  ----------------------------------------------------------------------------------
   pBPMV-R1A (2961)  GCAGTGAGCGCAACGCAATTAATGTGAGTTAGCTCACTCATTAGGCACCCCAGGCTTTACACTTTATGCTTCCGGCTCGT
   pBPMV-R1B (2961)  GCAGTGAGCGCAACGCAATTAATGTGAGTTAGCTCACTCATTAGGCACCCCAGGCTTTACACTTTATGCTTCCGGCTCGT
       K-Ho1    (1)  ----------------------------------------------------------------------------------
   II-Cb1 (II)  (1)  ----------------------------------------------------------------------------------
        K-Ha1   (1)  ----------------------------------------------------------------------------------
   Consensus (2961)
                                                                                                        Section 39
              (3041) 3041     3050      3060      3070      3080      3090      3100      3110      3120
   IL-Cb1 (I)   (1)  ----------------------------------------------------------------------------------
        K-G7    (1)  ----------------------------------------------------------------------------------
   pBPMV-R1A (3041)  ATGTTGTGTGGAATTGTGAGCGGATAACAATTTCACACAGGAAACAGCTATGACCATGATTACGCCAAGCTATTTAGGTG
   pBPMV-R1B (3041)  ATGTTGTGTGGAATTGTGAGCGGATAACAATTTCACACAGGAAACAGCTATGACCATGATTACGCCAAGCTATTTAGGTG
       K-Ho1    (1)  ----------------------------------------------------------------------------------
   II-Cb1 (II)  (1)  ----------------------------------------------------------------------------------
        K-Ha1   (1)  ----------------------------------------------------------------------------------
   Consensus (3041)
                                                                                                        Section 40
              (3121) 3121     3130      3140      3150      3160      3170      3180      3190      3200
   IL-Cb1 (I)   (1)  ----------------------------------------------------------------------------------
        K-G7    (1)  ----------------------------------------------------------------------------------
   pBPMV-R1A (3121)  ACACTATAGAATACTCAAGCGGCCGCCTACTCCAAGAATATCAAAGATACAGTCTCAGAAGACCAAAGGGCTATTGAGAC
   pBPMV-R1B (3121)  ACACTATAGAATACTCAAGCGGCCGCCTACTCCAAGAATATCAAAGATACAGTCTCAGAAGACCAAAGGGCTATTGAGAC
       K-Ho1    (1)  ----------------------------------------------------------------------------------
   II-Cb1 (II)  (1)  ----------------------------------------------------------------------------------
        K-Ha1   (1)  ----------------------------------------------------------------------------------
   Consensus (3121)
                                                                                                        Section 41
              (3201) 3201     3210      3220      3230      3240      3250      3260      3270      3280
   IL-Cb1 (I)   (1)  ----------------------------------------------------------------------------------
        K-G7    (1)  ----------------------------------------------------------------------------------
   pBPMV-R1A (3201)  TTTTCAACAAAGGGTAATATCGGGAAACCTCCTCGGATTCCATTGCCCAGCTATCTGTCACTTCATCAAAAGGACAGTAG
   pBPMV-R1B (3201)  TTTTCAACAAAGGGTAATATCGGGAAACCTCCTCGGATTCCATTGCCCAGCTATCTGTCACTTCATCAAAAGGACAGTAG
       K-Ho1    (1)  ----------------------------------------------------------------------------------
   II-Cb1 (II)  (1)  ----------------------------------------------------------------------------------
        K-Ha1   (1)  ----------------------------------------------------------------------------------
   Consensus (3201)
                                                                                                        Section 42
              (3281) 3281     3290      3300      3310      3320      3330      3340      3350      3360
   IL-Cb1 (I)   (1)  ----------------------------------------------------------------------------------
        K-G7    (1)  ----------------------------------------------------------------------------------
   pBPMV-R1A (3281)  AAAAGGAAGGTGGCACCTACAAATGCCATCATTGCGATAAAGGAAAGGCTATCGTTCAAGATGCCTCTGCCGACAGTGGT
   pBPMV-R1B (3281)  AAAAGGAAGGTGGCACCTACAAATGCCATCATTGCGATAAAGGAAAGGCTATCGTTCAAGATGCCTCTGCCGACAGTGGT
       K-Ho1    (1)  ----------------------------------------------------------------------------------
   II-Cb1 (II)  (1)  ----------------------------------------------------------------------------------
        K-Ha1   (1)  ----------------------------------------------------------------------------------
   Consensus (3281)
```

*FIG. 10G*

```
                                                                                                                    Section 43
              (3361) 3361     3370      3380      3390      3400      3410      3420      3430      3440
   IL-Cb1 (I)   (1) ----------------------------------------------------------------------------------
        K-G7    (1) ----------------------------------------------------------------------------------
    pBPMV-R1A (3361) CCCAAAGATGGACCCCCACCCACGAGGAGCATCGTGGAAAAAGAAGACGTTCCAACCACGTCTTCAAAGCAAGTGGATTG
    pBPMV-R1B (3361) CCCAAAGATGGACCCCCACCCACGAGGAGCATCGTGGAAAAAGAAGACGTTCCAACCACGTCTTCAAAGCAAGTGGATTG
        K-Ho1   (1) ----------------------------------------------------------------------------------
   II-Cb1 (II)  (1) ----------------------------------------------------------------------------------
        K-Ha1   (1) ----------------------------------------------------------------------------------
    Consensus (3361)
                                                                                                                    Section 44
              (3441) 3441     3450      3460      3470      3480      3490      3500      3510      3520
   IL-Cb1 (I)   (1) ----------------------------------------------------------------------------------
        K-G7    (1) ----------------------------------------------------------------------------------
    pBPMV-R1A (3441) ATGTGATCTACTCCAAGAATATCAAAGATACAGTCTCAGAAGACCAAAGGGCTATTGAGACTTTTCAACAAAGGGTAATA
    pBPMV-R1B (3441) ATGTGATCTACTCCAAGAATATCAAAGATACAGTCTCAGAAGACCAAAGGGCTATTGAGACTTTTCAACAAAGGGTAATA
        K-Ho1   (1) ----------------------------------------------------------------------------------
   II-Cb1 (II)  (1) ----------------------------------------------------------------------------------
        K-Ha1   (1) ----------------------------------------------------------------------------------
    Consensus (3441)
                                                                                                                    Section 45
              (3521) 3521     3530      3540      3550      3560      3570      3580      3590      3600
   IL-Cb1 (I)   (1) ----------------------------------------------------------------------------------
        K-G7    (1) ----------------------------------------------------------------------------------
    pBPMV-R1A (3521) TCGGGAAACCTCCTCGGATTCCATTGCCCAGCTATCTGTCACTTCATCAAAAGGACAGTAGAAAAGGAAGGTGGCACCTA
    pBPMV-R1B (3521) TCGGGAAACCTCCTCGGATTCCATTGCCCAGCTATCTGTCACTTCATCAAAAGGACAGTAGAAAAGGAAGGTGGCACCTA
        K-Ho1   (1) ----------------------------------------------------------------------------------
   II-Cb1 (II)  (1) ----------------------------------------------------------------------------------
        K-Ha1   (1) ----------------------------------------------------------------------------------
    Consensus (3521)
                                                                                                                    Section 46
              (3601) 3601     3610      3620      3630      3640      3650      3660      3670      3680
   IL-Cb1 (I)   (1) ----------------------------------------------------------------------------------
        K-G7    (1) ----------------------------------------------------------------------------------
    pBPMV-R1A (3601) CAAATGCCATCATTGCGATAAAGGAAAGGCTATCGTTCAAGATGCCTCTGCCGACAGTGGTCCCAAAGATGGACCCCCAC
    pBPMV-R1B (3601) CAAATGCCATCATTGCGATAAAGGAAAGGCTATCGTTCAAGATGCCTCTGCCGACAGTGGTCCCAAAGATGGACCCCCAC
        K-Ho1   (1) ----------------------------------------------------------------------------------
   II-Cb1 (II)  (1) ----------------------------------------------------------------------------------
        K-Ha1   (1) ----------------------------------------------------------------------------------
    Consensus (3601)
                                                                                                                    Section 47
              (3681) 3681     3690      3700      3710      3720      3730      3740      3750      3760
   IL-Cb1 (I)   (1) ----------------------------------------------------------------------------------
        K-G7    (1) ----------------------------------------------------------------------------------
    pBPMV-R1A (3681) CCACGAGGAGCATCGTGGAAAAAGAAGACGTTCCAACCACGTCTTCAAAGCAAGTGGATTGATGTGATATCTCCACTGAC
    pBPMV-R1B (3681) CCACGAGGAGCATCGTGGAAAAAGAAGACGTTCCAACCACGTCTTCAAAGCAAGTGGATTGATGTGATATCTCCACTGAC
        K-Ho1   (1) ----------------------------------------------------------------------------------
   II-Cb1 (II)  (1) ----------------------------------------------------------------------------------
        K-Ha1   (1) ----------------------------------------------------------------------------------
    Consensus (3681)
                                                                                                                    Section 48
              (3761) 3761     3770      3780      3790      3800      3810      3820      3830      3840
   IL-Cb1 (I)   (1) ----------------------------------------------------------------------------------TA
        K-G7    (1) ----------------------------------------------------------------------------------TA
    pBPMV-R1A (3761) GTAAGGGATGACGCACAATCCCACTATCCTTCGCAAGACCCTTCCTCTATATAAGGAAGTTCATTTCATTTGGAGAGGTA
    pBPMV-R1B (3761) GTAAGGGATGACGCACAATCCCACTATCCTTCGCAAGACCCTTCCTCTATATAAGGAAGTTCATTTCATTTGGAGAGGTA
        K-Ho1   (1) ----------------------------------------------------------------------------------TA
   II-Cb1 (II)  (1) ----------------------------------------------------------------------------------TA
        K-Ha1   (1) ----------------------------------------------------------------------------------TA
    Consensus (3761)                                                                                  TA
```

```
                      Section 61
              (4801) 4801      4810       4820       4830       4840       4850       4860       4870       4880
    IL-Cb1 (I) (956)  AAAGAATGGATAGAAGAAGCTGCGAAAGAAATTTCATGGTTCTTGCAAGGATGTAAAGAGCTGCTAGCCTGGGGAATGTG
         K-G7  (956)  AAAGAGTGGATAGAAGAAGCTACGAAAGAAATTTCATGGTTTTTGCAAGGATGTAAAGAGCTGCTAGCCTGGGGAATGTG
    pBPMV-R1A (4794)  AAAGAGTGGATAGAAGAAGCTGCGAAAGAGATTTCATGGTTTTTGCAAGGATGCAAAGAGTTGCTAGCCTGGGGAATGTG
    pBPMV-R1B (4794)  AAAGAGTGGATAGAAGAAGCTGCGAAAGAGATTTCATGGTTTTTGCAAGGATGCAAAGAGTTGCTAGCCTGGGGAATGTG
        K-Ho1  (956)  AAAGAATGGATAGAAGAAGCTGCGAAAGAAATTTCATGGTTCTTGCAAGGATGTAAAGAGCTGCTAGCCTGGGGAATGTG
    II-Cb1 (II) (958) AAAGAATGGATTGAAGAGGCTGCGAAAGAAATTTCTTGGTTCCTGCAAGGTTGTAAGGAATTGTTAGCTTGGGGAATGTG
        K-Ha1  (959)  AAAGAATGGATTGAAGAGGCTGCGAAGGAAATTTCTTGGTTCCTGCAGGGGTTGTAAGGAATTATTAGCTTGGGGAATGTG
    Consensus (4801)  AAAGAATGGATAGAAGAAGCTGCGAAAGAAATTTCATGGTTCTTGCAAGGATGTAAAGAGTTGCTAGCCTGGGGAATGTG
                                                                                                  Section 62
              (4881) 4881      4890       4900       4910       4920       4930       4940       4950       4960
    IL-Cb1 (I) (1036) CATTTTGGCTAGCTCCTGTGCTCTAGGATTGGTTGAAAAATGCCTTATCTCTTTGGGCATGATTTCTGAATCTTTTGATT
         K-G7 (1036)  TATTTTGGCTAGCTCCTGTGCTCTAGGATTGGTTGAAAAATGCCTTATTTCTTTGGGCATGATTTCCGAATCTTTTGATT
    pBPMV-R1A (4874)  TATTTTGGCTAGCTCCTGTGCTCTAGGATTGGTTGAAAAATGCCTTATCTCTTTGGGCATGATTTCCGAATCTTTTGATT
    pBPMV-R1B (4874)  TATTTTGGCTAGCTCCTGTGCTCTAGGATTGGTTGAAAAATGCCTTATCTCTTTGGGCATGATTTCCGAATCTTTTGATT
        K-Ho1 (1036)  CATTTTGGCTAGCTCCTGTGCTCTAGGATTGGTTGAAAAATGCCTTATCTCTTTGGGCATGATTTCTGAATCTTTTGATT
    II-Cb1 (II) (1038) TATTCTAGCTAGTTCCTGTGCTTTGGGATTGGTTGAAAAATGTCTCATTTCTCTAGGCATGATTTCTGAATCTTTTGATT
        K-Ha1 (1039)  TATTCTGGCTAGTTCCTGTGCTTTGGGATTGGTTGAAAAATGTCTCATTTCTTTAGGCATGATTTCTGAATCTTTTGATT
    Consensus (4881)  TATTTTGGCTAGCTCCTGTGCTCTAGGATTGGTTGAAAAATGCCTTATCTCTTTGGGCATGATTTCTGAATCTTTTGATT
                                                                                                  Section 63
              (4961) 4961      4970       4980       4990       5000       5010       5020       5030       5040
    IL-Cb1 (I) (1116) TGGTTGGTTTGTTTGTTCGATCTGCCATTGTGGGAGCTTTCTGTGTTTCCATAAAAACTGGTAAGTTCATCACAAACAGT
         K-G7 (1116)  TGGTTGGCTTGTTTGTCGATCTGCCATTGTGGGAGCTTTCTGTGTTTCCATAAAAACTGGCAAGTTCGTCACGAATAGT
    pBPMV-R1A (4954)  TGGTTGGTTTGTTTGTTCGATCTGCCATTGTGGGAGCTTTCTGTGTTTCCATAAAAACTGGCAAGTTCATCACGAATAGT
    pBPMV-R1B (4954)  TGGTTGGTTTGTTTGTTCGATCTGCCATTGTGGGAGCTTTCTGTGTTCCCATAAAAACTGGCAAGTTCATCACGAATAGT
        K-Ho1 (1116)  TGGTTGGTTTGTTTGTCGATCTGCCATTGTGGGAGCTTTCTGTGTTTCCATAAAAACTGGTAAGTTCGTCACGAACAGT
    II-Cb1 (II) (1118) TGGTTGGTTTGTTTGTTCGATCAGCCATTGTTGGAGCCTTCTGTGTTCTATCAAGACGGGCAAGTTGTTTCAAATAGT
        K-Ha1 (1119)  TGGTTGGTTTGTTTGTTCGATCAGCCATTGTTGGGGCCTTCTGTGTTCTATCAAGACGGGCAGGTTGTTTCAAATAGT
    Consensus (4961)  TGGTTGGTTTGTTTGTTCGATCTGCCATTGTGGGAGCTTTCTGTGTTCCATAAAAACTGGCAAGTTCGTCACGAATAGT
                                                                                                  Section 64
              (5041) 5041      5050       5060       5070       5080       5090       5100       5110       5120
    IL-Cb1 (I) (1196) GAGTGATTACTTGTGCTACCATTGCAGTTTCTACAATAGCAACTGTAATGTCTCAGGCTTTTAAGCCTTCTGAAGAGAT
         K-G7 (1196)  GAATTGATCACTTGTGCTACCATTGCAGTTCTACAATAGCAACTGTAATGTCTCAGGCTTTTAAGCCTTCTGAAGAGAT
    pBPMV-R1A (5034)  GAATTGGTCACTTGTGCTACCATTGCAGTTTCTACAATAGCAACTGTAATGTCTCAGGCTTTTAAGCCTTCTGAAGAGAT
    pBPMV-R1B (5034)  GAATTGGTCACTTGTGCTACCATTGCAGTTTCTACAATAGCAACTGTAATGTCTCAGGCTTTTAAGCCTTCTGAAGAGAT
        K-Ho1 (1196)  GAATTGATCACTTGTGCTACCATTGCAGTTTCTACAATAGCAACTGTAATGTCTCAGGCTTTTAAGCCTTCCGAAGAGAT
    II-Cb1 (II) (1198) GAGTTGATCACATGTGCTACCATTGCAGTTTCTACAATTGCAACTGTTATGTCTCAAGCTTTCAAACCTTCTGAAGAAAT
        K-Ha1 (1199)  GAGTTGATCACATGTGCTACCATTGCAGTTTCTACAATTGCAACTGTTATGTCTCCAAGCTTTCAAACCTTCTGAAGAAAT
    Consensus (5041)  GAATTGATCACTTGTGCTACCATTGCAGTTTCTACAATAGCAACTGTAATGTCTCAGGCTTTTAAGCCTTCTGAAGAGAT
                                                                                                  Section 65
              (5121) 5121      5130       5140       5150       5160       5170       5180       5190       5200
    IL-Cb1 (I) (1276) TAAGGGACAGTTCCAAGCCCTTTCAGTTCTAGAAGGGTTGGCAACACAGCTCACTTCATTTGTGACACATCTTTAGTTG
         K-G7 (1276)  TAAGGGACAGTTCCAAGCCCTTTCAGTTCTAGAAGGGTTGGCAACACAGCTCACTTCATTTGTGACACGTCCTTAGTTG
    pBPMV-R1A (5114)  TAAGGGGCAGTTCCAAGCCCTTTCAGTTCTAGAAGGGTTGGCAACACAGCTCACTTCGTTTGTGACACGTCTTTAGTTG
    pBPMV-R1B (5114)  TAAGGGGCAGTTCCAAGCCCTTTCAGTTCTAGAAGGGTTGGCAACACAGCTCACTTCGTTTGTGACACGTCTTTAGTTG
        K-Ho1 (1276)  TAAGGGACAGTTCCAAGCCCTTTCAGTTCTAGAAGGGTTGGCAACACAGCTCACTTCATTTGTGACACGTCTTTAGTTG
    II-Cb1 (II) (1278) TAAAGGGACAATTCCAAGCCCTTTTCGTTTTTAGAGGGGATTGGCAACACAACTCACTTCATTTGTGACACATCTTTGATTG
        K-Ha1 (1279)  TAAAGGGCAATTCCAGGCTCGTTTCGTGTTTAGAGGGATTGGCAACACAACTCACTTCATTTGTGACACATCTTTAGTTG
    Consensus (5121)  TAAGGGGCAGTTCCAAGCCCTTTCAGTTCTAGAAGGGTTGGCAACACAGCTCACTTCATTTGTGACACGTCTTTAGTTG
                                                                                                  Section 66
              (5201) 5201      5210       5220       5230       5240       5250       5260       5270       5280
    IL-Cb1 (I) (1356) CTATGGGAAAAACCTGCACAGCTTTTAATCAAATTTGCACTGCTGGCAAAAATGTTAAGGTGATTGCAGGTAGGTTACTA
         K-G7 (1356)  CTATGGGAAAAACCTGCACAGCTTTTAATCAAATTTGCACTGCTGGCAAAAATGTTAAGGTGATTGCAGGTAGGTTGCTG
    pBPMV-R1A (5194)  CTATGGGAAAAACCTGCACAGCTTTTAATCAAATTTGCACTGCTGGCAAAAATGTTAAGGTGATTGCAGGTAGGTTGCTG
    pBPMV-R1B (5194)  CTATGGGAAAAACCTGCACAGCTTTTAATCAAATTTGCACTGCTGGCAAAAATGTTAAGGTGATTGCAGGTAGGTTGCTG
        K-Ho1 (1356)  CTATGGGAAAAACCTGCACAGCTTTTAATCAAATTTGCACTGCTGGCAAAAATGTTAAGGTGATTGCAGGTAGGTTGCTA
    II-Cb1 (II) (1358) CCATGGGAAAAACTTGCACAGCATTTAATCAAATTTGTACTGCTGGAAAAAATGTTAAGGTGATTGCAGGCAGATTGTTG
        K-Ha1 (1359)  CCATGGGAAAAACCTGCACAGCATTTAATCAAATTTGTACTGCTGGGAAAAATGTTAAAGTGATTGCAGGCAGATTGTTG
    Consensus (5201)  CTATGGGAAAAACCTGCACAGCTTTTAATCAAATTTGCACTGCTGGCAAAAATGTTAAGGTGATTGCAGGTAGGTTGCTG
```

*FIG. 10K*

```
                                                                                                    Section 67
              (5281)  5281      5290       5300       5310       5320       5330       5340       5350       5360
   IL-Cb1 (I) (1436)  GAAGTTGTTTCCAATTTTGTCAGAAAATTATTAGGATTGGACAGTGTTTTTCTCAGAGATGCTGCACTCATCTTTTCTCA
        K-G7  (1436)  GAAGTTGTTTCTAATTTTGTTAGAAAATTATTAGGATTGGATAGTGCTTTTCTCAGAGATGCTGCACTCATTTTTTCTCA
   pBPMV-R1A  (5274)  GAAGTTGTTTCTAATTTTGTCAGAAAATTATTAGGATTGGATAGTGCTTTTCTCAGAGATGCTGCACTCATTTTTTCCCA
   pBPMV-R1B  (5274)  GAAGTTGTTTCTAATTTTGTCAGAAAATTATTAGGATTGGATAGTGCTTTTCTCAGAGATGCTGCACTCATTTTTTCCCA
        K-Ho1 (1436)  GAAGTTGTTTCTAATTTTGTCAGAAAATTATTAGGATTGGATAGTGCTTTTCTCAGAGATGCTGCACTCATTTTTTCTCA
  II-Cb1 (II) (1438)  GATGTAGTTTCCAATTTTGTAAGGAAACTTTTGGGATTGGATAGTGCTTTTCTTAGAGATGCAGCGCTCATCCTCTCTCA
        K-Ha1 (1439)  GATGTAGTTTCCAATTTTTGTAAGGAAACTTTTGGGATTGGATAGTGCTTTTCTTAGAGATGCAGCGCTTATTTTCTCTCA
   Consensus  (5281)  GAAGTTGTTTCTAATTTTGTCAGAAAATTATTAGGATTGGATAGTGCTTTTCTCAGAGATGCTGCACTCATTTTTTCTCA
                                                                                                    Section 68
              (5361)  5361      5370       5380       5390       5400       5410       5420       5430       5440
   IL-Cb1 (I) (1516)  AGATGTGGATGGGTGGTTGCGTAACATCAGTTGGTGCCAAGAACAGTTTTTGTTGAAAGCTTACATGTCACAAGATGATC
        K-G7  (1516)  AGATGTGGATGGATGGTTGCGTAACATTAGTTGGTGCCAAGAACAGTTTTTGTTGAAAGCTTACATGTCGCAAGATGATC
   pBPMV-R1A  (5354)  AGATGTGGATGGATGGTTGCGTAACATCAGTTGGTGCCAGGAACAGTTTTTGTTGAAAGCTTACATGTCGCAAGATGATC
   pBPMV-R1B  (5354)  AGATGTGGATGGATGGTTGCGTAACATCAGTTGGTGCCAGGAACAGTTTTTGTTGAAAGCTTACATGTCGCAAGATGATC
        K-Ho1 (1516)  AGATGTGGATGGATGGTTGCGTAACATCAGTTGGTGCCAAGAACAGTTTTTGTTGAAGGCTTACATGTCGCAAGATGATC
  II-Cb1 (II) (1518)  AGATGTTGATGGTGGCTGCGCAATATCAGCTGGTGTCAGGAACAATTCCTACTGAAAGCATACATGTCTCAAGATGATC
        K-Ha1 (1519)  AGATGTTGACGGTTGGTTGCGCAATATCAGCTGGTGTCAGGAACAATTCCTACTGAAAGCATACATGTCTCAAGATGATC
   Consensus  (5361)  AGATGTGGATGGATGGTTGCGTAACATCAGTTGGTGCCAGGAACAGTTTTTGTTGAAAGCTTACATGTCGCAAGATGATC
                                                                                                    Section 69
              (5441)  5441      5450       5460       5470       5480       5490       5500       5510       5520
   IL-Cb1 (I) (1596)  TTATTGTCCTGCGCTCTTTAGTTGTCAAAGGTGAAAGAATGAGGGAACAGATGCTTGAAGGAGAAGTTAAGGTGTCTCCA
        K-G7  (1596)  TTATTGTCTTACCGCTCTTTAGTTGTCAAAGGTGAAAGAATGAGGGAACAGATGCTTGAAGGAGAAGTTAAGGTGTCTCCA
   pBPMV-R1A  (5434)  TTATTGTCCTGCGCTCTTTAGTTGTTAAAGGTGAAAGAATGAGGGAACAGATGCTTGAAGGAGAAGTTAAGGTATCTCCA
   pBPMV-R1B  (5434)  TTATTGTCCTGCGCTCTTTAGTTGTTAAAGGTGAAAGAATGAGGGAACAGATGCTTGAAGGAGAAGTTAAGGTGTCTCCA
        K-Ho1 (1596)  TTATTGTCCTGCGCTCTTTAGTTGTCAAAGGTGAAAGAATGAGGGAACAGATGCTTGAAGGAGAAGTTAAGGTGTCTCCA
  II-Cb1 (II) (1598)  TTATTGTCTTGCGTTCCTTAGTTGTCAAAGGTGAAAGAATGAGAGAACAAATGTTGGAAGGAGAGGTTAAAGTGTCTCCC
        K-Ha1 (1599)  TTATTGTCTTGCGTTCCTTAGTTGTCAAAGGTGAAAGAAGCAAATGCTGGAGGAGAGGTTAAAGTGTCTCCT
   Consensus  (5441)  TTATTGTCCTGCGCTCTTTAGTTGTCAAAGGTGAAAGAATGAGGGAACAGATGCTTGAAGGAGAAGTTAAGGTGTCTCCA
                                                                                                    Section 70
              (5521)  5521      5530       5540       5550       5560       5570       5580       5590       5600
   IL-Cb1 (I) (1676)  AGTGTTTGCAACCTTATTGTCAAAGGCTGTGAAGAAGCAAATAAATTGATGCGTGAGAGCGCACTTCATTGTTCAAAAAC
        K-G7  (1676)  AGTGTTTGCAACCTTATTGTCAAAGGCTGTGAAGAAGCAAATAAATTGATGCGTGAGAGCGCACTTCATTGTTCAAAAAC
   pBPMV-R1A  (5514)  AGTGTTTGCAACCTTATTGTCAAAGGCTGTGAAGAAGCAAATAAATTGATGCGTGAGAGCGCACTTCATTGTTCAAAAAC
   pBPMV-R1B  (5514)  AGTGTTTGCAACCTTATTGTCAAAGGCTGTGAAGAAGCAAATAAATTGATGCGTGAGAGCGCACTTCATTGTTCAAAAAC
        K-Ho1 (1676)  AGTGTTTGCAACCTTATTGTCAAAGGCTGTGAAGAAGCAAATAAATTGATGCGTGAGAGCGCACTTCATTGTTCAAAAAC
  II-Cb1 (II) (1678)  AGTGTTTGTAATCTTATTGTAAAAGGTTGTGAAGAAGCAAGTAAGTTGATGAGAGAAAGTGTGCTACATTGTTCAAAGAC
        K-Ha1 (1679)  AGTGTTTGTAATCTTATTGTAAAAGGTTGTGAAGAAGCAAGTAAGTTGATGAGAGAAAGTGTGCTACATTGTTCAAAGAC
   Consensus  (5521)  AGTGTTTGCAACCTTATTGTCAAAGGCTGTGAAGAAGCAAATAAATTGATGCGTGAGAGCGCACTTCATTGTTCAAAAAC
                                                                                                    Section 71
              (5601)  5601      5610       5620       5630       5640       5650       5660       5670       5680
   IL-Cb1 (I) (1756)  AATTAGGAAGAATTCCTTTTGTTATTTTTGCTCACGGTGAATCCCGGGTTGGGAAATCTCTGCTGGTTGATAGGCTAATCA
        K-G7  (1756)  AATTAGGAAGAATTCCTTTTGTTATTTTTGCTCACGGTGAATCCCGAGTTGGGAAATCTCTGCTGGTTGATAAGCTAATCA
   pBPMV-R1A  (5594)  AATTAGGAAGATTCCTTTTGTTATTTTTGCTCACGGTGAATCCCGAGTTGGGAAATCTCTGTTGGTTGATAAGCTAATCA
   pBPMV-R1B  (5594)  AATTAGGAAGATTCCTTTTGTTATTTTTGCTCACGGTGAATCCCGGGTTGGGAAATCTCTGCTGGTTGATAGGCTAATCA
        K-Ho1 (1756)  AATTAGGAAGATTCCTTTTGTTATTTTTGCTCACGGTGAATCCCGGGTTGGGAAATCTCTGCTGGTTGATAGGCTAATCA
  II-Cb1 (II) (1758)  TGTACGAAAATTCCATTTGTCATTTTTGCACACGGTGATCTCGTGTTGGAAAATCTTTGCTAGTTGATAGACTTATCA
        K-Ha1 (1759)  TGTACGAAAATTCCATTTGTTATTTTTGCACACGGTGATTCTCGTGTTGGAAAATCTTTGCTAGTTGATAGACTTATCA
   Consensus  (5601)  AATTAGGAAGATTCCTTTTGTTATTTTTGCTCACGGTGAATCCCG GTTGGGAAATCTCTGCTGGTTGATAGGCTAATCA
                                                                                                    Section 72
              (5681)  5681      5690       5700       5710       5720       5730       5740       5750       5760
   IL-Cb1 (I) (1836)  CAGATTTCTGTGATCATTTGGAAATTGGAGAAGATGCTGTGTACTCAAGGAATCCATCAGATCCTTTCTGAGTGGATAT
        K-G7  (1836)  CAGATTTCTGTGATCATTTGGAAATTGGAGAAGATGCTGTGTACTCAAGGAATCCATCAGATCCTTTTTGAGTGGATAT
   pBPMV-R1A  (5674)  CAGATTTCTGTGATCATTTGGAAATTGGAGAAGATGCTGTGTACTCAAGGAATCCATCAGATCCTTTCTGAGTGGATAT
   pBPMV-R1B  (5674)  CAGATTTCTGTGATCATTTGGAAATTGGAGAAGATGCTGTGTACTCAAGGAATCCATCAGATCCTTTCTGAGTGGATAT
        K-Ho1 (1836)  CAGATTTCTGTGATCATTTGGAAATTGGAGAAGATGCTGTGTACTCAAGGAATCCATCAGATCCTTTCTGAGTGGATAT
  II-Cb1 (II) (1838)  CAGATTTTTGTGATCATCTGGAAATTGGGAGGATGCTGTTTATTCAAGGAATCCTTCGGATCCTTTCTGGAGTGGGTAT
        K-Ha1 (1839)  CAGATTTTTGTGATCATCTAGAAATTGGGAGGATGCTGTTTATTCAAGGAATCCTTCGGATCCTTTCTGGAGTGGGTAT
   Consensus  (5681)  CAGATTTCTGTGATCATTTGGAAATTGGAGAAGATGCTGTGTACTCAAGGAATCCATCAGATCCTTTCTGGAGTGGATAT
```

```
                                                                                                                    Section 91
              (7201) 7201      7210      7220      7230      7240      7250      7260      7270      7280
    IL-Cb1 (I) (3356) GATCCTGATAAATTTCAAATGTTTGATAACAGTGAAATCGGGTTGTATACAAATCCAACTTTGGAGGACATCCCACATTC
          K-G7 (3356) GATCCTGATAAATTTCAAATGTTTGATAACAGTGAAATTGGGTTGTATACAAATCCAACTTTGGAGGACATCCCACATTC
    pBPMV-R1A (7194) GATCCTGATAAATTTCAAATGTTTGATAACAGTGAAATCGGGTTGTATACAAATCCAACTTTGGAGGACATCCCACATTC
    pBPMV-R1B (7194) GATCCTGATAAATTTCAAATGTTTGATAACAGTGAAATCGGGTTGTATACAAATCCAACTTTGGAGGACATCCCACATTC
         K-Ho1 (3356) GATCCTGATAAATTTCAAATGTTTGATAACAGTGAAATCGGTTGTATACAAATCCAACTTTGGAGGACATCCCACATTC
    II-Cb1 (II) (3358) GATCCTGACAAGTTTCAGATGTTTGACAACAGTGAAATAGGCCTTTATTATAATCCCACTTTGGAAGATATCCCACATTC
         K-Ha1 (3359) GATCCTGACAAGTTTCAGATGTTTGACAACAGTGAAATAGGTCTTTATTCTAATCCCACTTTGGAAGATATCCCACATTC
    Consensus (7201) GATCCTGATAAATTTCAAATGTTTGATAACAGTGAAATCGGGTTGTATACAAATCCAACTTTGGAGGACATCCCACATTC
                                                                                                                    Section 92
              (7281) 7281      7290      7300      7310      7320      7330      7340      7350      7360
    IL-Cb1 (I) (3436) TGCTTGGGACCTTTTCTGCTGGGACAGTGAGAAAACTCTGCCAAATAATTTTTCTGCTGAATTGCTTTCCTGTAAATTGG
          K-G7 (3436) TGCTTGGGACCTTTTCTGCTGGGACAGTGAGAAAACTTTGCCAAACAATTTTTCTGCTGAATTGCTTTCCTGTAAATTGG
    pBPMV-R1A (7274) TGCTTGGGACCTTTTCTGCTGGGACAGTGAGAAAACTTTGCCAAACAATTTTTCTGCTGAACTGCTTTCCTGTAAATTGG
    pBPMV-R1B (7274) TGCTTGGGACCTTTTCTGCTGGGACAGTGAGAAAACTTTGCCAAACAATTTTTCTGCTGAACTGCTTTCCTGTAAATTGG
         K-Ho1 (3436) TGCTTGGGACCTTTTCTGCTGGGACAGTGAGAAAACTTTGCCAAATAATTTTTCTGCTGAATTGCTTTCCTGTAAATTGG
    II-Cb1 (II) (3438) AGCTTGGGACCTTTTTTGCTGGGACAGTGAGAAAACCTTGCCAAATAATTTTTCTGCAGAATTGCTCTCCTTGCAAATTGG
         K-Ha1 (3439) AGCTTGGGACCTTTTTTGCTGGGACAGTGAGAAAACTTTGCCAAATAATTTTTCTGCAGAATTGCTCTCTTGCAAATTGG
    Consensus (7281) TGCTTGGGACCTTTTCTGCTGGGACAGTGAGAAAACTTTGCCAAATAATTTTTCTGCTGAATTGCTTTCCTGTAAATTGG
                                                                                                                    Section 93
              (7361) 7361      7370      7380      7390      7400      7410      7420      7430      7440
    IL-Cb1 (I) (3516) ACACTGTTACGGGACAATATTA-CCCAGAATGGGCTCCAATAAATTGTCGAGTACATCGGCAACCAATTCACATAACTGA
          K-G7 (3516) ACACTGTTACGGGACAATATTATCCCAGAATGG-CTCCAATAAATTGTCGAGTACATCGGCAACCAATTCACATAACTGA
    pBPMV-R1A (7354) ACACCGTTACGGGACAATATTA-CCCAGAATGGGCTCCAATAAATTGTCGAGTACATCGGCAACCAATTCACATAACTGA
    pBPMV-R1B (7354) ACACCGTTACGGGACAATATTA-CCCAGAATGGGCTCCAATAAATTGTCGAGTACATCGGCAACCAATTCACATAACTGA
         K-Ho1 (3516) ACACTGTTACGGGACAGTATTA-CCCAGAATGGGCTCCAATAAATTGTCGAGTACATCGGCAACCAATTCACATAACTGA
    II-Cb1 (II) (3518) ATACTGTTACTGGCCAATATTA-TCCTGAGTGGGCTCCAATAAATTGTCGAGTTCATCGACAACCAATTCACATCACTGA
         K-Ha1 (3519) ATACTGTTACTGGCCAATACTA-TCCTGAGTGGGCTCCAATTAATTGTCGAGTTCATCGACAACCAATTCACATCACTGA
    Consensus (7361) ACACTGTTACGGGACAATATTA CCCAGAATGGGCTCCAATAAATTGTCGAGTACATCGGCAACCAATTCACATAACTGA
                                                                                                                    Section 94
              (7441) 7441      7450      7460      7470      7480      7490      7500      7510      7520
    IL-Cb1 (I) (3595) AGGGAATTATGTTAGGAAACAAGATGTAAGCATCGAATATGATGCCTGCACAATTCCTAATGATTGTGGATCTCTGGTGG
          K-G7 (3595) AGGGAATTATGTTAGGAAACAAGATGTAAGCATTGAATATGATGCCTGCACAATTCCCAATGATTGTGGATCTCTGGTGG
    pBPMV-R1A (7433) AGGGAATTATGTCAGGAAACAAGATGTGAGCATTGAATATGATGCCTGCACAATTCCTAATGATTGTGGATCTCTGGTGG
    pBPMV-R1B (7433) AGGGAATTATGTCAGGAAACAAGATGTGAGCATTGAATATGATGCCTGCACAATTCCTAATGATTGTGGATCTCTGGTGG
         K-Ho1 (3595) AGGGAATTATGTAGGAAACAAGATGTAAGCATCGAATATGATGCCTGCACAATTCCTAATGATTGTGGATCTCTGGTGG
    II-Cb1 (II) (3597) AGGAAATTATGTCAGAAACAAGATGTCAGCATTGAATATGATGCATGTACAATTCCAAATGATTGTGGTTCATTGGTTG
         K-Ha1 (3598) AGGAAATTATGTCAGAAAGCAAGATGTCAGTATTGAATATGATGCATGTACAATCCAAATGATTGTGGTTCATTGGTTG
    Consensus (7441) AGGGAATTATGTCAGGAAACAAGATGT AGCATTGAATATGATGCCTGCACAATTCCTAATGATTGTGGATCTCTGGTGG
                                                                                                                    Section 95
              (7521) 7521      7530      7540      7550      7560      7570      7580      7590      7600
    IL-Cb1 (I) (3675) TTGCTAAGGTCGGAAATCACAAGCAAGTTGTTGGTTTTCATGTTGCTGGAAGCAAAGGAAGATTGGGCTATGCTTCATTA
          K-G7 (3675) TTGCTAAGGTTGGAAATCACAAGCAAATTGTTGGTTTCCATGTTGCTGGAAGCAAAGGAAGATTGGGCTATGCTTCATTG
    pBPMV-R1A (7513) TTGCTAAGGTCGGAAATCACAAGCAAATTGTTGGTTTCCATGTTGCTGGAAGTAAAGGAAGATTGGGCTATGCTTCATTG
    pBPMV-R1B (7513) TTGCTAAGGTCGGAAATCACAAGCAAATTGTTGGTTTCCATGTTGCTGGAAGCAAAGGAAGATTGGGCTATGCTTCATTG
         K-Ho1 (3675) TTGCCAAGGTCGGAAATCACAAGCAAATTGTTGGTTTCATGTTGCTGGAAGCAAAGGAAGATTGGGCTATGCTTCATTA
    II-Cb1 (II) (3677) TTGCCAAGGTTGGAAATCACAAACAAATTGTTGGTTTCCATGTTGCTGGAAGTAAAGCAAGACTGGGATATGCTTCATTG
         K-Ha1 (3678) TTGCCAAGGTTGGAAATCACAAACAAATTGTTGGTTTCCATGTTGCTGGAAGCAAAGGAAGACTGGGATATGCTTCATTG
    Consensus (7521) TTGCTAAGGTCGGAAATCACAAGCAAATTGTTGGTTTCCATGTTGCTGGAAGCAAAGGAAGATTGGGCTATGCTTCATTG
                                                                                                                    Section 96
              (7601) 7601      7610      7620      7630      7640      7650      7660      7670      7680
    IL-Cb1 (I) (3755) ATACCATATGTTGAGCCTGTGGTACAAGCCCAAAGTGCTGAAGTCTATTTTGACTTTTTCCTGTGGAAGTTGATAGTCA
          K-G7 (3755) ATACCATATGTTGAGCCTGTGGTACAAGCCCAAAGTGCTGAAGTCTATTTGATTCTTTCCTGTGGAAGTTGATAGTCA
    pBPMV-R1A (7593) ATACCATATGTTGAGCCTGTGGTACAAGCCCAAAGTGCTGAAGTCTATTTTGATTTCTTTCCTGTGGAAGTTGATAGTCA
    pBPMV-R1B (7593) ATACCATATGTTGAGCCTGTGGTACAAGCCCAAAGTGCTGAAGTCTATTTTGATTCTTTCCTGTGGAAGTTGATAGTCA
         K-Ho1 (3755) ATACCATATGTTGAGCCTGTGGTACAAGCCCAAAGTGCTGAAGTCTATTTTGACTTCTTTCCTGTGGAAGTTGATAGTCA
    II-Cb1 (II) (3757) ATACCATATGTTGAGCCAGTTGTGCAAGCTCAAAGTGCTGAAGTTTACTTTGACTTCTTCCCTGTGGAGGTTGATAGTCA
         K-Ha1 (3758) ATACCATATGGTTGAGCCAGTCGTGCAAGCTCAAAGTGCTGAAGTTTACTTTGATTCTTCCCTGTGGAGGTTGATAGTCA
    Consensus (7601) ATACCATATGTTGAGCCTGTGGTACAAGCCCAAAGTGCTGAAGTCTATTTTGATTTCTTTCCTGTGGAAGTTGATAGTCA
```

*FIG. 10P*

```
                                                                                                                    Section 97
              (7681) 7681      7690      7700      7710      7720      7730      7740      7750      7760
    IL-Cb1 (I) (3835) AGAGGGAGTTGCTCATATTGGTGAACTCAAATCTGGAGTTTATGTACCACTGCCCACAAAAACTAATCTTGTGGAAACTC
         K-G7  (3835) AGAGGGAGTAGCTCATATTGGTGAACTCAAATCTGGAGTTTATGTACCACTGCCCACAAAAACTAATCTTGTGGAAACTC
    pBPMV-R1A (7673) AGAGGGAGTTGCTCATATTGGTGAACTCAAATCTGGAGTTTATGTACCATTGCCCACAAAAACTAATCTTGTGGAAACTC
    pBPMV-R1B (7673) AGAGGGAGTTGCTCATATTGGTGAACTCAAATCTGGAGTTTATGTACCATTGCCCACAAAAACTAATCTTGTGGAAACTC
         K-Ho1 (3835) AGAGGGAGTTGCTCATATTGGTGAACTCAAATCTGGAGTTTATGTACCATTGCCCACAAAAACTAATCTTGTGGAAACTC
    II-Cb1 (II) (3837) AGAAGGAGTTGCTCACATTGGTGAATTGAAATCTGGTGTCTATGTTCCACTGCCTACAAAAACCAATTTAGTGGAAACTC
         K-Ha1 (3838) AGAGGGAGTTGCTCACATTGGTGAATTGAAATCTGGTGTCTATGTTCCACTGCCTACAAAAACTAATTTGGTGGAAACTC
    Consensus (7681) AGAGGGAGTTGCTCATATTGGTGAACTCAAATCTGGAGTTTATGTACCACTGCCCACAAAAACTAATCTTGTGGAAACTC
                                                                                                                    Section 98
              (7761) 7761      7770      7780      7790      7800      7810      7820      7830      7840
    IL-Cb1 (I) (3915) CCAAAGAATGGCAGTTGGATTTGCCTTGTGATAAGATTCCAAGTGTGTTAACCACTACTGATGAGAGATTGGTTGGCACA
         K-G7  (3915) CCAAAGAATGGCAGTTGGATTTGCCTTGTGATAAGATTCCAAGTGTGTTAACCACTACTGATGAGAGATTGGTTGGCACA
    pBPMV-R1A (7753) CCAAAGAATGGCAGTTGGATTTGCCTTGTGATAAGATTCCAAGTGTGTTAACCACTACTGATGAGAGATTGGTTGGCACG
    pBPMV-R1B (7753) CCAAAGAATGGCAGTTGGATTTGCCTTGTGATAAGATTCCAAGTGTGTTAACCACTACTGATGAGAGATTGGTTGGCACA
         K-Ho1 (3915) CCAAAGAATGGCAGTTGGATTTGCCTTGTGATAAGATTCCAAGTGTGTTAACCACTACTGATGAGAGATTGGTTGGCACA
    II-Cb1 (II) (3917) CCAAAGAATGGCAACCGGATCTACCTTGTGACAAAATTCCTAGTGTCTTGACTACAACTGATGAGAGATTGGTAGGCACA
         K-Ha1 (3918) CCAAAGAATGGCAACTGGATCTACCTTGTGATAAAAATTCCTAGTGTCTTGACTACAACTGATGAGAGATTGGTGGGCACA
    Consensus (7761) CCAAAGAATGGCAGTTGGATTTGCCTTGTGATAAGATTCCAAGTGTGTTAACCACTACTGATGAGAGATTGGTTGGCACA
                                                                                                                    Section 99
              (7841) 7841      7850      7860      7870      7880      7890      7900      7910      7920
    IL-Cb1 (I) (3995) GAGCATGAAGGATATGACCCATTCTTGGTGGTATTCAAAAATATGCAACTCCCATGATGCCTCTTGATGAGGAGATTCT
         K-G7  (3995) GAGCATGAAG-ATATGCACCCATT-CTTGGTGGTATTCAAAA-TATGCAACTCCCATGATGCCTCTTGATGAGGAGATTCT
    pBPMV-R1A (7833) GAGCATGAAGGATATGACCCATTTCTTGGTGGTATTCAAAAATATGCAACTCCCATGATGCCTCTAGATGAGGAGATTCT
    pBPMV-R1B (7833) GAGCATGAAGGATATGACCCATTTCTTGGTGGTATTCAAAAATATGCAACTCCCATGATGCCTCTAGATGAGGAGATTCT
         K-Ho1 (3995) GAGCATGAAGGATATGACCCATTTCTTGGTGGTATTCAAAAATATGCAACTCCCATGATGCCTCTAGATGAGGAGATTCT
    II-Cb1 (II) (3997) GAACATGAGGGATATGATCCTTTTCTTGGTGGAATTCAAAAATATGCCACTCCCATGATGCCCCTAGATGAAGAAATTCT
         K-Ha1 (3998) GAACATGAGGGATATGATCCTTTTCTTGGTGGAATTCAAAAATATGCCACTCCCATGATGCCCCTAGATGAAGAAATTCT
    Consensus (7841) GAGCATGAAGGATATGACCCATTCTTGGTGGTATTCAAAAATATGCAACTCCCATGATGCCTCTAGATGAGGAGATTCT
                                                                                                                    Section 100
              (7921) 7921      7930      7940      7950      7960      7970      7980      7990      8000
    IL-Cb1 (I) (4075) TTCCAAAGTTGCACAAGACATGGTTGAAGAATGGTTTGATTGTGTTGATGAGGAGGATACATTTGAAGAAGTTTCTTTGA
         K-G7  (4072) TTCCAAAGTTGCACAAGACATGGTTGAAGAATGGTTTGATTGTGTTGATGAGGAGGATACATTTGAAGAAGTTTCTTTGA
    pBPMV-R1A (7913) TTCCAAAGTTGCACAAGACATGGTTGAAGAATGGTTTGATTGTGTTGATGAGGAGGATACATTTGAAGAAGTTTCTTTGA
    pBPMV-R1B (7913) TTCCAAAGTTGCACAAGACATGGTTGAAGAATGGTTTGATTGTGTTGATGAGGAGGATACATTTGAAGAAGTTTCTTTGA
         K-Ho1 (4075) TTCCAAAGTTGCACAAGACATGGTTGAAGAATGGTTTGATTGTGTTGATGAGGAGGATACATTTGAAGAAGTTTCTTTGA
    II-Cb1 (II) (4077) TTCTAAGGTTGCACAAGATATGGTTGAGGAATGGTTTGATTGTGTTGATGAGGAGGATTCCTTTGAGGAAGTTTCTTTAA
         K-Ha1 (4078) TTCTAAGGTTGCACAAGATATGGTTGAGGAATGGTTTGATTGTGTTGATGAGGAGGATTCCTTTGAGGAAGTTTCTTTAA
    Consensus (7921) TTCCAAAGTTGCACAAGACATGGTTGAAGAATGGTTTGATTGTGTTGATGAGGAGGATACATTTGAAGAAGTTTCTTTGA
                                                                                                                    Section 101
              (8001) 8001      8010      8020      8030      8040      8050      8060      8070      8080
    IL-Cb1 (I) (4155) GTGCTGCACTCAATGGTGTTGAAGGTTTGGATTACATGGAACGCATTCCTCTTGCCACTTCAGAGGGTTTTCCTCATGTT
         K-G7  (4152) GTGCTGCACTCAATGGTGTTGAAGGTTTGGATTACATGGAACGCATTCCTCTTGCCACTTCAGAGGGTTTTCCTCATGTT
    pBPMV-R1A (7993) GTGCTGCACTCAATGGTGTTGAAGGTTTGGATTACATGGAACGCATTCCTCTTGCCACTTCAGAGGGTTTTCCTCATGTT
    pBPMV-R1B (7993) GTGCTGCACTCAATGGTGTTGAAGGTTTGGATTACATGGAACGCATTCCTCTTGCCACTTCAGAGGGTTTTCCTCATGTT
         K-Ho1 (4155) GTGCTGCACTCAATGGTGTTGAAGGTTTGGATTACATGGAACGCATTCCTCTTGCCACTTCAGAGGGTTTTCCTCATGTT
    II-Cb1 (II) (4157) GTGCAGCACTCAATGGTGTTGAGGTTTGGACTATATGGAAAGAATTCCTCTTGCCACATCTGAGGGTTTTCCTCATGTG
         K-Ha1 (4158) GTGCAGCACTCAATGGTGTTGAGGGTTTGGACTATATGGAAAGAATTCCTCTTGCCACATCTGAGGGTTTTCCTCATGTG
    Consensus (8001) GTGCTGCACTCAATGGTGTTGAAGGTTTGGATTACATGGAACGCATTCCTCTTGCCACTTCAGAGGGTTTTCCTCATGTT
                                                                                                                    Section 102
              (8081) 8081      8090      8100      8110      8120      8130      8140      8150      8160
    IL-Cb1 (I) (4235) CTGTCCAGGAAAATGGTGAAAAAGGCAAGAGAAGATTTGTCACTGGAGATGGTGAAGAAATGTCACTAATTCCTGGTAC
         K-G7  (4232) CTGTCCAGGAAAATGGTGAAAAAGGCAAGAGAAGATTTGTCACTGGAGATGGTGAAGAAATGTCACTAATTCCTGGTAC
    pBPMV-R1A (8073) CTGTCCAGGAAAATGGTGAAAAAGGCAAGAGAAGATTTGTCACTGGAGATGGTGAAGAAATGTCACTAATTCCTGGTAC
    pBPMV-R1B (8073) CTGTCCAGGAAAATGGTGAAAAAGGCAAGAGAAGATTTGTCACTGGAGATGGTGAAGAAATGTCACTAATTCCTGGTAC
         K-Ho1 (4235) CTGTCCAGGAAAATGGTGAAAAAGGCAAGAGAAGATTTGTCACTGGAGATGGTGAAGAAATGTCACTAATTCCTGGTAC
    II-Cb1 (II) (4237) CTTTCACGCAAAAATGGCGAAAAAGGCAAAAGAGAGATTTGTCTCGGGGATGGTGAAGAGATGACATTGATTCCGGGAAC
         K-Ha1 (4238) CTTTCACGCAAAAATGGTGAAAAAGGCAAAGGAGATTTGTTTCTGGGGATGGTGAAGAGATGACATTGATTCCGGGAAC
    Consensus (8081) CTGTCCAGGAAAATGGTGAAAAAGGCAAGAGAAGATTTGTCACTGGAGATGGTGAAGAAATGTCACTAATTCCTGGTAC
```

*FIG. 10Q*

```
                                                                                               Section 103
            (8161) 8161      8170      8180      8190      8200      8210      8220      8230      8240
IL-Cb1 (I)  (4315) CAGTGTTGAAGAAGCATACAATAAATTGACTGTTGAACTAGAAAAGTGTGTTCCAACATTGGTTGGCATAGAATGTCCCA
      K-G7  (4312) CAGTGTTGAAGAAGCGTACAATAAATTGACTGTTGAATTAGAAAAGTGTGTTCCAACATTGGTTGGTATAGAATGTCCTA
 pBPMV-R1A  (8153) CAGTGTTGAAGAAGCATACAATAAATTGACTGTTGAACTAGAAAAGTGTGTTCCAACATTGGTTGGCATAGAATGTCCCA
 pBPMV-R1B  (8153) CAGTGTTGAAGAAGCATACAATAAATTGACTGTTGAACTAGAAAAGTGTGTTCCAACATTGGTTGGCATAGAATGTCCCA
     K-Ho1  (4315) CAGTGTTGAAGAAGCATACAATAAATTGACTGTTGAACTAGAAAAGTGTGTTCCAACATTGGTTGGCATAGAATGTCCCA
 II-Cb1 (II)(4317) CAGTGTTGAAGAAGCTTACAACAAGCTAATAGTTGAACTTGAAAAAAGTGTTCCTACATTGGTTGGCATTGAATGTCCCA
     K-Ha1  (4318) CAGTGTTGAACAGGCTTACAACAAGCTAATAGTTGAACTTGAAAAAAGTGTTCCTACATTAGTTGGCATTGAATGTCCCA
 Consensus  (8161) CAGTGTTGAAGAAGCATACAATAAATTGACTGTTGAACTAGAAAAGTGTGTTCCAACATTGGTTGGCATAGAATGTCCCA
                                                                                               Section 104
            (8241) 8241      8250      8260      8270      8280      8290      8300      8310      8320
IL-Cb1 (I)  (4395) AAGATGAAAAACTTCCCCGTCGCAAAATTTTTGATAAACCCAAGACGCGCTGCTTCACCATACTTTCTATGGAATTTAAT
      K-G7  (4392) AAGATGAAAAACTTCCCTCGTCGCAAAATTTTTGATAAACCCAAGACGCGCTGCTTCACCATACTTCCTATGGAATTTAAT
 pBPMV-R1A  (8233) AAGATGAAAAACTTCCCCGTCGCAAAATTTTTGATAAACCCAAGACGCGCTGCTTCACCATACTTCCTATGGAATTTAAT
 pBPMV-R1B  (8233) AAGATGAAAAACTTCCCCGTCGCAAAATTTTTGATAAACCCAAGACGCGCTGCTTCACCATACTTCCTATGGAATTTAAT
     K-Ho1  (4395) AGGATGAAAAACTTCCCCGTCGCAAAATTTTTGATAAACCCAAGACGCGCTGCTTCACCATACTTCCTATGGAATTTAAT
 II-Cb1 (II)(4397) AGGATGAGAAACTTCCTCGTCGCAAAATTTTTGACAAACCTAAGACGCGCTGCTTCACTATTCTCCCTATGGAGTTTAAT
     K-Ha1  (4398) AGGATGAGAAACTTCCTCGTCGCAAAATTTTTGACAAACCTAAGACGCGCTGCTTCACTATTCTCCCTATGGAGTTTAAT
 Consensus  (8241) AAGATGAAAAACTTCCCCGTCGCAAAATTTTTGATAAACCCAAGACGCGCTGCTTCACCATACTTCCTATGGAATTTAAT
                                                                                               Section 105
            (8321) 8321      8330      8340      8350      8360      8370      8380      8390      8400
IL-Cb1 (I)  (4475) CTAGTGGTGCGTCAAAAATTCTTGAATTTTGTGCGATTCATTATGAAGAAAGGGACAAATTGAGTGCCAAGTTGGAAT
      K-G7  (4472) TTAGTGGTGCGTCAAAAGTTCTTGAATTTTGTGCGATTCATTATGAAGAAAGGGACAAATTGAGTTGCCAAGTTGGAAT
 pBPMV-R1A  (8313) CTGGTGGTGCGTCAAAAATTCTTGAATTTTGTGCGATTCATTATGAAGAAAGGGACAAATTGAGTTGCCAAGTTGGAAT
 pBPMV-R1B  (8313) CTGGTGGTGCGTCAAAAATTCTTGAATTTTGTGCGATTCATTATGAAGAAAGGGACAAATTGAGTGCCAAGTTGGAAT
     K-Ho1  (4475) CTAGTGGTGCGTCAAAAATTCTTGAATTTTGTGCGATTCATTATGAAGAAAGGGACAAATTGAGTTGCCAAGTTGGAAT
 II-Cb1 (II)(4477) CTTGTGGTTCGTCAGAAGTTTTTAAATTTTGTGAGGTTCATTATGAAGAAAGGGACAAGCTTAGTTGTCAAGTTGGAAT
     K-Ha1  (4478) CTTGTGGTTCGTCAAAAGTTTTTAAATTTTGTGAGGTTCATTATGAAGAAAGGGACAAGCTTAGTTGTCAAGTCGGAAT
 Consensus  (8321) CT GTGGTGCGTCAAAAATTCTTGAATTTTGTGCGATTCATTATGAAGAAAGGGACAAATTGAGTTGCCAAGTTGGAAT
                                                                                               Section 106
            (8401) 8401      8410      8420      8430      8440      8450      8460      8470      8480
IL-Cb1 (I)  (4555) CAATCCATATTCTATGGAGTGGACTGGTTTGGCAAATAGACTGTTGAGCAAGGGAAATGACATTTTGTGTTGTGACTATG
      K-G7  (4552) CAATCCATATTCTATGGAGTGGACTGGTTTGGCAAATAGACTGTTGTGAGCAAGGGAAATGACATTTTGTGTTGTGACTATG
 pBPMV-R1A  (8393) CAATCCATATTCTATGGAGTGGACTGGTTTGGCAAATAGACTGTTGAGCAAGGGAAATGACATTTTGTGTTGTGACTATG
 pBPMV-R1B  (8393) CAATCCATATTCTATGGAGTGGACTGGTTTGGCAAATAGACTGTTGAGCAAGGGAAATGACATTTTGTGTTGTGACTATG
     K-Ho1  (4555) CAATCCATATTCTATGGAGTGGACTGGTTTGGCAAATAGACTGTTGAGCAAGGGAAATGACATTTTGTGTTGTGACTATG
 II-Cb1 (II)(4557) CAACCCATACTCCATGGAATGGACTGGTTTGGCCAATAGATTATTGAGTAAGGGCAACGATATTCTGTGTTGCGATTATG
     K-Ha1  (4558) CAACCCATACCCATGGAATGGACTGGTTTGGCCAATAGATTATTGAGTAAGGGCAACGATATTCTGTGTTGCGATTATG
 Consensus  (8401) CAATCCATATTCTATGGAGTGGACTGGTTTGGCAAATAGACTGTTGAGCAAGGGAAATGACATTTTGTGTTGTGATTATG
                                                                                               Section 107
            (8481) 8481      8490      8500      8510      8520      8530      8540      8550      8560
IL-Cb1 (I)  (4635) CTAGTTTTGATGGTCTGATAACTAAGCAAGTTATGAGCAAGATGGCAGAAATGATAAACAGTCTTTGTGGTGGAGATGAG
      K-G7  (4632) CTAGTTTTAGTGGTCTGATAACTAAGCAAGTTATGAGCAAGATGGCAGAAATGATAAACAGTCTTTGTGGTGGAGATGAG
 pBPMV-R1A  (8473) CTAGTTTTGATGGTCTGATAACTAAGCAAGTTATGAGCAAGATGGCAGAAATGATAAACAGTCTTTGTGGTGGAGATGAG
 pBPMV-R1B  (8473) CTAGTTTTGATGGTCTGATAACTAAGCAAGTTATGAGCAAGATGGCAGAAATGATAAACAGTCTTTGTGGTGGAGATGAG
     K-Ho1  (4635) CTAGTTTTGATGGTCTGATAACTAAGCAAGTCATGAGCAAGATGGCAGAAATGATAAACAGTCTTTGTGGTGGTGATGAA
 II-Cb1 (II)(4637) CTAGTTTTGATGGTTTGATTACCAAGCAAGTTATGAGCAAGATGGCAGAAATGATAAACAGTCTTTGTGGTGGTGATGAA
     K-Ha1  (4638) CTAGTTTTGATGGTTTGATTACCAAGCAAGTTATGAGCAAGATGGCAGAAATGATAAACAGTCTTTGTGGTGGTGATGAA
 Consensus  (8481) CTAGTTTTGATGGTCTGATAACTAAGCAAGTCATGAGCAAGATGGCAGAAATGATAAACAGTCTTTGTGGTGGAGATGAG
                                                                                               Section 108
            (8561) 8561      8570      8580      8590      8600      8610      8620      8630      8640
IL-Cb1 (I)  (4715) AAACTGATGCGTGAGAGAACACATCTTCTGTTAGCTTGTTGCTCCAGGATGGCAATCTGTAAAAAAATGTTTGGAGAGT
      K-G7  (4712) AAACTGATGCGTGAGAGAACACATCTTCTGTTAGCTTGTTGCTCCAGGATGGCAATCTGTAAAAAAGATATTTGGAGAGT
 pBPMV-R1A  (8553) AAACTGATGCGTGAGAGAACGCATCTTCTGTTAGCTTGTTGCTCCAGGATGGCAATCTGTAAAAAAGATGTTTGGAGAGT
 pBPMV-R1B  (8553) AAACTGATGCGTGAGAGAACACATCTTCTGTTAGCTTGTTGCTCCAGGATGGCAATCTGTAAAAAAGATGTTTGGAGAGT
     K-Ho1  (4715) AAACTGATGCGTGAGAGAACACATCTTCTGTTAGCTTGTTGCTCCAGGATGGCAATCTGTAAAAAAGATGTTTGGAGAGT
 II-Cb1 (II)(4717) AAATTGATGCGTGAAAGGACACACCTGCTGTTGGCTTGTTGTTCAAGGATGGCAATTTGTAAGAAAGATGTTTGGAGAGT
     K-Ha1  (4718) AAATTGATGCGTGAAAGGACACACCTACTGTTGGCTTGTTGTTCAAGGATGGCAATTTGTAAGAAAGATGTTTGGAGGGT
 Consensus  (8561) AAACTGATGCGTGAGAGAACACATCTTCTGTTAGCTTGTTGCTCCAGGATGGCAATCTGTAAAAAAGATGTTTGGAGAGT
```

```
                                                                                                                    Section 115
              (9121) 9121      9130      9140      9150      9160      9170      9180      9190      9200
    IL-Cb1 (I) (5275) CAGTCCAGAAGAAGCTCGTCAGTTGAGAAGAAAGGCTCTCTCTCGTATTGAGTGGTTGCAAAAAGCTGATGTGCCCACCA
          K-G7 (5272) TAGTCCAGAAGAAGCTCGTCGATTGAGAAGAAAGGCTCTCTCTTGTATTGAGTGGTTGCAAAAAGCTGATGTGCCCACCA
    pBPMV-R1A (9113) CAGTCCAGAAGAAGCTCGTCAATTGAGAAGAAAGGCTCTCTCTCGCATTGAGTGGTTGCAAAAAGCTGATGTGCCCACCA
    pBPMV-R1B (9113) CAGTCCAGAAGAAGCTCGTCAATTGAGAAGAAAGGCTCTCTCTCGTATTGAGTGGTTGCAAAAAGCTGATGTGCCCACCA
         K-Ho1 (5275) CAGTCCAGAAGAAGCTTGTCAGTTGAGAAGAAGGGCTCTCTCTCGTATTGAGTGGTTGCAAAAAGCTGATGTGCCCACCA
    II-Cb1 (II) (5277) CAGTCCAGAGGAAGCTCGCCAATTGAGAAGGAAAGCTCTCTCTCGTATTGAATGGCTGCAAAAAGCTGATGTGCCTACCA
         K-Ha1 (5278) CAGTCCAGAGGAAGCTCGCCAATTGAGAAGGAAAGCTCTCTCTCGATCGAATGGCTGCAAAAAGCTGATGTGCCTACCA
     Consensus (9121) CAGTCCAGAAGAAGCTCGTCAATTGAGAAGAAAGGCTCTCTCTCGTATTGAGTGGTTGCAAAAAGCTGATGTGCCCACCA
                                                                                                                    Section 116
              (9201) 9201      9210      9220      9230      9240      9250      9260      9270      9280
    IL-Cb1 (I) (5355) TAGCACAAATTGAAGAATTTCATTCAATGCAGAGGATTATGAATGCTCCTGATTCAAATGATAATATTGATCTCTTGTTG
          K-G7 (5352) TAGCACAAATTGAAGAATTTCATTCAATGCAGAGGATTATGAATGCTCCTGATTCAAATGATAATATTGATCTTTTGTTG
    pBPMV-R1A (9193) TAGCACAAATTGAAGAATTTCATTCAATGCAGAGGATTATGAATGCTCCTGACTCAAATGATAATATTGATCTTTTGTTG
    pBPMV-R1B (9193) TAGCACAAATTGAAGAATTTCATTCAATGCAGAGGATTATGAATGCTCCTGATTCAAATGATAATATTGATCTTTTGTTG
         K-Ho1 (5355) TAGCACAAATTGAAGAATTTCATTCAATGCAGAGGATTATGAATGCTCCTGATTCAAATGATAATATTGATCTTTTGTTG
    II-Cb1 (II) (5357) TAGCACAGATTGAAGAGTTTCATTCGATGCAGAGGATGATGAATGCTCCTGATTCAAATGATAATATTGATCTACTGTTG
         K-Ha1 (5358) TAGCACAGATTGAAGAGTTCCATTCGATGCAGAGGATGATGAATGCTCCTGATTCAAATGATAATATTGACCTACTGTTG
     Consensus (9201) TAGCACAAATTGAAGAATTTCATTCAATGCAGAGGATTATGAATGCTCCTGATTCAAATGATAATATTGATCTTTTGTTG
                                                                                                                    Section 117
              (9281) 9281      9290      9300      9310      9320      9330      9340      9350      9360
    IL-Cb1 (I) (5435) AGCATCGACTTGTTGGGTCTTCAGGGTGCAGGCAAGGCCTTCCCAAATAAGATTGTG-TTTGATGATAAATTGGTATTGG
          K-G7 (5432) AGCATTGACTTGTTGGGTCTTCAGGGTGCAG-CAAGGCCTTCCCAAATAAGATTGTGGTTTGATGATAAATTGGTATTGG
    pBPMV-R1A (9273) AGCATTGACTTGTTGGGTCTTCAGGGTGCAGGCAAGGCCTTCCCAAATAAGATTGTG-TTTGATGATAAATTGGTATTGG
    pBPMV-R1B (9273) AGCATTGACTTGTTGGGTCTTCAGGGTGCAGGCAAGGCCTTCCCAAATAAGATTGTG-TTTGATGATAAATTGGTATTGG
         K-Ho1 (5435) AGCATCGACTTGTTGGGTCTTCAGGGTGCAGGCAAGGCCTTCCCAAATAAGATTGTG-TTTGATGATAAATTGGTATTGG
    II-Cb1 (II) (5437) AGCATTGATTTGTTGGGTTTACAAGGAGCAGGTAAAGCTTTTCCAAACAAGATTGTT-TTTGATGATAAGCTTGTGTTGG
         K-Ha1 (5438) AGCATTGATTTGTTGGGTTTACAAGGAGCAGGTAAAGCTTTTCCAAACAAGATTGTT-TTTGATGATAAGCTTGTGTTGG
     Consensus (9281) AGCATTGACTTGTTGGGTCTTCAGGGTGCAGGCAAGGCCTTCCCAAATAAGATTGTG TTTGATGATAAATTGGTATTGG
                                                                                                                    Section 118
              (9361) 9361      9370      9380      9390      9400      9410      9420      9430      9440
    IL-Cb1 (I) (5514) CAAATACACAAGAATTTTTTGATGGAAATTTTCCAACAGATTCTTGGTTACCAATATTTGTTAATTGTCTTTACCCTGTG
          K-G7 (5511) CAAATACACAAGAATTTTTTGATGGAAATTTTCCAGCAGATTCTTGGTTACCAATATTTGTTAATTGTCTTTACCCTGTG
    pBPMV-R1A (9352) CAAATACACAAGAATTTTTTGATGGAAATTTTCCAACAGATTCTTGGTTACCAATATTTGTCAATTGTCTTTACCCTGTG
    pBPMV-R1B (9352) CAAATACACAAGAATTTTTTGATGGAAATTTTCCAACAGATTCTTGGTTACCAATATTGTCAATTGTCTTTACCCTGTG
         K-Ho1 (5514) CAAATACACAAGAATTTTTTGATGGAAATTTTCCAACAGATTCTTGGTTACCAATATTTGTCAATTGTCTTTACCCTGTG
    II-Cb1 (II) (5516) CTAACACACAAGAATTCTTTGATGGAAATTTTCCAGTAGATTCTTGGTTACCAATTTTTGTGAATTGTCTTTATCCTGTA
         K-Ha1 (5517) CTAACACACAAGAATTCTTTGATGGAAATTTTCCAGTGGATTCTTGGTTACCAATTTTTGTGAATTGTCTTTATCCTGTA
     Consensus (9361) CAAATACACAAGAATTTTTTGATGGAAATTTTCCAACAGATTCTTGGTTACCAATATTTGT AATTGTCTTTACCCTGTG
                                                                                                                    Section 119
              (9441) 9441      9450      9460      9470      9480      9490      9500      9510      9520
    IL-Cb1 (I) (5594) AGTCAATTGCCCGCAGAAGCTGTCATTGTTAATGTTGTTGTGGGAGTGGGCGTGGTGGTTGCCTACTACTGCTTGGAT
          K-G7 (5591) AGTCAATTGCCCGCAGAAGCTGTCATTGTTAATGTTGTTGTGGGAGTGGGCGTGGTGGTTTGCCTACTACTGCTTGGAT
    pBPMV-R1A (9432) AGTCAATTGCCCGCAGAGGCTGTCACTGTTAATGTTGTTTGTGGGAGTGGGCGTGGTGGTTTGCCTACTACTGCTTGGAT
    pBPMV-R1B (9432) AGTCAATTGCCCGCAGAAGCTGTCACTGTTAATGTTGTTTGTGGGAGTGGGCGTGGTGGTTTGCCTACTACTGCTTGGAT
         K-Ho1 (5594) AGTCAATTGCCCGCAGAAGCTGTCATTGTTAATGTTGTCTGTGGGAGTGGGCGGTGGTTTACCTACTACTGCTTGGAT
    II-Cb1 (II) (5596) AGTCAATTACCCTCAGAAGCTGTCGTTGTTAACATTGGTAGTGGACGTGGTGGTTTACCCACCACTGCTTGGAT
         K-Ha1 (5597) AGTCAATTACCCTTCAGAAGCTGTTGTTGTAAATGTCACATGTGGACTGGTGGTTTACCCACCACTGCTTGGAT
     Consensus (9441) AGTCAATTGCCCGCAGAAGCTGTCATTGTTAATGTTGTTTGTGGGAGTGGGCGTGGTGGTTTGCCTACTACTGCTTGGAT
                                                                                                                    Section 120
              (9521) 9521      9530      9540      9550      9560      9570      9580      9590      9600
    IL-Cb1 (I) (5674) TAGTTCTGCAGTTAACAATCGCTCCTCAGATATCAATAAGAAAATTCGGACAGCGCTTGGAAAAGGTAAGAAAATTGTCT
          K-G7 (5671) TAGTTCTGCAGTTAACAATCGCTCCTCAGATATCAATAAGAAAATTCGGACAGCGCTTGGAAAAGGTAAGAAAATTGTCT
    pBPMV-R1A (9512) TAGTTCTGCAGTTAACAATCGCTCCTCAGATATCAATAAGAAAATTCGGACAGCACTTGGAAAAGGTAAGAAAATTGTCT
    pBPMV-R1B (9512) TAGTTCTGCAGTTAACAATCGCTCCTCAGATATCAATAAGAAAATTCGGACAGCACTTGGAAAAGGTAAGAAAATTGTCT
         K-Ho1 (5674) TAGTTCTGCAGTTAACAATCGCTCCTCAGATATCAACAAGAAAATTCGGACAGCGCTTGGAAAAGGTAAGAAAATTGTCT
    II-Cb1 (II) (5676) TAGCAGCAGTTAACAATCGCTCCTCAGATATCAACAAAAAGATTCGCACAGCACTTGGGAAAGGTAAGAAAATTGTTT
         K-Ha1 (5677) TAGTTCTGCAGTTAACAATCGCTCCTCAGATATCAACAAAAAGATTCGCACAGCACTTGGGAAAGGTAAGAAAATTGTTT
     Consensus (9521) TAGTTCTGCAGTTAACAATCGCTCCTCAGATATCAATAAGAAAATTCGGACAGCACTTGGGAAAGGTAAGAAAATTGTCT
```

```
                                                                                                    Section 127
              (10081) 10081     ,10090     ,10100     ,10110     ,10120     ,10130     ,10140     ,10150  10160
   IL-Cb1 (I)  (5999) ------------------------------------------------------------------------------------------
       K-G7   (5996) ------------------------------------------------------------------------------------------
 pBPMV-R1A (10072) TTTAATACGCGATAGAAAACAAAATATAGCGCGCAAACTAGGATAAATTATCGCGCGCGGTGTCATCTATGTTACTAGAT
 pBPMV-R1B (10072) TTTAATACGCGATAGAAAACAAAATATAGCGCGCAAACTAGGATAAATTATCGCGCGCGGTGTCATCTATGTTACTAGAT
       K-Ho1  (5999) ------------------------------------------------------------------------------------------
   II-Cb1 (II) (6006) ------------------------------------------------------------------------------------------
       K-Ha1  (6007) ------------------------------------------------------------------------------------------
Consensus (10081)
                                                                                                    Section 128
              (10161) 10161         10178
   IL-Cb1 (I)  (5999) ------------------
       K-G7   (5996) ------------------
 pBPMV-R1A (10152) CGGGAATTCCAATTCGCC
 pBPMV-R1B (10152) CGGGAATTCCAATTCGCC
       K-Ho1  (5999) ------------------
   II-Cb1 (II) (6006) ------------------
       K-Ha1  (6007) ------------------
Consensus (10161)
```

*FIG. 10V*

SEQUENCE LISTING

<160> NUMBER OF SEQ ID NOS: 8

<210> SEQ ID NO 1
<211> LENGTH: 10169
<212> TYPE: DNA
<213> ORGANISM: Bean Pod Mottle Virus

<400> SEQUENCE: 1

| | | | | | |
|---|---|---|---|---|---|
| tatagtgagt | cgtattacaa | ttcactggcc | gtcgttttac | aacgtcgtga | ctgggaaaac | 60 |
| cctggcgtta | cccaacttaa | tcgccttgca | gcacatcccc | ctttcgccag | ctggcgtaat | 120 |
| agcgaagagg | cccgcaccga | tcgcccttcc | caacagttgc | gcagcctgaa | tggcgaatgg | 180 |
| acgcgccctg | tagcggcgca | ttaagcgcgg | cgggtgtggt | ggttacgcgc | agcgtgaccg | 240 |
| ctacacttgc | cagcgcccta | gcgcccgctc | ctttcgcttt | cttcccttcc | tttctcgcca | 300 |
| cgttcgccgg | ctttccccgt | caagctctaa | atcggggggct | cccttttaggg | ttccgattta | 360 |
| gtgctttacg | gcacctcgac | cccaaaaaac | ttgattaggg | tgatggttca | cgtagtgggc | 420 |
| catcgccctg | atagacggtt | tttcgccctt | tgacgttgga | gtccacgttc | tttaatagtg | 480 |

```
gactcttgtt ccaaactgga acaacactca accctatctc ggtctattct tttgatttat    540
aagggatttt gccgatttcg gcctattggt taaaaaatga gctgatttaa caaaaattta    600
acgcgaattt taacaaaata ttaacgctta caatttcctg atgcggtatt ttctccttac    660
gcatctgtgc ggtatttcac accgcatatg gtgcactctc agtacaatct gctctgatgc    720
cgcatagtta agccagcccc gacacccgcc aacacccgct gacgcgccct gacgggcttg    780
tctgctcccg gcatccgctt acagacaagc tgtgaccgtc tccgggagct gcatgtgtca    840
gaggttttca ccgtcatcac cgaaacgcgc gagacgaaag gcctcgtga tacgcctatt     900 tttataggtt aatgtcatga taataatggt ttcttagacg tcaggtggca cttttcgggg    960
aaatgtgcgc ggaacccct a tttgtttatt tttctaaata cattcaaata tgtatccgct   1020
catgagacaa taaccctgat aaatgcttca ataatattga aaaggaaga gtatgagtat    1080 tcaacatttc cgtgtcgccc ttattcccctt ttttgcggca ttttgccttc ctgttttttgc  1140 tcacccagaa acgctggtga agtaaaaga tgctgaagat cagttgggtg cacgagtggg    1200
ttacatcgaa ctggatctca acagcggtaa gatccttgag agttttcgcc ccgaagaacg   1260
ttttccaatg atgagcactt ttaaagttct gctatgtggc gcggtattat cccgtattga   1320
cgccgggcaa gagcaactcg gtcgccgcat acactattct cagaatgact tggttgagta   1380
ctcaccagtc acagaaaagc atcttacgga tggcatgaca gtaagagaat tatgcagtgc   1440
tgccataacc atgagtgata acactgcggc caacttactt ctgacaacga tcggaggacc   1500
gaaggagcta accgcttttt tgcacaacat ggggaatcat gtaactcgcc ttgatcgttg   1560
ggaaccggag ctgaatgaag ccataccaaa cgacgagcgt gacaccacga tgcctgtagc   1620
aatggcaaca acgttgcgca aactattaac tggcgaacta cttactctag cttcccggca   1680
acaattaata gactggatgg aggcggataa agttgcagga ccacttctgc gctcggccct   1740
tccggctggc tggtttattg ctgataaatc tggagccggt gagcgtgggt ctcgcggtat   1800
cattgcagca ctggggccag atggtaagcc ctcccgtatc gtagttatct acacgacggg   1860
gagtcaggca actatggatg aacgaaatag acagatcgct gagataggtg cctcactgat   1920
taagcattgg taactgtcag accaagttta ctcatatata ctttagattg atttaaaact   1980 tcattttttaa tttaaaagga tctaggtgaa gatcctttt gataatctca tgaccaaaat   2040
cccttaacgt gagttttcgt tccactgagc gtcagacccc gtagaaaaga tcaaaggatc   2100
ttcttgagat cctttttttc tgcgcgtaat ctgctgcttg caaacaaaaa aaccaccgct   2160
accagcggtg gtttgtttgc cggatcaaga gctaccaact ctttttccga aggtaactgg   2220
cttcagcaga gcgcagatac caaatactgt tcttctagtg tagccgtagt taggccacca   2280
cttcaagaac tctgtagcac cgcctacata cctcgctctg ctaatcctgt taccagtggc   2340
tgctgccagt ggcgataagt cgtgtcttac cgggttggac tcaagacgat agttaccgga   2400
taaggcgcag cggtcgggct gaacggggg ttcgtgcaca cagcccagct tggagcgaac   2460
gacctacacc gaactgagat acctacagcg tgagctatga gaaagcgcca cgcttcccga   2520
agggagaaag gcggacaggt atccggtaag cggcagggtc ggaacaggag agcgcacgag   2580
ggagcttcca gggggaaacg cctggtatct ttatagtcct gtcgggtttc gccacctctg   2640
acttgagcgt cgatttttgt gatgctcgtc agggggggcgg agcctatgga aaaacgccag   2700
caacgcggcc ttttttacggt tcctggcctt ttgctggcct tttgctcaca tgttctttcc   2760
tgcgttatcc cctgattctg tggataaccg tattaccgcc tttgagtgag ctgataccgc   2820
tcgccgcagc cgaacgaccg agcgcagcga gtcagtgagc gaggaagcgg aagagcgccc   2880
```

```
aatacgcaaa ccgcctctcc ccgcgcgttg gccgattcat taatgcagct ggcacgacag   2940
gtttcccgac tggaaagcgg gcagtgagcg caacgcaatt aatgtgagtt agctcactca   3000
ttaggcaccc caggctttac actttatgct tccggctcgt atgttgtgtg gaattgtgag   3060
cggataacaa tttcacacag gaaacagcta tgaccatgat tacgccaagc tatttaggtg   3120
acactataga atactcaagc ggccgcctac tccaagaata tcaaagatac agtctcagaa   3180
gaccaaaggg ctattgagac ttttcaacaa agggtaatat cgggaaacct cctcggattc   3240
cattgcccag ctatctgtca cttcatcaaa aggacagtag aaaaggaagg tggcacctac   3300
aaatgccatc attgcgataa aggaaaggct atcgttcaag atgcctctgc cgacagtggt   3360
cccaaagatg acccccacc cacgaggagc atcgtggaaa aagaagacgt tccaaccacg   3420
tcttcaaagc aagtggattg atgtgatcta ctccaagaat atcaaagata cagtctcaga   3480
agaccaaagg ctattgaga cttttcaaca aagggtaata tcgggaaacc tcctcggatt   3540
ccattgccca gctatctgtc acttcatcaa aggacagta gaaaaggaag gtggcaccta   3600
caaatgccat cattgcgata aaggaaaggc tatcgttcaa gatgcctctg ccgacagtgg   3660
tcccaaagat ggaccccac ccacgaggag catcgtggaa aagaagacg ttccaaccac   3720 gtcttcaaag caagtggatt gatgtgatat ctccactgac gtaagggatg acgcacaatc   3780
ccactatcct tcgcaagacc cttcctctat ataaggaagt tcatttcatt tggagagta   3840 ttaaaatttt cataagattt gaaattttga taaaccgcga tcataggttg ccgcaccta   3900 aaaccggaaa caaagcaat cgttacttga tttcaaagac ttctcaattt ctttctacat   3960
ttcttgtata cggctttcaa agtgaaagaa aatcactctc tgtgctggtc acagacttcg   4020
tgaatcattt tcttctgct ctcagttcat ttgctgaaca ctctcctatt tgatataaga   4080
cttcgtgtca gatttgaact tctcctatct cttttctcg gttcttcatt tgatttcaaa   4140
cttttctgaa atttaaatct cttttgacat tttgaacttt gtgttggctc catttgaaaa   4200
acaacatgaa gttctatcct ggtcaaaata tttccgaaat tgtttaccac tttcagagta   4260
atgagacagc caataggtta gatgcatatt ttgcttgtgg ctgtgaggag gatactgaag   4320
tcctcgctcg tttgaagcag tgtaatcctc gtctgcttca tctgtcatat gctgccttt   4380 gtttggaaat gggcagtcat tcaatagagg aaatggaata tgatgatggg gaattaattt   4440
tttcctattt ccaaaactt tttactttcca tcgtttccaa ttcttctaaa acaaccaaat   4500
tgagagcata cattcgttca gcatttgcat atcattttca gcattttgtt gaatttgatc   4560
aatatacaaa tgattctctc aatactgtgg atacaagtgt atcagcccaa gggatagcag   4620
acttggctct ctctatggtt agatggatac ccactcagat taaaaagtt gttaattttg   4680 gtgtgggatc tgttatagag tcttttttcag agcatttaaa taagctcttg atgcaatatt   4740
gtccaatagt ttttcaagct ttcagctggg tcaacaatat ttggacaatg gtcaaagagt   4800
ggatagaaga agctgcgaaa gagatttcat ggttttttgca aggatgcaaa gagttgctag   4860 cctgggggaat gtgtattttg gctagctcct gtgctctagg attggttgaa aaatgcctta   4920
tctctttggg catgattttcc gaatcttttg atttggttgg tttgtttgtt cgatctgcca   4980
ttgtgggagc tttctgtgtt tccataaaaa ctggcaagtt catcacgaat agtgaattgg   5040
tcacttgtgc taccattgca gttctacaa tagcaactgt aatgtctcag cttttaagc   5100 cttctgaaga gattaagggg cagttccaag ccctttcagt tctagaaggg ttggcaacac   5160
agctcacttc gttttgtgac acgtcttag ttgctatggg aaaaacctgc acagctttta   5220
atcaaatttg cactgctggc aaaaatgtta aggtgattgc aggtaggttg ctggaagttg   5280
```

```
tttctaattt tgtcagaaaa ttattaggat tggatagtgc ttttctcaga gatgctgcac    5340
tcattttttc ccaagatgtg gatggatggt tgcgtaacat cagttggtgc caggaacagt    5400
ttttgttgaa agcttacatg tcgcaagatg atcttattgt cctgcgctct ttagttgtta    5460
aaggtgaaag aatgagggaa cagatgcttg aaggagaagt taaggtatct ccaagtgttt    5520
gcaaccttat tgtcaaaggc tgtgaagaag caaataaatt gatgcgtgag agcgcacttc    5580
attgttcaaa aacaattagg aagattcctt ttgttatttt tgctcacggt gaatcccgag    5640
ttgggaaatc tctgttggtt gataagctaa tcacagattt ctgtgatcat ttggaaattg    5700
gagaagatgc tgtgtactca aggaatccat cagatccttt ctggagtgga tatagaaggc    5760
agccaattgt tactattgat gattttgctg ctgttgtttc ggagccatct gctgaagctc    5820
aattaattcc attagtttca agtgctcctt atccattaaa catggctggt ttagaggaga    5880
agggaatgca ctttgattcc cagatcatga tgtgttcttc aaatttctta gagccgtctc    5940
ctgaagctaa aattagagat gatatggctt ttagaaatcg gagacatgtg ctgatcacag    6000
ttgaactcaa acctggggtt gaatatgatg agagtgattt tactaaaaat cagcgatatt    6060
tgctgaaaac ttggtttcat gatcattatg ttgtagacca aacttttgag tcctatgctg    6120
atctgctggc acattgtttt accaagtggg agagacatgt taaggagcaa gagtcaaatc    6180
tgtctcaaat taagggcaag aaaagtgaaa gtggtcattt ttataatttt caacaactta    6240
tggatttggc tgtttcttgg aatcttaatg cagatatcat gaaaaacagg atcaaggctg    6300
agagaagtga catggtttat gttttttctg cagggaggaa ggataaaatt ttgcattgtt    6360
ttctgaacaa ggaaggcgag tgcacggttc gtcctgattc aatagatgat cctgaagcgc    6420
aagctttgct caaagcttca gagacaatgc tcatgaaagc ctatgccttc cttaaataca    6480
ataatgcaac aaatttgatt gtcagaaccc atttggcaga actagtgaat gaagattttt    6540
atgatgagaa attcaatttc attggaacaa ttggaacacc ggcttttcat cgccaaatag    6600
ctgcacattt ggaaaagatg ccattgtggc aaaaagcaat tttgtgtgga atgggacatt    6660
gtttgtctcg gaaaagcaaa gagacctggt atactggtat gaaggagaaa tttgtgcaga    6720
tgatgaaaag catctatgaa actgaagtca cagactggcc agtgccattg aaaatcattt    6780
ctggtactat tctagccacc attttgggaa caacttttgg gaagttattt tccttttaa    6840 gggatgctgg caatggaggt gttttgttg gtaatgttgc ttcagcattt accacatcaa    6900
gtgtgcttga ggcgcaaagc cgaaaaccca acagatatga ggtctctcaa tataggtatc    6960
gcaatgtgcc aataaagcgc agagcgtggg ttgagggtca aatgtctttt gatcaatcag    7020
tggtggcaat tatgtcaaaa tgtaaagcca gtatgagaat gggaaacact gatgctcaaa    7080
ttttgatggt tccagggcgt agattcattg cacatggtca ttttttaag aatctcaccc    7140 aaaaagttag agtccaaatt gttacttctg agaaaagcta ttggcatgtg tatgatcctg    7200
ataaatttca aatgtttgat aacagtgaaa tcgggttgta tacaaatcca actttggagg    7260
acatcccaca ttctgcttgg gaccttttct gctgggacag tgagaaaact ttgccaaaca    7320
atttttctgc tgaactgctt tcctgtaaat ggacaccgt tacgggacaa tattacccag    7380
aatgggctcc aataaattgt cgagtacatc ggcaaccaat tcacataact gaagggaatt    7440
atgtcaggaa acaagatgtg agcattgaat atgatgcctg cacaattcct aatgattgtg    7500
gatctctggt ggttgctaag gtcggaaatc acaagcaaat tgttggtttc catgttgctg    7560
gaagtaaagg aagattgggc tatgcttcat tgataccata tgttgagcct gtggtacaag    7620
cccaaagtgc tgaagtctat tttgatttct ttcctgtgga agttgatagt caagagggag    7680
```

```
ttgctcatat tggtgaactc aaatctggag tttatgtacc attgcccaca aaaactaatc    7740
ttgtggaaac tcccaaagaa tggcagttgg atttgccttg tgataagatt ccaagtgtgt    7800
taaccactac tgatgagaga ttggttggca cggagcatga aggatatgac ccatttcttg    7860
gtggtattca aaaatatgca actcccatga tgcctctaga tgaggagatt ctttccaaag    7920
ttgcacaaga catggttgaa gaatggtttg attgtgttga tgaggaggat acatttgaag    7980
aagtttcttt gagtgctgca ctcaatggtg ttgaaggttt ggattacatg gaacgcattc    8040
ctcttgccac ttcagagggt tttcctcatg ttctgtccag gaaaaatggt gaaaaaggca    8100
agagaagatt tgtcactgga gatggtgaag aaatgtcact aattcctggt accagtgttg    8160
aagaagcata caataaattg actgttgaac tagaaaagtg tgttccaaca ttggttggca    8220
tagaatgtcc caaagatgaa aaacttcccc gtcgcaaaat ttttgataaa cccaagacgc    8280
gctgcttcac catacttcct atggaattta atctggtggt gcgtcaaaaa ttcttgaatt    8340
ttgtgcgatt cattatgaag aaaagggaca aattgagttg ccaagttgga atcaatccat    8400
attctatgga gtggactggt ttggcaaata gactgttgag caagggaaat gacattttgt    8460
gttgtgatta tgctagtttt gatggtctga taactaagca agtcatgagc aagatggcag    8520
aaatgataaa cagtctttgt ggtggagatg agaaactgat gcgtgagaga acgcatcttc    8580
tgttagcttg ttgctccagg atggcaatct gtaaaaaaga tgtttggaga gttgagtgtg    8640
gtatcccttc tggatttcca ctcactgtta tctgcaatag cattttcaat gagatgctta    8700
tcagatatag ttatgaaaag ttgctgcgtc aagctaaggc tcctagtatg tttctccagt    8760
cttttaaaaa ttttatttct ttgtgtgttt atggagatga taatttaatt agtgttcatg    8820
agtatgttaa gccatatttt agtggttcta aattgaaaag tttcctagct agtcataaca    8880
tcaccattac tgatggaatt gacaaaacta gtgcaacttt acagtttaga aagttgtcag    8940
agtgtgattt tcttaaaaga aattttaagc aaatgtccaa tgttttgtgg gtagctcctg    9000
aagacaaagc tagtttgtgg tcacaattac actatgtttc atgtaacaat ttggaaatgc    9060
aagaagctta tcttgttaac ttggttaatg tgttgcgtga ttgtacctg cacagtccag    9120 aagaagctcg tcaattgaga agaaaggctc tctctcgcat tgagtggttg caaaaagctg    9180
atgtgcccac catagcacaa attgaagaat tcattcaat gcagaggatt atgaatgctc    9240
ctgactcaaa tgataatatt gatcttttgt tgagcattga cttgttgggt cttcagggtg    9300
caggcaaggc cttcccaaat aagattgtgt ttgatgataa attggtattg gcaaatacac    9360 aagaatttt tgatggaaat tttccaacag attcttggtt accaatattt gtcaattgtc    9420
tttaccctgt gagtcaattg cccgcagagg ctgtcactgt taatgttgtt tgtgggagtg    9480
ggcgtggtgg tttgcctact actgcttgga ttagttctgc agttaacaat cgctcctcag    9540
atatcaataa gaaaattcgg acagcacttg ggaaaggtaa gaaaattgtc tttttgacta    9600
gagttgatcc ttttcctgtg gccttgttag ctgttctttt tggtgttaag aacgaaattc    9660
tgagttctaa tgccacaaat ccaatgttga caaggcttct tgagaactgc aagagtctta    9720
aatatttggt tgatgagtgt cctttttgcat ttgttaacta gtttgtaata ttttgctcac    9780
ttaaataaag cgcattacta tgtgcaataa gtgtgtttaa atataaaaaa aaaaaaaaaa    9840
aaaatcgatg ggcctggatc ctaggttcac aaagtgtcat cgatagctcg aatttccccg    9900
atcgttcaaa catttggcaa taaagtttct taagattgaa tcctgttgcc ggtcttgcga    9960
tgattatcat ataatttctg ttgaattacg ttaagcatgt aataattaac atgtaatgca   10020
tgacgttatt tatgagatgg gtttttatga ttagagtccc gcaattatac atttaatacg   10080
```
cgatagaaaa caaaatatag cgcgcaaact aggataaatt atcgcgcgcg gtgtcatcta 10140
tgttactaga tcgggaattc caattcgcc 10169

<210> SEQ ID NO 2
<211> LENGTH: 1851
<212> TYPE: PRT
<213> ORGANISM: Bean Pod Mottle Virus

<400> SEQUENCE: 2

```
Met Lys Phe Tyr Pro Gly Gln Asn Ile Ser Glu Ile Val Tyr His Phe
1               5                   10                  15

Gln Ser Asn Glu Thr Ala Asn Arg Leu Asp Ala Tyr Phe Ala Cys Gly
            20                  25                  30

Cys Glu Glu Asp Thr Glu Val Leu Ala Arg Leu Lys Gln Cys Asn Pro
        35                  40                  45

Arg Leu Leu His Leu Ser Tyr Ala Ala Phe Cys Leu Glu Met Gly Ser
    50                  55                  60

His Ser Ile Glu Glu Met Glu Tyr Asp Asp Gly Glu Leu Ile Phe Ser
65                  70                  75                  80

Tyr Phe Gln Asn Phe Leu Leu Ser Ile Val Ser Asn Ser Ser Lys Thr
                85                  90                  95

Thr Lys Leu Arg Ala Tyr Ile Arg Ser Ala Phe Ala Tyr His Phe Gln
            100                 105                 110

His Phe Val Glu Phe Asp Gln Tyr Thr Asn Asp Ser Leu Asn Thr Val
        115                 120                 125

Asp Thr Ser Val Ser Ala Gln Gly Ile Ala Asp Leu Ala Leu Ser Met
    130                 135                 140

Val Arg Trp Ile Pro Thr Gln Ile Lys Lys Val Val Asn Phe Gly Val
145                 150                 155                 160

Gly Ser Val Ile Glu Ser Phe Ser Glu His Phe Asn Lys Leu Leu Met
                165                 170                 175

Gln Tyr Cys Pro Ile Val Phe Gln Ala Phe Ser Trp Val Asn Asn Ile
            180                 185                 190

Trp Thr Met Val Lys Glu Trp Ile Glu Glu Ala Ala Lys Glu Ile Ser
        195                 200                 205

Trp Phe Leu Gln Gly Cys Lys Glu Leu Leu Ala Trp Gly Met Cys Ile
    210                 215                 220

Leu Ala Ser Ser Cys Ala Leu Gly Leu Val Glu Lys Cys Leu Ile Ser
225                 230                 235                 240

Leu Gly Met Ile Ser Glu Ser Phe Asp Leu Val Gly Leu Phe Val Arg
                245                 250                 255

Ser Ala Ile Val Gly Ala Phe Cys Val Ser Ile Lys Thr Gly Lys Phe
            260                 265                 270

Ile Thr Asn Ser Glu Leu Val Thr Cys Ala Thr Ile Ala Val Ser Thr
        275                 280                 285

Ile Ala Thr Val Met Ser Gln Ala Phe Lys Pro Ser Glu Glu Ile Lys
    290                 295                 300

Gly Gln Phe Gln Ala Leu Ser Val Leu Glu Gly Leu Ala Thr Gln Leu
305                 310                 315                 320

Thr Ser Phe Cys Asp Thr Ser Leu Val Ala Met Gly Lys Thr Cys Thr
                325                 330                 335

Ala Phe Asn Gln Ile Cys Thr Ala Gly Lys Asn Val Lys Val Ile Ala
            340                 345                 350

Gly Arg Leu Leu Glu Val Val Ser Asn Phe Val Arg Lys Leu Leu Gly
```

-continued

```
                355                 360                 365
Leu Asp Ser Ala Phe Leu Arg Asp Ala Ala Leu Ile Phe Ser Gln Asp
            370                 375                 380

Val Asp Gly Trp Leu Arg Asn Ile Ser Trp Cys Gln Glu Gln Phe Leu
385                 390                 395                 400

Leu Lys Ala Tyr Met Ser Gln Asp Leu Ile Val Leu Arg Ser Leu
                405                 410                 415

Val Val Lys Gly Glu Arg Met Arg Glu Gln Met Leu Glu Gly Glu Val
            420                 425                 430

Lys Val Ser Pro Ser Val Cys Asn Leu Ile Val Lys Gly Cys Glu Glu
435                 440                 445

Ala Asn Lys Leu Met Arg Glu Ser Ala Leu His Cys Ser Lys Thr Ile
    450                 455                 460

Arg Lys Ile Pro Phe Val Ile Phe Ala His Gly Glu Ser Arg Val Gly
465                 470                 475                 480

Lys Ser Leu Leu Val Asp Lys Leu Ile Thr Asp Phe Cys Asp His Leu
                485                 490                 495

Glu Ile Gly Glu Asp Ala Val Tyr Ser Arg Asn Pro Ser Asp Pro Phe
            500                 505                 510

Trp Ser Gly Tyr Arg Arg Gln Pro Ile Val Thr Ile Asp Asp Phe Ala
            515                 520                 525

Ala Val Val Ser Glu Pro Ser Ala Glu Ala Gln Leu Ile Pro Leu Val
            530                 535                 540

Ser Ser Ala Pro Tyr Pro Leu Asn Met Ala Gly Leu Glu Glu Lys Gly
545                 550                 555                 560

Met His Phe Asp Ser Gln Ile Met Met Cys Ser Ser Asn Phe Leu Glu
                565                 570                 575

Pro Ser Pro Glu Ala Lys Ile Arg Asp Asp Met Ala Phe Arg Asn Arg
            580                 585                 590

Arg His Val Leu Ile Thr Val Glu Leu Lys Pro Gly Val Glu Tyr Asp
            595                 600                 605

Glu Ser Asp Phe Thr Lys Asn Gln Arg Tyr Leu Leu Lys Thr Trp Phe
    610                 615                 620

His Asp His Tyr Val Val Asp Gln Thr Phe Glu Ser Tyr Ala Asp Leu
625                 630                 635                 640

Leu Ala His Cys Phe Thr Lys Trp Glu Arg His Val Lys Glu Gln Glu
                645                 650                 655

Ser Asn Leu Ser Gln Ile Lys Gly Lys Lys Ser Glu Ser Gly His Phe
            660                 665                 670

Tyr Asn Phe Gln Gln Leu Met Asp Leu Ala Val Ser Trp Asn Leu Asn
            675                 680                 685

Ala Asp Ile Met Lys Asn Arg Ile Lys Ala Glu Arg Ser Asp Met Val
    690                 695                 700

Tyr Val Phe Ser Ala Gly Arg Lys Asp Lys Ile Leu His Cys Phe Leu
705                 710                 715                 720

Asn Lys Glu Gly Glu Cys Thr Val Arg Pro Asp Ser Ile Asp Asp Pro
                725                 730                 735

Glu Ala Gln Ala Leu Leu Lys Ala Ser Glu Thr Met Leu Met Lys Ala
            740                 745                 750

Tyr Ala Phe Leu Lys Tyr Asn Asn Ala Thr Asn Leu Ile Val Arg Thr
            755                 760                 765

His Leu Ala Glu Leu Val Asn Glu Asp Phe Tyr Asp Glu Lys Phe Asn
    770                 775                 780
```

-continued

Phe Ile Gly Thr Ile Gly Thr Pro Ala Phe His Arg Gln Ile Ala Ala
785                 790                 795                 800

His Leu Glu Lys Met Pro Leu Trp Gln Lys Ala Ile Leu Cys Gly Met
            805                 810                 815

Gly His Cys Leu Ser Arg Lys Ser Lys Glu Thr Trp Tyr Thr Gly Met
            820                 825                 830

Lys Glu Lys Phe Val Gln Met Met Lys Ser Ile Tyr Glu Thr Glu Val
        835                 840                 845

Thr Asp Trp Pro Val Pro Leu Lys Ile Ile Ser Gly Thr Ile Leu Ala
    850                 855                 860

Thr Ile Leu Gly Thr Thr Phe Trp Lys Leu Phe Ser Phe Leu Arg Asp
865                 870                 875                 880

Ala Gly Asn Gly Gly Val Phe Val Gly Asn Val Ala Ser Ala Phe Thr
                885                 890                 895

Thr Ser Ser Val Leu Glu Ala Gln Ser Arg Lys Pro Asn Arg Tyr Glu
            900                 905                 910

Val Ser Gln Tyr Arg Tyr Arg Asn Val Pro Ile Lys Arg Arg Ala Trp
        915                 920                 925

Val Glu Gly Gln Met Ser Phe Asp Gln Ser Val Val Ala Ile Met Ser
    930                 935                 940

Lys Cys Lys Ala Ser Met Arg Met Gly Asn Thr Asp Ala Gln Ile Leu
945                 950                 955                 960

Met Val Pro Gly Arg Arg Phe Ile Ala His Gly His Phe Lys Asn
                965                 970                 975

Leu Thr Gln Lys Val Arg Val Gln Ile Val Thr Ser Glu Lys Ser Tyr
            980                 985                 990

Trp His Val Tyr Asp Pro Asp Lys Phe Gln Met Phe Asp Asn Ser Glu
        995                 1000                1005

Ile Gly Leu Tyr Thr Asn Pro Thr Leu Glu Asp Ile Pro His Ser
    1010                1015                1020

Ala Trp Asp Leu Phe Cys Trp Asp Ser Glu Lys Thr Leu Pro Asn
    1025                1030                1035

Asn Phe Ser Ala Glu Leu Leu Ser Cys Lys Leu Asp Thr Val Thr
    1040                1045                1050

Gly Gln Tyr Tyr Pro Glu Trp Ala Pro Ile Asn Cys Arg Val His
    1055                1060                1065

Arg Gln Pro Ile His Ile Thr Glu Gly Asn Tyr Val Arg Lys Gln
    1070                1075                1080

Asp Val Ser Ile Glu Tyr Asp Ala Cys Thr Ile Pro Asn Asp Cys
    1085                1090                1095

Gly Ser Leu Val Val Ala Lys Val Gly Asn His Lys Gln Ile Val
    1100                1105                1110

Gly Phe His Val Ala Gly Ser Lys Gly Arg Leu Gly Tyr Ala Ser
    1115                1120                1125

Leu Ile Pro Tyr Val Glu Pro Val Val Gln Ala Gln Ser Ala Glu
    1130                1135                1140

Val Tyr Phe Asp Phe Pro Val Glu Val Asp Ser Gln Glu Gly
    1145                1150                1155

Val Ala His Ile Gly Glu Leu Lys Ser Gly Val Tyr Val Pro Leu
    1160                1165                1170

Pro Thr Lys Thr Asn Leu Val Glu Thr Pro Lys Glu Trp Gln Leu
    1175                1180                1185

Asp Leu Pro Cys Asp Lys Ile Pro Ser Val Leu Thr Thr Thr Asp
    1190                1195                1200

```
Glu Arg Leu Val Gly Thr Glu His Glu Gly Tyr Asp Pro Phe Leu
    1205            1210            1215

Gly Gly Ile Gln Lys Tyr Ala Thr Pro Met Met Pro Leu Asp Glu
    1220            1225            1230

Glu Ile Leu Ser Lys Val Ala Gln Asp Met Val Glu Glu Trp Phe
    1235            1240            1245

Asp Cys Val Asp Glu Glu Asp Thr Phe Glu Glu Val Ser Leu Ser
    1250            1255            1260

Ala Ala Leu Asn Gly Val Glu Gly Leu Asp Tyr Met Glu Arg Ile
    1265            1270            1275

Pro Leu Ala Thr Ser Glu Gly Phe Pro His Val Leu Ser Arg Lys
    1280            1285            1290

Asn Gly Glu Lys Gly Lys Arg Arg Phe Val Thr Gly Asp Gly Glu
    1295            1300            1305

Glu Met Ser Leu Ile Pro Gly Thr Ser Val Glu Glu Ala Tyr Asn
    1310            1315            1320

Lys Leu Thr Val Glu Leu Glu Lys Cys Val Pro Thr Leu Val Gly
    1325            1330            1335

Ile Glu Cys Pro Lys Asp Glu Lys Leu Pro Arg Arg Lys Ile Phe
    1340            1345            1350

Asp Lys Pro Lys Thr Arg Cys Phe Thr Ile Leu Pro Met Glu Phe
    1355            1360            1365

Asn Leu Val Val Arg Gln Lys Phe Leu Asn Phe Val Arg Phe Ile
    1370            1375            1380

Met Lys Lys Arg Asp Lys Leu Ser Cys Gln Val Gly Ile Asn Pro
    1385            1390            1395

Tyr Ser Met Glu Trp Thr Gly Leu Ala Asn Arg Leu Leu Ser Lys
    1400            1405            1410

Gly Asn Asp Ile Leu Cys Cys Asp Tyr Ala Ser Phe Asp Gly Leu
    1415            1420            1425

Ile Thr Lys Gln Val Met Ser Lys Met Ala Glu Met Ile Asn Ser
    1430            1435            1440

Leu Cys Gly Gly Asp Glu Lys Leu Met Arg Glu Arg Thr His Leu
    1445            1450            1455

Leu Leu Ala Cys Cys Ser Arg Met Ala Ile Cys Lys Lys Asp Val
    1460            1465            1470

Trp Arg Val Glu Cys Gly Ile Pro Ser Gly Phe Pro Leu Thr Val
    1475            1480            1485

Ile Cys Asn Ser Ile Phe Asn Glu Met Leu Ile Arg Tyr Ser Tyr
    1490            1495            1500

Glu Lys Leu Leu Arg Gln Ala Lys Ala Pro Ser Met Phe Leu Gln
    1505            1510            1515

Ser Phe Lys Asn Phe Ile Ser Leu Cys Val Tyr Gly Asp Asp Asn
    1520            1525            1530

Leu Ile Ser Val His Glu Tyr Val Lys Pro Tyr Phe Ser Gly Ser
    1535            1540            1545

Lys Leu Lys Ser Phe Leu Ala Ser His Asn Ile Thr Ile Thr Asp
    1550            1555            1560

Gly Ile Asp Lys Thr Ser Ala Thr Leu Gln Phe Arg Lys Leu Ser
    1565            1570            1575

Glu Cys Asp Phe Leu Lys Arg Asn Phe Lys Gln Met Ser Asn Val
    1580            1585            1590

Leu Trp Val Ala Pro Glu Asp Lys Ala Ser Leu Trp Ser Gln Leu
```

1595 1600 1605

His Tyr Val Ser Cys Asn Asn Leu Glu Met Gln Glu Ala Tyr Leu
1610 1615 1620

Val Asn Leu Val Asn Val Leu Arg Glu Leu Tyr Leu His Ser Pro
1625 1630 1635

Glu Glu Ala Arg Gln Leu Arg Arg Lys Ala Leu Ser Arg Ile Glu
1640 1645 1650

Trp Leu Gln Lys Ala Asp Val Pro Thr Ile Ala Gln Ile Glu Glu
1655 1660 1665

Phe His Ser Met Gln Arg Ile Met Asn Ala Pro Asp Ser Asn Asp
1670 1675 1680

Asn Ile Asp Leu Leu Leu Ser Ile Asp Leu Leu Gly Leu Gln Gly
1685 1690 1695

Ala Gly Lys Ala Phe Pro Asn Lys Ile Val Phe Asp Asp Lys Leu
1700 1705 1710

Val Leu Ala Asn Thr Gln Glu Phe Phe Asp Gly Asn Phe Pro Thr
1715 1720 1725

Asp Ser Trp Leu Pro Ile Phe Val Asn Cys Leu Tyr Pro Val Ser
1730 1735 1740

Gln Leu Pro Ala Glu Ala Val Thr Val Asn Val Val Cys Gly Ser
1745 1750 1755

Gly Arg Gly Gly Leu Pro Thr Thr Ala Trp Ile Ser Ser Ala Val
1760 1765 1770

Asn Asn Arg Ser Ser Asp Ile Asn Lys Lys Ile Arg Thr Ala Leu
1775 1780 1785

Gly Lys Gly Lys Lys Ile Val Phe Leu Thr Arg Val Asp Pro Phe
1790 1795 1800

Pro Val Ala Leu Leu Ala Val Leu Phe Gly Val Lys Asn Glu Ile
1805 1810 1815

Leu Ser Ser Asn Ala Thr Asn Pro Met Leu Thr Arg Leu Leu Glu
1820 1825 1830

Asn Cys Lys Ser Leu Lys Tyr Leu Val Asp Glu Cys Pro Phe Ala
1835 1840 1845

Phe Val Asn
1850

<210> SEQ ID NO 3
<211> LENGTH: 10169
<212> TYPE: DNA
<213> ORGANISM: Bean Pod Mottle Virus

<400> SEQUENCE: 3
tatagtgagt cgtattacaa ttcactggcc gtcgttttac aacgtcgtga ctgggaaaac 60
cctggcgtta cccaacttaa tcgccttgca gcacatcccc ctttcgccag ctggcgtaat 120
agcgaagagg cccgcaccga tcgcccttcc caacagttgc gcagcctgaa tggcgaatgg 180
acgcgccctg tagcggcgca ttaagcgcgg cgggtgtggt ggttacgcgc agcgtgaccg 240
ctacacttgc cagcgcccta gcgcccgctc ctttcgcttt cttcccttcc tttctcgcca 300
cgttcgccgg ctttccccgt caagctctaa atcgggggct ccctttaggg ttccgattta 360
gtgctttacg gcacctcgac cccaaaaaac ttgattaggg tgatggttca cgtagtgggc 420
catcgccctg atagacggtt tttcgccctt tgacgttgga gtccacgttc tttaatagtg 480
gactcttgtt ccaaactgga acaacactca accctatctc ggtctattct tttgatttat 540
aagggatttt gccgatttcg gcctattggt taaaaaatga gctgatttaa caaaaattta 600

```
acgcgaattt taacaaaata ttaacgctta caatttcctg atgcggtatt ttctccttac    660
gcatctgtgc ggtatttcac accgcatatg gtgcactctc agtacaatct gctctgatgc    720
cgcatagtta agccagcccc gacacccgcc aacacccgct gacgcgccct gacgggcttg    780
tctgctcccg gcatccgctt acagacaagc tgtgaccgtc tccgggagct gcatgtgtca    840
gaggttttca ccgtcatcac cgaaacgcgc gagacgaaag ggcctcgtga tacgcctatt    900
tttataggtt aatgtcatga taataatggt ttcttagacg tcaggtggca cttttcgggg    960
aaatgtgcgc ggaaccccta tttgtttatt tttctaaata cattcaaata tgtatccgct   1020
catgagacaa taaccctgat aaatgcttca ataatattga aaaggaaga gtatgagtat    1080 tcaacatttc cgtgtcgccc ttattcccct ttttgcggca ttttgccttc ctgttttgc    1140 tcacccagaa acgctggtga agtaaaaga tgctgaagat cagttgggtg cacgagtggg    1200
ttacatcgaa ctggatctca acagcggtaa gatccttgag agttttcgcc ccgaagaacg   1260
ttttccaatg atgagcactt ttaaagttct gctatgtggc gcggtattat cccgtattga    1320
cgccgggcaa gagcaactcg gtcgccgcat acactattct cagaatgact tggttgagta    1380
ctcaccagtc acagaaaagc atcttacgga tggcatgaca gtaagagaat tatgcagtgc    1440
tgccataacc atgagtgata acactgcggc caacttactt ctgacaacga tcggaggacc    1500
gaaggagcta accgcttttt tgcacaacat ggggatcat gtaactcgcc ttgatcgttg    1560
ggaaccggag ctgaatgaag ccataccaaa cgacgagcgt gacaccacga tgcctgtagc    1620
aatggcaaca acgttgcgca aactattaac tggcgaacta cttactctag cttcccggca    1680
acaattaata gactggatgg aggcggataa agttgcagga ccacttctgc gctcggccct    1740
tccggctggc tggtttattg ctgataaatc tggagccggt gagcgtgggt ctcgcggtat    1800
cattgcagca ctggggccag atggtaagcc ctcccgtatc gtagttatct acacgacggg    1860
gagtcaggca actatggatg aacgaaatag acagatcgct gagataggtg cctcactgat    1920
taagcattgg taactgtcag accaagttta ctcatatata ctttagattg atttaaaact    1980
tcatttttaa tttaaaagga tctaggtgaa gatcctttt gataatctca tgaccaaaat    2040
cccttaacgt gagttttcgt tccactgagc gtcagacccc gtagaaaaga tcaaaggatc    2100
ttcttgagat ccttttttc tgcgcgtaat ctgctgcttg caaacaaaaa aaccaccgct    2160
accagcggtg gtttgtttgc cggatcaaga gctaccaact ctttttccga aggtaactgg    2220
cttcagcaga gcgcagatac caaatactgt tcttctagtg tagccgtagt taggccacca    2280
cttcaagaac tctgtagcac cgcctacata cctcgctctg ctaatcctgt taccagtggc    2340
tgctgccagt ggcgataagt cgtgtcttac cgggttggac tcaagacgat agttaccgga    2400
taaggcgcag cggtcgggct gaacggggg ttcgtgcaca gcccagct tggagcgaac     2460 gacctacacc gaactgagat acctacagcg tgagctatga gaaagcgcca cgcttcccga    2520
agggagaaag gcggacaggt atccggtaag cggcagggtc ggaacaggag agcgcacgag    2580
ggagcttcca gggggaaacg cctggtatct ttatagtcct gtcgggtttc gccacctctg    2640
acttgagcgt cgatttttgt gatgctcgtc agggggggcg agcctatgga aaaacgccag    2700
caacgcggcc ttttacggt tcctggcctt ttgctggcct tttgctcaca tgttctttcc    2760
tgcgttatcc cctgattctg tggataaccg tattaccgcc tttgagtgag ctgataccgc    2820
tcgccgcagc cgaacgaccg agcgcagcga gtcagtgagc gaggaagcgg aagagcgccc    2880
aatacgcaaa ccgcctctcc ccgcgcgttg gccgattcat taatgcagct ggcacgacag    2940
gtttcccgac tggaaagcgg gcagtgagcg caacgcaatt aatgtgagtt agctcactca    3000
```

```
ttaggcaccc caggctttac actttatgct tccggctcgt atgttgtgtg gaattgtgag   3060
cggataacaa tttcacacag gaaacagcta tgaccatgat tacgccaagc tatttaggtg   3120
acactataga atactcaagc ggccgcctac tccaagaata tcaaagatac agtctcagaa   3180
gaccaaaggg ctattgagac ttttcaacaa agggtaatat cgggaaacct cctcggattc   3240
cattgcccag ctatctgtca cttcatcaaa aggacagtag aaaggaagg tggcacctac    3300 aaatgccatc attgcgataa aggaaaggct atcgttcaag atgcctctgc cgacagtggt   3360
cccaaagatg accccccacc cacgaggagc atcgtggaaa aagaagacgt tccaaccacg   3420
tcttcaaagc aagtggattg atgtgatcta ctccaagaat atcaaagata cagtctcaga   3480
agaccaaagg gctattgaga cttttcaaca aagggtaata tcgggaaacc tcctcggatt   3540
ccattgccca gctatctgtc acttcatcaa aggacagta gaaaaggaag gtggcaccta    3600
caaatgccat cattgcgata aaggaaaggc tatcgttcaa gatgcctctg ccgacagtgg   3660
tcccaaagat ggaccccac ccacgaggag catcgtggaa aagaagacg ttccaaccac     3720 gtcttcaaag caagtggatt gatgtgatat ctccactgac gtaagggatg acgcacaatc   3780
ccactatcct tcgcaagacc cttcctctat ataaggaagt tcatttcatt tggagaggta   3840
ttaaaatttt cataagattt gaaattttga taaaccgcga tcataggttg ccgcaccta    3900 aaaccggaaa caaaagcaat cgttacttga tttcaaagac ttctcaattt ctttctacat   3960
ttcttgtata cggctttcaa agtgaaagaa aatcactctc tgtgctggtc acagacttcg   4020
tgaatcattt tctttctgct ctcagttcat ttgctgaaca ctctcctatt tgatatagga   4080
cttcgtgtca gatttgaact tctcctatct ctttttctcg gttcttcatt tgatttcaaa   4140
cttttctgaa atttaaatct cttttgcat tttgaacttt tgttggctc catttgaaaa    4200 acaacatgaa gttctatcct ggtcaaaata tttccgaaat tgtttaccac tttcagagta   4260
atgagacagc caataggtta gatgcatatt ttgcttgtgg ctgtgaggag gatactgaag   4320
tcctcgctcg tttgaagcag tgtaatcctc gtctgcttca tctgtcatat gctgcctttt   4380
gtttggaaat gggcagtcat tcaatagagg aaatggaata tgatgatggg gaattaattt   4440
tttcctattt ccaaaacttt ttactttcca tcgtttccaa ttcttctaaa acaaccaaat   4500
tgagagcata cattcgttca gcatttgcat atcatttca gcattttgtt gaatttgatc    4560
aatatacaaa tgattctctc aatactgtgg atacaagtgt atcagcccaa gggatagcag   4620
acttggctct ctctatggtt agatggatac ccactcagat taaaaaagtt gttaattttg   4680
gtgtgggatc tgttatagag tcttttcag agcattttaa taagctcttg atgcaatatt    4740
gtccaatagt ttttcaagct ttcagctggg tcaacaatat ttggacaatg gtcaaagagt   4800
ggatagaaga agctgcgaaa gagatttcat ggttttgca aggatgcaaa gagttgctag    4860
cctggggaat gtgtatttg gctagctcct gtgctctagg attggttgaa aaatgcctta    4920
tctctttggg catgattttcc gaatcttttg atttggttgg tttgtttgtt cgatctgcca   4980
ttgtgggagc tttctgtgtt tccataaaaa ctggcaagtt catcacgaat agtgaattgg   5040
tcacttgtgc taccattgca gtttctacaa tagcaactgt aatgtctcag cttttaagc    5100 cttctgaaga gattaaggg cagttccaag ccctttcagt tctagaaggg ttggcaacac    5160
agctcacttc gttttgtgac acgtctttag ttgctatggg aaaaaccgtgc acagcttta   5220 atcaaatttg cactgctggc aaaaatgtta aggtgattgc aggtaggttg ctggaagttg   5280
tttctaattt tgtcagaaaa ttattaggat tggatagtgc ttttctcaga gatgctgcac   5340
tcattttttc ccaagatgtg gatggatggt tgcgtaacat cagttggtgc caggaacagt   5400
```

```
ttttgttgaa agcttacatg tcgcaagatg atcttattgt cctgcgctct ttagttgtta    5460
aaggtgaaag aatgagggaa cagatgcttg aaggagaagt taaggtatct ccaagtgttt    5520
gcaaccttat tgtcaaaggc tgtgaagaag caaataaatt gatgcgtgag agcgcacttc    5580
attgttcaaa aacaattagg aagattcctt ttgttatttt tgctcacggt gaatcccgag    5640
ttgggaaatc tctgttggtt gataagctaa tcacagattt ctgtgatcat ttggaaattg    5700
gagaagatgc tgtgtactca aggaatccat cagatccttt ctggagtgga tatagaaggc    5760
agccaattgt tactattgat gattttgctg ctgttgtttc ggagccatct gctgaagctc    5820
aattaattcc attagtttca agtgctcctt atccattaaa catggctggt ttagaggaga    5880
agggaatgca cttttgattcc cagatcatga tgtgttcttc aaatttctta gagccgtctc    5940
ctgaagctaa aattagagat gatatggctt ttagaaatcg gagacatgtg ctgatcacag    6000
ttgaactcaa acctggggtt gaatatgatg agagtgattt tactaaaaat cagcgatatt    6060
tgctgaaaac ttggtttcat gatcattatg ttgtagacca aacttttgag tcctatgctg    6120
atctgctggc acattgtttt accaagtggg agagacatgt taaggagcaa gagtcaaatc    6180
tgtctcaaat taagggcaag aaaagtgaaa gtggtcattt ttataatttt caacaactta    6240
tggatttggc tgtttcttgg aatcttaatg cagatatcat gaaaaacagg atcaaggctg    6300
agagaagtga catggtttat gttttttctg cagggaggaa ggataaaatt ttgcattgtt    6360
ttctgaacaa ggaaggcgag tgcacggttc gtcctgattc aatagatgat cctgaagcgc    6420
aagctttgct caaagcttca gagacaatgc tcatgaaagc ctatgccttc cttaaataca    6480
ataatgcaac aaatttgatt gtcagaaccc atttggcaga actagtgaat gaagattttt    6540
atgatgagaa attcaatttc attggaacaa ttggaacacc ggcttttcat cgccaaatag    6600
ctgcacattt ggaaaagatg ccattgtggc aaaaagcaat tttgtgtgga atgggacatt    6660
gtttgtctcg gaaaagcaaa gagacctggt atactggtat gaaggagaaa tttgtgcaga    6720
tgatgaaaag catctatgaa actgaagtca cagactggcc agtgccattg aaaatcattt    6780
ctggtactat tctagccacc attttgggaa caacttttg gaagttattt tccttttttaa    6840 gggatgctgg caatggaggt gttttttgttg gtaatgttgc ttcagcattt accacatcaa    6900
gtgtgcttga ggcgcaaagc cgaaaaccca acagatatga ggtctctcaa tataggtatc    6960
gcaatgtgcc aataaagcgc agagcgtggg ttgagggtca aatgtctttt gatcaatcag    7020
tggtggcaat tatgtcaaaa tgtaaagcca gtatgagaat gggaaacact gatgctcaaa    7080
ttttgatggt tccagggcgt agattcattg cacatggtca ttttttttaag aatctcaccc    7140 aaaaagttag agtccaaatt gttacttctg agaaaagcta ttggcatgtg tatgatcctg    7200
ataaatttca aatgtttgat aacagtgaaa tcgggttgta tacaaatcca actttggagg    7260
acatcccaca ttctgcttgg gacctttttct gctgggacag tgagaaaact ttgccaaaca    7320 attttttctgc tgaactgctt tcctgtaaat tggacaccgt tacgggacaa tattacccag    7380
aatgggctcc aataaattgt cgagtacatc ggcaaccaat tcacataact gaagggaatt    7440
atgtcaggaa acaagatgtg agcattgaat atgatgcctg cacaattcct aatgattgtg    7500
gatctctggt ggttgctaag gtcggaaatc acaagcaaat tgttggtttc catgttgctg    7560
gaagtaaagg aagattgggc tatgcttcat tgataccata tgttgagcct gtggtacaag    7620
cccaaagtgc tgaagtctat tttgatttct ttcctgtgga agttgatagt caagagggag    7680
ttgctcatat tggtgaactc aaatctggag tttatgtacc attgcccaca aaaactaatc    7740
ttgtggaaac tcccaaagaa tggcagttgg atttgccttg tgataagatt ccaagtgtgt    7800
```

```
taaccactac tgatgagaga ttggttggca cggagcatga aggatatgac ccatttcttg    7860
gtggtattca aaatatgca actcccatga tgcctctaga tgaggagatt ctttccaaag    7920
ttgcacaaga catggttgaa gaatggtttg attgtgttga tgaggaggat acatttgaag    7980
aagtttcttt gagtgctgca ctcaatggtg ttgaaggttt ggattacatg gaacgcattc    8040
ctcttgccac ttcagagggt tttcctcatg ttctgtccag gaaaaatggt gaaaaaggca    8100
agagaagatt tgtcactgga gatggtgaag aaatgtcact aattcctggt accagtgttg    8160
aagaagcata caataaattg actgttgaac tagaaaagtg tgttccaaca ttggttggca    8220
tagaatgtcc caaagatgaa aaacttcccc gtcgcaaaat ttttgataaa cccaagacgc    8280
gctgcttcac catacttcct atggaattta atctggtggt gcgtcaaaaa ttcttgaatt    8340
ttgtgcgatt cattatgaag aaaagggaca aattgagttg ccaagttgga atcaatccat    8400
attctatgga gtggactggt ttggcaaata gactgttgag caaggaaaat gacattttgt    8460
gttgtgatta tgctagtttt gatggtctga taactaagca agtcatgagc aagatggcag    8520
aaatgataaa cagtctttgt ggtggagatg agaaactgat gcgtgagaga acgcatcttc    8580
tgttagcttg ttgctccagg atggcaatct gtaaaaaaga tgtttggaga ttgagtgtg    8640 gtatcccttc tggatttcca ctcactgtta tctgcaatag catttcaat gagatgctta    8700 tcagatatag ttatgaaaag ttgctgcgtc aagctaaggc tcctagtatg tttctccagt    8760
cttttaaaaa ttttatttct ttgtgtgttt atggagatga taatttaatt agtgttcatg    8820
agtatgttaa gccatatttt agtggttcta aattgaaaag tttcctagct agtcataaca    8880
tcaccattac tgatggaatt gacaaaacta gtgcaacttt acagtttaga aagttgtcag    8940
agtgtgattt tctaaaaga aattttaagc aaatgtccaa tgttttgtgg gtagctcctg    9000
aagacaaagc tagtttgtgg tcacaattac actatgtttc atgtaacaat ttggaaatgc    9060
aagaagctta tcttgttaac ttggttaatg tgttgcgtga gttgtacctg cacagtccag    9120
aagaagctcg tcaattgaga agaaaggctc tctctcgcat tgagtggttg caaaaagctg    9180
atgtgcccac catagcacaa attgaagaat ttcattcaat gcagaggatt atgaatgctc    9240
ctgactcaaa tgataatatt gatcttttgt tgagcattga cttgttgggt cttcagggtg    9300
caggcaaggc cttcccaaat aagattgtgt ttgatgataa attggtattg gcaaatacac    9360
aagaattttt tgatggaaat tttccaacag attcttggtt accaatattt gtcaattgtc    9420
tttaccctgt gagtcaattg cccgcagagg ctgtcactgt taatgttgtt tgtgggagtg    9480
ggcgtggtgg tttgcctact actgcttgga ttagttctgc agttaacaat cgctcctcag    9540
atatcaataa gaaaattcgg acagcacttg ggaaaggtaa gaaaattgtc ttttgacta    9600 gagttgatcc ttttcctgtg gccttgttag ctgttctttt tggtgttaag aacgaaattc    9660
tgagttctaa tgccacaaat ccaatgttga caaggcttct tgagaactgc aagagtctta    9720
aatatttggt tgatgagtgt cctttttgcat ttgttaacta gtttgtaata ttttgctcac    9780
ttaaataaag cgcattacta tgtgcaataa gtgtgtttaa atataaaaaa aaaaaaaaa    9840 aaaatcgatg ggcctggatc ctaggttcac aaagtgtcat cgatagctcg aatttccccg    9900
atcgttcaaa catttggcaa taaagtttct taagattgaa tcctgttgcc ggtcttgcga    9960
tgattatcat ataatttctg ttgaattacg ttaagcatgt aataattaac atgtaatgca   10020
tgacgttatt tatgagatgg ttttttatga ttagagtccc gcaattatac atttaatacg   10080
cgatagaaaa caaatatag cgcgcaaact aggataaatt atcgcgcgcg gtgtcatcta   10140
tgttactaga tcgggaattc caattcgcc                                     10169
```

<210> SEQ ID NO 4
<211> LENGTH: 8067
<212> TYPE: DNA
<213> ORGANISM: Bean Pod Mottle Virus

<400> SEQUENCE: 4

| | | | | | |
|---|---|---|---|---|---|
| tatagtgagt | cgtattacaa | ttcactggcc | gtcgttttac | aacgtcgtga | ctgggaaaac | 60 |
| cctggcgtta | cccaacttaa | tcgccttgca | gcacatcccc | ctttcgccag | ctggcgtaat | 120 |
| agcgaagagg | cccgcaccga | tcgcccttcc | aacagttgc | gcagcctgaa | tggcgaatgg | 180 |
| acgcgccctg | tagcggcgca | ttaagcgcgg | cgggtgtggt | ggttacgcgc | agcgtgaccg | 240 |
| ctacacttgc | cagcgcccta | gcgcccgctc | ctttcgcttt | cttcccttcc | tttctcgcca | 300 |
| cgttcgccgg | ctttccccgt | caagctctaa | atcgggggct | ccctttaggg | ttccgattta | 360 |
| gtgctttacg | gcacctcgac | cccaaaaaac | ttgattaggg | tgatggttca | cgtagtgggc | 420 |
| catcgccctg | atagacggtt | tttcgccctt | tgacgttgga | gtccacgttc | tttaatagtg | 480 |
| gactcttgtt | ccaaactgga | acaacactca | accctatctc | ggtctattct | tttgatttat | 540 |
| aagggatttt | gccgatttcg | gcctattggt | taaaaaatga | gctgatttaa | caaaaattta | 600 |
| acgcgaattt | taacaaaata | ttaacgctta | caatttcctg | atgcggtatt | ttctccttac | 660 |
| gcatctgtgc | ggtatttcac | accgcatatg | gtgcactctc | agtacaatct | gctctgatgc | 720 |
| cgcatagtta | agccagcccc | gacacccgcc | aacacccgct | gacgcgccct | gacgggcttg | 780 |
| tctgctcccg | gcatccgctt | acagacaagc | tgtgaccgtc | tccgggagct | gcatgtgtca | 840 |
| gaggttttca | ccgtcatcac | cgaaacgcgc | gagacgaaag | gcctcgtga | tacgcctatt | 900 |
| tttataggtt | aatgtcatga | taataatggt | tccttagacg | tcaggtggca | cttttcgggg | 960 |
| aaatgtgcgc | ggaaccccta | tttgtttatt | tttctaaata | cattcaaata | tgtatccgct | 1020 |
| catgagacaa | taaccctgat | aaatgcttca | ataatattga | aaaggaaga | gtatgagtat | 1080 |
| tcaacatttc | cgtgtcgccc | ttattccctt | ttttgcggca | ttttgccttc | ctgttttgc | 1140 |
| tcacccagaa | acgctggtga | aagtaaaaga | tgctgaagat | cagttgggtg | cacgagtggg | 1200 |
| ttacatcgaa | ctggatctca | acagcggtaa | gatccttgag | agttttcgcc | ccgaagaacg | 1260 |
| ttttccaatg | atgagcactt | ttaaagttct | gctatgtggc | gcggtattat | cccgtattga | 1320 |
| cgccgggcaa | gagcaactcg | gtcgccgcat | acactattct | cagaatgact | tggttgagta | 1380 |
| ctcaccagtc | acagaaaagc | atcttacgga | tggcatgaca | gtaagagaat | tatgcagtgc | 1440 |
| tgccataacc | atgagtgata | acactgcggc | caacttactt | ctgacaacga | tcggaggacc | 1500 |
| gaaggagcta | accgcttttt | tgcacaacat | gggggatcat | gtaactcgcc | ttgatcgttg | 1560 |
| ggaaccggag | ctgaatgaag | ccataccaaa | cgacgagcgt | gacaccacga | tgcctgtagc | 1620 |
| aatggcaaca | acgttgcgca | aactattaac | tggcgaacta | cttactctag | cttcccggca | 1680 |
| acaattaata | gactggatgg | aggcggataa | agttgcagga | ccacttctgc | gctcggccct | 1740 |
| tccggctggc | tggtttattg | ctgataaatc | tggagccggt | gagcgtgggt | ctcgcggtat | 1800 |
| cattgcagca | ctggggccag | atggtaagcc | ctcccgtatc | gtagttatct | acacgacggg | 1860 |
| gagtcaggca | actatggatg | aacgaaatag | acagatcgct | gagataggtg | cctcactgat | 1920 |
| taagcattgg | taactgtcag | accaagttta | ctcatatata | ctttagattg | atttaaaact | 1980 |
| tcatttttaa | tttaaaagga | tctaggtgaa | gatcctttt | gataatctca | tgaccaaaat | 2040 |
| cccttaacgt | gagttttcgt | tccactgagc | gtcagacccc | gtagaaaaga | tcaaaggatc | 2100 |
| ttcttgagat | cctttttttc | tgcgcgtaat | ctgctgcttg | caaacaaaaa | aaccaccgct | 2160 |

```
accagcggtg gtttgtttgc cggatcaaga gctaccaact cttttttccga aggtaactgg    2220 cttcagcaga gcgcagatac caaatactgt tcttctagtg tagccgtagt taggccacca    2280
cttcaagaac tctgtagcac cgcctacata cctcgctctg ctaatcctgt taccagtggc    2340
tgctgccagt ggcgataagt cgtgtcttac cgggttggac tcaagacgat agttaccgga    2400
taaggcgcag cggtcgggct gaacgggggg ttcgtgcaca cagcccagct tggagcgaac    2460
gacctacacc gaactgagat acctacagcg tgagctatga gaaagcgcca cgcttcccga    2520
agggagaaag gcggacaggt atccggtaag cggcagggtc ggaacaggag agcgcacgag    2580
ggagcttcca gggggaaacg cctggtatct ttatagtcct gtcgggtttc gccacctctg    2640
acttgagcgt cgattttttgt gatgctcgtc agggggggcgg agcctatgga aaaacgccag    2700
caacgcggcc tttttacggt tcctggcctt ttgctggcct tttgctcaca tgttctttcc    2760
tgcgttatcc cctgattctg tggataaccg tattaccgcc tttgagtgag ctgataccgc    2820
tcgccgcagc cgaacgaccg agcgcagcga gtcagtgagc gaggaagcgg aagagcgccc    2880
aatacgcaaa ccgcctctcc ccgcgcgttg gccgattcat taatgcagct ggcacgacag    2940
gtttcccgac tggaaagcgg gcagtgagcg caacgcaatt aatgtgagtt agctcactca    3000
ttaggcaccc caggctttac actttatgct tccggctcgt atgttgtgtg gaattgtgag    3060
cggataacaa tttcacacag gaaacagcta tgaccatgat tacgccaagc tatttaggtg    3120
acactataga atactcaagc ggccgcctac tccaagaata tcaaagatac agtctcagaa    3180
gaccaaaggg ctattgagac ttttcaacaa agggtaatat cgggaaacct cctcggattc    3240
cattgcccag ctatctgtca cttcatcaaa aggacagtag aaaaggaagg tggcacctac    3300
aaatgccatc attgcgataa aggaaaggct atcgttcaag atgcctctgc cgacagtggt    3360
cccaaagatg gaccccacc cacgaggagc atcgtggaaa aagaagacgt tccaaccacg    3420
tcttcaaagc aagtggattg atgtgatcta ctccaagaat atcaaagata cagtctcaga    3480
agaccaaagg gctattgaga cttttcaaca aagggtaata tcgggaaacc tcctcggatt    3540
ccattgccca gctatctgtc acttcatcaa aaggacagta gaaaaggaag gtggcaccta    3600
caaatgccat cattgcgata aaggaaaggc tatcgttcaa gatgcctctg ccgacagtgg    3660
tcccaaagat ggaccccac ccacgaggag catcgtggaa aaagaagacg ttccaaccac    3720
gtcttcaaag caagtggatt gatgtgatat ctccactgac gtaagggatg acgcacaatc    3780
ccactatcct tcgcaagacc cttcctctat ataaggaagt tcatttcatt tggagaggta    3840
ttaaaatttt cataagattt gaaattttga taaaccgcga tcacaggttg ccgcaccta    3900 aaaccggaaa caaagcaat cgttacttga tttcaagaat cttccaattt cttcctactt    3960
cttggtgtac gatttcttaa gagaaagaaa atcactctct gtgctggcca cagacttcgt    4020
gaatcatttt cttttccact cttagtttat ttgctgaaca ctctcctatt tgatatagga    4080
cttcgtgtca gatttaaact ttttctgttt ctttctcagt tctctgctta atttcaagtt    4140
taagctggtg aaatcttgga ttagtgctcc cactctccta tctggtatag gacttcgtgg    4200
gtagactttt ctatttctgt cttttctttc actctcttct tctcactgat ccgcattgcc    4260
gttcaaagtg gtcttatttg aaaaacactt gggcgttggt gcaaatgttt gcttcgttaa    4320
ttttctctgg ggacaacagg ctcactgaga aaacaatttt tacttgcaga gatttggaca    4380
tcttggttgt ttattataca atagcaactc aatttagaaa atttctaccg cattacatta    4440
ggtggcatct gtatacctttg ttgatctaca ttctcccatc ttttctcact gctgaaatta    4500
aatataagcg gaatctgagt aatattcata tttctggctt attttacgac ggcagatata    4560
```

```
aattctggac taaacacgag aaaaatcttg ctttgacaga agaggaaaag atggaagtga   4620
ttagaaacaa aggcattcct gctgatgttc ttgcaaagcg agctcatgaa tttgaaaaac   4680
atgttgctca tgaaagcctc aaggatcaaa ttcctgctgt tgacaagttg tattctacta   4740
aggttaataa gtttgcaaaa attatgaacc ttagacaaag tgttgttggt gatcttaaac   4800
ttcttactga tgggaagttg tatgagggta agcatattcc tgtatctaat attagtgcag   4860
gggagaatca tgtagttcaa atacccctaa tggcacagga ggaaattctg tcttctagtg   4920
caagtgattt cagaactgca atggtgagta aaaatagcaa gcctcaagct actgcaatgc   4980
atgtaggagc tatagaaatt atcattgata gtttcgcaag tcctgactgc aacatagttg   5040
gtgcaatgct tttggttgat acttatcata ccaatcctga aaatgcagtt cgtagtattt   5100 tgttgcgcc tttcagaggc ggaaggccca ttcgggtggt tacatttccg aataccattg   5160
tgcagattga accagacatg aattcaaggt ttcagctttt gagtaccact accaatggtg   5220
attttgttca aggaaaagat ctcgcaatgg ttaaagttaa tgtagcatgt gctgctgttg   5280
gcttgacatc aagttacact ccaactccac tgttggaatc tggtttgcaa aaagacagag   5340
ggttaattgt ggatattttt ggaaggatgt cttacgttgc tcataacgtt aatcagcccc   5400
aagagaaaga tttgttggag ggaaattttt cctttgatat taaatctcgc tctagattgg   5460
aaaaagtttc ttctactaaa gcacaatttg ttagtgaaaa accttcaaa tatgatataa   5520 ttggtgctgg ttcacattct tcagaagatt ttcctaaaaa agaagatcaa gaaaaaccca   5580
aaaagattga tgccagattg agacaaagaa tagatcccca atacaatgag gttcaggctc   5640
agatggaaac aaatttgttt aaattgtctc ttgatgatgt tgaaactcct aaaggttcca   5700
tgttggatct taaaatttct caatctaaaa ttgcacttcc caaaaacaca gttggaggaa   5760
ccattctgcg tagtgatcta ttggcaaatt ttttgacaga gggcaatttt agagcaagtg   5820
ttgatttgca gcgcactcat cgtattaaag gaatgattaa atggtggcc acagttggta   5880 ttcctgagaa tacaggtata tcattggcct gtgctatgaa tagttctttt aggggggcgtg   5940 ccagttctga tatttacacc atctgctctc aagactgtga attatggaat cctgcttgca   6000
caaaagcaat gactatgtca tttaatccaa acccgtgttc tgatgcatgg agtttggaat   6060
ttttgaagcg taccggattt cattgtgata tcatttgtgt cactggatgg actgccaccc   6120
caatgcagga tgttcaggtt acaattgatt ggtttatttc ctctcaggaa tgtgttccca   6180
ggacctattg tgttttaaat ccacaaaatc cttttgtgtt aaataggtgg atgggcaaac   6240 tgacttccc ccagggcact tcccgaagtg ttaaaagaat gcctctttct ataggggag   6300 gagctggtgc aaagaatgct attctcatga atatgccaaa tgctgttctt tcaatgtgga   6360
gatattttgt tggagatctc gtctttgaag tttctaagat gacttctccc tacattaaat   6420
gtacagtctc tttcttcata gcatttggaa atttggctga tgcaccatt aattttgagg   6480 cttttcccca aagctggtg cagtttggag aaattcagga aaaagttgta ttgaaattt   6540 cacaagagga atttcttaca gcttggtcaa ctcaggtgcg tcctgcaaca actctgttgg   6600
ctgatgggtg tccatatttg tatgctatgg tgcatgatag ttcagtgtct acaataccag   6660
gtgattttgt cattggtgtt aagttggcaa ccataaacaa tatgtgtgca tatgggctca   6720
atcctggtat tcaggttct cgtctttttgg gcaccattcc tcagtccatt tcacagcaaa   6780
ctgtttggaa tcagatggca acagtgagaa caccattgaa ttttgatcct agcaagcaga   6840
gcttttgtca atttctctatt gaccttctcg gtggaggaat tttagtggac aaaactggag   6900
attggatcac acttatacaa aattctccaa ttagtaactt gttgagagtt gctgcttgga   6960
```
agaaaggctg tttaatggtt aagattgtga tgtctgggaa tgcagcagtc aaaaggagtg 7020
attgggcctc attggtacaa gtgtttttaa caaacagcaa cagtacagag cattttgatg 7080
catgtaagtg gacaaaatcg gaaccacatt cctgggaatt gatcttccca atagaggtgt 7140
gtggtcctaa caatggtttt gaaatgtgga gttctgagtg ggcaaatcaa acttcatggc 7200
atttgagttt ccttattgac aatcccaaac agtctacagt tttgacattt ctcctgggaa 7260
tttcccaaga ttttgaaatt gctggtaata ctcttatgcc agctttttct gttccacagg 7320
ctactgccag atcttctgaa aatgcggaat cctctgcatg aggatccgcg tcgactccag 7380
gcctcgagag atctctggaa tttgtgtttt ctttcgtttg ttcgcttgtt taattcaata 7440
aaggaaatta ggcatgaccc tctcgttgag tatgctctgt ctatttgaaa atttccacac 7500
ctcttttaat tgtcgtaatg atgtgtgaag tgtgtgttat tttaaaaaaa aaaaaaaaaa 7560
aatcgatagc tcgaatttcc ccgatcgttc aaacatttgg caataaagtt tcttaagatt 7620
gaatcctgtt gccggtcttg cgatgattat catataattt ctgttgaatt acgttaagca 7680
tgtaataatt aacatgtaat gcatgacgtt atttatgaga tgggttttta tgattagagt 7740
cccgcaatta tacatttaat acgcgataga aaacaaaata tagcgcgcaa actaggataa 7800
attatcgcgc gcggtgtcat ctatgttact agatcgggaa ttccaattcg ccctatagtg 7860
agtcgtatta caattcactg gccgtcgttt tacaacgtcg tgactgggaa aaccctggcg 7920
ttacccaact taatcgcctt gcagcacatc ccccttttcgc cagctggcgt aatagcgaag 7980
aggcccgcac cgatcgccct tcccaacagt tgcgcagcct gaatggcgaa tggacgcgcc 8040
ctgtagcggc gcattaagcg cggcggg 8067

<210> SEQ ID NO 5
<211> LENGTH: 9014
<212> TYPE: DNA
<213> ORGANISM: Bean Pod Mottle Virus

<400> SEQUENCE: 5
tatagtgagt cgtattacaa ttcactggcc gtcgttttac aacgtcgtga ctgggaaaac 60
cctggcgtta cccaacttaa tcgccttgca gcacatcccc ctttcgccag ctggcgtaat 120
agcgaagagg cccgcaccga tcgcccttcc caacagttgc gcagcctgaa tggcgaatgg 180
acgcgccctg tagcggcgca ttaagcgcgg cgggtgtggt ggttacgcgc agcgtgaccg 240
ctacacttgc cagcgcccta gcgcccgctc ctttcgcttt cttcccttcc tttctcgcca 300
cgttcgccgg ctttccccgt caagctctaa atcgggggct ccctttaggg ttccgattta 360
gtgctttacg gcacctcgac cccaaaaaac ttgattaggg tgatggttca cgtagtgggc 420
catcgccctg atagacggtt tttcgccctt tgacgttgga gtccacgttc tttaatagtg 480
gactcttgtt ccaaactgga acaacactca accctatctc ggtctattct tttgatttat 540
aagggatttt gccgatttcg gcctattggt taaaaaatga gctgatttaa caaaaattta 600
acgcgaattt taacaaaata ttaacgctta caatttcctg atgcggtatt ttctccttac 660
gcatctgtgc ggtatttcac accgcatatg gtgcactctc agtacaatct gctctgatgc 720
cgcatagtta agccagcccc gacacccgcc aacacccgct gacgcgccct gacgggcttg 780
tctgctcccg gcatccgctt acagacaagc tgtgaccgtc tccgggagct gcatgtgtca 840
gaggttttca ccgtcatcac cgaaacgcgc gagacgaaag ggcctcgtga tacgcctatt 900
tttataggtt aatgtcatga taataatggt ttcttagacg tcaggtggca cttttcgggg 960
aaatgtgcgc ggaaccccta tttgtttatt tttctaaata cattcaaata tgtatccgct 1020

```
catgagacaa taaccctgat aaatgcttca ataatattga aaaggaaga gtatgagtat   1080 tcaacatttc cgtgtcgccc ttattccctt ttttgcggca ttttgccttc ctgttttttgc  1140 tcacccagaa acgctggtga aagtaaaaga tgctgaagat cagttgggtg cacgagtggg   1200
ttacatcgaa ctggatctca acagcggtaa gatccttgag agttttcgcc ccgaagaacg   1260
ttttccaatg atgagcactt ttaaagttct gctatgtggc gcggtattat cccgtattga   1320
cgccgggcaa gagcaactcg gtcgccgcat acactattct cagaatgact tggttgagta   1380
ctcaccagtc acagaaaagc atcttacgga tggcatgaca gtaagagaat tatgcagtgc   1440
tgccataacc atgagtgata acactgcggc caacttactt ctgacaacga tcggaggacc   1500
gaaggagcta accgcttttt tgcacaacat gggggatcat gtaactcgcc ttgatcgttg   1560
ggaaccggag ctgaatgaag ccataccaaa cgacgagcgt gacaccacga tgcctgtagc   1620
aatggcaaca acgttgcgca aactattaac tggcgaacta cttactctag cttcccggca   1680
acaattaata gactggatgg aggcggataa agttgcagga ccacttctgc gctcggccct   1740
tccggctggc tggtttattg ctgataaatc tggagccggt gagcgtgggt ctcgcggtat   1800
cattgcagca ctggggccag atggtaagcc ctcccgtatc gtagttatct acacgacggg   1860
gagtcaggca actatggatg aacgaaatag acagatcgct gagataggtg cctcactgat   1920
taagcattgg taactgtcag accaagttta ctcatatata ctttagattg atttaaaact   1980 tcattttta tttaaaagga tctaggtgaa gatcctttt gataatctca tgaccaaaat   2040
cccttaacgt gagttttcgt tccactgagc gtcagacccc gtagaaaaga tcaaaggatc   2100
ttcttgagat cctttttttc tgcgcgtaat ctgctgcttg caaacaaaaa aaccaccgct   2160
accagcggtg gtttgtttgc cggatcaaga gctaccaact ctttttccga aggtaactgg   2220
cttcagcaga gcgcagatac caaatactgt tcttctagtg tagccgtagt taggccacca   2280
cttcaagaac tctgtagcac cgcctacata cctcgctctg ctaatcctgt taccagtggc   2340
tgctgccagt ggcgataagt cgtgtcttac cgggttggac tcaagacgat agttaccgga   2400
taaggcgcag cggtcgggct gaacggggggg ttcgtgcaca cagcccagct tggagcgaac   2460
gacctacacc gaactgagat acctacagcg tgagctatga gaaagcgcca cgcttcccga   2520
agggagaaag gcggacaggt atccggtaag cggcagggtc ggaacaggag agcgcacgag   2580
ggagcttcca gggggaaacg cctggtatct ttatagtcct gtcgggtttc gccacctctg   2640
acttgagcgt cgatttttgt gatgctcgtc aggggggcgg agcctatgga aaaacgccag   2700
caacgcggcc ttttacggt tcctggcctt ttgctggcct tttgctcaca tgttctttcc   2760
tgcgttatcc cctgattctg tggataaccg tattaccgcc tttgagtgag ctgataccgc   2820
tcgccgcagc cgaacgaccg agcgcagcga gtcagtgagc gaggaagcgg aagagcgccc   2880
aatacgcaaa ccgcctctcc ccgcgcgttg gccgattcat taatgcagct ggcacgacag   2940
gtttcccgac tggaaagcgg gcagtgagcg caacgcaatt aatgtgagtt agctcactca   3000
ttaggcaccc caggctttac actttatgct tccggctcgt atgttgtgtg gaattgtgag   3060
cggataacaa tttcacacag gaaacagcta tgaccatgat tacgccaagc tatttaggtg   3120
acactataga atactcaagc ggccgcctac tccaagaata tcaaagatac agtctcagaa   3180
gaccaaaggg ctattgagac ttttcaacaa agggtaatat cggaaaacct cctcggattc   3240
cattgcccag ctatctgtca cttcatcaaa aggacagtag aaaaggaagg tggcacctac   3300
aaatgccatc attgcgataa aggaaggct atcgttcaag atgcctctgc cgacagtggt   3360
cccaaagatg gaccccccacc cacgaggagc atcgtggaaa aagaagacgt tccaaccacg   3420
```

```
tcttcaaagc aagtggattg atgtgatcta ctccaagaat atcaaagata cagtctcaga    3480
agaccaaagg gctattgaga cttttcaaca aagggtaata tcgggaaacc tcctcggatt    3540
ccattgccca gctatctgtc acttcatcaa aaggacagta gaaaaggaag gtggcaccta    3600
caaatgccat cattgcgata aaggaaaggc tatcgttcaa gatgcctctg ccgacagtgg    3660
tcccaaagat ggaccccac ccacgaggag catcgtggaa aaagaagacg ttccaaccac    3720
gtcttcaaag caagtggatt gatgtgatat ctccactgac gtaagggatg acgcacaatc    3780
ccactatcct tcgcaagacc cttcctctat ataaggaagt tcatttcatt tggagaggta    3840
ttaaaatttt cataagattt gaaattttga taaaccgcga tcacaggttg ccgcaccta    3900 aaaccggaaa caaagcaat cgttacttga tttcaagaat cttccaattt cttcctactt    3960
cttggtgtac gatttcttaa gagaaagaaa atcactctct gtgctggcca cagacttcgt    4020
gaatcatttt cttttccact cttagtttat ttgctgaaca ctctcctatt tgatataggga    4080 cttcgtgtca gatttaaact ttttctgttt cttttctcagt tctctgctta atttcaagtt    4140
taagctggtg aaatcttgga ttagtgctcc cactctccta tctggtatag gacttcgtgg    4200
gtagactttt ctatttctgt cttttctttc actctcttct tctcactgat ccgcattgcc    4260
gttcaaagtg gtcttatttg aaaaacactt gggcgttggt gcaaatgttt gcttcgttaa    4320
ttttctctgg gacaacagg ctcactgaga aaacaatttt tacttgcaga gatttggaca    4380
tcttggttgt ttattataca atagcaactc aatttagaaa atttctaccg cattacatta    4440
ggtggcatct gtataccttg ttgatctaca ttctcccatc ttttctcact gctgaaatta    4500
aatataagcg gaatctgagt aatattcata tttctggctt attttacgac ggcagatata    4560
aattctggac taaacacgag aaaaatcttg ctttgacaga agaggaaaag atggaagtga    4620
ttagaaacaa aggcattcct gctgatgttc ttgcaaagcg agctcatgaa tttgaaaaac    4680
atgttgctca tgaaagcctc aaggatcaaa ttcctgctgt tgacaagttg tattctacta    4740
aggttaataa gtttgcaaaa attatgaacc ttagacaaag tgttgttggt gatcttaaac    4800
ttcttactga tgggaagttg tatgagggta agcatattcc tgtatctaat attagtgcag    4860
gggagaatca tgtagttcaa ataccctaa tggcacagga ggaaattctg tcttctagtg    4920
caagtgattt cagaactgca atggtgagta aaaatagcaa gcctcaagct actgcaatgc    4980
atgtaggagc tatagaaatt atcattgata gtttcgcaag tcctgactgc aacatagttg    5040
gtgcaatgct tttggttgat acttatcata ccaatcctga aaatgcagtt cgtagtattt    5100
ttgttgcgcc tttcagaggc ggaaggccca ttcgggtggt tacatttccg aataccattg    5160
tgcagattga accagacatg aattcaaggt ttcagctttt gagtaccact accaatggtg    5220
attttgttca aggaaaagat ctcgcaatgg ttaaagttaa tgtagcatgt gctgctgttg    5280
gcttgacatc aagttacact ccaactccac tgttggaatc tggtttgcaa aaagacagag    5340
ggttaattgt ggaatatttt ggaaggatgt cttacgttgc tcataacgtt aatcagcccc    5400
aagagaaaga tttgttggag ggaaattttt cctttgatat taaatctcgc tctagattgg    5460
aaaaagtttc ttctactaaa gcacaatttg ttagtggaaa aaccttcaaa tatgatataa    5520
ttggtgctgg ttcacattct tcagaagatt ttcctaaaaa agaagatcaa gaaaaaccca    5580
aaaagattga tgccagattg agacaaagaa tagatcccca atacaatgag gttcaggctc    5640
agatggagac caacctcttc aagctcagct tggacgacgt agagacacca aagggaagcc    5700
tcgagatgag taaaggagaa gaacttttca ctggagttgt cccaattctt gttgaattag    5760
atggtgatgt taatgggcac aaattttctg tcagtggaga gggtgaaggt gatgcaacat    5820
```

```
acggaaaact taccottaaa tttatttgca ctactggaaa actacctgtt ccatggccaa    5880
cacttgtcac tactttctct tatggtgttc aatgcttttc aagataccca gatcatatga    5940
agcggcacga cttcttcaag agcgccatgc ctgagggata cgtgcaggag aggaccatct    6000 cttcaagga cgacgggaac tacaagacac gtgctgaagt caagtttgag ggagacaccc    6060
tcgtcaacag gatcgagctt aagggaatcg atttcaagga ggacggaaac atcctcggcc    6120
acaagttgga atacaactac aactcccaca acgtatacat cacggcagac aaacaaaaga    6180
atggaatcaa agctaacttc aaaattagac acaacattga agatgaagc gttcaactag    6240 cagaccatta tcaacaaaat actccaattg gcgatggccc tgtccttta ccagacaacc    6300 attacctgtc cacacaatct gccctttcga aagatcccaa cgaaaagaga gaccacatgg    6360
tccttcttga gtttgtaaca gctgctggga ttacacatgg catggatgaa ctatacaaac    6420
ccggggcccc agctaagcaa ttgctgaatt tcgatctctt gaaactggct ggagatgtag    6480
aatcaaatcc aggcccgatg gaaacaaatt tgtttaaatt gtctcttgat gatgttgaaa    6540
ctcctaaagg ttccatgttg gatcttaaaa tttctcaatc taaaattgca cttcccaaaa    6600
acacagttgg aggaaccatt ctgcgtagtg atctattggc aaattttttg acagagggca    6660
attttagagc aagtgttgat ttgcagcgca ctcatcgtat taaaggaatg attaaaatgg    6720
tggccacagt tggtattcct gagaatacag gtatatcatt ggcctgtgct atgaatagtt    6780
cttttagggg gcgtgccagt tctgatattt acaccatctg ctctcaagac tgtgaattat    6840
ggaatcctgc ttgcacaaaa gcaatgacta tgtcatttaa tccaaacccg tgttctgatg    6900
catggagttt ggaattttg aagcgtaccg gatttcattg tgatatcatt tgtgtcactg    6960
gatggactgc cacccaatg caggatgttc aggttacaat tgattggttt atttcctctc    7020
aggaatgtgt tcccaggacc tattgtgttt taaatccaca aaatcctttt gtgttaaata    7080
ggtggatggg caaactgact ttcccccagg gcacttcccg aagtgttaaa agaatgcctc    7140
tttctatagg gggaggagct ggtgcaaaga atgctattct catgaatatg ccaaatgctg    7200
ttctttcaat gtggagatat tttgttggag atctcgtctt tgaagtttct aagatgactt    7260
ctccctacat taaatgtaca gtctctttct tcatagcatt tggaaatttg gctgatgaca    7320
ccattaattt tgaggctttt ccccacaagc tggtgcagtt tggagaaatt caggaaaaag    7380
ttgtattgaa atttcacaa gaggaatttc ttacagcttg gtcaactcag gtgcgtcctg    7440
caacaactct gttggctgat gggtgtccat atttgtatgc tatggtgcat gatagttcag    7500
tgtctacaat accaggtgat tttgtcattg gtgttaagtt ggcaaccata aacaatatgt    7560
gtgcatatgg gctcaatcct ggtatttcag gttctcgtct tttgggcacc attcctcagt    7620
ccatttcaca gcaaactgtt tggaatcaga tggcaacagt gagaacacca ttgaattttg    7680
atcctagcaa gcagagcttt tgtcaattt ctattgacct tctcggtgga ggaattttag    7740
tggacaaaac tggagattgg atcacactta tacaaaattc tccaattagt aacttgttga    7800
gagttgctgc ttggaagaaa ggctgtttaa tggttaagat tgtgatgtct gggaatgcag    7860
cagtcaaaag gagtgattgg gcctcattgg tacaagtgtt tttaacaaac agcaacagta    7920
cagagcattt tgatgcatgt aagtggacaa aatcggaacc acattcctgg gaattgatct    7980
tcccaataga ggtgtgtggt cctaacaatg gttttgaaat gtggagttct gagtgggcaa    8040
atcaaacttc atggcatttg agtttcctta ttgacaatcc caaacagtct acagttttg    8100 acattctcct gggaatttcc caagattttg aaattgctgg taatactctt atgccagctt    8160
tttctgttcc acaggctact gccagatctt ctgaaaatgc ggaatcctct gcatgaggat    8220
```

```
cccagaaaga acagcgcctt ccattgaagc taaatatttt tgttttgtgt aatctccagc    8280
taaatagaaa ccttctatag gagatctttg aatgggtcga caaggttcac aatttggaac    8340
agttttgtaa accgaccttg gtgttttaac aacatggtac ttgagaatct tagctttgct    8400
ttggtctgca gaaatttcat caggaaagag tttggcaagc tcagtcatcg tggcttgaat    8460
aatatcatcg tcactacgtg aaatccattc ttcggctggt gcaaaaacca actctaacat    8520
tgactggttt gggctataat attccttgcg gatcctctgg aatttgtgtt ttctttcgtt    8580
tgttcgcttg tttaattcaa taaaggaaat taggcatgac cctctcgttg agtatgctct    8640
gtctatttga aaatttccac acctctttta attgtcgtaa tgatgtgtga agtgtgtgtt    8700
attttaaaaa aaaaaaaaaa aaaatcgata gctcgaattt ccccgatcgt tcaaacatttt   8760 ggcaataaag tttcttaaga ttgaatcctg ttgccggtct tgcgatgatt atcatataat    8820
ttctgttgaa ttacgttaag catgtaataa ttaacatgta atgcatgacg ttatttatga    8880
gatgggtttt tatgattaga gtcccgcaat tatacattta atacgcgata gaaaacaaaa    8940
tatagcgcgc aaactaggat aaattatcgc gcgcggtgtc atctatgtta ctagatcggg    9000
aattccaatt cgcc                                                      9014

<210> SEQ ID NO 6
<211> LENGTH: 9311
<212> TYPE: DNA
<213> ORGANISM: Bean Pod Mottle Virus

<400> SEQUENCE: 6
tatagtgagt cgtattacaa ttcactggcc gtcgttttac aacgtcgtga ctgggaaaac      60
cctggcgtta cccaacttaa tcgccttgca gcacatcccc ctttcgccag ctggcgtaat    120
agcgaagagg cccgcaccga tcgcccttcc caacagttgc gcagcctgaa tggcgaatgg    180
acgcgccctg tagcggcgca ttaagcgcgg cgggtgtggt ggttacgcgc agcgtgaccg    240
ctacacttgc cagcgcccta gcgcccgctc ctttcgcttt cttcccttcc tttctcgcca    300
cgttcgccgg ctttccccgt caagctctaa atcgggggct ccctttaggg ttccgattta    360
gtgctttacg gcacctcgac cccaaaaaac ttgattaggg tgatggttca cgtagtgggc    420
catcgccctg atagacggtt tttcgccctt tgacgttgga gtccacgttc tttaatagtg    480
gactcttgtt ccaaactgga acaacactca accctatctc ggtctattct tttgatttat    540
aagggatttt gccgatttcg gcctattggt taaaaatga gctgatttaa caaaatttta   600
acgcgaattt taacaaaata ttaacgctta caatttcctg atgcggtatt ttctccttac    660
gcatctgtgc ggtatttcac accgcatatg gtgcactctc agtacaatct gctctgatgc    720
cgcatagtta agccagcccc gacacccgcc aacacccgct gacgcgccct gacgggcttg    780
tctgctcccg gcatccgctt acagacaagc tgtgaccgtc tccgggagct gcatgtgtca    840
gaggttttca ccgtcatcac cgaaacgcgc gagacgaaag gcctcgtga tacgcctatt      900 tttataggtt aatgtcatga taataatggt ttcttagacg tcaggtggca cttttcgggg    960
aaatgtgcgc ggaaccccta tttgtttatt tttctaaata cattcaaata tgtatccgct   1020
catgagacaa taaccctgat aaatgcttca ataatattga aaaggaaga gtatgagtat    1080 tcaacatttc cgtgtcgccc ttattccctt ttttgcggca ttttgccttc ctgttttgc    1140 tcacccagaa acgctggtga agtaaaaga tgctgaagat cagttgggtg cacgagtggg    1200
ttacatcgaa ctggatctca acagcggtaa gatccttgag agttttcgcc ccgaagaacg    1260
ttttccaatg atgagcactt ttaaagttct gctatgtggc gcggtattat cccgtattga    1320
```

```
cgccgggcaa gagcaactcg gtcgccgcat acactattct cagaatgact tggttgagta    1380
ctcaccagtc acagaaaagc atcttacgga tggcatgaca gtaagagaat tatgcagtgc    1440
tgccataacc atgagtgata acactgcggc caacttactt ctgacaacga tcggaggacc    1500
gaaggagcta accgcttttt tgcacaacat gggggatcat gtaactcgcc ttgatcgttg    1560
ggaaccggag ctgaatgaag ccataccaaa cgacgagcgt gacaccacga tgcctgtagc    1620
aatggcaaca acgttgcgca aactattaac tggcgaacta cttactctag cttcccggca    1680
acaattaata gactggatgg aggcggataa agttgcagga ccacttctgc gctcggccct    1740
tccggctggc tggtttattg ctgataaatc tggagccggt gagcgtgggt ctcgcggtat    1800
cattgcagca ctggggccag atggtaagcc ctcccgtatc gtagttatct acacgacggg    1860
gagtcaggca actatggatg aacgaaatag acagatcgct gagataggtg cctcactgat    1920
taagcattgg taactgtcag accaagttta ctcatatata ctttagattg atttaaaact    1980
tcattttttaa tttaaaagga tctaggtgaa gatcctttttt gataatctca tgaccaaaat    2040
cccttaacgt gagttttcgt tccactgagc gtcagacccc gtagaaaaga tcaaaggatc    2100
ttcttgagat cctttttttc tgcgcgtaat ctgctgcttg caaacaaaaa aaccaccgct    2160
accagcggtg gtttgtttgc cggatcaaga gctaccaact cttttttccga aggtaactgg    2220
cttcagcaga gcgcagatac caaatactgt tcttctagtg tagccgtagt taggccacca    2280
cttcaagaac tctgtagcac cgcctacata cctcgctctg ctaatcctgt taccagtggc    2340
tgctgccagt ggcgataagt cgtgtcttac cgggttggac tcaagacgat agttaccgga    2400
taaggcgcag cggtcgggct gaacgggggg ttcgtgcaca cagcccagct tggagcgaac    2460
gacctacacc gaactgagat acctacagcg tgagctatga aaagcgcca cgcttcccga    2520
agggagaaag gcggacaggt atccggtaag cggcagggtc ggaacaggag agcgcacgag    2580
ggagcttcca gggggaaacg cctggtatct ttatagtcct gtcgggtttc gccacctctg    2640
acttgagcgt cgatttttgt gatgctcgtc aggggggcgg agcctatgga aaaacgccag    2700
caacgcggcc ttttttacggt tcctggcctt ttgctggcct tttgctcaca tgttcttttcc    2760
tgcgttatcc cctgattctg tggataaccg tattaccgcc tttgagtgag ctgataccgc    2820
tcgccgcagc cgaacgaccg agcgcagcga gtcagtgagc gaggaagcgg aagagcgccc    2880
aatacgcaaa ccgcctctcc ccgcgcgttg gccgattcat taatgcagct ggcacgacag    2940
gtttcccgac tggaaagcgg gcagtgagcg caacgcaatt aatgtgagtt agctcactca    3000
ttaggcaccc caggctttac actttatgct tccggctcgt atgttgtgtg gaattgtgag    3060
cggataacaa tttcacacag gaaacagcta tgaccatgat tacgccaagc tatttaggtg    3120
acactataga atactcaagc ggccgcctac tccaagaata tcaaagatac agtctcagaa    3180
gaccaaaggg ctattgagac ttttcaacaa agggtaatat cgggaaacct cctcggattc    3240
cattgcccag ctatctgtca cttcatcaaa aggacagtag aaaaggaagg tggcacctac    3300
aaatgccatc attgcgataa aggaaaggct atcgttcaag atgcctctgc cgacagtggt    3360
cccaaagatg gaccccccacc cacgaggagc atcgtggaaa aagaagacgt tccaaccacg    3420
tcttcaaagc aagtggattg atgtgatcta ctccaagaat atcaaagata cagtctcaga    3480
agaccaaagg gctattgaga cttttcaaca agggtaata tcgggaaacc cctcggatt    3540
ccattgccca gctatctgtc acttcatcaa aaggacagta gaaaaggaag gtggcaccta    3600
caaatgccat cattgcgata aaggaaaggc tatcgttcaa gatgcctctg ccgacagtgg    3660
tcccaaagat ggaccccccac ccacgaggag catcgtggaa aagaagacg ttccaaccac    3720
```

```
gtcttcaaag caagtggatt gatgtgatat ctccactgac gtaagggatg acgcacaatc   3780
ccactatcct tcgcaagacc cttcctctat ataaggaagt tcatttcatt tggagaggta   3840
ttaaaatttt cataagattt gaaattttga taaaccgcga tcacaggttg ccgcacctta   3900
aaaccggaaa caaaagcaat cgttacttga tttcaagaat cttccaattt cttcctactt   3960
cttggtgtac gatttcttaa gagaaagaaa atcactctct gtgctggcca cagacttcgt   4020
gaatcatttt cttttccact cttagtttat ttgctgaaca ctctcctatt tgatatagga   4080
cttcgtgtca gatttaaact ttttctgttt cttttctcagt tctctgctta atttcaagtt   4140
taagctggtg aaatcttgga ttagtgctcc cactctccta tctggtatag gacttcgtgg   4200
gtagactttt ctatttctgt cttttctttc actctcttct tctcactgat ccgcattgcc   4260
gttcaaagtg gtcttatttg aaaaacactt gggcgttggt gcaaatgttt gcttcgttaa   4320
ttttctctgg ggacaacagg ctcactgaga aaacaatttt tacttgcaga gatttggaca   4380
tcttggttgt ttattataca atagcaactc aatttagaaa atttctaccg cattacatta   4440
ggtggcatct gtataccttg ttgatctaca ttctcccatc ttttctcact gctgaaatta   4500
aatataagcg gaatctgagt aatattcata tttctggctt attttacgac ggcagatata   4560
aattctggac taaacacgag aaaaatcttg ctttgacaga gaggaaaag atggaagtga   4620 ttagaaacaa aggcattcct gctgatgttc ttgcaaagcg agctcatgaa tttgaaaaac   4680
atgttgctca tgaaagcctc aaggatcaaa ttcctgctgt tgacaagttg tattctacta   4740
aggttaataa gtttgcaaaa attatgaacc ttagacaaag tgttgttggt gatcttaaac   4800
ttcttactga tgggaagttg tatgagggta agcatattcc tgtatctaat attagtgcag   4860
gggagaatca tgtagttcaa ataccctaa tggcacagga ggaaattctg tcttctagtg   4920
caagtgattt cagaactgca atggtgagta aaaatagcaa gcctcaagct actgcaatgc   4980
atgtaggagc tatagaaatt atcattgata gtttcgcaag tcctgactgc aacatagttg   5040
gtgcaatgct tttggttgat acttatcata ccaatcctga aaatgcagtt cgtagtattt   5100
ttgttgcgcc tttcagaggc ggaaggccca ttcgggtggt tacatttccg aataccattg   5160
tgcagattga accagacatg aattcaaggt ttcagctttt gagtaccact accaatggtg   5220
attttgttca aggaaaagat ctcgcaatgg ttaaagttaa tgtagcatgt gctgctgttg   5280
gcttgacatc aagttacact ccaactccac tgttggaatc tggtttgcaa aaagacagag   5340
ggttaattgt ggaatatttt ggaaggatgt cttacgttgc tcataacgtt aatcagcccc   5400
aagagaaaga tttgttggag ggaaattttt cctttgatat taaatctcgc tctagattgg   5460
aaaaagtttc ttctactaaa gcacaattg ttagtggaaa aaccttcaaa tatgatataa   5520
ttggtgctgg ttcacattct tcagaagatt ttcctaaaaa agaagatcaa gaaaaaccca   5580
aaaagattga tgccagattg agacaaagaa tagatcccca atacaatgag gttcaggctc   5640
agatggagac caacctcttc aagctcagct tggacgacgt agagacacca aagggaagcc   5700
tcgacggatc catgagtaaa ggagaagaac ttttcactgg agttgtccca attcttgttg   5760
aattagatgg tgatgttaat gggcacaaat tttctgtcag tggagagggt gaaggtgatg   5820
caacatacgg aaaacttacc cttaaattta tttgcactac tggaaaacta cctgttccat   5880
ggccaacact tgtcactact ttctcttatg gtgttcaatg cttttcaaga tacccagatc   5940
atatgaagcg gcacgacttc ttcaagagcg ccatgcctga gggatacgtg caggagagga   6000
ccatctcttt caaggacgac gggaactaca agacacgtgc tgaagtcaag tttgagggag   6060
acaccctcgt caacaggatc gagcttaagg gaatcgattt caaggaggac ggaaacatcc   6120
```

```
tcggccacaa gttggaatac aactacaact cccacaacgt atacatcacg gcagacaaac    6180
aaaagaatgg aatcaaagct aacttcaaaa ttagacacaa cattgaagat ggaagcgttc    6240
aactagcaga ccattatcaa caaaatactc caattggcga tggccctgtc cttttaccag    6300
acaaccatta cctgtccaca caatctgccc tttcgaaaga tcccaacgaa aagagagacc    6360
acatggtcct tcttgagttt gtaacagctg ctgggattac acatggcatg gatgaactat    6420
acaaaggatc cgcgcctgca aaacagctct taaactttga cctacttaag ttagcaggtg    6480
acgttgagtc caaccctggg cccctcgaga gcccagaacg acgcccggcc gacatccgcc    6540
gtgccaccga ggcggacatg ccggcggtct gcaccatcgt caaccactac atcgagacaa    6600
gcacggtcaa cttccgtacc gagccgcagg aaccgcagga gtggacggac gacctcgtcc    6660
gtctgcggga gcgctatccc tggctcgtcg ccgaggtgga cggcgaggtc gccggcatcg    6720
cctacgcggg ccccctggaag gcacgcaacg cctacgactg gacggccgag tcgaccgtgt    6780
acgtctcccc ccgccaccag cggacgggac tgggctccac gctctacacc cacctgctga    6840
agtccctgga ggcacagggc ttcaagagcg tggtcgctgt catcgggctg cccaacgacc    6900
cgagcgtgcg catgcacgag gcgctcggat atgcccccg cggcatgctg cgggcggccg    6960
gcttcaagca cgggaactgg catgacgtgg gtttctggca gctggacttc agcctgccgg    7020
taccgccccg tccggtcctg cccgtcaccg agatccccgg ggccccagct aagcaattgc    7080
tgaatttcga tctcttgaaa ctggctggag atgtagaatc aaatccaggc ccgatggaaa    7140
caaatttgtt taaattgtct cttgatgatg ttgaaactcc taaaggttcc atgttggatc    7200
ttaaaatttc tcaatctaaa attgcacttc ccaaaaacac agttggagga accattctgc    7260
gtagtgatct attggcaaat ttttgacag agggcaattt tagagcaagt gttgatttgc    7320
agcgcactca tcgtattaaa ggaatgatta aaatggtggc cacagttggt attcctgaga    7380
atacaggtat atcattggcc tgtgctatga atagttcttt tagggggcgt gccagttctg    7440
atatttacac catctgctct caagactgtg aattatggaa tcctgcttgc acaaaagcaa    7500
tgactatgtc atttaatcca aacccgtgtt ctgatgcatg gagtttggaa ttttgaagc    7560 gtaccggatt tcattgtgat atcatttgtg tcactggatg gactgccacc ccaatgcagg    7620
atgttcaggt tacaattgat tggttttattt cctctcagga atgtgttccc aggacctatt    7680
gtgttttaaa tccacaaaat ccttttgtgt taaataggtg gatgggcaaa ctgactttcc    7740
cccagggcac ttcccgaagt gttaaaagaa tgcctctttc tatagggga ggagctggtg    7800 caaagaatgc tattctcatg aatatgccaa atgctgttct ttcaatgtgg agatattttg    7860
ttggagatct cgtcttttgaa gtttctaaga tgacttctcc ctacattaaa tgtacagtct    7920
ctttcttcat agcatttgga aatttggctg atgacaccat taattttgag gcttttcccc    7980
acaagctggt gcagttttgga gaaattcagg aaaaagttgt attgaaattt tcacaagagg    8040
aatttcttac agcttggtca actcaggtgc gtcctgcaac aactctgttg gctgatgggt    8100
gtccatattt gtatgctatg gtgcatgata gttcagtgtc tacaatacca ggtgattttg    8160
tcattggtgt taagttggca accataaaca atatgtgtgc atatgggctc aatcctggta    8220
tttcaggttc tcgtcttttg ggcaccattc ctcagtccat ttcacagcaa actgtttgga    8280
atcagatggc aacagtgaga acaccattga atttgatcc tagcaagcag agcttttgtc    8340
aattttctat tgaccttctc ggtggaggaa ttttagtgga caaaactgga gattggatca    8400
cacttataca aaattctcca attagtaact tgttgagagt tgctgcttgg aagaaaggct    8460
gtttaatggt taagattgtg atgtctggga atgcagcagt caaaaggagt gattgggcct    8520
```

-continued

```
cattggtaca agtgttttta acaaacagca acagtacaga gcattttgat gcatgtaagt      8580
ggacaaaatc ggaaccacat tcctgggaat tgatcttccc aatagaggtg tgtggtccta      8640
acaatggttt tgaaatgtgg agttctgagt gggcaaatca aacttcatgg catttgagtt      8700
tccttattga caatcccaaa cagtctacag ttttgacat tctcctggga atttcccaag       8760
attttgaaat tgctggtaat actcttatgc cagcttttc tgttccacag gctactgcca       8820
gatcttctga aaatgcggaa tcctctgcat gatctggaat ttgtgttttc tttcgtttgt      8880
tcgcttgttt aattcaataa aggaaattag gcatgaccct ctcgttgagt atgctctgtc      8940
tatttgaaaa tttccacacc tcttttaatt gtcgtaatga tgtgtgaagt gtgtgttatt      9000
ttaaaaaaaa aaaaaaaaaa atcgatagct cgaatttccc cgatcgttca aacatttggc      9060
aataaagttt cttaagattg aatcctgttg ccggtcttgc gatgattatc atataatttc      9120
tgttgaatta cgttaagcat gtaataatta acatgtaatg catgacgtta tttatgagat      9180 gggttttat gattagagtc ccgcaattat acatttaata cgcgatagaa aacaaaatat       9240
agcgcgcaaa ctaggataaa ttatcgcgcg cggtgtcatc tatgttacta gatcgggaat      9300
tccaattcgc c                                                           9311

<210> SEQ ID NO 7
<211> LENGTH: 10169
<212> TYPE: DNA
<213> ORGANISM: Bean Pod Mottle Virus

<400> SEQUENCE: 7
tatagtgagt cgtattacaa ttcactggcc gtcgttttac aacgtcgtga ctgggaaaac        60
cctggcgtta cccaacttaa tcgccttgca gcacatcccc ctttcgccag ctggcgtaat       120
agcgaagagg cccgcaccga tcgcccttcc caacagttgc gcagcctgaa tggcgaatgg       180
acgcgccctg tagcggcgca ttaagcgcgg cgggtgtggt ggttacgcgc agcgtgaccg       240
ctacacttgc cagcgcccta gcgcccgctc ctttcgcttt cttcccttcc tttctcgcca       300
cgttcgccgg ctttccccgt caagctctaa atcgggggct ccctttaggg ttccgattta       360
gtgctttacg gcacctcgac cccaaaaaac ttgattaggg tgatggttca cgtagtgggc       420
catcgccctg atagacggtt tttcgccctt gacgttgga gtccacgttc tttaatagtg        480
gactcttgtt ccaaactgga acaacactca accctatctc ggtctattct tttgatttat       540
aagggatttt gccgatttcg gcctattggt taaaaatga gctgatttaa caaaaattta       600
acgcgaattt taacaaaata ttaacgctta caatttcctg atgcggtatt ttctccttac       660
gcatctgtgc ggtatttcac accgcatatg gtgcactctc agtacaatct gctctgatgc       720
cgcatagtta agccagcccc gacacccgcc aacacccgct gacgcgccct gacgggcttg       780
tctgctcccg gcatccgctt acagacaagc tgtgaccgtc tccggagct gcatgtgtca        840 gaggttttca ccgtcatcac cgaaacgcgc gagacgaaag gcctcgtga tacgcctatt        900 tttataggtt aatgtcatga taataatggt tcttagacg tcaggtggca cttttcgggg        960
aaatgtgcgc ggaacccta tttgtttatt tttctaaata cattcaaata tgtatccgct       1020
catgagacaa taaccctgat aaatgcttca ataatattga aaaggaaga gtatgagtat       1080 tcaacatttc cgtgtcgccc ttattccctt ttttgcggca ttttgccttc ctgttttgc       1140 tcacccagaa acgctggtga agtaaaaga tgctgaagat cagttgggtg cacgagtggg       1200
ttacatcgaa ctggatctca acagcggtaa gatccttgag agttttcgcc ccgaagaacg      1260
ttttccaatg atgagcactt ttaaagttct gctatgtggc gcggtattat cccgtattga      1320
```

```
cgccgggcaa gagcaactcg gtcgccgcat acactattct cagaatgact tggttgagta    1380
ctcaccagtc acagaaaagc atcttacgga tggcatgaca gtaagagaat tatgcagtgc    1440
tgccataacc atgagtgata acactgcggc caacttactt ctgacaacga tcggaggacc    1500
gaaggagcta accgcttttt tgcacaacat gggggatcat gtaactcgcc ttgatcgttg    1560
ggaaccggag ctgaatgaag ccataccaaa cgacgagcgt gacaccacga tgcctgtagc    1620
aatggcaaca acgttgcgca aactattaac tggcgaacta cttactctag cttcccggca    1680
acaattaata gactggatgg aggcggataa agttgcagga ccacttctgc gctcggccct    1740
tccggctggc tggtttattg ctgataaatc tggagccggt gagcgtgggt ctcgcggtat    1800
cattgcagca ctggggccag atggtaagcc ctcccgtatc gtagttatct acacgacggg    1860
gagtcaggca actatggatg aacgaaatag acagatcgct gagataggtg cctcactgat    1920
taagcattgg taactgtcag accaagttta ctcatatata ctttagattg atttaaaact    1980
tcatttttaa tttaaaagga tctaggtgaa gatcctttt gataatctca tgaccaaaat    2040
cccttaacgt gagttttcgt tccactgagc gtcagacccc gtagaaaaga tcaaaggatc    2100
ttcttgagat cctttttttc tgcgcgtaat ctgctgcttg caaacaaaaa aaccaccgct    2160
accagcggtg gtttgtttgc cggatcaaga gctaccaact cttttccga aggtaactgg    2220
cttcagcaga gcgcagatac caaatactgt tcttctagtg tagccgtagt taggccacca    2280
cttcaagaac tctgtagcac cgcctacata cctcgctctg ctaatcctgt taccagtggc    2340
tgctgccagt ggcgataagt cgtgtcttac cgggttggac tcaagacgat agttaccgga    2400
taaggcgcag cggtcgggct gaacggggggg ttcgtgcaca cagcccagct tggagcgaac    2460
gacctacacc gaactgagat acctacacgc tgagctatga gaaagcgcca cgcttcccga    2520
agggagaaag gcggacaggt atccggtaag cggcagggtc ggaacaggag agcgcacgag    2580
ggagcttcca gggggaaacg cctggtatct ttatagtcct gtcgggtttc gccacctctg    2640
acttgagcgt cgatttttgt gatgctcgtc aggggggcgg agcctatgga aaaacgccag    2700
caacgcggcc ttttttacggt tcctggcctt ttgctggcct tttgctcaca tgttctttcc    2760
tgcgttatcc cctgattctg tggataaccg tattaccgcc tttgagtgag ctgataccgc    2820
tcgccgcagc cgaacgaccg agcgcagcga gtcagtgagc gaggaagcgg aagagcgccc    2880
aatacgcaaa ccgcctctcc ccgcgcgttg gccgattcat taatgcagct ggcacgacag    2940
gtttcccgac tggaaagcgg gcagtgagcg caacgcaatt aatgtgagtt agctcactca    3000
ttaggcaccc caggctttac actttatgct tccggctcgt atgttgtgtg gaattgtgag    3060
cggataacaa tttcacacag gaaacagcta tgaccatgat tacgccaagc tatttaggtg    3120
acactataga atactcaagc ggccgcctac tccaagaata tcaaagatac agtctcagaa    3180
gaccaaaggg ctattgagac ttttcaacaa agggtaatat cgggaaacct cctcggattc    3240
cattgcccag ctatctgtca cttcatcaaa aggacagtag aaaaggaagg tggcacctac    3300
aaatgccatc attgcgataa aggaaaggct atcgttcaag atgcctctgc cgacagtggt    3360
cccaaagatg gacccccacc cacgaggagc atcgtggaaa aagaagacgt tccaaccacg    3420
tcttcaaagc aagtggattg atgtgatcta ctccaagaat atcaaagata cagtctcaga    3480
agaccaaagg gctattgaga cttttcaaca agggtaata tcgggaaacc tcctcggatt    3540
ccattgccca gctatctgtc acttcatcaa aaggacagta gaaaaggaag gtggcaccta    3600
caaatgccat cattgcgata aaggaaaggc tatcgttcaa gatgcctctg ccgacagtgg    3660
tcccaaagat ggacccccac ccacgaggag catcgtggaa aagaagacg ttccaaccac    3720
```

```
gtcttcaaag caagtggatt gatgtgatat ctccactgac gtaagggatg acgcacaatc   3780
ccactatcct tcgcaagacc cttcctctat ataaggaagt tcatttcatt tggagaggta   3840
ttaaaatttt cataagattt gaaattttga taaaccgcga tcataggttg ccgcaccttg   3900
aaaccggaaa caaaagcaat cgttacttga tttcaaagac ttctcaattt ctttctacat   3960
ttcttgtata cggctttcaa agtgaaagaa atcactctc tgtgctggtc acagacttcg    4020
tgaatcattt tctttctgct ctcagttcat ttgctgaaca ctctcctatt tgatataggg   4080
cttcgtgtca gatttgaact tctcctatct cttttttctcg gttcttcatt tgatttcaaa   4140
cttttctgaa atttaaatct cttttgacat tttgaacttt gtgttggctc catttgaaaa   4200
acaacatgaa gttctatcct ggtcaaaata tttccgaaat tgtttaccac tttcagagta   4260
atgagacagc caataggtta gatgcatatt ttgcttgtgg ctgtgaggag gatactgaag   4320
tcctcgctcg tttgaagcag tgtaatcctc gtctgcttca tctgtcatat gctgcctttt   4380
gtttggaaat gggcagtcat tcaatagagg aaatggaata tgatgatggg gaattaattt   4440
tttcctattt ccaaaacttt ttactttcca tcgtttccaa ttcttctaaa acaaccaaat   4500
tgagagcata cattcgttca gcatttgcat atcatttttca gcattttgtt gaatttgatc   4560
aatatacaaa tgattctctc aatactgtgg atacaagtgt atcagcccaa gggatagcag   4620
acttggctct ctctatggtt agatggatac ccactcagat taaaaaagtt gttaatttg    4680 gtgtgggatc tgttatagag tcttttttcag agcatttaa taagctcttg atgcaatatt   4740
gtccaatagt ttttcaagct ttcagctggg tcaacaatat ttggacaatg gtcaaagagt   4800
ggatagaaga agctgcgaaa gagatttcat ggttttgca aggatgcaaa gagttgctag    4860
cctggggaat gtgtattttg gctagctcct gtgctctagg attggttgaa aaatgcctta   4920
tctcttgggg catgatttcc gaatcttttg atttggttgg tttgtttgtt cgatctgcca   4980
ttgtgggagc tttctgtgtt tccataaaaa ctggcaagtt catcacgaat agtgaattgg   5040
tcacttgtgc taccattgca gtttctacaa tagcaactgt aatgtctcag gcttttaagc   5100
cttctgaaga gattaagggg cagttccaag ccctttcagt tctagaaggg ttggcaacac   5160
agctcacttc gttttgtgac acgtctttag ttgctatggg aaaaacctgc acagctttta   5220
atcaaatttg cactgctggc aaaaatgtta aggtgattgc aggtaggttg ctggaagttg   5280
tttctaattt tgtcagaaaa ttattaggat tggatagtgc ttttctcaga gatgctgcac   5340 tcatttttttc ccaagatgtg gatggatggt tgcgtaacat cagttggtgc caggaacagt   5400
ttttgttgaa agcttacatg tcgcaagatg atcttattgt cctgcgctct ttagttgtta   5460
aaggtgaaag aatgagggaa cagatgcttg aaggagaagt taaggtatct ccaagtgttt   5520
gcaaccttat tgtcaaaggc tgtgaagaag caaataaatt gatgcgtgag agcgcacttc   5580
attgttcaaa aacaattagg aagattcctt ttgttatttt tgctcacggt gaatcccgag   5640
ttgggaaatc tctgttggtt gataagctaa tcacagattt ctgtgatcat ttggaaattg   5700
gagaagatgc tgtgtactca aggaatccat cagatccttt ctggagtgga tatagaaggc   5760
agccaattgt tactattgat gattttgctg ctgttgtttc ggagccatct gctgaagctc   5820
aattaattcc attagtttca agtgctcctt atccattaaa catggctggt ttagaggaga   5880
agggaatgca ctttgattcc cagatcatga tgtgttcttc aaatttctta gagccgtctc   5940
ctgaagctaa aattagagat gatatggctt ttagaaatcg gagacatgtg ctgatcacag   6000
ttgaactcaa acctggggtt gaatatgatg agagtgattt tactaaaaat cagcgatatt   6060
tgctgaaaac ttggtttcat gatcattatg ttgtagacca aacttttgag tcctatgctg   6120
```

```
atctgctggc acattgtttt accaagtggg agagacatgt taaggagcaa gagtcaaatc    6180
tgtctcaaat taagggcaag aaaaatgaaa gtggtcattt taataatttt caacaactta    6240
tggatttggc tgtttcttgg aatcttaatg cagatatcat gaaaaacagg atcaaggctg    6300
agagaagtga catggtttat gttttttctg cagggaggaa ggataaaatt ttgcattgtt    6360
ttctgaacaa ggaaggcgag tgcacggttc gtcctgattc aatagatgat cctgaagcgc    6420
aagctttgct caaagcttca gagacaatgc tcatgaaagc ctatgccttc cttaaataca    6480
ataatgcaac aaatttgatt gtcagaaccc atttggcaga actagtgaat gaagattttt    6540
atgatgagaa attcaatttc attggaacaa ttggaacacc ggcttttcat cgccaaatag    6600
ctgcacattt ggaaaagatg ccattgtggc aaaaagcaat tttgtgtgga atgggacatt    6660
gtttgtctcg gaaaagcaaa gagacctggt atactggtat gaaggagaaa tttgtgcaga    6720
tgatgaaaag catctatgaa actgaagtca cagactggcc agtgccattg aaaatcattt    6780
ctggtactat tctagccacc attttgggaa caacttttg gaagttatt tcctttttaa    6840 gggatgctgg caatggaggt gttttgttg gtaatgttgc ttcagcattt accacatcaa    6900
gtgtgcttga ggcgcaaagc cgaaaaccca acagatgatga ggtctctcaa tataggtatc    6960
gcaatgtgcc aataaagcgc agagcgtggg ttgagggtca aatgtctttt gatcaatcag    7020
tggtggcaat tatgtcaaaa tgtaaagcca gtatgagaat gggaaacact gatgctcaaa    7080
ttttgatggt tccagggcgt agattcattg cacatggtca ttttttaag aatctcaccc    7140 aaaaagttag agtccaaatt gttacttctg agaaaagcta ttggcatgtg tatgatcctg    7200
ataaatttca aatgtttgat aacagtgaaa tcggggttgta tacaaatcca actttggagg    7260
acatcccaca ttctgcttgg gaccttttct gctgggacag tgagaaaact ttgccaaaca    7320 attttttctgc tgaactgctt tcctgtaaat tggacaccgt tacgggacaa tattacccag    7380
aatgggctcc aataaattgt cgagtacatc ggcaaccaat tcacataact gaagggaatt    7440
atgtcaggaa acaagatgtg agcattgaat atgatgcctg cacaattcct aatgattgtg    7500
gatctctggt ggttgctaag gtcggaaatc acaagcaaat tgttggttt catgttgctg    7560 gaagtaaagg aagattgggc tatgcttcat tgataccata tgttgagcct gtggtacaag    7620
cccaaagtgc tgaagtctat tttgattct ttcctgtgga agttgatagt caagagggag    7680
ttgctcatat tggtgaactc aaatctggag tttatgtacc attgcccaca aaaactaatc    7740
ttgtggaaac tcccaaagaa tggcagttgg atttgccttg tgataagatt ccaagtgtgt    7800
taaccactac tgatgagaga ttggttggca cggagcatga aggatatgac ccatttcttg    7860
gtggtattca aaaatatgca actcccatga tgcctctaga tgaggagatt ctttccaaag    7920
ttgcacaaga catggttgaa gaatggtttg attgtgttga tgaggaggat acatttgaag    7980
aagtttcttt gagtgctgca ctcaatggtt ttgaaggttt ggattacatg gaacgcattc    8040
ctcttgccac ttcagagggt tttcctcatg ttctgtccag gaaaaatggt gaaaaaggca    8100
agagaagatt tgtcactgga gatggtgaag aaatgtcact aattcctggt accagtgttg    8160
aagaagcata caataaattg actgttgaac tagaaaagtg tgttccaaca ttggttggca    8220
tagaatgtcc caaagatgaa aaacttcccc gtcgcaaaat ttttgataaa cccaagacgc    8280
gctgcttcac catacttcct atggaattta atctggtggt gcgtcaaaaa ttcttgaatt    8340
ttgtgcgatt cattatgaag aaaagggaca aattgagttg ccaagttgga atcaatccat    8400
attctatgga gtggactggt ttggcaaata gactgttgag caagggaaat gacatttgt    8460 gttgtgatta tgctagtttt gatggtctga taactaagca agtcatgagc aagatggcag    8520
```

```
aaatgataaa cagtctttgt ggtggagatg agaaactgat gcgtgagaga acgcatcttc   8580
tgttagcttg ttgctccagg atggcaatct gtaaaaaaga tgtttggaga gttgagtgtg   8640
gtatcccttc tggatttcca ctcactgtta tctgcaatag cattttcaat gagatgctta   8700
tcagatatag ttatgaaaag ttgctgcgtc aagctaaggc tcctagtatg tttctccagt   8760
cttttaaaaa ttttatttct ttgtgtgttt atggagatga taatttaatt agtgttcatg   8820
agtatgttaa gccatatttt agtggttcta aattgaaaag tttcctagct agtcataaca   8880
tcaccattac tgatggaatt gacaaaacta gtgcaacttt acagtttaga aagttgtcag   8940
agtgtgattt tcttaaaaga aattttaagc aaatgtccaa tgttttgtgg gtagctcctg   9000
aagacaaagc tagtttgtgg tcacaattac actatgtttc atgtaacaat ttggaaatgc   9060
aagaagctta tcttgttaac ttggttaatg tgttgcgtga gttgtacctg cacagtccag   9120
aagaagctcg tcaattgaga agaaaggctc tctctcgcat tgagtggttg caaaaagctg   9180
atgtgcccac catagcacaa attgaagaat ttcattcaat gcagaggatt atgaatgctc   9240
ctgactcaaa tgataatatt gatcttttgt tgagcattga cttgttgggt cttcagggtg   9300
caggcaaggc cttcccaaat aagattgtgt ttgatgataa attggtattg gcaaatacac   9360
aagaattttt tgatggaaat tttccaacag attcttggtt accaatattt gtcaattgtc   9420
tttaccctgt gagtcaattg cccgcagagg ctgtcactgt taatgttgtt tgtgggagtg   9480
ggcgtggtgg tttgcctact actgcttgga ttagttctgc agttaacaat cgctcctcag   9540
atatcaataa gaaaattcgg acagcacttg ggaaaggtaa gaaaattgtc tttttgacta   9600
gagttgatcc ttttcctgtg gccttgttag ctgttctttt tggtgttaag aacgaaattc   9660
tgagttctaa tgccacaaat ccaatgttga caaggcttct tgagaactgc aagagtctta   9720
aatatttggt tgatgagtgt ccttttgcat ttgttaacta gtttgtaata ttttgctcac   9780
ttaaataaag cgcattacta tgtgcaataa gtgtgtttaa atataaaaaa aaaaaaaaaa   9840
aaaatcgatg ggcctggatc ctaggttcac aaagtgtcat cgatagctcg aatttccccg   9900
atcgttcaaa catttggcaa taaagtttct taagattgaa tcctgttgcc ggtcttgcga   9960
tgattatcat ataatttctg ttgaattacg ttaagcatgt aataattaac atgtaatgca  10020
tgacgttatt tatgagatgg gtttttatga ttagagtccc gcaattatac atttaatacg  10080
cgatagaaaa caaaatatag cgcgcaaact aggataaatt atcgcgcgcg gtgtcatcta  10140
tgttactaga tcgggaattc caattcgcc                                    10169
```

<210> SEQ ID NO 8
<211> LENGTH: 1851
<212> TYPE: PRT
<213> ORGANISM: Bean Pod Mottle Virus

<400> SEQUENCE: 8

```
Met Lys Phe Tyr Pro Gly Gln Asn Ile Ser Glu Ile Val Tyr His Phe
1               5                   10                  15

Gln Ser Asn Glu Thr Ala Asn Arg Leu Asp Ala Tyr Phe Ala Cys Gly
            20                  25                  30

Cys Glu Glu Asp Thr Glu Val Leu Ala Arg Leu Lys Gln Cys Asn Pro
        35                  40                  45

Arg Leu Leu His Leu Ser Tyr Ala Ala Phe Cys Leu Glu Met Gly Ser
    50                  55                  60

His Ser Ile Glu Glu Met Glu Tyr Asp Asp Gly Glu Leu Ile Phe Ser
65                  70                  75                  80
```

```
Tyr Phe Gln Asn Phe Leu Leu Ser Ile Val Ser Asn Ser Ser Lys Thr
                85                  90                  95

Thr Lys Leu Arg Ala Tyr Ile Arg Ser Ala Phe Ala Tyr His Phe Gln
            100                 105                 110

His Phe Val Glu Phe Asp Gln Tyr Thr Asn Asp Ser Leu Asn Thr Val
        115                 120                 125

Asp Thr Ser Val Ser Ala Gln Gly Ile Ala Asp Leu Ala Leu Ser Met
130                 135                 140

Val Arg Trp Ile Pro Thr Gln Ile Lys Lys Val Val Asn Phe Gly Val
145                 150                 155                 160

Gly Ser Val Ile Glu Ser Phe Ser Glu His Phe Asn Lys Leu Leu Met
                165                 170                 175

Gln Tyr Cys Pro Ile Val Phe Gln Ala Phe Ser Trp Val Asn Asn Ile
            180                 185                 190

Trp Thr Met Val Lys Glu Trp Ile Glu Glu Ala Ala Lys Glu Ile Ser
        195                 200                 205

Trp Phe Leu Gln Gly Cys Lys Glu Leu Leu Ala Trp Gly Met Cys Ile
    210                 215                 220

Leu Ala Ser Ser Cys Ala Leu Gly Leu Val Glu Lys Cys Leu Ile Ser
225                 230                 235                 240

Leu Gly Met Ile Ser Glu Ser Phe Asp Leu Val Gly Leu Phe Val Arg
                245                 250                 255

Ser Ala Ile Val Gly Ala Phe Cys Val Ser Ile Lys Thr Gly Lys Phe
            260                 265                 270

Ile Thr Asn Ser Glu Leu Val Thr Cys Ala Thr Ile Ala Val Ser Thr
        275                 280                 285

Ile Ala Thr Val Met Ser Gln Ala Phe Lys Pro Ser Glu Glu Ile Lys
    290                 295                 300

Gly Gln Phe Gln Ala Leu Ser Val Leu Glu Gly Leu Ala Thr Gln Leu
305                 310                 315                 320

Thr Ser Phe Cys Asp Thr Ser Leu Val Ala Met Gly Lys Thr Cys Thr
                325                 330                 335

Ala Phe Asn Gln Ile Cys Thr Ala Gly Lys Asn Val Lys Val Ile Ala
            340                 345                 350

Gly Arg Leu Leu Glu Val Val Ser Asn Phe Val Arg Lys Leu Leu Gly
        355                 360                 365

Leu Asp Ser Ala Phe Leu Arg Asp Ala Ala Leu Ile Phe Ser Gln Asp
    370                 375                 380

Val Asp Gly Trp Leu Arg Asn Ile Ser Trp Cys Gln Glu Gln Phe Leu
385                 390                 395                 400

Leu Lys Ala Tyr Met Ser Gln Asp Asp Leu Ile Val Leu Arg Ser Leu
                405                 410                 415

Val Val Lys Gly Glu Arg Met Arg Glu Gln Met Leu Glu Gly Glu Val
            420                 425                 430

Lys Val Ser Pro Ser Val Cys Asn Leu Ile Val Lys Gly Cys Glu Glu
        435                 440                 445

Ala Asn Lys Leu Met Arg Glu Ser Ala Leu His Cys Ser Lys Thr Ile
    450                 455                 460

Arg Lys Ile Pro Phe Val Ile Phe Ala His Gly Glu Ser Arg Val Gly
465                 470                 475                 480

Lys Ser Leu Leu Val Asp Lys Leu Ile Thr Asp Phe Cys Asp His Leu
                485                 490                 495

Glu Ile Gly Glu Asp Ala Val Tyr Ser Arg Asn Pro Ser Asp Pro Phe
            500                 505                 510
```

```
Trp Ser Gly Tyr Arg Arg Gln Pro Ile Val Thr Ile Asp Asp Phe Ala
            515                 520                 525

Ala Val Val Ser Glu Pro Ser Ala Glu Ala Gln Leu Ile Pro Leu Val
            530                 535                 540

Ser Ser Ala Pro Tyr Pro Leu Asn Met Ala Gly Leu Glu Glu Lys Gly
545                 550                 555                 560

Met His Phe Asp Ser Gln Ile Met Met Cys Ser Ser Asn Phe Leu Glu
            565                 570                 575

Pro Ser Pro Glu Ala Lys Ile Arg Asp Asp Met Ala Phe Arg Asn Arg
            580                 585                 590

Arg His Val Leu Ile Thr Val Glu Leu Lys Pro Gly Val Glu Tyr Asp
            595                 600                 605

Glu Ser Asp Phe Thr Lys Asn Gln Arg Tyr Leu Leu Lys Thr Trp Phe
            610                 615                 620

His Asp His Tyr Val Val Asp Gln Thr Phe Glu Ser Tyr Ala Asp Leu
625                 630                 635                 640

Leu Ala His Cys Phe Thr Lys Trp Glu Arg His Val Lys Glu Gln Glu
            645                 650                 655

Ser Asn Leu Ser Gln Ile Lys Gly Lys Asn Glu Ser Gly His Phe
            660                 665                 670

Asn Asn Phe Gln Gln Leu Met Asp Leu Ala Val Ser Trp Asn Leu Asn
            675                 680                 685

Ala Asp Ile Met Lys Asn Arg Ile Lys Ala Glu Arg Ser Asp Met Val
            690                 695                 700

Tyr Val Phe Ser Ala Gly Arg Lys Asp Lys Ile Leu His Cys Phe Leu
705                 710                 715                 720

Asn Lys Glu Gly Glu Cys Thr Val Arg Pro Asp Ser Ile Asp Asp Pro
            725                 730                 735

Glu Ala Gln Ala Leu Leu Lys Ala Ser Glu Thr Met Leu Met Lys Ala
            740                 745                 750

Tyr Ala Phe Leu Lys Tyr Asn Asn Ala Thr Asn Leu Ile Val Arg Thr
            755                 760                 765

His Leu Ala Glu Leu Val Asn Glu Asp Phe Tyr Asp Glu Lys Phe Asn
            770                 775                 780

Phe Ile Gly Thr Ile Gly Thr Pro Ala Phe His Arg Gln Ile Ala Ala
785                 790                 795                 800

His Leu Glu Lys Met Pro Leu Trp Gln Lys Ala Ile Leu Cys Gly Met
            805                 810                 815

Gly His Cys Leu Ser Arg Lys Ser Lys Glu Thr Trp Tyr Thr Gly Met
            820                 825                 830

Lys Glu Lys Phe Val Gln Met Met Lys Ser Ile Tyr Glu Thr Glu Val
            835                 840                 845

Thr Asp Trp Pro Val Pro Leu Lys Ile Ile Ser Gly Thr Ile Leu Ala
850                 855                 860

Thr Ile Leu Gly Thr Thr Phe Trp Lys Leu Phe Ser Phe Leu Arg Asp
865                 870                 875                 880

Ala Gly Asn Gly Gly Val Phe Val Gly Asn Val Ala Ser Ala Phe Thr
            885                 890                 895

Thr Ser Ser Val Leu Glu Ala Gln Ser Arg Lys Pro Asn Arg Tyr Glu
            900                 905                 910

Val Ser Gln Tyr Arg Tyr Arg Asn Val Pro Ile Lys Arg Arg Ala Trp
            915                 920                 925

Val Glu Gly Gln Met Ser Phe Asp Gln Ser Val Val Ala Ile Met Ser
```

-continued

```
               930                 935                 940
Lys Cys Lys Ala Ser Met Arg Met Gly Asn Thr Asp Ala Gln Ile Leu
945                 950                 955                 960

Met Val Pro Gly Arg Arg Phe Ile Ala His Gly His Phe Phe Lys Asn
                965                 970                 975

Leu Thr Gln Lys Val Arg Val Gln Ile Val Thr Ser Glu Lys Ser Tyr
            980                 985                 990

Trp His Val Tyr Asp Pro Asp Lys Phe Gln Met Phe Asp Asn Ser Glu
                995                 1000                1005

Ile Gly Leu Tyr Thr Asn Pro Thr Leu Glu Asp Ile Pro His Ser
    1010                1015                1020

Ala Trp Asp Leu Phe Cys Trp Asp Ser Glu Lys Thr Leu Pro Asn
    1025                1030                1035

Asn Phe Ser Ala Glu Leu Leu Ser Cys Lys Leu Asp Thr Val Thr
    1040                1045                1050

Gly Gln Tyr Tyr Pro Glu Trp Ala Pro Ile Asn Cys Arg Val His
    1055                1060                1065

Arg Gln Pro Ile His Ile Thr Glu Gly Asn Tyr Val Arg Lys Gln
    1070                1075                1080

Asp Val Ser Ile Glu Tyr Asp Ala Cys Thr Ile Pro Asn Asp Cys
    1085                1090                1095

Gly Ser Leu Val Val Ala Lys Val Gly Asn His Lys Gln Ile Val
    1100                1105                1110

Gly Phe His Val Ala Gly Ser Lys Gly Arg Leu Gly Tyr Ala Ser
    1115                1120                1125

Leu Ile Pro Tyr Val Glu Pro Val Val Gln Ala Gln Ser Ala Glu
    1130                1135                1140

Val Tyr Phe Asp Phe Phe Pro Val Glu Val Asp Ser Gln Glu Gly
    1145                1150                1155

Val Ala His Ile Gly Glu Leu Lys Ser Gly Val Tyr Val Pro Leu
    1160                1165                1170

Pro Thr Lys Thr Asn Leu Val Glu Thr Pro Lys Glu Trp Gln Leu
    1175                1180                1185

Asp Leu Pro Cys Asp Lys Ile Pro Ser Val Leu Thr Thr Thr Asp
    1190                1195                1200

Glu Arg Leu Val Gly Thr Glu His Glu Gly Tyr Asp Pro Phe Leu
    1205                1210                1215

Gly Gly Ile Gln Lys Tyr Ala Thr Pro Met Met Pro Leu Asp Glu
    1220                1225                1230

Glu Ile Leu Ser Lys Val Ala Gln Asp Met Val Glu Glu Trp Phe
    1235                1240                1245

Asp Cys Val Asp Glu Glu Asp Thr Phe Glu Glu Val Ser Leu Ser
    1250                1255                1260

Ala Ala Leu Asn Gly Val Glu Gly Leu Asp Tyr Met Glu Arg Ile
    1265                1270                1275

Pro Leu Ala Thr Ser Glu Gly Phe Pro His Val Leu Ser Arg Lys
    1280                1285                1290

Asn Gly Glu Lys Gly Lys Arg Arg Phe Val Thr Gly Asp Gly Glu
    1295                1300                1305

Glu Met Ser Leu Ile Pro Gly Thr Ser Val Glu Glu Ala Tyr Asn
    1310                1315                1320

Lys Leu Thr Val Glu Leu Glu Lys Cys Val Pro Thr Leu Val Gly
    1325                1330                1335
```

```
Ile Glu Cys Pro Lys Asp Glu Lys Leu Pro Arg Arg Lys Ile Phe
1340                1345                1350

Asp Lys Pro Lys Thr Arg Cys Phe Thr Ile Leu Pro Met Glu Phe
1355                1360                1365

Asn Leu Val Val Arg Gln Lys Phe Leu Asn Phe Val Arg Phe Ile
1370                1375                1380

Met Lys Lys Arg Asp Lys Leu Ser Cys Gln Val Gly Ile Asn Pro
1385                1390                1395

Tyr Ser Met Glu Trp Thr Gly Leu Ala Asn Arg Leu Leu Ser Lys
1400                1405                1410

Gly Asn Asp Ile Leu Cys Cys Asp Tyr Ala Ser Phe Asp Gly Leu
1415                1420                1425

Ile Thr Lys Gln Val Met Ser Lys Met Ala Glu Met Ile Asn Ser
1430                1435                1440

Leu Cys Gly Gly Asp Glu Lys Leu Met Arg Glu Arg Thr His Leu
1445                1450                1455

Leu Leu Ala Cys Cys Ser Arg Met Ala Ile Cys Lys Lys Asp Val
1460                1465                1470

Trp Arg Val Glu Cys Gly Ile Pro Ser Gly Phe Pro Leu Thr Val
1475                1480                1485

Ile Cys Asn Ser Ile Phe Asn Glu Met Leu Ile Arg Tyr Ser Tyr
1490                1495                1500

Glu Lys Leu Leu Arg Gln Ala Lys Ala Pro Ser Met Phe Leu Gln
1505                1510                1515

Ser Phe Lys Asn Phe Ile Ser Leu Cys Val Tyr Gly Asp Asp Asn
1520                1525                1530

Leu Ile Ser Val His Glu Tyr Val Lys Pro Tyr Phe Ser Gly Ser
1535                1540                1545

Lys Leu Lys Ser Phe Leu Ala Ser His Asn Ile Thr Ile Thr Asp
1550                1555                1560

Gly Ile Asp Lys Thr Ser Ala Thr Leu Gln Phe Arg Lys Leu Ser
1565                1570                1575

Glu Cys Asp Phe Leu Lys Arg Asn Phe Lys Gln Met Ser Asn Val
1580                1585                1590

Leu Trp Val Ala Pro Glu Asp Lys Ala Ser Leu Trp Ser Gln Leu
1595                1600                1605

His Tyr Val Ser Cys Asn Asn Leu Glu Met Gln Glu Ala Tyr Leu
1610                1615                1620

Val Asn Leu Val Asn Val Leu Arg Glu Leu Tyr Leu His Ser Pro
1625                1630                1635

Glu Glu Ala Arg Gln Leu Arg Arg Lys Ala Leu Ser Arg Ile Glu
1640                1645                1650

Trp Leu Gln Lys Ala Asp Val Pro Thr Ile Ala Gln Ile Glu Glu
1655                1660                1665

Phe His Ser Met Gln Arg Ile Met Asn Ala Pro Asp Ser Asn Asp
1670                1675                1680

Asn Ile Asp Leu Leu Leu Ser Ile Asp Leu Leu Gly Leu Gln Gly
1685                1690                1695

Ala Gly Lys Ala Phe Pro Asn Lys Ile Val Phe Asp Asp Lys Leu
1700                1705                1710

Val Leu Ala Asn Thr Gln Glu Phe Phe Asp Gly Asn Phe Pro Thr
1715                1720                1725

Asp Ser Trp Leu Pro Ile Phe Val Asn Cys Leu Tyr Pro Val Ser
1730                1735                1740
```

-continued

```
Gln Leu Pro Ala Glu Ala Val Thr Val Asn Val Val Cys Gly Ser
    1745            1750            1755

Gly Arg Gly Gly Leu Pro Thr Thr Ala Trp Ile Ser Ser Ala Val
    1760            1765            1770

Asn Asn Arg Ser Ser Asp Ile Asn Lys Lys Ile Arg Thr Ala Leu
    1775            1780            1785

Gly Lys Gly Lys Lys Ile Val Phe Leu Thr Arg Val Asp Pro Phe
    1790            1795            1800

Pro Val Ala Leu Leu Ala Val Leu Phe Gly Val Lys Asn Glu Ile
    1805            1810            1815

Leu Ser Ser Asn Ala Thr Asn Pro Met Leu Thr Arg Leu Leu Glu
    1820            1825            1830

Asn Cys Lys Ser Leu Lys Tyr Leu Val Asp Glu Cys Pro Phe Ala
    1835            1840            1845

Phe Val Asn
    1850
```

BPMV-BASED VIRAL CONSTRUCTS USEFUL FOR VIGS AND EXPRESSION OF HETEROLOGOUS PROTEINS IN LEGUMES

CROSS-REFERENCE TO RELATED APPLICATIONS

This application claims priority under 35 U.S.C. §119 to provisional application Ser. No. 61/281,469 filed Nov. 18, 2009, herein incorporated by reference in its entirety.

GRANT REFERENCE

This invention was made with government support under Grant Nos. 2006-31100-06019, and 2007-31100-06019, awarded by USDA/CSREES. The government has certain rights in the invention.

FIELD OF THE INVENTION

This invention relates generally to the area of plant molecular biology and more specifically to plant viral expression vectors.

BACKGROUND OF THE INVENTION

Plant virus-based vectors for expressing heterologous proteins in plants present promising biotechnological tools to supplement conventional breeding and transgenic technology. Considering the speed with which a virus infection becomes established throughout a plant and the high yield of viral-encoded proteins that accumulate in plants, the use of viral vectors provides an attractive and cost effective means for the overproduction of valuable proteins in plants and for rapid evaluation of new traits.

Plant virus-based vectors have been recently developed to express heterologous proteins in plants for the study of gene function, production of pharmaceuticals, analysis of plant-microbe interactions, fungicide and insecticide screening, metabolic engineering and nutrient improvement and represent valuable means to supplement conventional breeding and transgenic technology.

Several different types of positive sense RNA plant viruses have been developed as vectors for production of recombinant proteins and peptides (Pogue et al., Annu. Rev. Phytopathol. 40:45-74 (2002); Scholthof et al., Annu. Rev. Phytopathol. 34:299-323 (1996)). Depending on the structure of the viruses involved and their genome replication and expression strategies, a number of approaches including gene replacement, gene insertion, epitope presentation, and complementation have been utilized. Plant viral vectors are presently available for recombinant protein expression in a wide range of host plants including *Nicotiana benthamiana*, tobacco, squash, cucumber, wheat, barley, cowpea, *Nicotiana clevelandii*, *Chenopodium quinoa*, and *Arabidopsis* (Allison et al., J. Virol. 62:3581-3588 (1998); Brisson et al., Nature 310:511-514 (1984); Choi et al., Plant J. 23:547-555 (2000); Constantin et al., Plant J. 40:622-631 (2004); Dolja et al., Proc. Natl. Acad. Sci. U.S.A. 89:10208-10212 (1992); Fernandez-Fernandez et al., Virology 280:283-291 (2001); French et al., Science 231:1294-1297 (1986); Gopinath et al., Virology 267:159-173 (2000); Hagiwara et al., J. Virol. 73:7988-7993 (1999); Haupt et al., Plant Physiol. 125:209-218 (2001); Lacomme et al., Plant J. 34:543-553 (2003); Turnage et al., Plant J. 30:107-117 (2002)). Even with these advances, there are only a limited number of plant viral vectors that are suitable for systemic expression of foreign proteins in major legume crops like soybean. Soybean is a main source of oil and high-quality protein worldwide, and there is critical need for tools that allow for rapid evaluation of new traits involving expression of valuable proteins that confer disease/pest resistance and/or those that enhance the commercial value of soybean.

Plant viral vectors can be also used as virus-induced gene silencing (VIGS) reverse genetics tools to study gene function (Burch-Smith et al., 2004). VIGS can specifically down regulate a single gene, members of a gene family, or sets of distinct genes (Lu et al., 2003; Peele et al., 2001; Turnage et al., 2002). Due to these advantages, many positive sense RNA plant viruses have been developed as vectors for production of recombinant proteins or as VIGS vectors for many plant species (Burch-Smith et al., 2004; Ding et al., 2006; Grønlund et al., 2008; Igarashi et al., 2009; Meng et al., 2009; Pogue et al., 2002; Zhang et al., 2009). With readily increasing genomic information, VIGS vectors have substantial potential to advance functional genomics for both monocots and dicots. Methods to understand and analyze plant gene function are employed by using loss-of-function or gain-of-function techniques at present. Gene function analyzed by gain-of-function is generally accomplished through gene transformation, while loss-of-function is conducted through mutagen, transposon tagging, T-DNA insertion or homologous recombination. However, the abovementioned approaches are complicated, time-consuming and difficult to scale up the gene analysis.

Alternatively, gene silencing is recently used to analyze gene function. Virus induced gene silencing (VIGS) is an efficient and reliable method though there are many techniques being conducted to induce gene silencing. Gene transformation is not required in the VIGS process, which provides a quick and feasible way for plants with lengthy life cycle and transformation difficulties. VIGS is an RNA silencing process that exploits a host defense mechanisms to defend against foreign viral RNAs or transposon(s). Small interfering RNA (siRNA) has been observed in plants when foreign viruses invade plants. These siRNAs binds foreign viral RNAs and trigger degradation of viral RNA. Virus-induced gene silencing (VIGS) is a type of RNA silencing that is initiated by recombinant virus vectors carrying fragments of host genes being analyzed. The plants are infected with the recombinant viruses to activate the RNA silencing of endogenous target gene of host plants. Virus-induced gene silencing (VIGS) is an RNA silencing process that targets host defense against viruses. Many plant VIGS vectors have been developed as reverse genetics tools for functional genomics studies. VIGS is especially useful for plants, such as soybean, that are recalcitrant to transformation.

Depending on the genome replication and expression strategy of the virus employed, there are two primary approaches for foreign gene sequence expression by plant viruses. The first is through insertion of foreign gene sequences into the viral genome by substitution of a viral gene or fusion with a viral gene(s) to express the foreign gene as a fusion protein precursor. The second approach is to insert the foreign gene after a viral sub-genomic promoter and express the foreign gene sequence through a viral sub-genomic RNA.

VIGS does not require the whole gene. It was reported that 23 nucleotides was enough to induce gene silencing (Plant J. 25, 417-25, 2001). The use of small fragments alleviates problems of acquiring the whole cDNA and can enhance the specificity of virus induced gene silencing (VIGS). Compared with transformation of plants with sense and/or anti-sense gene approaches, the advantage of VIGS is the relative speed. Moreover it suppresses the target gene RNA level after the seedling is established, which allows the functions of the essential genes to be tested upon silencing.

Previously, two generations of Bean pod mottle virus (BPMV, genus Comovirus) VIGS vectors have been demonstrated to be effective and efficient soybean functional genomics tools. However, there are critical limitations to the design of the previous vectors. For example, the fragment of the host gene to be silenced must be expressed as a fusion protein that is in the same reading frame as the viral polyprotein. The expression of this peptide may be undesirable for VIGS applications as this feature limits design of VIGS inserts to translatable regions rather than to any region of interest. Further, in the previous design, only one gene can be expressed.

It is an object of the present invention to provide a new DNA-based BPMV vector to facilitate applications of the BPMV vector for soybean functional genomics.

It is yet another object of the present invention to provide a novel BPMV-based vector which accommodates simultaneous expression of foreign genes as well as insertion of non-coding sequences for VIGS.

It is yet another object of the present invention to provide a plant VIGS RNA1 helper vector that has ideal symptom phenotype that does not interfere with the VIGS phenotype.

It is yet a further object of the invention to provide a novel vector for over-expression and accumulation of heterologous proteins in legumes such as soybean as well as for VIGS for loss of function analysis.

SUMMARY OF INVENTION

The invention provides Bean pod mottle virus (BPMV) vectors useful for expression of heterologous proteins or for virus-induced gene silencing. The invention also provides methods for expressing a heterologous polypeptide in a legume plant such as soybean as well as provides methods for virus-induced gene silencing, to determine the function of a gene of interest.

Applicants provide herein novel designs for BPMV vectors to further enhance the potential of BPMV as a viral vector for functional genomics. According to the invention, the new designs provide vectors with the flexibility for use in VIGS and for expression of heterologous proteins in legumous plants, particularly soybean. Previous BPMV vectors are based solely on insertion of constructs between the movement protein and large coat protein of BPMV for expression of the same. This reduces gene silencing protocols to those of co-suppression constructs or other coding constructs for gene silencing. Further, this insertion strategy requires that the foreign sequences be in frame with the BPMV RNA2 open reading frame. Because of the translation requirement, primer design, particularly for high throughput applications, is laborious with the previous vectors. In addition, potential interference of the translated peptide from the foreign sequence may result in unanticipated phenotypes. Applicants have overcome these inconveniences, by providing BPMV vectors with an insertion site after the BPMV RNA2 translation stop codon. Such placement, via an engineered restriction site, and/or multiple cloning site allows insertion of non-coding sequences into the BPMV vector for functional analysis which does not require translation. Applicants vectors pBPMV V1 (pBPMV-IA-V1; SEQ ID NO:3) and pBPMV V2 (pBPMV-IA-V2; SEQ ID NO:3) provide this improvement.

In a preferred embodiment, the BPMV vectors of the invention include the RNA2 post-translation insertion site as well as the traditional site for heterologous protein expression between the movement protein and long coat protein, such as vector pBPMV V4 (pBPMV-IA-V4; SEQ ID NO:5). Other improvements include the addition of a second insertion site between the movement protein and long coat protein for double gene expression as in vector pBPMV V5 (pBPMV-IA-V5; SEQ ID NO:6). This novel design provides a BPMV vector that can be used for VIGS as well as for heterologous gene expression including applications such as cDNA library screening, promoter silencing, and silencing of un-translated regions of messenger RNAs. Further, RNA silencing and foreign gene expression can be achieved in a single BPMV viral construct making marker gene assisted silencing possible. The new BPMV vectors, similar to the previously reported high efficiency DNA-based BPMV vectors, have the viral genome under control of the CaMV 35S promoter and Nos terminator to overcome the disadvantage of an inefficient RNA-based vector.

Applicants also have used Foot and Mouth Disease Virus 2A proteinase (FMDV 2A) as a proteinase for excision of the heterologous proteins. Use of these rather than truncated portions of native BPMV sequences provides greater efficiency by reducing the possibility of recombination of the vector among native sequences.

In yet another embodiment, applicant has prepared novel BPMV RNA1 sequences to be used with RNA2 vectors to generate infectious clones. The novel RNA1 sequences allow for suitable visualization of viral infection symptoms and result in improved phenotypic visualization of the VIGS affects. According to the invention, applicants have found that modifying a strain of BPMV RNA1 (I-Di1) protein at positions 359 and 365 to a serine and tyrosine respectively produces BPMV infections with only moderate symptoms. The novel amino acid sequence is disclosed as SEQ ID NO:2, the nucleotide sequence is disclosed as SEQ ID NO:1 (pBPMV-IA-R1M).

In accordance with the present invention, an efficient viral vector system capable of rapidly producing significant amounts of heterologous proteins and of VIGS in higher plants is provided which comprises the use of exemplary bipartite transgene/viral vectors.

Thus, in one aspect of the invention, a plant gene expression system is provided which comprises a first gene construct comprising a truncated RNA2 of a bipartite BPMV genome carrying at least one foreign gene encoding a heterologous protein of interest operably linked to promoter and terminator sequences; or a nontranslated sequence designed for VIGS, and a second gene construct comprising RNA1 of said bipartite BPMV virus genome operably linked to promoter and terminator sequences. In another embodiment, RNA1 is modified for only moderate disease symptoms after infection. The constructs may be expressed transiently or stably incorporated in plant cells. Alternatively, constructs may be introduced into plant cells via crossing or agro infiltration. In a preferred embodiment, at least one construct is expressed transiently or at least one construct is stably integrated into the genome of said plant cell. Most preferably, the RNA2 of the system is truncated such that no infectious virus is produced.

In another aspect of the invention, a gene construct encoding a truncated RNA2 molecule operably linked to a nucleic acid encoding a heterologous protein of interest, each being further optionally linked to promoter and terminator sequences functional in a plant cell is provided.

In another aspect of the invention, a VIGS construct encoding a truncated RNA2 molecule linked to a non-coding or nucleic acid designed for VIGS. In some embodiments the nucleic acid which needs to be transcribed for VIGS will be further optionally linked to promoter and terminator sequences functional in a plant cell. Exemplary truncated RNA2 molecules include, for example, those having a deletion of greater than 2700 nucleotides in the RNA2 sequence. Heterologous proteins of interest include, without limitation, multimeric proteins, cytokines, vaccines, enzymes, growth factors, receptors, interferons, hematopoeitic agents, pituitary hormones, thyroid hormones, hypothalamic hormones, albumin, insulin and pancreatic hormones. In a preferred aspect of the invention, the system is employed to produce antibodies with affinity for proteins having commercial or therapeutic value.

Also included in the present invention are plants comprising the gene expression system described above, and plant cells or progeny obtained therefrom.

In yet another aspect of the invention, a method for expressing a foreign gene or for VIGS in a plant cell is provided by using the BPMV vectors of the invention. An exemplary method comprises providing a first gene construct, said construct comprising at least one truncated RNA2 construct of a bipartite BPMV genome and at least one nucleic acid encoding a heterologous protein of interest operably linked to promoter and terminator sequences or a VIGS construct which in certain embodiments may be operably linked to promoter and terminator sequences; providing a second gene construct, said construct comprising RNA1 of said BPMV bipartite virus genome; and introducing said first and second constructs into a plant cell, thereby producing said heterologous protein of interest or, alternatively transcription and/or translation of the VIGS construct. In some embodiments the same RNA2 may include both protein expression and VIGS in the same construct.

In a preferred embodiment the RNA1 is modified so that the plant only experiences moderate symptoms of BPMV. The constructs of the invention may be introduced into said plant cell simultaneously or sequentially. They may be expressed transiently, or stably incorporated into the plant cell genome. Alternatively, the constructs may be introduced via crossing with plant cells harboring said construct. Most preferably, the truncation of RNA2 prevents the production of infectious viral particles in the presence of functional RNA1. The constructs of the invention may each possess discrete promoter and terminator sequences. Alternatively, they may be operably linked in a polycistronic fashion such that a single promoter and a single terminator control the expression of at least two coding regions.

DESCRIPTION OF THE FIGURES

The patent or application file contains at least one drawing executed in color. Copies of this patent or patent application publication with color drawing(s) will be provided by the Office upon request and payment of the necessary fee.

FIG. 1 is a schematic representation of the CaMV 35S promoter driven BPMV vector. A, BPMV genomic RNA1 and RNA2 are expressed under control of the CaMV 35S promoter and Nos terminator. B, Cloning site for insertion of foreign sequences into BPMV RNA2. MP, movement protein; L-CP, large coat protein subunit; S-CP, small coat protein subunit; FMDV-2A, Foot and mouth disease virus 2A proteinase.

Figure 2:
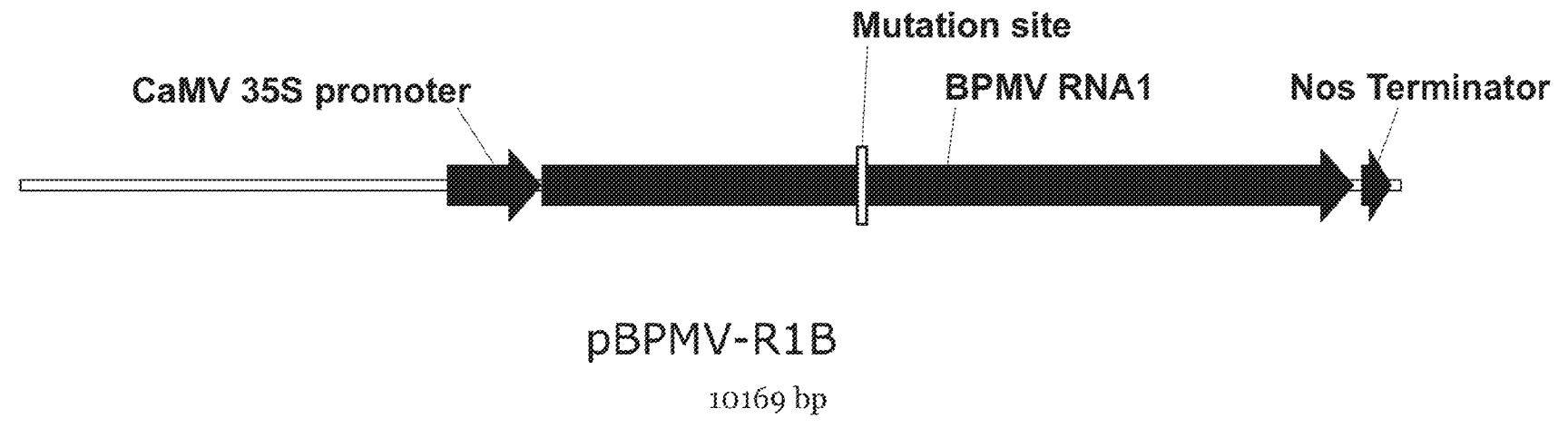

FIG. 2 is a linear map depicting the R1B (pBPMV-IA-R1M) vector with the modifications of the invention.

Figure 7:
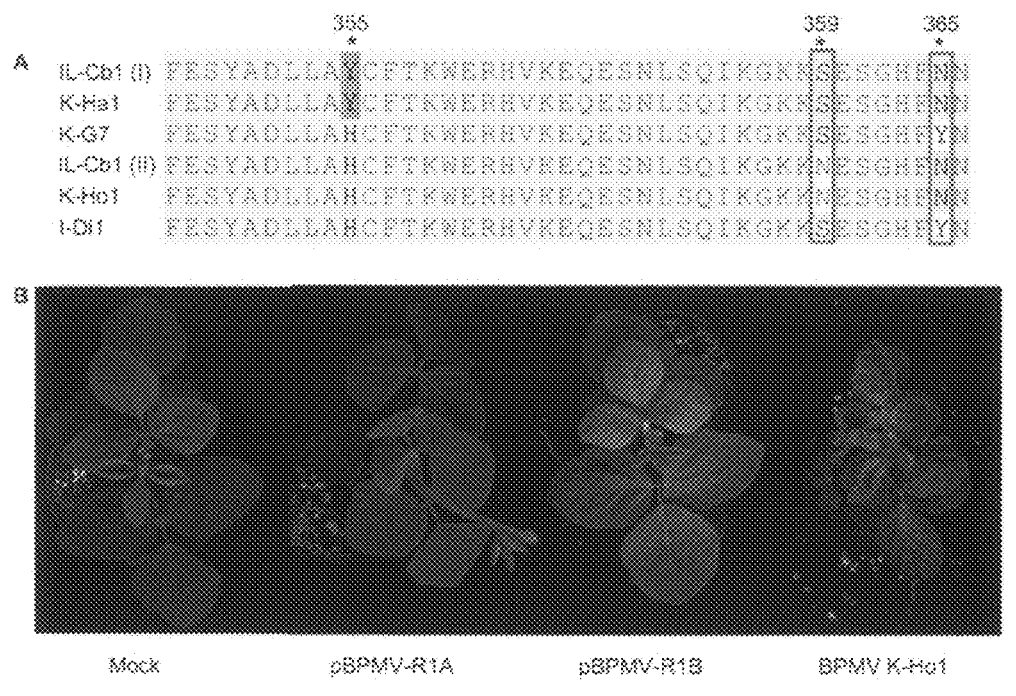

FIG. 7 depicts modification of BPMV RNA1 with moderate symptoms. A, Alignment of the helicase gene amino acid of selected BPMV strains and isolates. The three differences are highlighted with * and relative positions are indicated above *. The GeneBank accession numbers for the BPMV RNA1s are IL-Cb1 (I) (AY744931), K-Ha1 (AF394606), K-G7 (U70866), IL-Cb1 (II) (AY744932) and K-Ho1 (AF394608). The Iowa isolate I-Di1 (amino acids 634-74 of SEQ ID NO:2) is also shown. B, shoot phenotypes on the Williams soybean cultivar induced by different BPMV infectious RNA1 clones. Plants were photographed at 3 weeks post inoculation. Mock, mock-inoculated control. Infectious BPMV RNA 2 clone pBPMV-R2 was used as the RNA2 component for all infectious RNA1 clones. All plants were maintained in a growth chamber at 20° C. with a photoperiod of 16 hours.

FIG. 8 is an alignment of the amino acid sequences of variant BPMV RNA1 proteins including the modified RNA1 proteins of the invention pBPMV-R1A (SEQ ID NO:2) and pBPMV-R1B (SEQ ID NO:8).

FIG. 9 is a comparison of K-G7 and the R1A. (pBPMV-IA-R.1) (SEQ ID NO:1) sequence of the invention.

FIG. 10 is an alignment of the nucleotide sequences encoding the variant BPMV RNA1 pBPMV-R1A (SEQ ID NO:1) and pBPMV-R1B (SEQ ID NO:7) in FIG. 8.

FIG. 11 is a series of photographs depicting the soybean PDS gene silencing induced by different fragments and insertion orientations. A, Diagram of soybean PDS gene organization. Primers for amplification of different regions are indicated by hollow arrows on PDS gene. The single ORF is illustrated above the gene. The middle region between primers pF1130 and pR1520 is used as template for probe preparation. B, Soybean PDS gene silencing induced by different VIGS constructs. Plants were photographed at 3 weeks post inoculation. pBPMV-R1B (pBPMV-IA-R1M) was used as RNA1 clone for all inoculations. The RNA2 VIGS constructs used are PDS-F1 (pBPMV-PDS-F1, sense insertion), PDS-R1 (pBPMV-PDS-R1, antisense insertion), PDS-F2 (pBPMV-PDS-F2, sense insertion), PDS-R2 (pBPMV-PDS-R2, antisense insertion), PDS-F3 (pBPMV-PDS-F3, sense insertion), PDS-R3 (pBPMV-PDS-R3, antisense insertion), PDS-F4 (pBPMV-PDS-F4, sense insertion) and PDS-R4 (pBPMV-PDS-R4, antisense insertion). Mock, mock-inoculated control. Vector, empty vector control inoculated with pBPMV-R2. PDS-R3 induced the strongest PDS photobleaching phenotype. All plants were maintained in a growth chamber at 20° C. with a photoperiod of 16 hours.

FIG. 12 is a series of photographs depicting the BPMV RNA2 accumulations and changes in the soybean PDS gene mRNA levels induced by VIGS. Northern blot analysis was used to assess the PDS mRNA levels in soybean plants inoculated by different soybean PDS gene silencing constructs targeting different regions and with different insertion orientations. A, equivalent RNA loading was assessed by ethidium bromide staining of total RNA extracted from the third and fourth trifoliolates of infected plants by the BPMV VIGS constructs shown in FIG. 11. B, Northern blot analysis of BPMV RNA2 accumulation using probes prepared from the PCR products using primer pair R2-1548F and R2-2688R (Table I). C, Northern blot analysis of PDS mRNA levels induced by different VIGS constructs. The PDS Probe was prepared from middle region using primers pF1130 and pR1520 (FIG. 11A). D, Percentage of the BPMV RNA2 accumulation levels of each VIGS construct compared to the levels in vector control plants. The relative levels of the BPMV RNA2 accumulation were calculated by dividing the radioactivity signal of the VIGS treatments by the signal for the vector control. E. Percentage of the PDS mRNA levels induced by each VIGS construct compared to the levels in vector control plants. The relative levels of the PDS mRNA accumulation were calculated by dividing the radioactivity signal of the VIGS treatments by the signal for the vector control.

Figure 3:
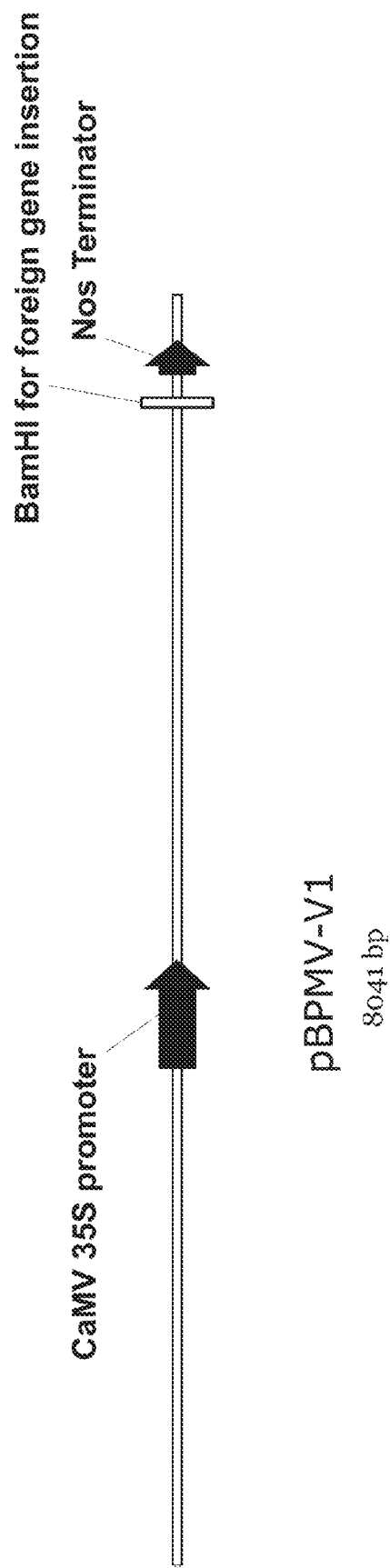
FIG. 3 is a linear map depicting the pBPMV V1 (pBPMV-IA-V1) vector of the invention.

FIG. 13 is a series of photographs showing the diverse symptoms induced by BPMV vector recombinants expressing foreign genes. pBPMV-R1B (pBPMV-IA-R1M) was used as the RNA1 clone for all inoculations. Plants were photographed at 3 weeks post inoculation. The BPMV viral gene expression and VIGS constructs are GFP (pBPMV-GFP2), BAR (pBPMV-BAR), BAR+PDS (pBPMV-BAR-PDS), pBPMV-P19 (pBPMV-P19), TBSV-P19+PDS (pBPMV-P19-PDS), GFP+BAR (pBPMV-GFP+BAR) and GFP+PDS (pBPMV-GFP-PDS). Mock and Vector are describe in FIG. 11. All plants were maintained in a growth chamber at 20° C. with a photoperiod of 16 hours. Note TBSV-P19 and TBSV-P19+PDS both induced massive necrosis.

FIG. 14 includes photographs showing BAR gene expression by BPMV vector provides herbicide resistance. pBPMV-R1B (pBPMV-IA-R1M) was used as the RNA1 clone for all inoculations. The BPMV viral gene expression constructs are BAR (pBPMV-BAR) and GFP+BAR (pBPMV-GFP+BAR). Mock and Vector are describe in FIG. 11 All plants were maintained in a greenhouse room with a photoperiod of 16 hours. Soybean seedlings were inoculated when the primary leaves are fully expanded. Three weeks post-inoculation, plants were treated with the herbicide (0.05% amino glufosinate in deionized water). Photographs were taken three weeks after the herbicide treatment. BAR and GFP+BAR conferred herbicide resistance while the mock and vector treated plants were killed.

FIG. 15 is a group of photographs demonstrating GFP gene expression in soybean. Green fluorescence on systemic leaves of soybean plants was examined by epifluorescence photography. pBPMV-R1B (pBPMV-IA-R1M) was used as the RNA1 clone for all inoculations. The BPMV viral gene expression constructs are GFP (pBPMV-GFP2), GFP+BAR (pBPMV-GFP+BAR) and GFP+PDS (pBPMV-GFP+PDS). Mock and Vector are describe in FIG. 11. All plants were maintained in a growth chamber at 20° C. with a photoperiod of 16 hours. Soybean seedlings were inoculated when the primary leaves are fully expanded. The third trifoliolates were photographed three weeks post inoculation for all treatments except for GFP+PDS which is the fourth trifoliolate. A, Pictures were taken under natural light. B, The same leaves in A were photographed under UV excitation for GFP fluorescence. Note the green fluorescence in panel B for constructs GFP, GFP+BAR and GFP+PDS.

FIG. 16 is a series of photographs showing GFP gene expression in soybean roots. Green fluorescence in soybean roots was examined by epifluorescence photography. pBPMV-R1B (pBPMV-IA-R1M) was used as the RNA1 clone for all inoculations. Mock and Vector are describe in FIG. 11. All plants were maintained in a growth chamber at 20° C. with a photoperiod of 16 hours. Soybean plants were inoculated when the primary leaves are fully expanded. Three weeks post-inoculation, soybean roots were rinsed with water and photographed under either natural light (upper panel) or UV excitation for GFP fluorescence (lower panel). Note the green fluorescence in panel B for constructs pBPMV-GFP2 and pBPMV-GFP+BAR.

DETAILED DESCRIPTION OF THE INVENTION

The following definitions are provided to facilitate an understanding of the present invention.

The phrase "bipartite transgene containing viral vector" refers to a two part viral replication system for production of heterologous proteins of interest. Exemplified herein are members of the Comovirus BPMV, which are in the picornavirus superfamily and possess non-enveloped, icosahedral capsids, and bipartite, single stranded positive sense RNA genomes. BPMV strains useful in the practice of the invention and their respective GenBank accession numbers are as follows: DQ 139274, AY 744933, AY744932, AY 744931, NC 003496, NC003495, FJ 185223, FJ 185222, EF 528583, AJ 269536, AF394609, AF394608, AF394607, AF 394606, AF330210, AF330209, AF330208, AF330207, AF 330206, AF 448497, AF 070866, M62738. RNA1 and RNA1 sequences isolated from these other BPMV can be truncated and operably linked to a heterologous sequences, or modified to provide only moderate symptoms according to the invention as described herein.

"Plant" species of interest include, but are not limited to, soybean (*Glycine max*), common bean (*Phaseolus vulgaris*), Peanuts (*Arachis hypogaea*), *Medicago sativa*, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*)), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers. The skilled person will appreciate that the tropism of the viral vectors disclosed herein varies. However, determining susceptibility to such viruses is well within the purview of the skilled person. Moreover, it may be possible to alter such specificity by recombinantly expressing receptors which facilitate viral entry into a plant cell.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An "isolated nucleic acid" (either DNA or RNA) may further represent a molecule produced directly by biological or synthetic means and separated from other components present during its production.

The terms "percent similarity", "percent identity" and "percent homology" when referring to a particular sequence are used as set forth in the University of Wisconsin GCG software program.

As is known in the art, a number of different programs can be used to identify whether a nucleic acid has sequence identity of similarity to a known sequence. Sequence identity and/or similarity may be determined using standard techniques known in the art, including, but not limited to, the local sequence identity algorithm of Smith & Waterman, Adv. Appl. Math. 2, 482 (1981), by the sequence identity alignment algorithm of Needleman & Wunsch, J. Mol. Biol. 48, 443 (1970), by the search for similarity method of Pearson & Lipman, Proc. Natl. Acad. Sci. USA 85, 2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res. 12, 387-395 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment, PILEUP uses a simplification of the progressive alignment method of Feng & Doolittle, J. Mol. Evol. 35, 351-360 (1987); the method is similar to that described by Higgins & Sharp CABIOS 5, 151-153 (1989).

Another example of a useful algorithm is the BLAST algorithm, described in Altschul et al., J. Mol. Biol. 215, 403-410, (1990) and Karlin et al., Proc. Natl. Acad. Sci. USA 90, 5873-5787 (1993). A particularly useful BLAST program is the WU-BLAST-2 program which was obtained from Altshul et al., Methods in Enzymology, 266, 460-480 (1996): http://blast.wustl/edu/blast/README.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

The term "substantially pure" refers to a preparation comprising at least 50-60% by weight of a given material (e.g., nucleic acid, oligonucleotide, protein, etc.)., More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like).

A "replicon" is any genetic element, for example, a plasmid, cosmid, bacmid, plastid, phage or virus that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "oligonucleotide" as used herein refers to sequences, primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The phrase "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and method of use. For example, for diagnostic applications, depending on the complexity of the target sequence, the oligonucleotide probe typically contains 15-25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as appropriate temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by calorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell or plant. A number of "selectable marker genes" are known in the art and several antibiotic resistance markers satisfy these criteria, including those resistant to kanamycin (nptII), hygromycin B (aph IV) and gentamycin (aac3 and aacC4). Useful dominant selectable marker genes include genes encoding antibiotic resistance genes (e.g., resistance to hygromycin, kanamycin, bleomycin, G418, streptomycin or spectinomycin); and herbicide resistance genes (e.g., phosphinothricin acetyltransferase). A useful strategy for selection of transformants for herbicide resistance is described, e.g., in Vasil, Cell Culture and Somatic Cell Genetics of Plants, Vols. I III, Laboratory Procedures and Their Applications Academic Press, New York, 1984. Particularly preferred selectable marker genes for use in the present invention would be genes which confer resistance to compounds such as antibiotics like kanamycin, and herbicides like glyphosate (Della-Cioppa et al., Bio/Technology 5(6), 1987, U.S. Pat. Nos. 5,463,175, 5,633,435). Other selection devices can also be implemented and would still fall within the scope of the present invention.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

"Native" refers to a naturally occurring ("wild-type") nucleic acid sequence.

"Heterologous" sequence refers to a sequence which originates from a foreign source or species or, if from the same source, is modified from its original form.

A "coding sequence" or "coding region" refers to a nucleic acid molecule having sequence information necessary to produce a gene product, when the sequence is expressed.

"Genetic component" refers to any nucleic acid sequence or genetic element which may also be a component or part of an expression vector. Examples of genetic components include, but are not limited to promoter regions, 5' untranslated leaders or promoters, introns, genes, 3' untranslated regions or terminators, and other regulatory sequences or sequences which affect transcription or translation of one or more nucleic acid sequences.

"Complementary" refers to the natural association of nucleic acid sequences by base-pairing (A-G-T pairs with the complementary sequence T-C-A). Complementarity between two single-stranded molecules may be partial, if only some of the nucleic acids pair are complementary; or complete, if all bases pair are complementary. The degree of complementarity affects the efficiency and strength of hybridization and amplification reactions.

"Homology" refers to the level of similarity between nucleic acid or amino acid sequences in terms of percent nucleotide or amino acid positional identity, respectively, i.e., sequence similarity or identity. Homology also refers to the concept of similar functional properties among different nucleic acids or proteins.

"Promoter" refers to a nucleic acid sequence located upstream or 5' to a translational start codon of an open reading frame (or protein-coding region) of a gene and that is involved in recognition and binding of RNA polymerase II and other proteins (trans-acting transcription factors) to initiate transcription. A "plant promoter" is a native or non-native promoter that is functional in plant cells. Constitutive promoters are functional in most or all tissues of a plant throughout plant development. Tissue-, organ- or cell-specific promoters are expressed only or predominantly in a particular tissue, organ, or cell type, respectively. Rather than being expressed "specifically" in a given tissue, organ, or cell type, a promoter may display "enhanced" expression, i.e., a higher level of expression, in one part (e.g., cell type, tissue, or organ) of the plant compared to other parts of the plant. Temporally regulated promoters are functional only or predominantly during certain periods of plant development or at certain times of day, as in the case of genes associated with circadian rhythm, for example. Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

When fused to heterologous DNA sequences, such promoters typically cause the fused sequence to be transcribed in a manner that is similar to that of the gene sequence with which the promoter is normally associated. Promoter fragments that include regulatory sequences can be added (for example, fused to the 5' end of, or inserted within, an active promoter having its own partial or complete regulatory sequences (Fluhr et al., Science 232:1106 1112, 1986; Ellis et al., EMBO J. 6:1116, 1987; Strittmatter and Chua, Proc. Nat. Acad. Sci. USA 84:8986 8990, 1987; Poulsen and Chua, Mol. Gen. Genet. 214:16 23, 1988; Comai et al., Plant Mol. Biol. 15:373 381, 1991).

The 3' non-translated region of the gene constructs of the invention contain a transcriptional terminator, or an element having equivalent function, and, optionally, a polyadenylation signal, which functions in plants to cause the addition of polyadenylated nucleotides to the 3' end of the RNA. Examples of suitable 3' regions are (1) the 3' transcribed, non-translated regions containing the polyadenylation signal of *Agrobacterium* tumor-inducing (Ti) plasmid genes, such as the nopaline synthase (Nos) gene, and (2) plant genes such as the soybean storage protein genes and the small subunit of the ribulose-1,5-bisphosphate carboxylase (ssRUBISCO) gene. An example of another 3' region is that from the ssRUBISCO E9 gene from pea (European Patent Application 385,962, herein incorporated by reference in its entirety).

Typically, DNA sequences located a few hundred base pairs downstream of the polyadenylation site serve to terminate transcription. The DNA sequences are referred to herein as transcription-termination regions. The regions are required for efficient polyadenylation of transcribed messenger RNA (mRNA) and are known as 3' non-translated regions. RNA polymerase transcribes a coding DNA sequence through a site where polyadenylation occurs.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the basic and novel characteristics of the sequence.

The phrase "suppressor of gene silencing" refers to virally encoded proteins expressed in plants that suppress PTGS. An exemplary suppressor of PTGS, the helper component-proteinase (Hc-Pro) protein encoded by a plant potyvirus, is described herein. Sequence information for HcPro is found in GeneBank accession number PVY NC_001616 and PVY HCPro: AY518295.

An "antibody" or "antibody molecule" is any immunoglobulin, including antibodies and fragments thereof, that binds to a specific antigen, such as epitopes of an apoptosis modulator protein. The term includes polyclonal, monoclonal, chimeric, and bispecific antibodies. As used herein, antibody or antibody molecule contemplates both an intact immunoglobulin molecule and an immunologically active portion of an immunoglobulin molecule such as those portions known in the art as Fab, Fab', F(ab')$_2$ and F(v).

As used herein, "transgenic plant" includes reference to a plant that comprises within its nuclear genome a heterologous polynucleotide. Generally, the heterologous polynucleotide is stably integrated within the nuclear genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "VIGS" means virus-induced gene silencing.

As used herein, "viral silencing vector" means a DNA construct comprising (i) a sufficient portion of a viral genome to induce VIGS and (ii) a nucleotide sequence that is similar (i.e., a sequence that has a sufficient percent identity or a sufficient percent complementarity to effect down regulation) to at least a fragment of a target gene, wherein the target gene is down-regulated when the viral silencing vector is introduced into a cell. For example, in order to affect VIGS in a plant, the portion of the viral genome required to affect VIGS may include that portion responsible for viral movement and viral replication in the plant. As is known to those skilled in the art, each virus/host combination should be optimized for producing effective silencing vectors. In the present invention, the viral genome includes all genes except those encoding the coat protein. However, it is to be understood that other optimized vectors can be used and are included within the scope of the applicant's teachings. For example, the silencing vector may include the origin of replication, the genes necessary for replication in a plant cell, and one or more nucleotide sequences with similarity to one or more target genes. The vector may also include those genes necessary for viral movement. In the case of bipartite viruses, for example geminiviruses, the A and B components may be carried in the same silencing vector. Alternatively, the plant may be transformed with both components on separate vectors. Further, in one example, the A genome component of a geminivirus (which replicates autonomously) was shown to be sufficient for VIGS, as was the B component (WO 01/94694 and US Patent Application Publication Number 2002/0148005, both of which are incorporated herein by reference). Other silencing vectors are disclosed in U.S. Pat. No. 6,759,571 and US Patent Application Publication Number 2004/0019930, both of which are herein incorporated by reference. The nucleotide sequence that is similar to at least a fragment of a target gene may replace any coding or non-coding region that is nonessential for the present purposes of gene silencing, may be inserted into the vector outside the viral sequences, or may be inserted just downstream of an endogenous viral gene, such that the viral gene and the nucleotide sequence are cotranscribed. The size of the nucleotide sequence that is similar to the target gene may depend on the site of insertion or replacement within the viral genome. Accordingly, there are many ways of producing silencing vectors, as known to those skilled in the art.

BPMV is a member of the genus Comovirus in the family Comoviridae (Lomonossoff and Ghabrial, Encyclopedia of Plant Pathology, Vol. 1 (2001)). BPMV has a bipartite positive-strand RNA genome consisting of RNA1 (approximately 6.0 kb) and RNA2 (approximately 3.6 kb) that are separately encapsidated in isometric particles 28 nm in diameter. The BPMV genome is expressed via the synthesis and subsequent proteolytic processing of polyprotein precursors. BPMV RNA1 codes for five mature proteins required for replication, whereas RNA2 codes for a putative cell-to-cell movement protein (MP) and the two coat proteins (L-CP and SCP). As disclosed herein, stable VIGS BPMV-based vectors can be generated by inserting the VIGS construct after the translation truncation signal of the RNA2-encoded polyprotein open reading frame. Additionally, stable BPMV-based vectors which can be used for either VIGS or heterologous protein expression can be generated by optionally inserting the foreign gene construct into the RNA2 sequence between the MP and L-CP coding regions, and constructing additional proteinase cleavage sites to flank the foreign protein. In a preferred embodiment the proteinase cleavage sites are FMDV-2A.

Plant virus-based vectors provide valuable tools for expression of foreign proteins in plants and for gene function studies. As disclosed herein, Bean pod mottle virus (BPMV)-based vectors are useful for gene expression and virus-induced gene silencing (VIGS) in plants such as soybean. The genes of interest or the VIGS construct are inserted into the RNA2-encoded polyprotein open reading frame not only between the movement protein (MP) and the large coat protein (L-CP) coding regions as previous vectors, but after the BPMV RNA2 stop codon. There may or may not be an insertion between the movement protein and large coat protein as in other previous BPMV vectors. The placement of the insertion site after the stop codon avoids the requirement of in frame reading of the foreign sequences. It also allows the insertion of noncoding sequences for functional analysis. The novel recombinant BPMV constructs were stable following several serial passages in soybean and relatively high levels of protein expression were attained. Successful VIGS was also demonstrated. The results disclosed herein indicate that the BPMV-based vectors are suitable for expression of foreign proteins in soybean and for functional genomics applications.

In one embodiment, the invention provides a Bean pod mottle virus (BPMV) vector containing a nucleic acid sequence encoding an RNA2 polyprotein open reading frame (ORF), wherein the RNA2 polyprotein ORF comprises a first and second protease cleavage site such as a FMDV 2A, wherein the nucleic acid sequences encoding the first and second protease cleavage site differ sufficiently to reduce homologous recombination between the nucleic acid sequences. The protease cleavage sites are located after the RNA2 polyprotein stop codon and optionally between the movement protein (MP) and large coat protein (L-CP) and. The vector can contain restriction sites for insertion of a heterologous sequence between the protease cleavage sites.

As used herein, a "Bean pod mottle virus vector" or "BPMV vector" refers to a nucleic acid vector that, on its own or in combination with other nucleic acids, is capable of generating BPMV when expressed in a host cell or organism. A BPMV vector can be, for example, a BPMV genome such as a genome contained in a whole virus. In addition, a BPMV vector can be a plasmid encoding a portion of a BPMV genome. For example, as disclosed herein, a plasmid encoding one of the two RNAs that comprise the BPMV genome can be used as a BPMV vector that, when combined with a second plasmid that contains the other RNA, results in the production of BPMV virus (see Examples).

As used herein, an "RNA2 polyprotein" refers to the open reading frame encoded by an approximately 3.6 kb RNA, designated RNA2, found in BPMV, as previously described (see Gu et al., Phytopathology 92:446-452 (2002; Gu and Ghabrial, Virology 333:271-283 (2005)). A schematic representations of the genome organization of BPMV vectors of the invention is shown in FIGS. 1A-1C.

As used herein, a "protease cleavage site" refers to an amino acid sequence recognized and cleaved by a site-specific protease, for example, a virally-encoded site-specific protease. Site-specific proteases are well known in the art. In the case where an expression vector such as a BPMV vector of the invention is to be used in a host plant such as soybean, it is understood that the site-specific protease cleavage sites should be recognized by a site-specific protease, for example, a site-specific protease encoded by BPMV RNA1, as disclosed herein. For example, in BPMV, the two RNA viral genomes express polyprotein precursors, which are processed post-translationally to produce mature proteins. Thus, appropriate proteases are expressed that allow proper processing of the polyprotein to mature proteins. An example of such a protease cleavage site is the FMDV 2A proteinase site between the movement protein (MP) and large coat protein (L-CP) of the RNA2 polyprotein and at the end of the stop codon of the same (see FIG. 1).

Applicants have engineered novel RNA1 sequences which can be used according to the invention. RNA1 contains the coding regions of five proteins: from the 5'-end protease-cofactor (Co-pro), helicase (Hel), VPg, protease (Pro) and RNA-dependent RNA polymerase (RdRp). The intermediate polyproteins Hel+VPg and Pro+RdRp play important roles in replication. The modifications as showing in SEQ ID NOS:1 and 2, and in FIGS. 7-10.

As used herein, the phrase "differ sufficiently to reduce homologous recombination," refers to a difference in homology between two nucleic acid sequences such that the amount of homologous recombination between the sequences is reduced. For example, in an embodiment of the invention in which a protease cleavage site is present as two copies, the nucleic acid sequences encoding the protease cleavage sites can be similar or identical if the protease cleavage sites are similar or identical. In such a case, the homology between the nucleic acid sequences encoding the protease cleavage site can undergo homologous recombination. In the case where a nucleic acid encoding a heterologous polypeptide is inserted between the protease cleavage sites, homologous recombination would result in loss of the heterologous sequence and therefore decreased expression of the heterologous polypeptide. To minimize the chance of recombination, the nucleic acid sequences encoding the two copies of the protease cleavage site can be modified based on the degeneracy of the genetic code such that the same amino acids are encoded. For example, in a particular embodiment the third nucleotide of each codon is changed in one copy of protease cleavage site so that the encoded amino acids remain the same. Although exemplified with one of the nucleic acid sequences encoding one of the protease cleavage sites being modified, it is understood that one or both sequences can be modified so long as there is a sufficient difference in homology to reduce homologous recombination between the sequences. For example, instead of modifying one copy, it is possible to modify both nucleic acids, by alternating modified codons in the two copies, which would similarly result in reduced homology between the two sequences and therefore reduce homologous recombination.

One skilled in the art can readily determine a difference in homology sufficient to reduce homologous recombination, for example, by using vectors of the invention, inoculating a suitable host plant such as soybean and determining the amount of homologous recombination that has occurred. If homologous recombination has occurred at a level that makes a particular BPMV vector unsuitable for a particular use, one skilled in the art can make further changes in homologous sequences in order to reduce the amount of recombination that occurs.

Thus, in a particular embodiment, the invention provides a vector in which each codon encoding the protease cleavage site differs between the nucleic acid sequences encoding the first protease cleavage site and the second protease cleavage site. In one embodiment, one of the protease cleavage sites can comprise the FMDV 2A proteinase inserted after the translation stop codon. In still another embodiment, the vector can optionally contain a nucleic acid sequence encoding a heterologous polypeptide inserted between the first and second protease cleavage sites, for example, between BPMV movement protein (MP) and large coat protein (L-CP).

The vectors of the invention may optionally include other sequences known to those of skill in the art such as marker genes, regulatory elements, terminators, antibiotic resistance genes, and the like.

Regulatory Elements

Exemplary promoters for expression of a nucleic acid sequence in plants include the CaMV 35S promoter (Odell et al., 1985), CaMV 19S (Lawton et al., 1987), nos (Ebert et al., 1987), Adh (Walker et al., 1987), sucrose synthase (Yang and Russell, 1990), a-tubulin, actin (Wang et al., 1992), cab (Sullivan et al., 1989), PEPCase (Hudspeth and Grula, 1989) or R gene complex associated promoters (Chandler et al., 1989). Tissue specific promoters such as root cell promoters (Conkling et al., 1990) and tissue specific enhancers (Fromm et al., 1986) are also contemplated to be useful, as are inducible promoters such as ABA- and turgor-inducible promoters. In one embodiment of the invention, the native promoter of an isoflavone biosynthesis sequence is used. In another embodiment, a heterologous sequence is used.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

It is envisioned that nucleic acids encoding a polypeptide as provided herein may be introduced under the control of novel promoters or enhancers, etc., or homologous or tissue specific promoters or control elements. Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue.

Terminators

Transformation constructs prepared in accordance with the invention will typically include a 3' end DNA sequence that acts as a signal to terminate transcription and allow for the poly-adenylation of the mRNA produced by coding sequences operably linked to a promoter. Alternatively, a heterologous 3' end may enhance the expression of coding sequences. Examples of terminators that are deemed to be useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired.

Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Included within the terms selectable or screenable markers also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity.

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154,204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; or a gene encoding for green fluorescent protein (Sheen et al., 1995; Haseloff et al., 1997; Reichel et al., 1996; Tian et al., 1997; WO 97/41228).

A heterologous nucleotide sequence of the present invention can be provided as its wild-type sequence. Alternatively, a synthetic sequence, such as a "plant-optimized" sequence mentioned above can be employed. A nucleotide sequence having a high degree of homology to these sequences, so that the encoded amino acid sequence remains substantially unchanged, are also contemplated. In particular, sequences at least 80%, more preferably 90%, homologous with an aforementioned nucleotide sequence are contemplated. It should be noted, however, that only that those epitopes of an expressed antigenic protein essential for generating the desired immune response need be present in the translated molecule. Accordingly, C- and/or N-terminal fragments, including portions of fusion proteins, presenting the essential epitopes are contemplated within the invention. Such fragments can be encoded in a vector construct of the invention or can be generated in vivo or in vitro by post-translation cleavage processes.

A transgenic plant transformed with a BPMV vector described hereinabove is another aspect of the present invention. Particularly preferred plant hosts for the vector include soybean and other legumes.

The Vectors of the invention had many uses in plant transformation and research technologies. Examples of such uses include the following.

A. Gene Amplification

The constructs of the present invention can be used to amplify a gene of interest. According to the method of the invention, a gene of interest is amplified in the presence of a Rep protein, preferably about 10-fold, more preferably about 30-fold and most preferably about 100-fold, as compared to a gene of interest in the absence of a Rep protein.

B. Protein Production

The constructs of the present invention can be used to overproduce a protein of interest. According to the method of the invention, a protein of interest is overproduced in the presence of a Rep protein such that the amount of protein produced is preferably about 2%, more preferably about 10% and most preferably about 30% of the total protein of a cell comprising a construct of the invention that includes a nucleotide sequence encoding the protein of interest, and wherein the cell further comprises a Rep protein.

The invention also provides a method for expressing a heterologous polypeptide in a plant such as a soybean plant. The method can include the step of inoculating a soybean plant with Bean pod mottle virus (BPMV) RNA1 and recombinant RNA2, wherein the recombinant BPMV RNA2 comprises a nucleic acid sequence encoding an RNA2 polyprotein open reading frame (ORF), wherein the RNA2 polyprotein ORF comprises a first and second protease cleavage site such as a FDMV 2A cleavage site after the RNA translation stop codon, wherein the nucleic acid sequences encoding the first and second protease cleavage site differ sufficiently to reduce homologous recombination between the protease cleavage site, encoding nucleic acid sequences and wherein a nucleic acid sequence encoding a heterologous polypeptide is inserted between the first and second protease cleavage sites. In a particular embodiment, the method can be performed with a vector in which the first protease cleavage sites are located after the movement protein (MP) and large coat protein (L-CP) encoded by the RNA2 polyprotein. The recombinant RNA2 can contain restriction sites for inserting the nucleic acid sequence encoding the heterologous polypeptide between or after the first and second protease cleavage sites. Other BPMV vectors, as disclosed herein, can also be used in a method for expressing a heterologous polypeptide in a plant such as soybean. Such a method can be used, for example, to produce large quantities of a polypeptide of interest. Production of such heterologous polypeptides can be used to produce large quantities of proteins at relatively low cost, for example, to produce a therapeutic polypeptide. A polypeptide can be purified from the plant and used for therapeutic or other purposes. In addition, expression of a heterologous polypeptide such as an antigen can provide a plant or plant-derived product containing the antigen, which can provide a potential low cost oral vaccine containing an appropriate antigen.

C. Gene Function Studies

Another important application of plant viral vector systems is in studies on host gene function. With more plant genomic information available, a high throughput tool is required. Virus-induced gene silencing (VIGS) is an exceptional reverse genetics tool that can be employed to generate mutant phenotypes for conveying function to unknown genes. VIGS has many advantages over other methods, for example, it is quick and does not require plant transformation (Burch-Smith et al., 2004). In VIGS systems, viruses are designed to carry partial sequence of known or candidate genes in order to link their function to the mutant phenotype. Replication of the recombinant virus and generation of dsRNA intermediates trigger the RNA-mediated host defense system, resulting in degradation of RNA with sequence identity to the recombinant virus including mRNA of the gene of interest. The targets of VIGS can be a single gene, several members of a gene family, or several distinct genes (Lu et al., EMBO J. 22, 5690-5699 (2003a); Peele, et al., Plant J. 27:357-366 (2001); Turnage, et al., Plant J. 30:107-117 (2002)). Many model host plants including *N. benthamiana*, tomato, tobacco, *Arabidopsis*, and cassava have been explored (Burch-Smith, et al., Plant J. 39:734-746 (2004)). With the current abundance of genomic information on soybean and model legume species (Stacey, et al., Plant Physiol. 135:59-70 (2004)), it is timely to apply VIGS to soybean to enhance knowledge of gene function in such a major legume crop. As disclosed herein, BPMV vectors of the invention can be used as a VIGS vector for studies on gene function in soybean.

The invention additionally provides a method for virus-induced gene silencing in a soybean plant and vectors useful in a method for virus-induced gene silencing. Such a method can include the step of inoculating a soybean plant with Bean pod mottle virus (BPMV) RNA, wherein the BPMV RNA comprises a nucleic acid sequence encoding at least a portion of a gene endogenous to the soybean plant. For virus-induced gene silencing, a partial or entire sequence of an endogenous gene can also be located in the untranslated regions (UTRs) of RNA2, or in RNA1 if the sequence is small enough to be accommodated, as discussed above, since it is the expression of the nucleic acid encoding at least a portion of an endogenous gene that results in gene silencing. For a virus-induced gene silencing vector, the insertion in the UTRs can be facilitated by engineering appropriate restriction sites for insertion of the endogenous gene, so long as the inserted endogenous sequence does not impair viral RNA replication and a sufficient amount of infective BPMV is produced.

As used herein, the term "endogenous," when used in reference to a polypeptide, nucleic acid or gene, refers to a polypeptide, nucleic acid or gene that is expressed by a host. For example, using a BPMV vector of the invention for a method of virus-induced gene silencing, a BPMV vector is engineered to express at least a portion of a gene endogenous to the host plant such as soybean. In such a case, the endogenous gene is already expressed in the host plant.

The results disclosed herein represent the first report to demonstrate that BPMV-based vectors are suitable for VIGS of non-translatable gene sequences in soybean. The level of foreign gene expression, as exemplified by the BPMV-GFP vector, was estimated to account for 1% of total soluble proteins (see Example III). This level is comparable to that reported for the PVX-based vectors (Culver, Virology 226: 228-235 (1996)).

The BPMV-based vector is suitable for use as a VIGS vector to study gene function in soybean. Soybean is a major oilseed crop and an important source of food and feed protein. It is subject to a wide range of pathogens and VIGS is an ideal reverse genetics tool for soybean functional genomics aimed at understanding host-microbe interactions (Jackson et al., 2006; Stacey et al., 2004). Recently, BPMV VIGS was successfully used for identification of the soybean rust resistance gene Rpp4 (Meyer et al., 2009). Three viruses, Apple latent spherical virus (ALSV), Cucumber mosaic virus (CMV) and BPMV have been developed as soybean functional genomics tools (Igarashi et al., 2009; Nagamatsu et al., 2007; Zhang and Ghabrial 2006). Fusion protein expression was used for both ALSV and BPMV gene expression as well as for VIGS studies. The fusion protein strategy used for the previous BPMV VIGS vectors (Zhang and Ghabrial 2006; Zhang et al., 2009) requires that foreign sequences be in translation frame with the RNA2 open reading frame. This design strategy restricts the vector's usefulness for RNA silencing as it cannot target genes such as short transcription factors and non-coding sequences as well as promoter regions and untranslated regions. In addition, it cannot discern if RNA polarity influences the efficiency of target gene silencing and there is always a short peptide expressed that may confound the interpretation of the silencing result. To overcome these shortcomings, foreign sequences were inserted after the viral RNA2 ORF. The soybean PDS gene was selected for testing this novel strategy because of the obvious photobleaching phenotype as well as the opportunity to compare with previous results (Igarashi et al., 2009; Nagamatsu et al., 2007; Zhang et al., 2009). In our results, sense orientation insertion had minimal effect on PDS silencing. These results are consistent with those using ALSV in soybean where the 5' end PDS sense insertion had little PDS silencing effect (Igarashi et al., 2009). Similar results were also reported in *Arabidopsis* where sense insertion in TYMV had minimal effect on *Arabidopsis* GUS and PDS silencing (Pflieger et al., 2008). However, the ALSV report could not test the silencing effect of RNA polarity due to the fusion protein strategy. Here we found that generally antisense resulted in stronger silencing. Two antisense PDS VIGS constructs, pBPMV-PDS-R3 and pBPMV-PDS-R4, resulted in a 10 fold reduction. This contrasts with the 2.5-3 fold reduction we observed when testing other genes using the sense orientation (Zhang et al., 2009). Similar to the ALSV results, we found that the middle to 3' end PDS gene region resulted in stronger silencing, particularly in the antisense orientation.

It has been reported that gene fragments of 23-80 nt can be sufficient for VIGS induction (Thomas et al., 2001; Burch-Smith et al., 2004; Pflieger et al., 2008). Since the insert size for the BPMV PDS silencing construct in this study is about 300 nt, it is theoretically possible to achieve VIGS of multiple soybean genes. This is important because soybean has genetic redundancy and genes function in parallel signaling pathways (Blanc and Wolfe 2004; Lawrence and Pikaard 2003; Schlueter et al., 2004; Shoemaker et al., 1996) making simultaneous testing of different combinations of genes or homologs desirable (Zhang et al., 2009).

Another amenable feature for multiple gene silencing is that there is no limit on translation requirement for foreign gene insertion with the new BPMV VIGS vector. Further, the interesting finding that the 3' PDS antisense insertion gave the best silencing phenotype in soybean makes the new BPMV VIGS vector applicable for constructing a cDNA VIGS library because a version of the new BPMV VIGS vector was developed so that directional insertion can be achieved.

It will generally be desirable that vectors provided by the invention be capable of systemic spread in an infected plant. However, such a systemic spread may not be essential for efficient gene silencing. A recombinant vector provided by the invention may or may not therefore include all cis-elements required for vascular movement of the vector or even its cell-to-cell spread. In this manner, modulation of plant gene expression in a collection of plant cells may be more efficiently carried out. Methods for inoculating plants and plant cells with recombinant viral vectors or viral particles are well known to those of skill in the art. Such vectors may, for example, be administered in a solution and may also contain any other desired ingredients including buffers, cis-elements, surfactants, solvents and similar components.

Vector Construction

Construction of vectors for use with the invention will be well known to those of skill in light of the current disclosure.

Recombinant constructs preferably comprise restriction endonuclease sites to facilitate vector construction. Particularly useful are unique restriction endonuclease recognition sites. Examples of such restriction sites include sites for the restriction endonucleases HindIII, Tth 1111, BsmI, KpnI and XhoI. Endonucleases preferentially break the internal phosphodiester bonds of polynucleotide chains. They may be relatively unspecific, cutting polynucleotide bonds regardless of the surrounding nucleotide sequence. However, the endonucleases which cleave only a specific nucleotide sequence are called restriction enzymes. Restriction endonucleases generally internally cleave nucleic acid molecules at specific recognition sites, making breaks within "recognition" sequences that in many, but not all, cases exhibit two-fold symmetry around a given point. Such enzymes typically create double-stranded breaks.

Many of these enzymes make a staggered cleavage, yielding DNA fragments with protruding single-stranded 5' or 3' termini. Such ends are said to be "sticky" or "cohesive" because they will hydrogen bond to complementary 3' or 5' ends. As a result, the end of any DNA fragment produced by an enzyme, such as EcoRI, can anneal with any other fragment produced by that enzyme. This properly allows splicing of foreign genes into plasmids, for example. Some restriction endonucleases that may be particularly useful with the current invention include HindIII, Tth 111 1, BsmI, KpnI and XhoI.

Some endonucleases create fragments that have blunt ends, that is, that lack any protruding single strands. An alternative way to create blunt ends is to use a restriction enzyme that leaves overhangs, but to fill in the overhangs with a polymerase, such as Klenow, thereby resulting in blunt ends. When DNA has been cleaved with restriction enzymes that cut across both strands at the same position, blunt end ligation can be used to join the fragments directly together. The advantage of this technique is that any pair of ends may be joined together, irrespective of sequence.

Those nucleases that preferentially break off terminal nucleotides are referred to as exonucleases. For example, small deletions can be produced in any DNA molecule by treatment with an exonuclease which starts from each 3' end of the DNA and chews away single strands in a 3' to 5' direction, creating a population of DNA molecules with single-stranded fragments at each end, some containing terminal nucleotides. Similarly, exonucleases that digest DNA from the 5' end or enzymes that remove nucleotides from both strands have often been used. Some exonucleases which may be particularly useful in the present invention include Bal31, S1, and ExoIII. These nucleolytic reactions can be controlled by varying the time of incubation, the temperature, and the enzyme concentration needed to make deletions. Phosphatases and kinases also may be used to control which fragments have ends which can be joined. Examples of useful phosphatases include shrimp alkaline phosphatase and calf intestinal alkaline phosphatase. An example of a useful kinase is T4 polynucleotide kinase.

Once the source DNA sequences and vector sequences have been cleaved and modified to generate appropriate ends, they are incubated together with enzymes capable of mediating the ligation of the two DNA molecules. Particularly useful enzymes for this purpose include T4 ligase, *E. coli* ligase, or other similar enzymes. The action of these enzymes results in the sealing of the linear DNA to produce a larger DNA molecule containing the desired fragment (see, for example, U.S. Pat. Nos. 4,237,224; 4,264,731; 4,273,875; 4,322,499 and 4,336,336, which are specifically incorporated herein by reference).

It is to be understood that the termini of the linearized plasmid and the termini of the DNA fragment being inserted must be complementary or blunt in order for the ligation reaction to be successful. Suitable complementary ends can be achieved by choosing appropriate restriction endonucleases (i.e., if the fragment is produced by the same restriction endonuclease or one that generates the same overhang as that used to linearize the plasmid, then the termini of both molecules will be complementary). As discussed previously, in one embodiment of the invention, at least two classes of the vectors used in the present invention are adapted to receive the foreign oligonucleotide fragments in only one orientation. After joining the DNA segment to the vector, the resulting hybrid DNA can then be selected from among the large population of clones or libraries.

Once a DNA vector has been prepared, it will be readily understood to those of skill in the art that infective RNA transcripts may be made therefrom. For example, commercial kits are available for production of RNA transcripts. On example of such a kit that was used by the inventors is the mMeSSAGE mMACHINE transcription kit from Ambion (Austin, Tex.).

In certain embodiments of the invention, techniques may thus be used to assay gene expression and generally, the efficacy of a given gene silencing construct. While this may be carried out by visual observation of a change in plant phenotype, molecular tools may also be used. For example, expression may be evaluated by specifically identifying the nucleic acid or protein products of genes. Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Very frequently, the expression of a gene product is determined by evaluating the phenotypic results of its expression. These assays also may take many forms including but not limited to, analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may be observed, such as plant stature or growth.

Production and Characterization Of Stably Transformed Plants

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

Selection

It is believed that DNA is introduced into only a small percentage of target cells in any one study. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphotransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*.

Another example of a herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on polypeptides encoded by the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103. The best characterized mutant EPSPS gene conferring glyphosate resistance comprises amino acid changes at residues 102 and 106, although it is anticipated that other mutations will also be useful (PCT/W097/4103).

To use a bar-bialaphos or the EPSPS-glyphosate selective system, for example, transformed tissue can be cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate may be preferred, it is proposed that ranges of 0.1-50 mg/l bialaphos or 0.1-50 mM glyphosate will find utility.

Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber, for example, at about 85% relative humidity, 600 ppm $CO_2$, and 25-250 microeinsteins $m^{-2}s^{-1}$ of light. Plants may be matured in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plant Cons. Regenerating plants can be grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 µl agarose. In embryo rescue, large embryos (defined as greater than 3 mm in length) are germinated directly on an appropriate media. Embryos smaller than that may be cultured for 1 wk on media containing the above ingredients along with $10^{-5M}$ abscisic acid and then transferred to growth regulator-free medium for germination.

Characterization

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

DNA Integration, RNA Expression and Inheritance

Genomic DNA may be isolated from cell lines or any plant parts to determine the presence of the exogenous gene through the use of techniques well known to those skilled in the art. Note, that intact sequences will not always be present, presumably due to rearrangement or deletion of sequences in the cell. The presence of DNA elements introduced through the methods of this invention may be determined, for example, by polymerase chain reaction (PCR™). Using this technique, discrete fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR™ analysis. In addition, it is not typically possible using PCR™ techniques to determine whether transformants have exogenous genes introduced into different sites in the genome, i.e., whether transformants are of independent origin. It is contemplated that using PCR™ techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR™, e.g., the presence of a gene.

Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot Northern hybridizations. These techniques are modifications of Northern blotting and will only demonstrate the presence or absence of an RNA species.

Gene Expression

While Southern blotting and PCR™ may be used to detect the gene(s) in question, they do not provide information as to whether the corresponding protein is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

Breeding Plants

In addition to direct transformation of a particular plant genotype with a construct prepared according to the current invention, transgenic plants may be made by crossing a plant having a selected DNA of the invention to a second plant lacking the construct. For example, a selected polypeptide coding sequence can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:

(a) plant seeds of the first (starting line) and second (donor plant line that comprises a transgene of the invention) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

Although exemplified herein with soybean, it is understood that a BPMV vector of the inventions can be used in other suitable host plant organisms that support the propagation of BPMV. For example, other cultivars of bean and leguminous weeds are also known to be hosts for BPMV (Geisler et al., Plant Dis. 86:1280-1289 (2002)). Therefore, the vectors of the invention can be used in methods in other suitable host plants as with soybean.

It is understood that modifications which do not substantially affect the activity the various embodiments of this invention are also provided within the definition of the invention provided herein. Accordingly, the following examples are intended to illustrate but not limit the present invention.

The foregoing invention has been described in detail by way of illustration and example for purposes of clarity and understanding. However, it will be obvious that certain changes and modifications such as single gene modifications and mutations, somoclonal variants, variant individuals selected from large populations of the plants of the instant variety and the like may be practiced within the scope of the invention, as limited only by the scope of the appended claims.

Example I

Bean pod mottle virus (BPMV, genus Comovirus) has a bipartite positive RNA genome consisting of RNA1 (≈6 kb) and RNA2 (≈3.6 kb). Both BPMV RNA1 and RNA2 are expressed as a single polyprotein precursor and subsequent proteolysis to yield mature viral gene products. Based on the fusion protein expression strategy, Zhang and Ghabrial (2006) reported the first generation BPMV foreign gene expression and VIGS vector for functional genomics of soybean. However, the RNA-based first generation BPMV plant viral vector is not amenable for efficient use because of the requirement for in vitro RNA transcription and RNA inoculation. Recently, a more efficient DNA-based BPMV VIGS vector was reported that is an effective and efficient functional genomics tool applicable for high throughput large-scale functional genomics experiments in soybean (Zhang et al., 2009).

To further enhance the potential of BPMV as a viral vector for functional genomics, we describe here a BPMV vector that employs a novel design for foreign gene expression. With the new design, two foreign genes can be inserted into the BPMV genomic RNA2 for simultaneous systemic expression in plants. This makes in vivo protein-protein study feasible in soybean. The previously reported BPMV VIGS vectors are based on insertion of a gene fragment between the movement protein and large coat protein of BPMV. That design requires the foreign sequences to be in frame with the BPMV RNA2 open reading frame. Because of the translation requirement, primer design, particularly for high throughput applications, is laborious with the previous vector. In addition, potential interference of the translated peptide from the foreign sequence may result in unanticipated phenotypes. To overcome these inconveniences, we insert VIGS foreign gene fragments after the BPMV RNA2 translation stop codon to avoid the requirement of in frame reading of the foreign sequences. The new BPMV VIGS vector design also allows insertion of non-coding sequences into the BPMV VIGS vector for functional analysis. This novel design provides the potential that the BPMV VIGS vector can be used for applications such as cDNA library screening, promoter silencing, and silencing of un-translated regions of messenger RNAs. Further, RNA silencing and foreign gene expression can be achieved in a single BPMV viral construct making marker gene assisted silencing possible. The new BPMV vector was developed in a manner similar to the previously reported DNA-based BPMV vector in that the viral genome is under control of the CaMV 35S promoter and Nos terminator to overcome the disadvantage of an inefficient RNA-based vector.

Materials And Methods

Virus Strains, Inoculation, and BPMV Virus Detection

The BPMV isolate, I-Di1, was isolated in Iowa in 2006 (Bradshaw et al., 2007) and maintained in the soybean cultivar Williams (Zhang et al., 2009), which was used in all experiments in this study. Mechanical inoculation of plants dusted with 600-mesh Carborundum was done by using 50 mM potassium phosphate buffer, pH 7.0. All seeds used in the study were harvested from greenhouse grown plants previously indexed for the absence of BPMV and SMV. BPMV viral infection was verified by DAS-ELISA (Bradshaw et al., 2007).

DNA-based BPMV constructs were biolistically introduced into the primary leaves following methods described by Zhang et al. (2009). Following bombardment, plants were maintained in the greenhouse or growth chamber at 20° C. with a photoperiod of 16 hours.

Infectious BPMV I-Di1 RNA1 and RNA2 Constructs

Unless otherwise stated, all plasmids were propagated in ElectroMax DH5α-E cells (Invitrogen, Carlsbad, Calif., USA) and purified using the QiaPrep Spin MiniPrep kit (Qiagen, Valencia, Calif., USA). All PCR was performed using Takara PrimeSTAR™ HS DNA Polymerase (TaKaRa Bio Inc., Otsu, Shiga, Japan). Nucleotide sequencing was done using the Big Dye Terminator DNA Sequencing Kit (Applied Biosystems, Foster City, Calif., USA) and the ABI Prism 310 genetic analyzer. Sequence analysis was performed using the Vector NTI program (Invitrogen).

The fragment containing transcription elements from pBR322-35S (Wang et al., 2006) was released by digestion with EcoRI and NoI and ligated into similarly digested pGEM 11zf(+) vector (Promega Corporation, Madison, Wis., USA) to generate the pGEM-35S vector. pGEM-35S was digested with MscI and EcoRI, Klenow treated, and self ligated to remove MscI from the pGEM 11zf(+) vector backbone. The resultant vector was named pGEM-35S-M1.

Total RNA was extracted from BPMV-infected soybean leaves by the Trizol method (Invitrogen). First-strand cDNA was synthesized using 0.5 µg of mRNA, 0.5 µg oligo(dT)$_{20}$ primer, 1 µl 10 mM dNTP, and Superscript III reverse transcriptase (Invitrogen) to a final volume of 20 µl. A 2-µl aliquot of first-strand cDNA reverse transcription product was used as template in a 100 µl PCR reaction for amplification of full length RNA1 with primer pair BPMV-5end-F and BP-R1-3Cla. The PCR conditions were 1, one minute of denaturing at 98° C. followed by three cycles of denaturing at 98° C. for 10 seconds, annealing at 40° C. for 12 seconds and extending at 68° C. for 6 and half minutes; 2, thirty cycles of denaturing at 98° C. for 10 seconds, annealing at 52° C. for 12 seconds and extending at 68° C. for 6 and half minutes; 3, extra 10 minutes of extending at 68° C. The 6 kb PCR product was gel extracted, treated with T4 DNA kinase and ligated into StuI digested and dephosphorylated pGEM-35S-M1 vector to generate construct pBPMV-R1A (pBPMV-IA-R1). Clones were screened by PCR with primer pair BP-R1-5708F and Nos-Rev for correct insertion direction. Insertion orientation of pBPMV-R1A (pBPMV-IA-R1) was further confirmed by sequencing with primer 35-Seq (Table I) and the entire genomic BPMV RNA1 insertions were sequenced with primers for RNA1 listed in Table I.

Following the same procedure as described for RNA1, the full length BPMV RNA2 was amplified from the above cDNA template using the primer pair BP-5endF and R2-3Cla (Table I). The 3.6 kb PCR product was gel extracted, treated with T4 DNA kinase and ligated into StuI digested pGEM-35S-M1 to generate construct pBPMV-R2. Clones were screened by PCR with primer pair R2-3303F and Nos-Rev for correct insertion direction (Table I). Clone pBPMV-R2 was fully sequenced with primers for RNA2 listed in Table I.

Figure 6:
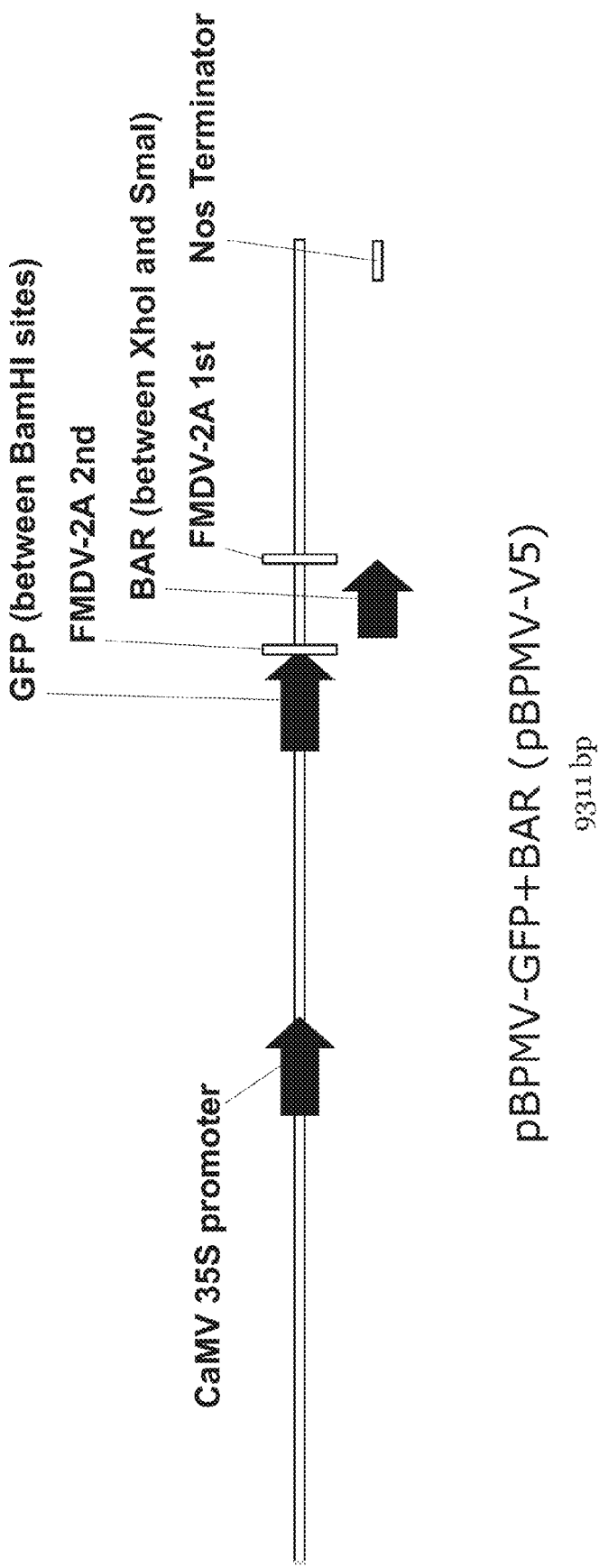
FIG. 6 is a linear map depicting the pBPMV V5 (pBPMV-IA-V5) vector of the invention.
Figure 9F:
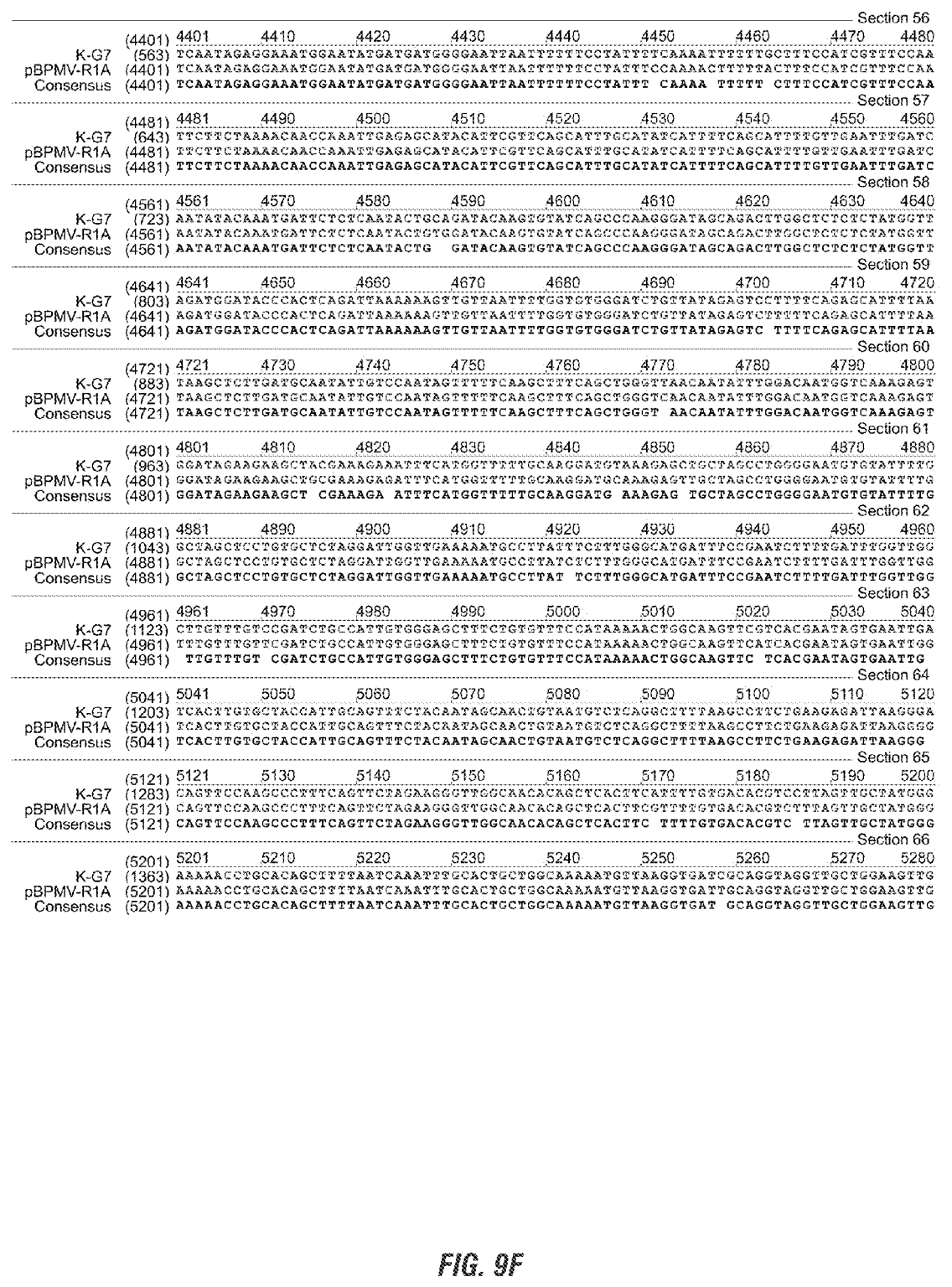
Figure 10I:
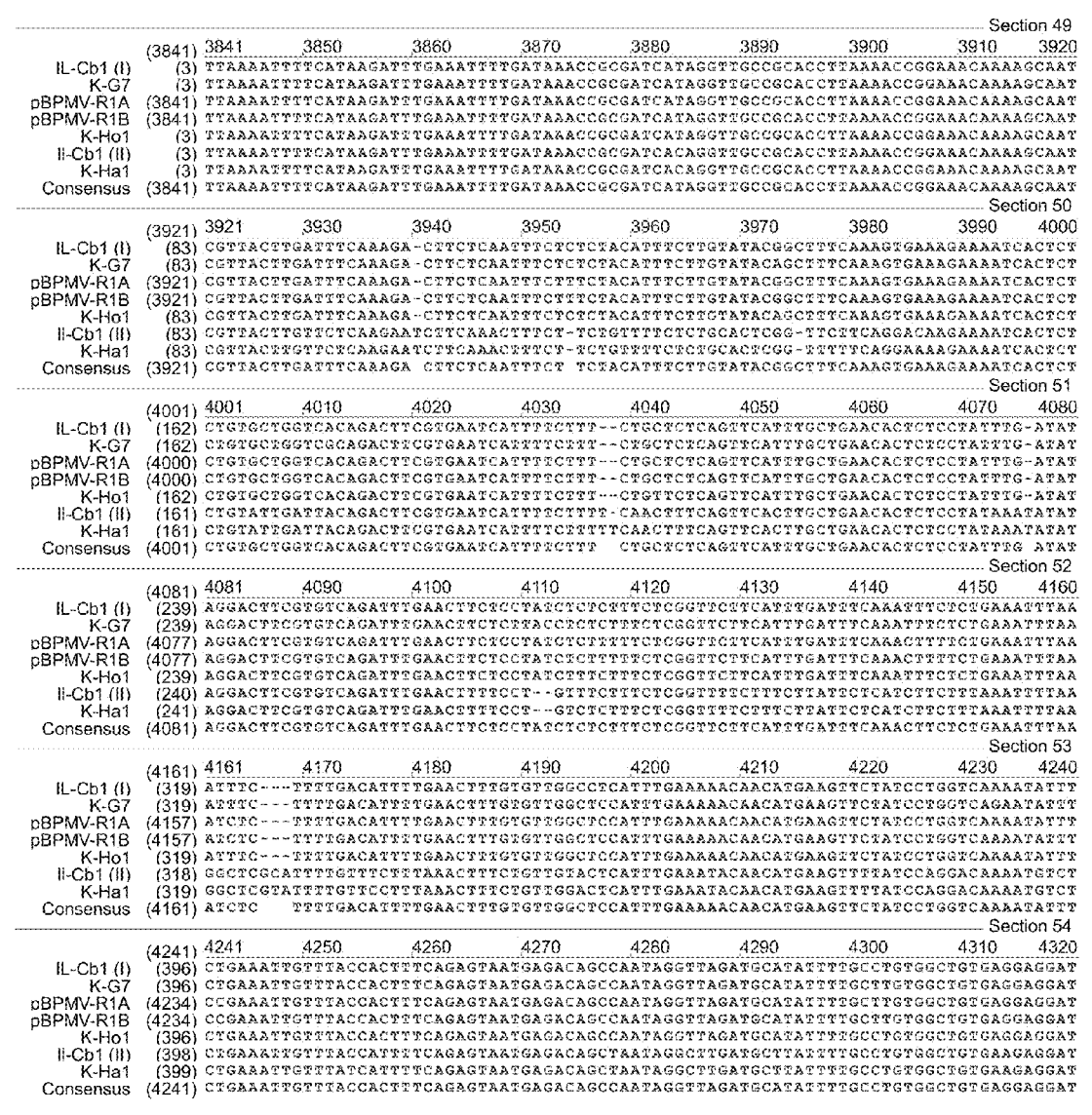
Figure 10J:
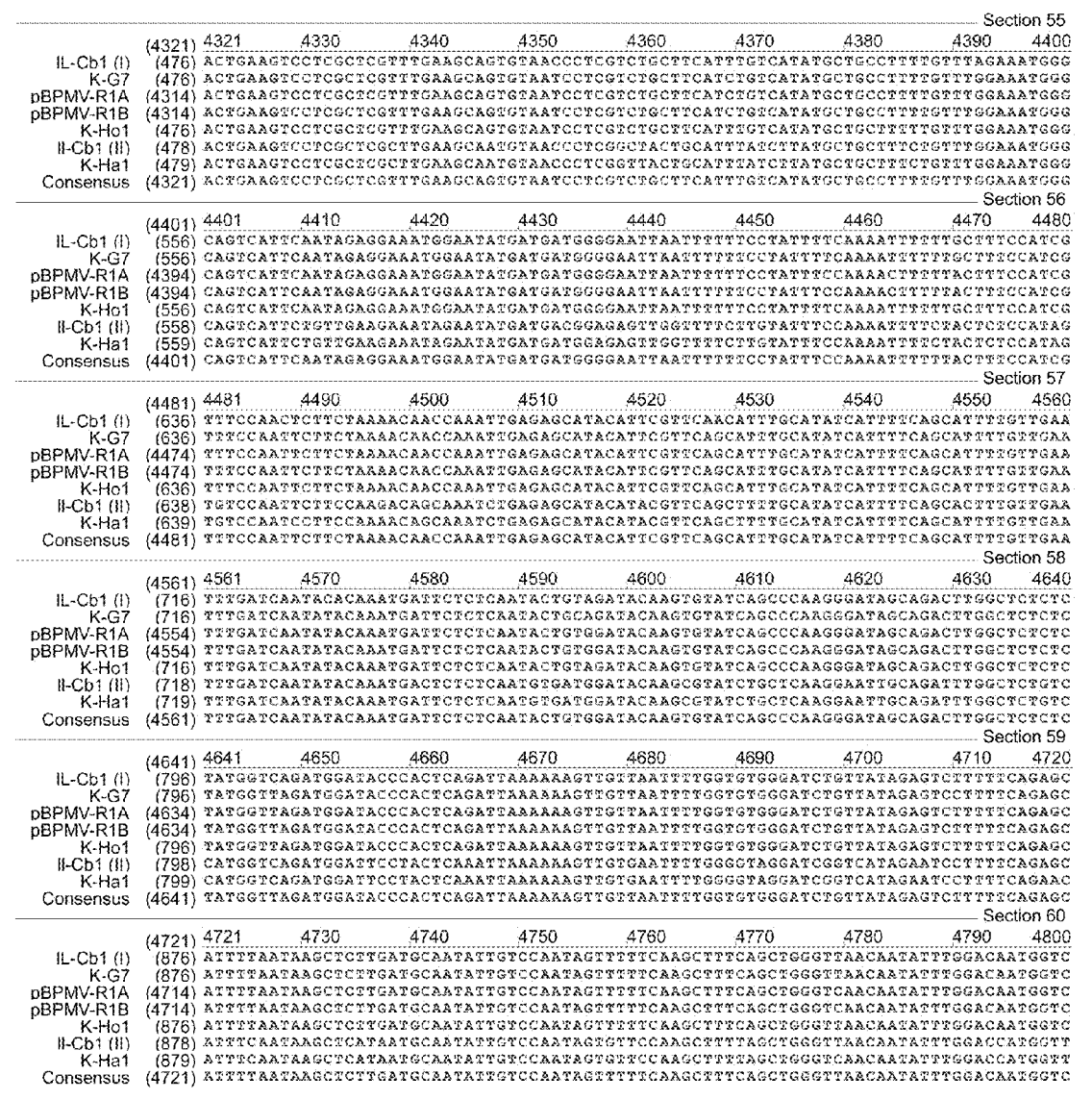
Figure 10M:
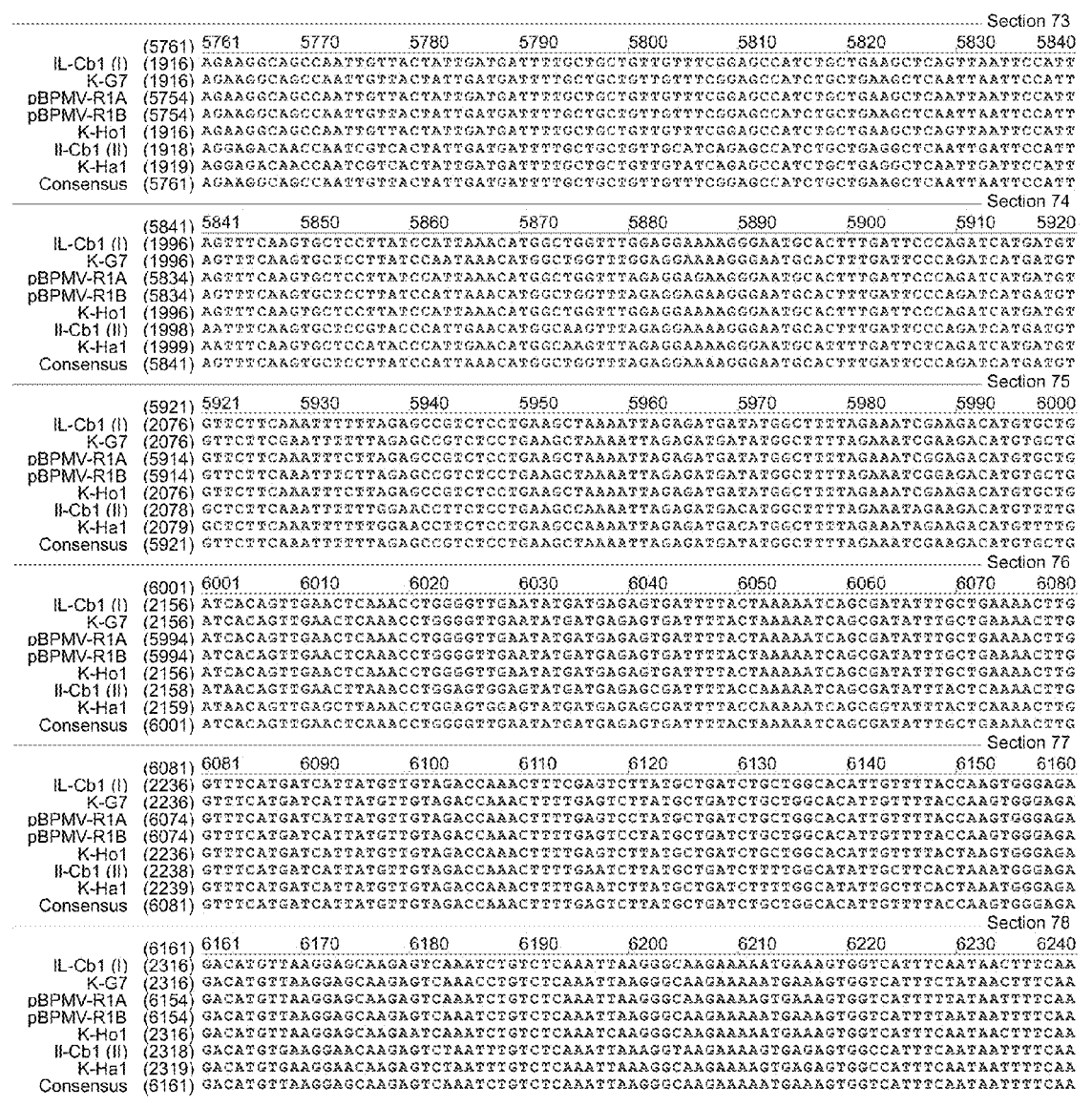
Figure 10N:
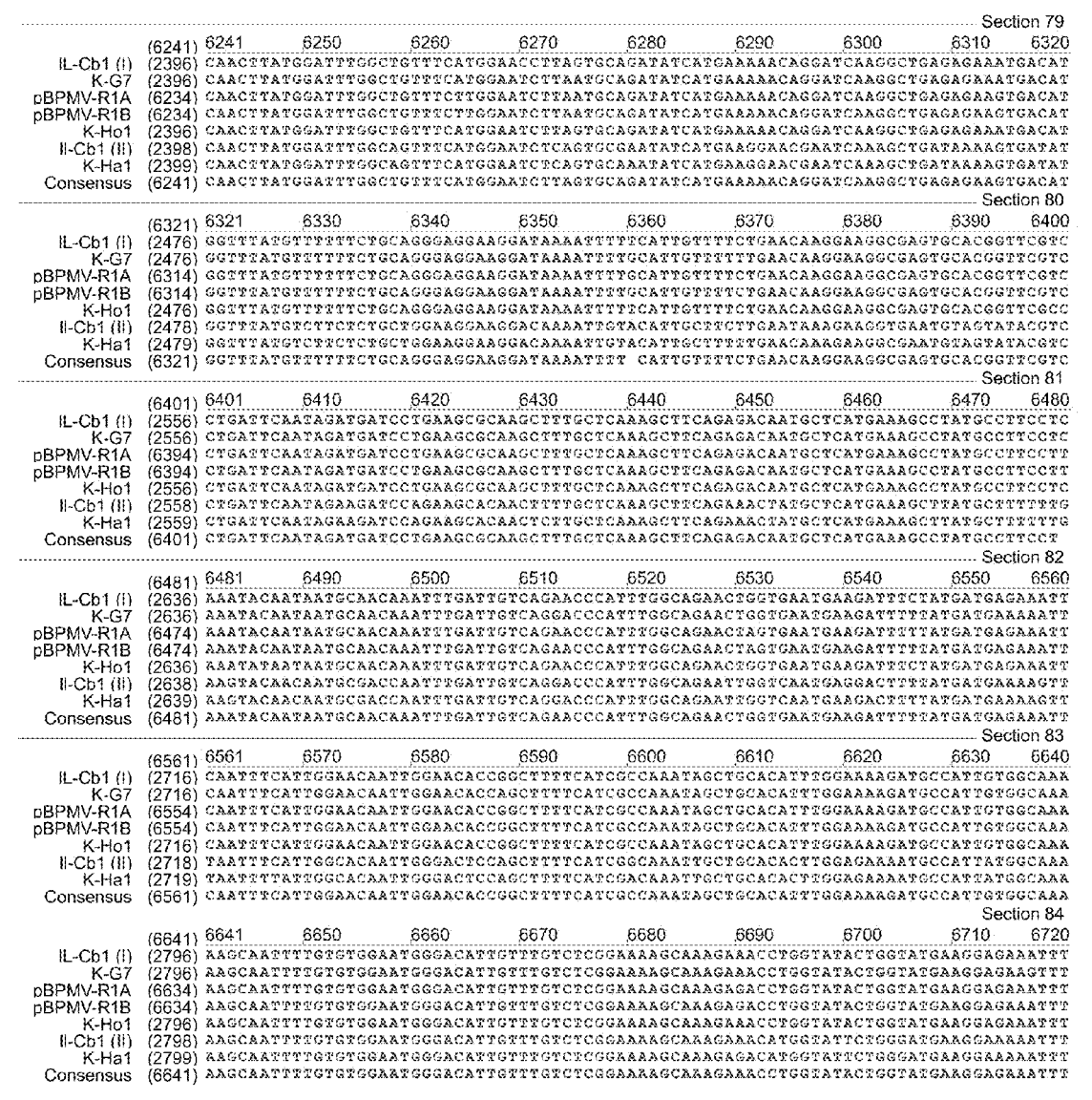
Figure 10S:
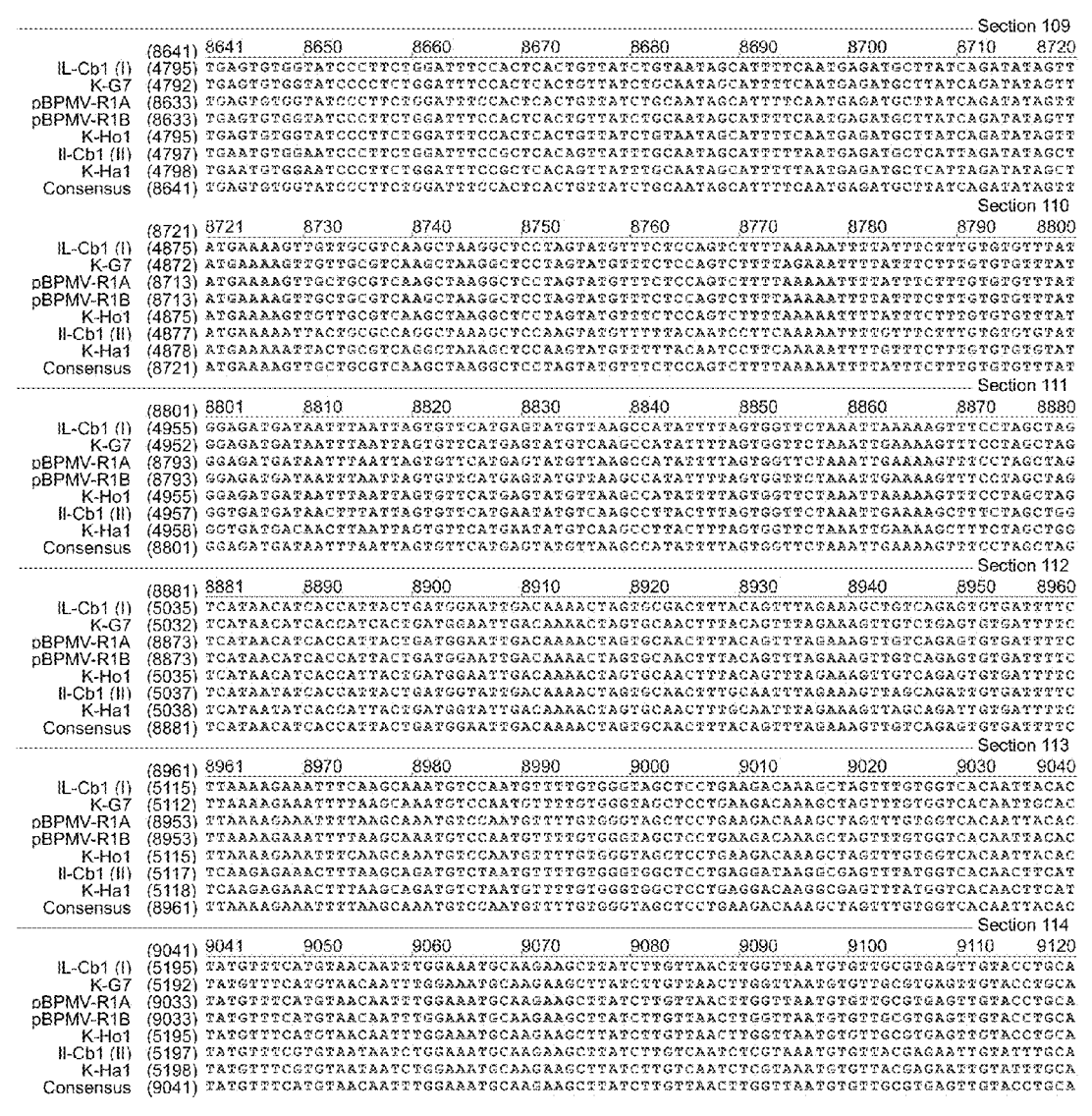
Figure 10U:
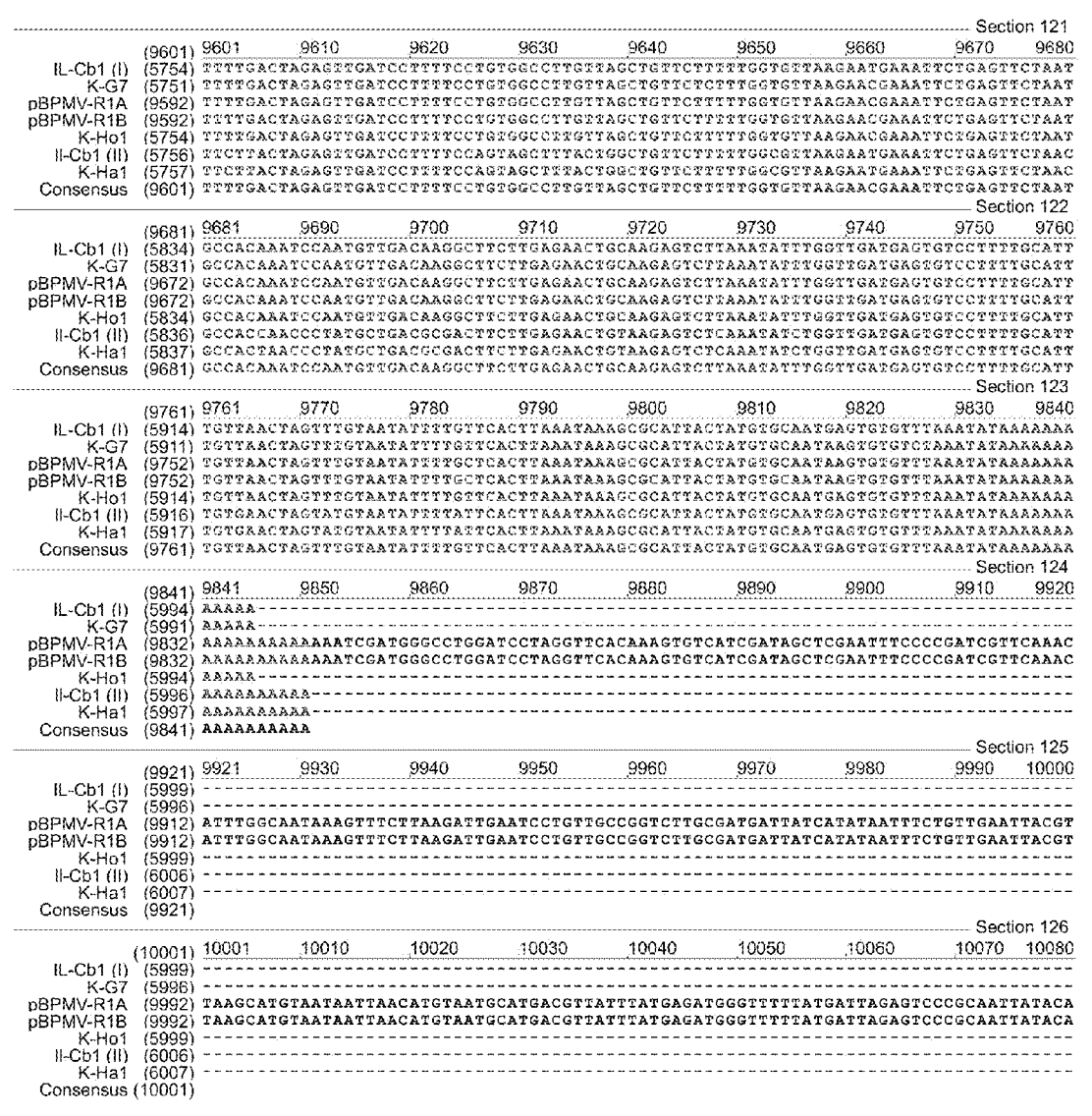

Modification of BPMV RNA1 to Provide a Vector with Moderate Symptoms pBPMV-R1A (pBPMV-IA-R1) was selected using overlapping PCR for further BPMV RNA1 modification. The first PCR reaction was performed with pBPMV-R1A (pBPMV-IA-R1) as template and primer pair R1-235F and R1-Modi-R. The second PCR reaction was performed with pBPMV-R1A (pBPMV-IA-R1) as template and primer pair R1-Modi-F and R1-3344R. The third PCR reaction was performed using PCR products of the previous two reactions as template and primer pair R1-235F and R1-Modi-R. Products of the third PCR reaction were digested with SwaI and MscI and ligated into similarly treated pBPMV-R1A (pBPMV-IA-R1) to yield pBPMV-R1B (pBPMV-IA-R1M) (FIG. 2). Insertion orientation was confirmed by PCR with primer pair R1-235F and R1-2245R. pBPMV-R1B (pBPMV-IA-R1M) was sequenced using primers listed in Table I (See also FIGS. 8-10 for sequence data).

BPMV RNA2 Vector Construction and Modification

BPMV RNA2 was selected for foreign gene insertion. The same reagents were used in BPMV vector modification as were used for generating infectious BPMV RNA1 and RNA2 clones. All PCR was performed with primers listed in Table I and Table II.

A set of overlapping PCR reactions was used to introduce the BamHI restriction site after the stop codon of BPMV RNA2 polyprotein coding sequence. PCR reaction A was performed with pBPMV-R2 as template and primer pair R2-2133F and R2-Rev 1. PCR reaction B was performed using pBPMV-R2 as template and overlapping primer pair R2-For1 and Nos-Rev. PCR reaction C was performed with PCR products of A and B as template and primer pair R2-2133F and Nos-Rev. The product of PCR reaction C was digested with BsrGI and ClaI and ligated into similarly digested pBPMV-R2 to yield pBPMV-V1 (pBPMV-IA-V1; FIG. 1B). Self annealing primer pair R2-For2 and R2-Rev2 was used for PCR without template and the PCR product was digested with BglII and BamHI. The digested PCR product was gel purified and ligated to BamHI digested and dephosphorylated pBPMV-V1 (pBPMV-IA-V1). Insertion orientation was confirmed by PCR with R2-For2 and Nos-Rev and the clone is designated as pBPMV-V2 (pBPMV-IA-V2; FIG. 1B, FIG. 4).

A set of overlapping PCR reactions was used to introduce the FMDV 2A proteinase sequence after the small coat protein subunit gene for foreign gene expression. PCR reaction D was performed with pBPMV-R2 as template and primer pair R2-For3 and Nos-Rev. PCR reaction E was performed with overlapping primer pair R2-For4 and R2-Rev3. PCR reaction F was performed with pBPMV-R2 as template and primer pair R2-2133F and R2-Rev4. PCR reaction G was performed with PCR products of D and E as template and primer pair R2-For4 and Nos-Rev. PCR reaction H was performed with PCR products of F and G as template and primer pair R2-2133F and Nos-Rev. The product of PCR reaction H was digested with BsrGI and ClaI and ligated into similarly digested pBPMV-R2 to yield pBPMV-M1 (FIG. 1B). A FMDV 2A proteinase site was introduced between the movement and large coat protein genes using a similar overlapping PCR method. PCR reaction I was performed with pBPMV-M1 as template and primer pair R2-1548F and R2-Rev5. PCR reaction J was performed with pBPMV-M1 as template and primer pair R2-For5 and R2-2688R. PCR reaction K was performed with PCR products of I and J as template and primer pair R2-1548F and 8P-R2-2688R. The product of PCR reaction K was digested with XbaI and BsrGI and ligated into similarly digested pBPMV-R2 to yield pBPMV-V3 (pBPMV-IA-V3; FIG. 1B, FIG. 4). The product of PCR reaction K was digested with XbaI and BsrGI and ligated into similarly digested pBPMV-V1 (pBPMV-IA-V1) to yield pBPMV-V4 (pBPMV-IA-V4; FIG. 1B, FIG. 5).

CaMV 35S Promoter Driven BPMV Viral Gene Expression and VIGS Constructs

SMV-N-GFP (Wang et al., 2006) was used as template with primer pair GFP-BamF and GFP-BamR for a PCR reaction. The PCR product was digested with BamHI and inserted into BamHI digested and dephosphorylated pBPMV-M1 (pBPMV-IA-M1) to yield construct pBPMV-M1-GFP. Insertion orientation was confirmed by sequencing with primer R2-3303F (Table I). pBPMV-M1-GFP was used as template with primer pairs GFP-Xho and GFP-Sma for PCR. The products were digested with XhoI and SmaI and inserted into similarly treated pBPMV-V3 (pBPMV-IA-V3) to create constructs pBPMV-GFP1 for GFP expression. The digested full GFP gene PCR product was also put into XhoI and SmaI digested pBPMV-V4 (pBPMV-IA-V4) to create pBPMV-GFP2 for GFP expression with insertion site for silencing. TBSV P19 gene was amplified from plasmid PZP-TBSVp19 (Qu et al., 2003) using primer pair TBSV-P19-Xho and TBSV-P19-Sma (Table II) and the PCR product was digested with XhoI and SmaI and inserted into similarly digested pBPMV-V4 (pBPMV-IA-V4) to create pBPMV-P19 for TBSV P19 gene expression with insertion site for silencing. Herbicide resistance BAR gene was amplified from plasmid pCB302 (Xiang et al., 1999) using primer pair BAR-Xho and BAR-Sma (Table II) and the PCR product was digested with XhoI and SmaI and inserted into similarly digested pBPMV-V4 (pBPMV-IA-V4) to create pBPMV-BAR for BAR gene expression with insertion site for silencing.

For the second FMDV-2A insertion into the BPMV RNA2 for two gene expression, overlapping PCR was used to generate double gene expression. PCR reaction L was performed using pBPMV-M1-GFP as template with primer pair GFP-modi-1F and GFP-modi-1R. PCR reaction M was performed using pBPMV-M1 as template with primer pair GFP-modi-2F and GFP-modi-2R. Overlapping PCR reaction N was performed using PCR products L and M as template with primer pair GFP-modi-1F and GFP-modi-2R. The product of PCR reaction N was digested with XhoI and SalI and inserted into XhoI digested pBPMV-BAR to create pBPMV-GFP-BAR. Insertion orientation was confirmed by sequencing with primer R2-1548F. The construct pBPMV-GFP-BAR has the features illustrated for pBPMV-V5 (FIG. 1B; pBPMV-IA-V5; FIG. 6).

Total RNA extraction and cDNA synthesis followed the previously described method for generating infectious BPMV clones. The cDNA was used for PCR with primers described below to amplify corresponding soybean PDS gene fragments (FIG. 11A) and the PCR products were digested with BamHI and inserted into similarly digested and dephosphorylated pBPMV-V1 (pBPMV-IA-V1) to generate the PDS VIGS constructs. The primers Gm-PDS-pF1 and Gm-PDS-pR1 were used for generating VIGS constructs pBPMV-PDS-F1 (sense insertion) and pBPMV-PDS-R1 (antisense insertion). The primers Gm-PDS-pF2 and Gm-PDS-pR2 were used for generating VIGS constructs pBPMV-PDS-F2 (sense insertion) and pBPMV-PDS-R2 (antisense insertion). The primers Gm-PDS-pF3 and Gm-PDS-pR3 were used for generating VIGS constructs pBPMV-PDS-F3 (sense insertion) and pBPMV-PDS-R3 (antisense insertion). The primers Gm-PDS-pF4 and Gm-PDS-pR4 were used for generating VIGS constructs pBPMV-PDS-F4 (sense insertion) and pBPMV-PDS-R4 (antisense insertion). The primers Gm-PDS-pF1130 and Gm-PDS-pR1520 were used for generating pBPMV-PDS-5 which was used as template for PDS gene probe preparation. All PDS gene fragment insertions were confirmed by sequencing with primer R2-3303F. The PDS gene fragment insert in construct pBPMV-PDS-R4 was released by BamHI digestion and inserted into BamHI digested and dephosphorylated constructs pBPMV-BAR and pBPMV-P19 to yield pBPMV-BAR-PDS and pBPMV-P19-PDS. Insertion orientation was confirmed by sequencing with primer R2-3303F.

RNA Extraction and Northern Hybridization Analysis

Total RNA extraction and reverse transcription were done following methods described by Zhang et al. (2009). For Northern hybridization analysis, following RNA extraction, hybridization was performed according to the description by Zhang and Ghabrial (2006). The probe for PDS was prepared by PCR with primer pair Gm-PDS-F5 and Gm-PDS-R5 using pBPMV-PDS-5 as template. Probes were labeled using Prime-a-Gene labeling system (Promega). Northern blot was assessed using ImageQuant v5.2 (Amersham, Piscataway, N.J., U.S.A.).

Herbicide Treatment and GFP Imaging

The fully expanded primary leaves of soybean seedlings were inoculated with the BPMV viral gene expression or VIGS constructs. Four weeks later, the infected soybean plants were sprayed with the herbicide Liberty, which contains glufosinate-ammonium (GA) as the active ingredient (Aventis CropScience, Research Triangle PK, NC, USA), at a concentration of 0.05% GA (w/v) in deionized water. The soybean plants were photographed 3 weeks after herbicide treatment. Foliar GFP expression was examined by visualizing with UV illumination (100-W Blak-Ray longwave UV lamp; UVP, Upland, Calif., USA) and photographs were taken using a Nikon D70 digital camera fitted with a yellow filter. For root GFP observation, four weeks after inoculation, soybean roots from each construct were rinsed and photographed using a Zeiss Stemi SV11 stereoscope (Zeiss, Jena, Germany). GFP expression was monitored with a Piston GFP filter set (Chroma, Rockingham, Vt.). Pictures were taken with a Zeiss Axiocam MRc5 digital camera and processed with Zeiss Axiovision software (Zeiss, Jena, Germany).

Results

Construction of CaMV 35S Promoter Driven BPMV Vectors

The previously developed RNA-based BPMV vector requires in vitro RNA transcription and mechanical inoculation of RNA (Zhang and Ghabrial, 2006). Increased throughput can be achieved by placing the cDNAs of BPMV genomic RNA1 and RNA2 under control of the CaMV 35S promoter and Nos terminator (Zhang et al., 2009) to circumvent the need for making in vitro RNA transcripts (FIG. 1). The newly developed BPMV viral vector described here was directly introduced into soybean plants by biolistic inoculation with efficiency greater than 80%. The BPMV isolate I-Di1 used for development of the new vector induced mild symptoms on three different soybean cultivars (Williams, Clark and Essex, data not shown). This feature makes this isolate suitable as a VIGS vector without interference from a severe viral phenotype.

After biolistic inoculation, the wild type infectious clones pBPMV-R1A (pBPMV-IA-R1) with pBPMV-R2 produced mild symptoms on the cultivar Williams (FIG. 7B). The mild infection was confirmed by mechanical inoculation to a new set of soybean seedlings and infection was confirmed by ELISA. Previously, the helicase gene on BPMV RNA1 was shown to be a pathogenicity factor (Gu and Ghabrial, 2005). They further suggested that amino acid position 359 of the helicase maybe critical for severe symptoms induced by severe strain K-Ho1. As a result of amino acid sequence comparison of the C-terminal region of the helicase gene, two amino acids (position 359 and 365) of I-Di1 RNA1 were mutated to that of the severe RNA1 of BPMV strain K-Ho1 (FIG. 7A (see FIGS. 8-11 for comparison of RNA1 amino acid and nucleotide sequences). Unlike the wild type RNA1 clone pBPMV-R1A (pBPMV-IA-R1), the mutant pBPMV-R1B (pBPMV-IA-R1M), upon inoculation with wild type RNA2 clone pBPMV-R2 produced obvious moderate symptoms on the soybean cultivar Williams (FIG. 7B). The moderate infection phenotype of pBPMV-R1B (pBPMV-IA-R1M) was confirmed by mechanical inoculation to a new set of soybean seedlings and followed by ELISA. Interestingly, the enhanced symptoms are not as severe as that of the severe strain K-Ho1 RNA1. Because the infection by pBPMV-R1A (pBPMV-IA-R1) only induced very mild visual symptoms that are almost indistinguishable from the uninfected mock control, it is necessary to confirm the positive infection by ELISA. However, infection by pBPMV-R1B (pBPMV-IA-R1M) is evident by the moderate visual symptoms. Thus, the ELISA confirmation step is not necessary and the vector is convenient for high throughput applications used in the following studies.

BPMV RNA2 Vector Modification for VIGS Study of Soybean PDS Gene

Figure 4:
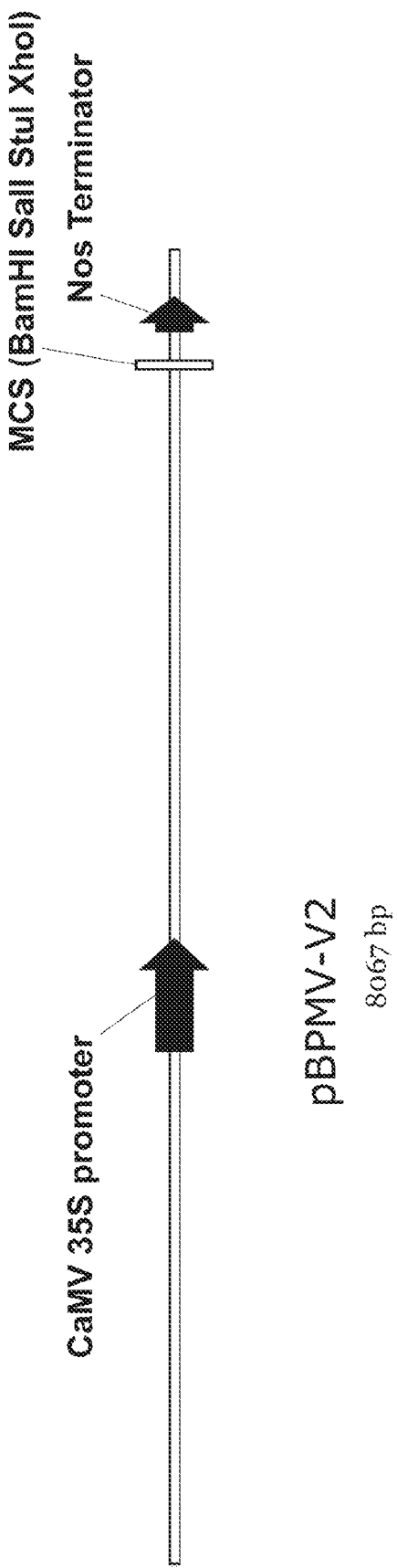
FIG. 4 is a linear map depicting the pBPMV V2 (pBPMV-IA-V2) vector of the invention.

A series of modifications were used to evaluate different designs of BPMV viral vectors for foreign gene expression and VIGS studies (FIG. 1B). First, a BamHI restriction site was introduced after the stop codon of RNA2 open reading frame to insert the target gene fragment for silencing (pBPMV-V1, FIG. 1B) (pBPMV-IA-V1). This strategy of engineering BPMV as a VIGS vector was tested by silencing the soybean PDS gene (FIG. 11). Further, to facilitate directional insertion, a multiple cloning site was introduced into the BamHI site to generate the VIGS vector pBPMV-V2 (pBPMV-IA-V2; FIG. 1B, FIG. 4).

The previous VIGS vector design (Zhang and Ghabrial, 2006) applied a fusion protein expression strategy that requires the foreign sequences to be in translation frame with the RNA2 open reading frame. This constraint limits the vector's usefulness for RNA silencing of genes such as those with short open reading frames as well as non-coding sequences such as promoter regions and untranslated regions. The insertion orientation of foreign gene inserts in the VIGS vector might influence the efficiency of silencing. For example, antisense mRNAs always have multiple stop codons but cannot be tested by the fusion protein strategy previously used for BPMV VIGS. Another disadvantage of the fusion strategy is there is always a short peptide expressed that could potentially confound the interpretation of the silencing result. To circumvent these issues in the new vector, we tested the possibility of inserting foreign sequences for silencing after the stop codon of the BPMV RNA2 open reading frame (FIG. 1; FIG. 11). Four sets of primers were designed to amply four different regions of soybean PDS, 5' UTR, 5' ORF, 3' ORF and 3' UTR. Because we inserted each of the four regions into the pBPMV-V1 (pBPMV-IA-V1) BamHI site, we could select clones with either sense or antisense orientation to test whether insert orientation affected the efficiency of PDS gene silencing. In three repeated experiments, we found that antisense insertion of the 3' ORF provided the best silencing (pBPMV-PDS-R3, FIG. 11B). The third and fourth trifoliolates of soybean plants infected by pBPMV-PDS-R3 were almost totally bleached while the same sequence inserted in the sense orientation only induced mosaic bleaching. In a comparison between 5' ORF and 3' ORF, the 3' end insertion was better for PDS VIGS in antisense orientation. This positional effect was more evident in the antisense than in the sense orientation. While the antisense 3' UTR gave mosaic type bleaching, the sense insertion of the 3' UTR of PDS gene showed little photobleaching. It is interesting that the 5' UTR in either sense or antisense insertion did not show photobleaching under the same conditions (FIG. 11B).

Northern blot analysis was used to evaluate PDS gene mRNA levels in soybean plants infected by the PDS VIGS constructs. Total RNA was extracted from the third and fourth trifoliolates at three weeks post inoculation. Twenty five µg of total RNAs were loaded for each treatment and equal loading was confirmed by ethidium bromide staining (FIG. 12A). Initially, to examine the accumulation of BPMV RNA2 transcripts, a partial sequence of I-Di1 RNA2 was PCR amplified with primer pair R2-1548F and R2-2688R (Table I). The probe using the PCR products was used to test the accumulation of BPMV RNA2 accumulation in each treatment (FIG. 12C). Results showing a single band for each PDS VIGS construct, as opposed to multiple bands, demonstrated no significant loss of the PDS insert (FIG. 12B). Further, RT-PCR was performed with forward primer R2-1548F and each reverse primer corresponding to the 3' end of PDS to confirm the PDS gene insertion on BPMV RNA2 (data not shown). Interestingly, all antisense insertions resulted in a significant reduction of BPMV RNA2. For the sense orientation insertion, only the 5' ORF caused a similar reduction. The remainder of the sense insertions had minimal impact on BPMV RNA2 accumulation as compared to the wild type empty vector (FIGS. 12, B and D). The 3' ORF and 3' UTR antisense gave the lowest RNA2 abundance which is about five to seven fold reduction as compared with the empty vector infection.

A central region of soybean PDS gene was amplified using primer pair Gm-PDS-F1130 and Gm-PDS-R1520. This region was used to probe the PDS mRNA accumulation level in plants infected with each PDS construct as well as with the empty vector control. Based upon band intensity relative to the empty vector control, PDS gene expression ranged from 8.6% to 23.1% of the empty vector control for the antisense construct but 58.8% to 124.3% for the sense construct. Significantly, there was a general correlation between the level of RNA2 accumulation and the target gene PDS mRNA level with the antisense orientation yielding the highest reduction of PDS gene mRNA level. Similar results were obtained twice (FIGS. 12, C and E).

Diverse Foliar Symptoms Induced by Expressing Different Genes

Cowpea mosaic virus (CPMV) was previously shown to express a foreign gene by inserting the foreign gene sequence after foot-and-mouth disease virus (FMDV) 2A proteinase peptide fused to the C-terminus of the small coat protein (Gopinath et al., 2000). Similarly, we synthesized the FMDV-2A proteinase coding region and placed it immediately after the C-terminus of the small coat protein gene of BPMV. A BamHI restriction site was introduced after FMDV-2A to facilitate foreign gene insertion for expression (pBPMV-M1, FIG. 1B). To test this strategy, the GFP gene was introduced into pBPMV-M1 to generate construct pBPMV-M1-GFP. After three repetitions with controls, we did not achieve infection with either pBPMV-M1 or pBPMV-M1-GFP when biolistically inoculated with either pBPMV-R1A (pBPMV-IA-R1) or pBPMV-R1B (pBPMV-IA-R1M) (data not shown). We ruled out the possibility of faulty inoculation because the biolistic inoculation method was optimized to routinely achieve almost 100% infection. At the same time, the wild type control pBPMV-R2 was highly infectious and it was handled concurrently with pBPMV-M1 and pBPMV-M1-GFP. Further, pBPMV-M1 and pBPMV-M1-GFP were fully re-sequenced and no nucleotide mutations were found as compared with pBPMV-R2.

The previous BPMV gene expression vectors (Zhang and Ghabrial, 2006; Zhang et al., 2009) duplicate the cleavage site between the C-terminus of MP and N-terminus of L-CP. In the new vector, instead of duplicating the cleavage site, we introduced a FMDV-2A proteinase peptide between the MP and L-CP cistrons (pBPMV-V3, FIG. 1B) (pBPMV-IA-V3). The vector is designed to insert foreign genes before the FMDV-2A proteinase peptide. The synthesized FMDV-2A proteinase peptide has autocleavage activity at the penultimate amino acid (Gopinath et al., 2000) leaving the mature L-CP with one extra proline at the N-terminus. This design was tested by inserting GFP, BAR and TBSV-P19 genes.

Figure 5:
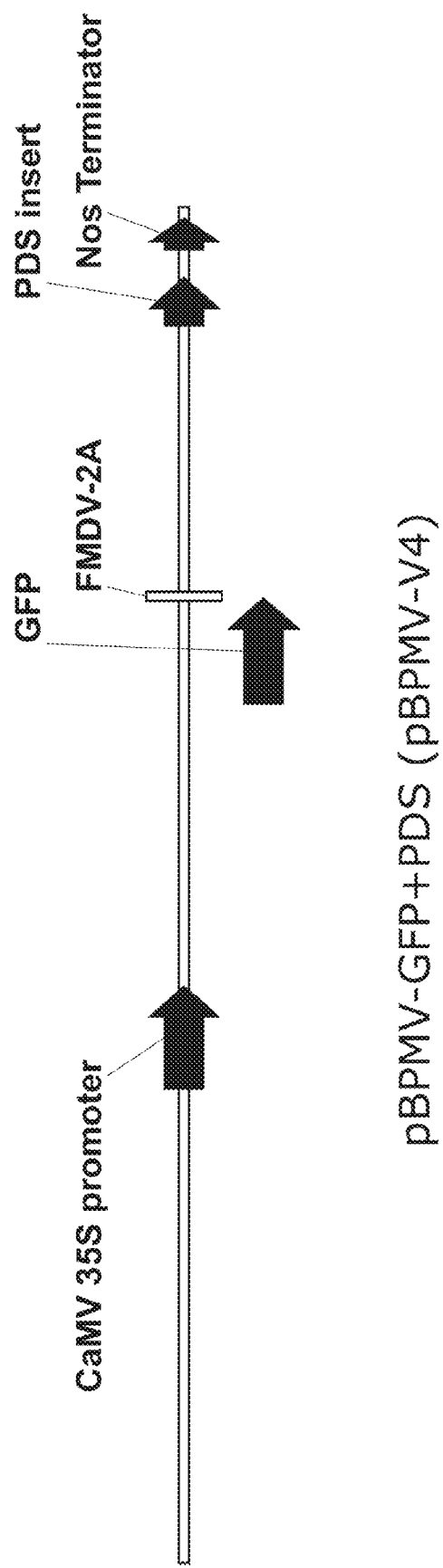
FIG. 5 is a linear map depicting the pBPMV V4 (pBPMV-IA-V4) vector of the invention.

Another BPMV viral vector was created to test the possibility of expressing a foreign gene and at the same time silence a target gene (pBPMV-V4, FIG. 1B FIG. 5) (pBPMV-IA-V4). Finally, a second FMDV-2A proteinase peptide was introduced after the first FMDV-2A sequence for double gene expression (pBPMV-V5, FIG. 1B FIG. 6) (pBPMV-IA-V5). To reduce instability of the introduced genetic elements, the sequence identity of the second FMDV 2A site was altered by taking advantage of codon degeneracy. The Xho I and Sma I restriction sites were used for the first gene insertion and BamHI was used for the second gene insertion (pBPMV-V5, FIG. 1B, FIG. 6) (pBPMV-IA-V5). Previously, double gene silencing was achieved by combining two constructs (Zhang et al., 2009). Similarly, the vector pBPMV-V2 (pBPMV-IA-V2) was designed to combine more than one construct for simultaneously silencing multiple genes.

Three genes, including fluorescence marker gene GFP, herbicide resistance gene BAR and RNA silencing suppressor TBSV P19 were expressed independently by the new BPMV gene expression vector. Three weeks post inoculation, typical mosaic symptoms were seen on pBPMV-GFP2 and pBPMV-BAR inoculated plants. However, severe symptoms including necrosis were induced by pBPMV-P19 which expresses TBSV P19 RNA silencing suppressor (FIG. 13). Similarly, the double gene expression construct pBPMV-GFP+BAR induced mosaic symptoms (FIG. 13). The activities of GFP and BAR gene were tested by green fluorescence and herbicide resistance (FIG. 14, FIG. 15). Both constructs pBPMV-BAR and pBPMV-GFP+BAR showed herbicide resistance whereas the mock and empty vector infected soybean plants were killed by herbicide treatment. This demonstrated that the BAR gene expressed by either the single gene or double gene expression vector is actively expressed (FIG. 16). Examination of GFP fluorescence showed that either the GFP single gene expression construct or the double gene expression construct pBPMV-GFP+BAR demonstrate GFP activity in the systemically infected leaves (FIG. 15). By examination of both BAR gene and GFP gene for the double gene expression construct pBPMV-GFP+BAR, it is shown that the activity of the expressed genes are biologically active when doubly expressed.

We further tested the potential for simultaneous gene expression and silencing by making the pBPMV-V4 (pBPMV-IA-V4) vector. Constructs pBPMV-P19-PDS which expresses TBSV P19, a potent RNA silencing suppressor, induced severe symptoms similar to pBPMV-P19. There was no visible photobleaching phenotype typical of PDS gene silencing (FIG. 13). However, pBPMV-BAR-PDS and pBPMV-GFP-PDS both induced visible photobleaching on soybean plants as expected if PDS was silenced (FIG. 13). The construct pBPMV-GFP-PDS was examined for GFP expression and PDS silencing more closely. Interestingly, the visible phenotypic expression of photobleaching of the PDS gene silencing overlaps visible fluorescence from GFP expression (FIG. 15).

Gene Expression in Roots

To investigate the possibility of foreign gene expression by the BPMV viral gene expression vector in soybean roots, GFP was tested for green fluorescence in roots. Three weeks post inoculation, soybean roots were rinsed and photographed (FIG. 16). Both the single GFP expression construct pBPMV-GFP2 and the double gene expression construct pBPMV-GFP+BAR gave readily detectable green fluorescence while the empty vector control produced no fluorescence. It is interesting to note that root tips generally show stronger green fluorescence (FIG. 16).

Discussion

Construction of CaMV 35S Promoter Driven BPMV Vector

Two distinct subgroups of BPMV RNA1 and RNA2 have been described (Zhang et al., 2007). Infectious clones were developed previously for several BPMV isolates of both subgroups using either T7 promoter driven in vitro RNA transcription and inoculation or DNA-based direct biolistic inoculation (Zhang and Ghabrial 2006; Zhang et al., 2009). Enhanced infection efficiency was achieved by placing the BPMV genomic RNA1 and RNA2 under control of the CaMV 35S promoter and Nos terminator (Zhang et al., 2009). The bypassing of RNA in vitro transcription and RNA rub inoculation increased throughput to make feasible the use of high throughput RNA silencing for soybean functional genomics.

While the biolistic inoculation is highly efficient, inoculation by direct DNA rubbing may make use of the BPMV vectors more facile as was reported for Soybean mosaic virus (SMV) (Seo et al., 2009) and Turnip yellow mosaic virus (TYMV, Pflieger et al., 2008). We evaluated direct DNA rubbing of soybean seedlings for two constructs, the TBSV P19 RNA silencing suppressor expression construct pBPMV-P19 and the soybean PDS silencing construct pBPMV-PDS-R3. In two attempts, infection by pBPMV-P19 was successful but was not by pBPMV-PDS-R3 (data not shown). The *Arabidopsis* plants used for one-step DNA rubbing by the TYMV PDS silencing construct were placed in the dark for 24 hours before inoculation (Pflieger et al., 2008). It is possible that further optimization of the method may result in higher infection efficiency for BPMV vectors. Because soybean is not amenable for agroinfiltration, we did not test agroinfiltration inoculation. Nevertheless, the previous work has shown that the DNA-based BPMV vectors described have the advantage of long term storage at −20° C. and easy distribution for large scale collaborations (Zhang et al., 2009).

The I-Di1 BPMV isolate has subgroup I RNA1 and subgroup II RNA2 (Bradshaw, unpublished) for which infectious clones were developed in this report. The infectious I-Di1 clones induced very mild symptoms indistinguishable from the phenotype of the mock control under the experimental conditions. While the mild symptoms are amenable for VIGS study, a disadvantage is that the infection has to be confirmed by either ELISA assay or RT-PCR. Gu and Ghabrial (2005) previously developed infectious clones for two subgroup I BPMV RNA1s, K-Ho1 and K-G7. BPMV K-Ho1 RNA1 induces severe symptoms but K-G7 RNA1 only causes mild symptoms. By recombination between the two RNA1s, the helicase cistron of subgroup I BPMV RNA1 was shown to encode the pathogenicity determinant for foliar symptom severity of subgroup I RNA1. They further suggested that amino acid position 359 of the helicase may be critical for the severe symptoms induced by K-Ho1. By amino acid sequence comparison of the C-terminus region of the helicase gene, two amino acids (position 359 and 365) of 1-Di1 RNA1 were mutated to that of the severe RNA1 of BPMV strain K-Ho1 (FIG. 7A (see FIGS. 8-11 for comparison of RNA1 amino acid and nucleotide sequences)). Unlike the wild type RNA1 clone pBPMV-R1A (pBPMV-IA-R1), the mutant pBPMV-R1B (pBPMV-IA-R1M), upon inoculation with wild type RNA2 clone pBPMV-R2, produced visible moderate symptoms on the soybean cultivar Williams (FIG. 7B). pBPMV-R1B (pBPMV-IA-R1M) was subsequently used in this study for gene expression as well as for VIGS and consistently gave visible symptoms that were not as severe as those caused by the severe strain K-Ho1. This feature makes pBPMV-R1B (pBPMV-IA-R1M) convenient for high throughput applications, because assays are not required to confirm infection and the moderate symptoms are less likely to interfere with phenotypic tests than a severe isolate. In addition, the availability of infectious BPMV RNA1 clones that can induce a range of symptom severity phenotypes provides options for diverse applications in the future.

The New DNA-Based BPMV VIGS Vector Allows Diverse Design for Gene Silencing in Soybean Soybean is a major oilseed crop and an important source of food and feed protein. It is subject to a wide range of pathogens and VIGS is an ideal reverse genetics tool for soybean functional genomics aimed at understanding host-microbe interactions (Jackson et al., 2006; Stacey et al., 2004). Recently, BPMV VIGS was successfully used for identification of the soybean rust resistance gene Rpp4 (Meyer et al., 2009). Three viruses, Apple latent spherical virus (ALSV), Cucumber mosaic virus (CMV) and BPMV have been developed as soybean functional genomics tools (Igarashi et al., 2009; Nagamatsu et al., 2007; Zhang and Ghabrial 2006). Fusion protein expression was used for both ALSV and BPMV gene expression as well as for VIGS studies. The fusion protein strategy used for the previous BPMV VIGS vectors (Zhang and Ghabrial 2006; Zhang et al., 2009) requires that foreign sequences be in translation frame with the RNA2 open reading frame. This design strategy restricts the vector's usefulness for RNA silencing as it cannot target genes such as those with very short reading frames and non-coding sequences as well as promoter regions and untranslated regions. In addition, it cannot discern if RNA polarity influences the efficiency of target gene silencing and there is always a short peptide expressed that may confound the interpretation of the silencing result. To overcome these shortcomings, foreign sequences were inserted after the viral RNA2 ORF. The soybean PDS gene was selected for testing this novel strategy because of the obvious photobleaching phenotype as well as the opportunity to compare with previous results (Igarashi et al., 2009; Nagamatsu et al., 2007; Zhang et al., 2009). In our results, sense orientation insertion had minimal effect on PDS silencing. These results are consistent with those using ALSV in soybean where the 5' end PDS sense insertion had little PDS silencing effect (Igarashi et al., 2009). Similar results were also reported in *Arabidopsis* where sense insertion in TYMV had minimal effect on *Arabidopsis* GUS and PDS silencing (Pflieger et al., 2008). However, the ALSV report could not test the silencing effect of RNA polarity due to the fusion protein strategy. Here we found that generally antisense resulted in stronger silencing. Two antisense PDS VIGS constructs, pBPMV-PDS-R3 and pBPMV-PDS-R4, resulted in a 10 fold reduction of PDS mRNA levels. This contrasts with the 2 to 3 fold reduction we observed when testing other genes using the sense orientation (Zhang et al., 2009). Similar to the ALSV results, we found that the middle to 3' end of the PDS gene coding region resulted in stronger silencing, particularly in the antisense orientation.

It has been reported that gene fragments of 23-80 nt can be sufficient for VIGS induction (Thomas et al., 2001; Burch-Smith et al., 2004; Pflieger et al., 2008). Since the insert size for the BPMV PDS silencing construct in this study is about 300 nt, it is theoretically possible to achieve VIGS of multiple soybean genes. This is important because soybean has genetic redundancy and genes function in parallel signaling pathways (Blanc and Wolfe 2004; Lawrence and Pikaard 2003; Schlueter et al., 2004; Shoemaker et al., 1996) making simultaneous testing of different combinations of genes or homologs desirable (Zhang et al., 2009).

Another amenable feature for multiple gene silencing is that there is no limit on translation requirement for foreign gene insertion with the new BPMV VIGS vector. Further, the interesting finding that the 3' PDS antisense insertion gave the best silencing phenotype in soybean makes the new BPMV VIGS vector applicable for constructing a cDNA VIGS library because a version of the new BPMV VIGS vector was developed so that directional insertion can be achieved (data not shown).

Interestingly, we observed that in general greater reduction in PDS mRNA is correlated with reduced BPMV RNA2 accumulation (FIG. 12). This is not surprising because viral RNA2 carries the inserts for the target gene. We hypothesize that when soybean activates defenses against viral infections, there is an added effect from the siRNAs for the host PDS gene targeting RNA2 for degradation. However, demonstration that this correlation is a general feature will require studies targeting a wide range of genes involved in different pathways.

The New BPMV Vectors are Useful for Single or Double Gene Expressions

To evaluate the potential of BPMV for double gene expression, we first tested adding the second foreign gene after the small coat protein cistron since previously it was shown before that a single foreign gene can be expressed between the movement protein and large coat protein cistrons (Zhang and Ghabrial 2006). To our surprise, with repeated attempts, the constructs pBPMV-M1 and its derivative pBPMV-M1-GFP did not infect soybean systemically. BPMV belongs to viral genus Comovirus of which CPMV is the type member and a similar strategy for CPMV was successful. However, RNA transcripts for CPMV were first introduced into cowpea protoplasts while the two BPMV constructs were directly inoculated to soybean plants (Gopinath et al., 2000). The difference in infection could be due to the different method of inoculation, difference in virus species, or potential trace amounts of back mutations to wild type in the CPMV GFP expression construct when it was passed from protoplasts to cowpea plants. Therefore, double gene expression was tested by inserting two foreign genes between the movement protein and large coat protein cistrons. After inserting the FMDV-2A autocleavage peptide, biological functions of several genes including GPF, BAR and TBSV-P19 were demonstrated. Subsequently, the second non-homologous FMDV-2A autocleavage peptide sequence was inserted for double gene expression. Both GFP and BAR in the construct pBPMV-GFP+BAR were biologically active. The FMDV-2A autocleavage peptide used in this study belongs to a family termed CHYSEL (cis-acting hydrolase element). Typical CHYSELs have about 20-30 amino acids and show direct co-translational separation of the nascent chain into two independent parts. Other FMDV-2A like CHYSEL peptides are encoded by some picornaviruses as well as a number of other single- and double-stranded RNA viruses (Doronina et al., 2008; Felipe 2004; Halpin et al., 1999). If multiple gene expression is required, other members of the CHYSEL peptide family can be selected to disrupt sequence homology to help maintain foreign gene insert stability. Plant viral vectors that can express two (or more) foreign genes may be advantageous for many applications. As one potential example, protein-protein interactions such as R-gene and avirulence genes may be simultaneously introduced into plants for studies of signaling pathways involved in biotic stress. For some applications, marker genes such as PDS for silencing and GFP for expression may be useful. This study suggested that gene expression and silencing in soybean appear to overlap (FIG. 15). Because both the silencing and expression phenotype can be patchy as shown in FIG. 15, marker genes may be helpful to determine more precisely where silencing of the target gene is occurring. We termed this marker gene assisted silencing.

As in shoots, the application of foreign gene expression and silencing is important for understanding of water and nutrient uptake as well as for microbial- and nematode-root interactions in roots (Constantin et al., 2008; Rosso et al., 2005; Ryu et al., 2004). BPMV was shown previously to be effective for root silencing (Zhang et al., 2009). Here we showed GFP gene expression in soybean roots demonstrating that BPMV is useful for a variety of applications for soybeans.

In summary, this new BPMV-derived vector system has potential to be a high throughput functional genomics tool to enable efficient, cost-effective and simplified screening of soybean plants for gene expression and silencing. Depending on characteristics of the viruses adopted, the same design principles can be applied or adapted to other plant viral vectors. This will substantially advance our understanding of soybean as well as other important crop plants.

LITERATURE CITED

Blanc G, Wolfe K H (2004), Widespread paleopolyploidy in model plant species inferred from age distributions of duplicate genes. Plant Cell 16: 1667-1678

Bradshaw J D, Rice M E, Hill J H (2007), No-choice preference of *Cerotoma trifurcata* (Coleoptera: Chrysomelidae) to potential host plants of Bean pod mottle virus (Comoviridae) in Iowa. J Econ Entomol 100: 808-814

Burch-Smith T M, Anderson J C, Martin G B, Dinesh-Kumar S P (2004), Applications and advantages of virus-induced gene silencing for gene function studies in plants. Plant J. 39:734-746

Constantin G D, Krath B N, MacFarlane S A, Nicolaisen M, Johansen I E, Lund O S (2004), Virus-induced gene silencing as a tool for functional genomics in a legume species. Plant J 40: 622-631

Ding X S, Schneider W L, Chaluvadi S R, Rouf M A, Nelson R A (2006), Characterization of a Brome mosaic virus strain and its use as a vector for gene silencing in monocotyledonous hosts. Mol Plant-Microbe Interact 19: 1229-1239

Doronina V A, de Felipe P, Wu C, Sharma P, Sachs M S, Ryan M D, Brown J D. (2008) Dissection of a co-translational nascent chain separation event. Biochem Soc Trans. 36: 712-716

Felipe P D (2004), Skipping the co-expression problem: the new 2A "CHYSEL" technology. Genet Vaccines Ther. 2: 13

Gopinath K, Wellink J, Porta C, Taylor K M, Lomonossoff G P, van Kammen A, (2000), Engineering Cowpea mosaic virus RNA-2 into a vector to express heterologous proteins in plants. Virology 267: 159-173

Grønlund M, Constantin G, Piednoir E, Kovacev J, Johansen I E, Lund O S (2008), Virus-induced gene silencing in *Medicago truncatula* and *Lathyrus odorata*. Virus Research 135: 345-349

Gu H, Ghabrial S A (2005), The Bean pod mottle virus proteinase cofactor and putative helicase are symptom severity determinants. Virology 333: 271-283

Halpin C, Cooke S E, Barakate A, Amrani A E, Ryan M D (1999), Self-processing 2A-polyproteins—a system for co-ordinate expression of multiple proteins in transgenic plants. Plant J 17: 453-459

Igarashi A, Yamagata K, Sugai T, Takahashi Y, Sugawara E, Tamura A, Yaegashi H, Yamagishi N, Takahashi T, Isogai M, Takahashi H, Yoshikawa N (2009), Apple latent spherical virus vectors for reliable and effective virus-induced gene silencing among a broad range of plants including tobacco, tomato, *Arabidopsis thaliana*, cucurbits, and legumes. Virology 386: 407-416

Jackson S A, Rokhsar D, Stacey G, Shoemaker R C, Schmutz J, Grimwood J (2006), Toward a reference sequence of the soybean genome: a multiagency effort. Crop Sci 46: S55-S61

Lawrence R J, Pikaard C S (2003), Transgene-induced RNA interference: a strategy for overcoming gene redundancy in polyploids to generate loss-of-function mutations. Plant J 36: 114-121

Lu R, Malcuit I, Moffett P, Ruiz M T, Peart J, Wu A J, Rathjen J P, Bendahmane A, Day L, Baulcombe D C (2003), High throughput virus-induced gene silencing implicates heat shock protein 90 in plant disease resistance. EMBO J. 22: 5690-5699

Meng Y, Moscou M J, Wise R P (2009), Blufensin1 negatively impacts basal defense in response to barley powdery mildew. Plant Physiol 149: 271-285

Meyer J D F, Silva D C G, Yang C, Zhang C, Mortel M V D, Pedley K F, Hill J H, Shoemaker R C, Abdelnoor R V, Whitham S A, Graham M A (2009), Identification and analyses of candidate genes for Rpp4 mediated resistance to Asian soybean rust in soybean (*Glycine max*). Plant Physiol 150: 295-307

Nagamatsu A, Masuta C, Senda M, Matsuura H, Kasai A, Hong J-S, Kitamura K, Abe J, Kanazawa A (2007), Functional analysis of soybean genes involved in flavonoid biosynthesis by virus-induced gene silencing. Plant Biotechnol J 5: 778-790

Peele C, Jordan C V, Muangsan N, Turnage M, Egelkrout E, Eagle P, Hanley-Bowdoin L, Robertson D (2001), Silencing of a meristematic gene using geminivirus-derived vectors. Plant J. 27: 357-366

Pflieger S, Blanchet S, Camborde L, Drugeon G, Rousseau A, Noizet M, Planchais S, Jupin I (2008), Efficient virus-induced gene silencing in *Arabidopsis* using a 'one-step' TYMV-derived vector. Plant J 56: 678-690

Pogue G P, Lindbo J A, Garger S J, Fitzmaurice W P (2002), Making an ally from an enemy: plant virology and the new agriculture. Ann Rev Phytopathol 40: 45-74

Qu F, Ren T, Morris T J (2003), The coat protein of Turnip crinkle virus suppresses posttranscriptional gene silencing at an early initiation step. J. Virol. 77: 511-522.

Rosso M-N, Dubrana M P, Cimbolini N, Jaubert S, Abad P (2005), Application of RNA interference to root-knot nematode genes encoding esophageal gland proteins. Mol Plant-Microbe Interact 18: 615-620

Ryu C-M, Anand A, Kang L, Mysore K S (2004) Agrodrench: a novel and effective agroinoculation method for virus-induced gene silencing in roots and diverse Solanaceous species. Plant J 40: 322-331

Schlueter J A, Dixon P, Granger C, Grant D, Clark L, Doyle J J, Shoemaker R C (2004), Mining EST databases to resolve evolutionary events in major crop species. Genome 47: 868-876

Seo J K, Lee H G, Kim K H (2009), Systemic gene delivery into soybean by simple rub-inoculation with plasmid DNA of a Soybean mosaic virus-based vector. Arch. Virol. 154: 87-99

Shoemaker R C, Polzin K, Labate J, Specht J, Brummer E C, Olson T, Young N, Concibido V, Wilcox J, Tamulonis J P, Kochert G, Boerma H R (1996), Genome duplication in soybean (*Glycine* subgenus *soja*). Genetics 144: 329-338

Stacey G, Vodkin L, Parrott W A, Shoemaker R C 2004. National Science Foundation-sponsored workshop report: draft plan for soybean genomics. Plant Physiol 135: 59-70.

Thomas C L, Jones L, Baulcombe D C, Maule A J (2001), Size constraints for targeting post-transcriptional gene silencing and for RNA-directed methylation in *Nicotiana benthamiana* using a Potato virus X vector. Plant J. 25: 417-425

Turnage M A, Muangsan N, Peele C G, Robertson D (2002), Geminivirus-based vectors for gene silencing in *Arabidopsis*. Plant J 30: 107-117

Wang L, Eggenberger A, Hill J H, Bogdanove A J (2006), *Pseudomonas syringae* effector avrB confers soybean cultivar-specific avirulence on Soybean mosaic virus adapted for transgene expression but effector avrPto does not. Mol Plant-Microbe Interact 19: 304-312

Xiang C, Han P, Lutziger I, Wang K, Oliver D J (1999), A mini binary vector series for plant transformation. *Plant Molecular Biology* 40: 711-717

Zhang C, Ghabrial S A (2006), Development of Bean pod mottle virus-based vectors for stable protein expression and sequence-specific virus-induced gene silencing in soybean. Virology 344: 401-411

Zhang C, Gu H, Ghabrial S A (2007), Molecular characterization of naturally occurring RNA1 recombinants of the Comovirus Bean pod mottle virus. Phytopathology 97: 1255-1262

Zhang C, Yang C, Whitham S A, Hill J R (2009), Development and use of an efficient DNA-based viral gene-silencing vector for soybean. *Mol Plant-Microbe Interact* 22: 123-31

TABLE I

Primers for constructing and sequencing infectious BPMV VIGS vectors

| Name | Sequence (5' → 3') |
| --- | --- |
| BP-5endF | TATTAAAATTTTCATAAGATTTGAAATTTTG |
| R1-235F | ATATAGGACTTCGTGTCAGATT |
| R1-688F | TGCATATCATTTTCAGCATTTTGT |
| R1-1208F | TGTGCTACCATTGCAGTTTCTA |
| R1-2245R | AAGTTTGGTCTACAACATAATGA |
| R1-2797R | TCCCATTCCACACAAAATTGCT |
| R1-3344R | TCAGGATCATACACATGCCA |
| R1-3824R | ACTCCCTCTTGACTATCAAC |
| R1-3746F | GCTTCATTAATACCATATGTTGA |
| R1-4707R | CCACCACAAAGACTGTTTATCA |
| R1-5238R | ACAAGATAAGCTTCTTGCATTT |
| R1-5708F | CAATAAGAAAATTCGGACAGCGCTT |

TABLE I-continued

Primers for constructing and sequencing infectious BPMV VIGS vectors

| Name | Sequence (5' → 3') |
| --- | --- |
| R1-5759R | GGAAAAGGATCAACTCTAGT |
| R1-3Cla | CCATCGATTTTTTTTTTTTTTTTTTATAT TTAAACAC |
| R2-454F | ACTTGGGCATTGGTGCAAATGT |
| R2-948F | ACTTCTTACTGATGGGAAGTTGTA |
| R2-1548F | CAAGAGAAAGATTTATTGGAGGGA |
| R2-1786F | AAGCTCAAATGGAAACAAATCT |
| R2-2133F | TGGAATCCTGCTTGTACAAAAGCA |
| R2-2688R | TGTGAGAAACTCCTCTTGTGA |
| R2-2746F | TGGCTGATGGGTGCCCATATT |
| R2-3303F | ATGGTTTCGAAATGTGGAGTTCTGA |
| R2-3Cla | CCATCGATTTTTTTTTTTTTTTTTAAAA TAACACAC |
| R1-Modi-F | AAAAATGAAAGTGGTCATTTTAATAAT |
| R1-Modi-R | ATTATTAAAATGACCACTTTCATTTTT |
| 35S-Seq | ACG CAC AAT CCC ACT ATC |
| Nos-Rev | AGA CCG GCA ACA GGA TTC A |
| CaMV-35FP | (5-phos)CCGCCCTCCAAAAATATCAAAGA |
| Nos-RP | (5-phos)GAATTCCCGATCTAGTAACATAGA |
| pCB0380-6455F | GTTTCAAACCCGGCAGCT |
| pCB0380-506R | CTGAACGTCAGAAGCCGACT |

TABLE II

Primers used for vector modification and foreign gene cloning

| Primer name | Primer sequence (5' → 3') |
| --- | --- |
| R2-For1 | TGCATGAGGATCCTGATCTGGAATTTGTGT |
| R2-Rev1 | CCAGATCAGGATCCTCATGCAGAGGATTCCGCA |
| R2-For2 | TCTGGATCCGCGTCGACTCCAGGCCTCGA |
| R2-Rev2 | GGAAGATCTCTCGAGGCCTGGAGTCGAC |
| R2-For3 | TTGAGTCCAACCCTGGGCCCGGATCCTGATCTGGAATTTGTGTTT |
| R2-Rev3 | CCAGGGTTGGACTCAACGTCACCTGCTAACTTAAGTAGGTCAAAGT |
| R2-For4 | TCTGCAGCGCCTGCAAAACAGCTCTTAAACTTTGACCTACTTAAG |
| R2-Rev4 | TGCAGGCGCTGCAGAGGATTCCGCATTTT |
| R2-For5 | CCCGTCGACCCCGGGGCCCAGCTAAGCAATTGCTGAATTTCGATC TCTTGAAACTGGCTGGAGATGTAGAATCAAATCCAGGCCCGATGGA AACAAATTTGTTTAAATTGT |
| R2-Rev5 | ACAATGAGGTTCAGGCTCAGATGGAGACCAACCTCTTCAAGCTCAG CTTGGACGACGTAGAGACACCAAAGGGAAGCCTCGAGCCCGTCGA CCCCGGG |

TABLE II-continued

| | |
|---|---|
| GFP-Bam-For | CCTTGGATCCATGAGTAAAGGAGAAGAACTTTTCA |
| GFP-Bam-Rev | TCCGGATCCTTATTTGTATAGTTCATCCATGCCA |
| GFP-Xho | CCGCTCGAGATGAGTAAAGGAGAAGAACTTT |
| GFP-Sma | TCCCCCGGGTTTGTATAGTTCATCCATGCCA |
| TBSV-P19-Xho | CCTCGAGATGGAACGAGCTATACAAGG |
| TBSV-P19-Sma | TCCCCCGGGCTCGCTTTCTTTTTCGAAGGT |
| BAR-Xho | CCGCTCGAGAGCCCAGAACGACGCC |
| BAR-Sma | TCCCCCGGGGATCTCGGTGACGGGCA |
| GFP-modi-1F | ACGCGTCGACGGATCCATGAGTAAAGGAGAAGAACTTT |
| GFP-modi-1R | AGGCGCGGATCCTTTGTATAGTTCATCCATGCCA |
| GFP-modi-2F | CTATACAAAGGATCCGCGCCTGCAAAACAGCTCT |
| GFP-modi-2R | CCGCTCGAGGGGCCCAGGGTTGGACTCAACGT |
| Gm-PDS-pF1 | CGCGGATCCCGTGGTGCTTTCACCACTGCT |
| Gm-PDS-pR1 | CGCGGATCCCACTTTGAAAGTAGATTTGGGA |
| Gm-PDS-pF2 | CGCGGATCCGCCGCTTGTGGCTATATAT |
| Gm-PDS-pR2 | CGCGGATCCTCCTGCACCGGCAATAACGA |
| Gm-PDS-pF3 | CGCGGATCCGCAAGGAATATTATAGCCCAAA |
| Gm-PDS-pR3 | CGCGGATCCCAGAAAGAACAGCGCCTTCCA |
| Gm-PDS-pF4 | CGCGGATCCCAAGAATTGAAAGAGTCATGGT |
| Gm-PDS-pR4 | CGCGGATCCCCAATACAAACATTGATCCAGA |
| Gm-PDS-pF1130 | CGCGGATCCTGGATGGCAATCCACCCGA |
| Gm-PDS-pR1520 | CGCGGATCCTTTGGGCTATAATATTCCTTGC |

BPMV sequences.txt

```
@551656AS34@
ISERF
267|Demo User
212
25|pBPMV-GFP + BAR (pBPMV-V5)
27|1
222|3
33|9311
236|472234174
26|8569
28|0
219|0
220|1
221|1
29|0
30|0
217|0
31|0
32|1
255
224|Demo User
50
256
224|Demo User
50
1001|0
45
51|43
52|Nos Terminator
53|0
55|9027
56|9302
57|0
281|1
```

TABLE II-continued

```
282|1
283|1
284|1
50
45
51|21
52|FMDV-2A 1st
53|0
55|7062
56|7133
57|0
281|1
282|1
283|1
284|1
50
45
51|21
52|GFP (between BamHI sites)
53|0
55|5712
56|6425
57|0
281|1
282|1
283|1
284|1
50
45
51|21
52|FMDV-2A 2nd
53|10
55|6432
56|6503
57|0
281|1
282|1
283|1
284|1
50
45
51|21
52|BAR (between XhoI and SmaI)
53|0
55|6510
56|7055
57|0
281|1
282|1
283|1
284|1
50
45
51|21
52|CaMV 35S promoter
53|0
55|3147
56|3838
57|0
281|1
282|1
283|1
284|1
50
205
37|0
38|0
39|0
40|0
24
```

209|tatagtgagtcgtattacaattcactggccgtcgttttacaacgtcgtgactgggaaaaccctggcgttacccaacttaatcgcc
ttgcagcacatccccctttcgccagctggcgtaatagcgaagaggcccgcaccgatcgcccttcccaacagttgcgcagcctgaat
ggcgaatggacgcgccctgtagcggcgcattaagcgcggcgggtgtggtggttacgcgcagcgtgaccgctacacttgccagc
gccctagcgcccgctcctttcgctttcttcccttcctttctcgccacgttcgccggctttccccgtcaagctctaaatcggggggctccc
tttagggttccgatttagtgctttacggcacctcgaccccaaaaaacttgattagggtgatggttcacgtagtgggccatcgccctgat
agacggtttttcgccctttgacgttggagtccacgttctttaatagtggactcttgttccaaactggaacaacactcaacccatctcg
gtctattcttttgatttataagggattttgccgatttcggcctattggttaaaaaatgagctgatttaacaaaaatttaacgcgaattt
taacaaaatattaacgcttacaatttcctgatgcggtattttctccttacgcatctgtgcggtatttcacaccgcatatggtgcactct
cagtacaatctgctctgatgccgcatagttaagccagccccgacacccgccaacacccgctgacgcgccctgacgggcttgtctgctcc TABLE II-continued cggcatccgcttacagacaagctgtgaccgtctccgggagctgcatgtgtcagaggttttcaccgtcatcaccgaaacgcgcgagacga
aagggcctcgtgatacgcctattttataggttaatgtcatgataataatggtttcttagacgtcaggtggcacttttcggggaaatgt
gcgcggaaccccctatttgtttattttctaaatacattcaaatatgtatccgctcatgagacaataaccctgataaatgcttcaataat
attgaaaaaggaagagtatgagtattcaacattccgtgtcgcccttattccctttttgcggcattttgccttcctgttttgctcac
ccagaaacgctggtgaaagtaaaagatgctgaagatcagttgggtgcacgagtgggttacatcgaactggatctcaacagcggtaagat
ccttgagagttttcgccccgaagaacgttttccaatgatgagcacttttaaagttctgctatgtggcgcggtattatcccgtattgacg
ccgggcaagagcaactcggtcgccgcatacactattctcagaatgacttggttgagtactcaccagtcacagaaaagc 209|atcttacggatggcatgacagtaagagaattatgcagtgctgccataaccatgagtgataacactgcggccaacttacttctga
caacgatcggaggaccgaaggagctaaccgcttttttgcacaacatgggggatcatgtaactcgccttgatcgttgggaaccggag
ctgaatgaagccataccaaacgacgagcgtgacaccacgatgcctgtagcaatggcaacaacgttgcgcaaactattaactggcg
aactacttactctagcttcccggcaacaattaatagactggatggaggcggataaagttgcaggaccacttctgcgctcggccttc
cggctggctggtttattgctgataaatctggagccggtgagcgtgggtctcgcggtatcattgcagcactgggcgcagatggtaag
ccctcccgtatcgtagttatctacacgacggggagtcaggcaactatggatgaacgaaatagacagatcgctgagataggtgcctc
actgattaagcattggtaactgtcagaccaagttactcatatatactttagattgatttaaaacttcatttttaatttaaaaggatct
aggtgaagatcctttttgataatctcatgaccaaaatcccttaacgtgagttttcgttccactgagcgtcagaccccgtagaaaagatc
aaaggatcttcttgagatccttttttttctgcgcgtaatctgctgcttgcaaacaaaaaaaccaccgctaccagcggtggtttgtttgcc
ggatcaagagctaccaactctttttccgaaggtaactggcttcagcagagcgcagataccaaatactgttcttctagtgtagccgtagt
taggccaccacttcaagaactctgtagcaccgcctacatacctcgctctgctaatcctgttaccagtggctgctgccagtggcgataag
tcgtgtcttaccgggttggactcaagacgatagttaccggataaggcgcagcggtcgggctgaacggggggtcgtgcacacagcccag
cttggagcgaacgacctacaccgaactgagatacctacagcgtgagctatgagaaagcgccacgcttcccgaaggggagaaaggc
ggacaggtatccggtaagcggcagggtcggaacaggagagcgcacgagggagcttccaggggggaaacgcctggtatctttata
gtcctgtcgggtttcgccacctctgacttgagcgtcgatttttgtgatgctcgtcaggggggcggagcctatggaaaaacgccagca
acgcggcctttttacggttcctggccttttgctggccttttgctcacatgttctttcctgcgttatcccctgattctgtggataaccgt
attaccgcc 209|tttgagtgagctgataccgctcgccgcagccgaacgaccgagcgcagcgagtcagtgagcgaggaagcggaagagcgc
ccaatacgcaaaccgcctctccccgcgcgttggccgattcattaatgcagctggcacgacaggtttcccgactggaaagcgggca
gtgagcgcaacgcaattaatgtgagttagctcactcattaggcaccccaggctttacactttatgcttccggctcgtatgttgtgtgga
attgtgagcggataacaatttcacacaggaaacagctatgaccatgattacgccaagctatttaggtgacactatagaatactcaagc
ggccgcctactccaagaatatcaaagatacagtctcagaagaccaaaggctattgagactttcaacaaagggtaatatcgggaa
acctcctcggattccattgcccagctatctgtcacttcatcaaaaggacagtagaaaaggaaggtggcacctacaaatgccatcatt
gcgataaaggaaaggctatcgttcaagatgcctctgccgacagtggtcccaaagatggaccccacccacgaggagcatcgtgg
aaaaagaagacgttccaaccacgtcttcaaagcaagtggattgatgatctactccaagaatatcaaagatacagtctcagaagac
caaagggctattgagactttcaacaaagggtaatatcgggaaacctcctcggattccattgcccagctatctgtcacttcatcaaaag
gacagtagaaaaggaaggtggcacctacaaatgccatcattgcgataaaggaaaggctatcgttcaagatgcctctgccgacagt
ggtcccaaagatggaccccacccacgaggagcatcgtggaaaaagaagacgttccaaccacgtcttcaaagcaagtggattga
tgtgatatctccactgacgtaagggatgacgcacaatcccactatctctatataaggaagttcatttcattt
ggagaggtattaaaattttcataagatttgaattttgataaaccgcgatcacaggttgccgcaccttaaaaccggaaacaaaagcaat
cgttacttgatttcaagaatcttccaatttcttcctacttcttggtgtacgatttcttaagagaaagaaaatcactctctgtgctggcc
acagacttcgtgaatcatttctttttccactcttagtttatttgctgaacactctcctatttgatataggacttcgtgtcagatttaaa
cttttttctgtttctttctcagttctctgcttaatttcaagtttaagctggtgaaatcttggattagtgctcccactctcctatctggta
taggacttcgtgg 209|gtagacttttctatttctgtcttttctttcactctcttcttctcactgatccgcattgccgttcaaagtggtcttatttgaaaaa
cacttgggcgttggtgcaaatgtttgcttcgttaattttctctgggacaacaggctcactgagaaaacaattttttacttgcagagatt
tggacatcttggttgtttattatacaatagcaactcaatttagaaaaatttctaccgcattacattaggtggcatctgtataccttgttg
atctacattctcccatcttttctcactgctgaaattaaatataagcggaatctgagtaatattcatatttctggcttattttacgacgg
cagatataaattctggactaaacacgagaaaaatcttgctttgacagaagaggaaaagatggaagtgattagaaacaaaggcattcctg
ctgatgttcttgcaaagcgagctcatgaatttgaaaaacatgttgctcatgaacttcaaggatcaaattcctgctgttgacaagttg
tattctactaaggttaataagtttgcaaaaattatgaacctttagacaaagtgttgttggtgatcttaaacttcttactgatgggaagtt
gtatgagggtaagcatattcctgtatctaatattagtgcaggggagaatcatgtagttcaaatacccctaatggcacaggaggaaattc
tgtcttctagtgcaagtgatttcagaactgcaatggtgagtaaaaatagcaagcctcaagctactgcaatgcatgtaggagctatagaa
attatcattgatagttttcgcaagtcctgactgcaacatagttggtgcaatgctttttggttgatacttatcataccaatcctgaaaatgc
agttcgtagtattttttgttgcgcctttcagaggcggaaggcccattcgggtggttacatttccgaataccattgtgcagattgaaccag
acatgaattcaaggtttcagcttttgagtaccactaccaatggtgattttgttcaaggaaaagatctcgcaatggttaaagttaatgta
gcatgtgctgctgttggcttgacatcaagttacactccaactccactgttggaatctggtttgcaaaaagacagagggtaattgtgga
atattttggaaggatgtcttacgttgctcataacgttaatcagccccaagagaaagatttgttggagggaaatttttcctttgatatta
aatctcgctctagattggaaaagtttcttctactaaagcacaatttgttagtgaaaaccttcaaatatgatataattggtgctggt
tcacattcttcagaagattttcctaaaaagaagatcaagaaaaacccaaaaagattgatgccagattg 209|agacaaagaatagatccccaatacaatgaggttcaggctcagatggagaccaacctcttcaagctcagcttggacgacgta
gagacaccaaagggaagcctcgacggatccatgagtaagggagaagaacttttcactggagttgtcccaattcttgttgaattagat
ggtgatgttaatgggcacaaattttctgtcagtggagagggtgaaggtgatgcaacatacggaaaacttacccttaaattttatttgcac
tactggaaaactacctgttccatggccaacacttgtcactactttctcttatggtgttcaatgcttttcaagatacccagatcatatga
agcggcacgacttcttcaagagcgccatgcctgagggatacgtgcaggagaccatctctttcaaggacgacgggaactacaaga
cacgtgctgaagtcaagtttgagggagacacccctcgtcaacaggatcgagcttaagggaatcgatttcaaggaggacggaaacat
cctcggccacaagttggaatacaactacaactcccacaacgtatacatcacggcagacaaacaaaagaatggaatcaaagctaac
ttcaaaattagacacaacattgaagatggaagcgttcaactagcagaccattatcaacaaaatactccaattggcgatggccctgtcc
ttttaccagacaaccattacctgtccacacaatctgccctttcgaaagatcccaacgaaaagagagaccacatggtccttcttgagttt
gtaacagctgctgggattacacatggcatggatgaactatacaaaggatccgcgcctgcaaaacagctcttaaactttgacctactta
agttagcaggtgacgttgagtccaaccctgggcccctcgagagcccagaacgacgcccggccgacatccgccgtgccaccgag
gcggacatgccggcggtctgcaccatcgtcaaccactacatcgagacaagcacggtcaacttccgtaccgagccgcaggaacc
gcaggagtggacgacgacctcgttccgtctgcgggagcgctatcctggctcgtcgcgaggtgacggcgaggtcgccggc
atcgcctacgcggggcccctggaaggcacgcaacgcctacgactgacggccgagtcgaccgtgtacgtctcccccgccacca
gcggacgggactggctccacgctctacacccacctgctgaagtccctggaggcacagggcttcaagagcgtggtcgctgtcat
cgggctgcccaacgacccgagcgtgcgcatgcacgaggcgctcggatatgccccccgcggcatgctgcgggcggccggcttc
aagcacgggaactggcatgacgtgggtttctggca TABLE II-continued

```
209|gctggacttcagcctgccggtaccgccccgtccggtcctgcccgtcaccgagatcccggggcccagctaagcaattgct
gaatttcgatctcttgaaactggctggagatgtagaatcaaatccaggcccgatggaaacaaatttgtttaaattgtctcttgatgatg
ttgaaactcctaaaggttccatgttggatcttaaaatttctcaatctaaaattgcacttcccaaaaacacagttggaggaaccattctg
cgtagtgatctattggcaaatttttttgacagagggcaattttagagcaagtgttgatttgcagcgcactcatcgtattaaaggaatgat
taaaatggtggccacagttggtattcctgagaatacaggtatatcattggcctgtgctatgaatagttcttttaggggcgtgccagtt
ctgatatttacaccatctgctctcaagactgtgaattatgaatcctgcttgcacaaaagcaatgactatgtcatttaatccaaacccg
tgttctgatgcatggagtttggaattttttgaagcgtaccggatttcattgtgatatcatttgtgtcactggatggactgccaccccaat
gcaggatgttcaggttacaattgattggtttatttcctctcaggaatgtgttcccaggacctattgtgttttaaatccacaaaatcctt
ttgtgttaaataggtggatgggcaaactgactttcccccagggcacttcccgaagtgttaaaagaatgcctctttctataggggagga
gctggtgcaaagaatgctattctcatgaatatgccaaatgctgtttcttcaatgtggagatattttgttggagatctcgtctttgaagt
ttctaagatgacttctccctacattaaatgtacagtctctttcttcatagcatttggaaatttggctgatgacaccattaattttgagg
cttttccccacaagctggtgcagtttggagaaattcaggaaaaagttgtattgaaattttcacaagaggaatttcttacagcttggtca
actcaggtgcgtcctgcaacaactctgttggctgatgggtgtccatatttgtatgctatggtgcatgatagttcagtgtctacaatacc
aggtgatttgtcattggtgttaagttggcaaccataaacaatatgtgtgcatatgggctcaatcctgctatttcaggttctcgtctttt
tgggcaccattcctcagtccatttcacagcaaactgtttggaatcagatggcaacagtgagaacaccattgaattttgatcctagcaag
cagagcttttgtcaattttctattgaccttctcggtggaggaattttagtggacaaaactggagattggatca 209|cacttatacaaaattctccaattagtaacttgagagagagctgatggaagaaaggctgtttaatggttaagattgtgatgtctg
ggaatgcagcagtcaaaaggagtgattgggcctcattggtacaagtgttttaacaaacagcaacagtacagagcattttgatgcat
gtaagtggacaaaatcggaaccacattcctgggaattgatcttcccaatagaggtgtgtggtcctaacaatggttttgaaatgtggag
ttctgagtgggcaaatcaaacttc  atggcatttgagatccttattgacaatcccaaacagtctacagatttgacattctcctgggaat
ttcccaagattttgaaattgctggtaatactcttatgccagctttttctgttccacaggctactgccagatcttctgaaaatgcggaat
cctctgcatgatctggaatttgtgttttctttcgtttgttcgcttgtttaattcaataaaggaaattaggcatgaccctctcgttgagt
atgctctgtctatttgaaaatttccacacctcttttaattgtcgtaatgatgtgtgaagtgtgtgttatttaaaaaaaaaaaaaaaaaa
aatcgatagctcgaatttccccgatcgttcaaacatttggcaataaagtttcttaagattgaatcctgttgccggtcttgcgatgatta
tcatataatttctgttgaattacgtaagcatgtaataattaacatgtaatgcatgacgttatttatgagatgggttttttatgattaga
gtcccgcaattatacatttaatacgcgatagaaaacaaaatatagcgcgcaaactaggataaattatcgcgcgcggtgtcatctatgtt
actagatcgggaattccaattcgcc 210
212
25|pBPMV-GFP + PDS (pBPMV-V4)
27|1
222|3
33|9014
236|472234174
26|8565
28|0
219|0
220|1
221|1
29|0
30|0
217|0
31|0
32|1
255
224|Demo User
50
256
224|Demo User
50
1001|0
45
51|21
52|FMDV-2A
53|0
55|6426
56|6497
57|0
281|1
282|1
283|1
284|1
50
45
51|21
52|PDS insert
53|0
55|8223
56|8549
57|0
281|1
282|1
283|1
284|1
50
45
51|21
52|GFP
```

TABLE II-continued

```
53|0
55|5706
56|6419
57|0
281|1
282|1
283|1
284|1
50
45
51|21
52|CaMV 35S promoter
53|0
55|3147
56|3838
57|0
281|1
282|1
283|1
284|1
50
45
51|21
52|Nos Terminator
53|0
55|8730
56|8945
57|0
281|1
282|1
283|1
284|1
50
205
37|0
38|0
39|0
40|0
24

209|tatagtgagtcgtattacaattcactggccgtcgttttacaacgtcgtgactgggaaaaccctggcgttacccaacttaatcgcc
ttgcagcacatccccctttcgccagctggcgtaatagcgaagaggcccgcaccgatcgcccttcccaacagttgcgcagcctgaat
ggcgaatggacgcgccctgtagcggcgcattaagcgcggcgggtgtggtggttacgcgcagcgtgaccgctacacttgccagc
gccctagcgcccgctcctttcgctttcttcccttcctttctcgccacgttcgccggctttccccgtcaagctctaaatcggggctccc
tttagggttccgatttagtgctttacggcacctcgaccccaaaaaacttgattagggtgatggttcacgtagtgggccatcgccctgat
agacggtttttcgccctttgacgttggagtccacgttctttaatagtggactcttgttccaaactggaacaacactcaaccctatctcg
gtctattcttttgatttataagggattttgccgatttcggcctattggttaaaaaatgagctgatttaacaaaaatttaacgcgaatttt
taacaaaatattaacgcttacaatttcctgatgcggtattttctccttacgcatctgtgcggtatttcacaccgcatatggtgcactct
cagtacaatctgctctgatgccgcatagttaagccagccccgacacccgccaacacccgctgacgcgccctgacgggcttgtctgctcc
cggcatccgcttacagacaagctgtgaccgtctccgggagctgcatgtgtcagaggttttcaccgtcatcaccgaaacgcgcgagacga
aagggcctcgtgatacgcctatttttataggttaatgtcatgataataatggtttcttagacgtcaggtggcacttttcggggaaatgt
gcgcggaacccctatttgtttatttttctaaatacattcaaatatgtatccgctcatgagacaataaaccctgataaatgcttcaataat
attgaaaaaggaagagtatgagtattcaacatttccgtgtcgcccttattcccttttttgcggcattttgccttcctgtttttgctcac
ccagaaacgctggtgaaagtaaaagatgctgaagatcagttgggtgcacgagtgggttacatcgaactggatctcaacagcggtaagat
ccttgagagttttcgccccgaagaacgttttccaatgatgagcacttttaaagttctgctatgtggcgcggtattatcccgtattgacg
ccgggcaagagcaactcggtcgccgcatacactattctcagaatgacttggttgagtactcaccagtcacagaaaagc 209|atcttacggatggcatgacagtaagagaattatgcagtgctgccataaccatgagtgataacactgcggccaacttacttctga
caacgatcggaggaccgaaggagctaaccgcttttttgcacaacatgggggatcatgtaactcgccttgatcgttgggaaccggag
ctgaatgaagccataccaaacgacgagcgtgacaccacgatgcctgtagcaatggcaacaacgttgcgcaaactattaactggcg
aactacttactctagcttcccggcaacaattaatagactggatggaggcggataaagttgcaggaccacttctgcgctcggcccttc
cggctggctggtttattgctgataaatctggagccggtgagcgtgggtctcgcggtatcattgcagcactggggccagatggtaag
ccctcccgtatcgtagttatctacacgacggggagtcaggcaactatggatgaacgaaatagacagatcgctgagataggtgcctc
actgattaagcattggtaactgtcagaccaagtttactcatatatactttagattgatttaaaacttcatttttaatttaaaaggatct
aggtgaagatcctttttgataatctcatgaccaaaatcccttaacgtgagttttcgttccactgagcgtcagaccccgtagaaaagatc
aaaggatcttcttgagatcctttttttctgcgcgtaatctgctgcttgcaaacaaaaaaaccaccgctaccagcggtggtttgtttgcc
ggatcaagagctaccaactctttttccgaaggtaactggcttcagcagagcgcagataccaaatactgttcttctagtgtagccgtagt
taggccaccacttcaagaactctgtagcaccgcctacatacctcgctctgctaatcctgttaccagtggctgctgccagtggcgataag
tcgtgtcttaccgggttggactcaagacgatagttaccggataaggcgcagcggtcgggctgaacggggggttcgtgcacacagcccag
cttggagcgaacgacctacaccgaactgagatacctacagcgtgagctatgagaaagcgccacgcttcccgaagggagaaaggc
ggacaggtatccggtaagcggcagggtcggaacaggagagcgcacgagggagcttccaggggggaaacgcctggtatctttata
gtcctgtcgggtttcgccacctctgacttgagcgtcgatttttgtgatgctcgtcaggggggcggagcctatgaaaaacgccagca
acgcggcctttttacggttcctggccttttgctggccttttgctcacatgttctttcctgcgttatcccctgattctgtggataaccgt
attaccgcc 209|tttgagtgagctgataccgctcgccgcagccgaacgaccgagcgcagcgagtcagtgagcgaggaagcggaagagcgc
ccaatacgcaaaccgcctctccccgcgcgttggccgattcattaatgcagctggcacgacaggtttcccgactggaaagcgggca
gtgagcgcaacgcaattaatgtgagttagctcactcattaggcaccccaggctttacactttatgcttccggctcgtatgttgtgtgga
attgtgagcggataacaatttcacacaggaaacagctatgaccatgattacgccaagctatttaggtgacactatagaatactcaagc
ggccgcctactccaagaatatcaaagatacagtctcagaagaccaaagggctattgagacttttcaacaaagggtaatatcgggaa
```

TABLE II-continued

```
     acctcctcggattccattgcccagctatctgtcacttcatcaaaaggacagtagaaaaggaaggtggcacctacaaatgccatcatt
     gcgataaaggaaaggctatcgttcaagatgcctctgccgacagtggtcccaaagatggaccccccacccacgaggagcatcgtgg
     aaaaagaagacgttccaaccacgtcttcaaagcaagtggattgatgtgatctactccaagaatatcaaagatacagtctcagaagac
     caaagggctattgagactttcaacaaagggtaatatcgggaaacctcctcggattccattgcccagctatctgtcacttcatcaaaag
     gacagtagaaaaggaaggtggcacctacaaatgccatcattgcgataaaggaaaggctatcgttcaagatgcctctgccgacagt
     ggtcccaaagatggaccccccacccacgaggagcatcgtggaaaagaagacgttccaaccacgtcttcaaagcaagtggattga
     tgtgatatctccactgacgtaagggatgacgcacaatcccactatccttcgcaagacccttcctctatataaggaagttcatttcattt
     ggagaggtattaaaattttcataagatttgaaattttgataaaccgcgatcacaggttgccgcaccttaaaaccggaaacaaaagcaat
     cgttacttgatttcaagaatcttccaatttcttcctacttcttggtgtacgatttcttaagagaaagaaaatcactctctgtgctggcc
     acagacttcgtgaatcattttcttttccactcttagtttatttgctgaacactctcctatttgatataggacttcgtgtcagatttaaa
     cttttttctgtttctttctcagttctctgcttaatttcaagtttaagctggtgaaatcttggattagtgctcccactctcctatctggta
     taggacttcgtgg 209 |gtagactatctatttctgtatttctttcactctcttcttctcactgatccgcattgccgttcaaagtggtcttatttgaaaaaca
     cttgggcgttggtgcaaatgtttgcttcgttaattttctctggggacaacaggctcactgagaaaacaattttttacttgcagagattg
     gacatcttggttgtttattatacaatagcaactcaatttagaaaattctaccgcattacattaggtggcatctgtataccttgttgat
     ctacattctcccatcttttctcactgctgaaattaaatataagcggaatctgagtaatattcatatttctggcttatttttacgacggca
     gatataaattctggactaaacacgagaaaatcttgctttgacagaagaggaaaagatggaagtgattagaaacaaaggcattcctgct
     gatgttcttgcaaagcgagctcatgaatttgaaaaacatgttgctcatgaaagcctcaaggatcaaattcctgctgttgacaagttgta
     ttctactaaggttaataagtttgcaaaaattatgaaccttagacaaagtgttgttggtgatcttaaacttcttactgatgggaagttgt
     atgagggtaagcatattcctgtatctaatattagtgcagggggaatcatgtagttcaaataccccaatggcacaggaggaaattctg
     tcttctagtgcaagtgatttcagaactgcaatggtgagtaaaaatagcaagcctcaagctactgcaatgcatgtaggagctatagaaat
     tatcattgatagtttcgcaagtcctgactgcaacatagttggtgcaatgcttttggttgatacttatcataccaatcctgaaaatgcag
     ttcgtagtattttgttgcgcctttcagaggcggaaggcccattcgggtggtacatttccgaataccattgtgcagattgaaccagac
     atgaattcaaggtttcagcttttgagtaccactaccaatggtgattttgttcaaggaaaagatctcgcaatggttaaagttaatgtagc
     atgtgctgctgttggcttgacatcaagttacactccaactccactgttggaatctggttttgcaaaaagacagagggttaattgtgaat
     attttggaaggatgtcttacgttgctcataacgttaatcagcccaagagaaagatttgttggagggaaattttttcctttgatattaaa
     tctcgctctagattggaaaagtttcttctactaaagcacaatttgttagtggaaaaaccttcaaatatgatataattggtgctggttc
     acattcttcagaagattttcctaaaaaagaagatcaagaaaaacccaaaaagattgatgccagattg 209 |agacaaagaatagatccccaatacaatgaggttcaggctcagatggagaccaacctcacaagctcagcttggacgacgta
     gagacaccaaagggaagcctcgagatgagtaaaggagaagaacttttcactggagttgtcccaattcttgttgaattagatggtgat
     gttaatgggcacaaattttctgtcagtggagagggtgaaggtgatgcaacatacggaaaacttacccttaaatttatttgcactactgg
     aaaactacctgttccatggccaacacttgtcactacttctcttatggtgttcaatgcttttcaagataccccagatcatatgaagcggc
     acgacttcttcaagagcgccatgcctgagggatacgtgcaggagaggaccatctcttttcaaggacgacgggaactacaagacacgtg
     ctgaagtcaagtttgagggagacaccctcgtcaacaggatcgagcttaagggaatcgatttcaaggaggacggaaacatcctcgg
     ccacaagttggaatacaactacaactcccacaacgtatacatcacggcagacaaacaaaagaatggaatcaaagctaacttcaaaa
     ttagacacaacattgaagatggaagcgttcaactagcagaccattatcaacaacacctatggacgacttggcgatggccctgtccttacc
     agacaaccattacctgtccacacaatctgcccttcgaaagatcccaacgaaaagagagaccacatggtccttcttgagtttgtaaca
     gctgctgggattacacatggcatggatgaactatacaaaccggggccccagctaagcaattgctgaatttcgatctcttgaaactg
     gctggagatgtagaatcaaatccaggcccgatggaaacaaatttgtttaaattgtctcttgatgatgttgaaactcctaaaggttccat
     gttggatcttaaaattcctcaatctaaaattgcacttcccaaaaaacacagttggaggaaccattctgcgtagtgatctattggcaaatt
     ttttgacagagggcaattttagagcaagtgttgatttgcagcgcactcatcgtattaaaggaatgattaaaatggtggccacagttggt
     attcctgagaatacaggtatatcattggcctgtgctatgaatagttcttttaggggggcgtgccagttctgatatttacaccatctgctc
     tcaagactgtgaattatggaatcctgcttgcacaaaagcaatgactatgtcatttaatccaaacccgtgttctgatgcatggagtttgg
     aattttttgaagcgtaccggatttcattgtgatatcatttgtgtcactggatggactgccaccccaatgcaggatgttcaggttacaat 209 |tgattggtttatttcctctcaggaatgtgttcccaggacctattgtgttttaaatccacaaaatccattgtgttaaataggtgga
     tgggcaaactgactttcccccagggcacttcccgaagtgttaaaagaatgcctcttctataggggggaggagctggtgcaaagaatgct
     attctcatgaatatgccaaatgctgttctttcaatgtggagatattttgttggagatgctcgttgaagttctaagatgactttctcc
     ctacattaaatgtacagtctctttcttcatagcatttggaaattttggctgatgacaccattaattttgaggcttttccccacaagctgg
     tgcagtttggagaaattcaggaaaaagttgtattgaaattttcacaagaggaatttcttacagctttggtcaactcaggtgcgtcctgca
     acaactctgttggctgatgggtgtccatatttgtatgctatggtgcatgatagttcagtgtctacaataccaggtgattagtcattggt
     gttaagaggcaaccataaacaatatgtgtgcatatgggctcaatcctggtatttcaggttctcgtcttttgggcaccattcctcagtcc
     atttcacagcaaactgtttggaatcagatggcaacagtgagaacaccattgaattttgatcctagcaagcagagcttttgtcaattttc
     tattgaccttctcggtggaggaattttagtggacaaaactggagattggatcacacttatacaaaattctccaattagtaacttgttga
     gagttgctgcttggaagaaaggctgtttaatggttaagattgtgatgtctgggaatgcagcagtcaaaaggagtgattgggcctcattg
     gtacaagtgtttttaacaaacagcaacagtacagagcattttgatgcatgtaagtggacaaaatcggaaccacattcctgggaattgat
     cttcccaatagaggtgtggtcctaacaatggttttgaaatgtgagttctgagtgggcaaatcaaacttcatggcatttgagtttcc
     ttattgacaatcccaaacagtctacagtttttgacattctcctgggaatttcccaagattttgaaattgctggtaatactcttatgcca
     gcttttctgttccacaggctactgccagatcttctgaaaatgcggaatcctctgcatgaggatcccagaaagaacagcgccttccatt
     gaagctaaatattttttgttttgtgtaatctccagctaaatagaaaccttctataggagatctttgaatgggtcgacaaggttcacaatt
     tggaacagttttgtaaaccgaccttggtgttttaacaacatggtacttgagaatcttagctttgct 209 |ttggtctgcagaaatttcatcaggaaagagtttggcaagctcagtcatcgtggcttgaataatatcatcgtcactacgtgaaatc
     cattcttcggctggtgcaaaaaccaactctaacattgactggtttgggctataatattccttgcggatcctctggaatttgtgttttct
     ttcgtttgttcgcttgtttaattcaataaaggaaattaggcatgactgactctctcgttggtatgtctgtctatttgaaaatttccacacc
     tcattaattgtcgtaatgatgtgtgaagtgtgtgttattttaaaaaaaaaaaaaaaaaaatcgatagctcgaatttccccgatcgttca
     aacatttggcaataaagtttcttaagattgaatcctgttgccggtcttgcgatgattatcatataatttctgttgaattacgttaagca
     tgtaataattaacatgtaatgcatgacgttatttgagatgggttttatgattagagtcccgcaattatacatttaatacgcgatag
     aaaacaaatatagcgcgcaaactaggataaattatcgcgcgcggtgtcatctatgttactagatcgggaattccaattcgcc 210
212
25|pBPMV-GFP1
27|1
222|3
33|8618
236|470921559
26|8578
```

TABLE II-continued

```
28|0
219|0
220|1
221|1
29|0
30|0
217|0
31|0
32|1
255
224|Demo User
50
256
224|Demo User
50
1001|0
45
51|38
52|FMDV 2A
53|0
55|7359
56|7430
57|0
281|1
282|1
283|1
284|1
50
45
51|43
52|Nos terminator
53|0
55|8334
56|8609
57|0
281|1
282|1
283|1
284|1
50
45
51|21
52|CaMV 35S promoter
53|0
55|3147
56|3838
57|0
281|1
282|1
283|1
284|1
50
45
51|21
52|GFP (between BamHI)
53|0
55|7437
56|8150
57|0
281|1
282|1
283|1
284|1
50
205
37|0
38|0
39|0
40|0
24
209|tatagtgagtcgtattacaattcactggccgtcgattacaacgtcgtgactgggaaaaccctggcgttacccaacttaatcgcc
ttgcagcacatccccctttcgccagctggcgtaatagcgaagaggcccgcaccgatcgcccttcccaacagttgcgcagcctgaat
ggcgaatggacgcgccctgtagcggcgcattaagcgcggcgggtgtggtggttacgcgcagcgtgaccgctacacttgccagc
gccctagcgcccgctcctttcgctttcttcccttcctttctcgccacgttcgccggctttccccgtcaagctctaaatcgggggctccc
tttagggttccgatttagtgctttacggcacctcgaccccaaaaaacttgattagggtgatggttcacgtagtgggccatcgccctgat
agacggtttttcgccctttgacgttggagtccacgttctttaatagtggactcttgttccaaactggaacaacactcaaccctatctcg
gtctattcttagatttataagggattttgccgatttcggcctattggttaaaaaatgagctgatttaacaaaaatttaacgcgaatata
acaaaatattaacgcttacaatttcctgatgcggtattttctccttacgcatctgtgcggtatttcacaccgcatatggtgcactctca
gtacaatctgctctgatgccgcatagttaagccagccccgacacccgccaacacccgctgacgcgccctgacgggcttgtctgctcccg
```

TABLE II-continued gcatccgcttacagacaagctgtgaccgtctccgggagctgcatgtgtcagaggttttcaccgtcatcaccgaaacgcgcgagacgaaa
gggcctcgtgatacgcctattttttataggttaatgtcatgataataatggtttcttagacgtcaggtggcacttttcggggaaatgtgc
gcggaacccctatttgtttattttttctaaatacattcaaatatgtatccgctcatgagacaataaccctgataaatgcttcaataatat
tgaaaaaggaagagtatgagtattcaacattccgtgtcgccctattccctttttttgcggcattttgccttcctgttttttgctcaccc
agaaacgctggtgaaagtaaaagatgctgaagatcagttgggtgcacgagtgggttacatcgaactggatctcaacagcggtaagatcc
ttgagagttttcgccccgaagaacgttttccaatgatgagcacttttaaagttctgctatgtggcgcggtattatcccgtattgacgcc
gggcaagagcaactcggtcgccgcatacactattctcagaatgacttggttgagtactcaccagtcacagaaaagc 209|atcttacggatggcatgacagtaagagaattatgcagtgctgccataaccatgagtgataacactgcggccaacttacttctga
caacgatcggaggaccgaaggagctaaccgcttttttgcacaacatgggggatcatgtaactcgccttgatcgttgggaaccggag
ctgaatgaagccataccaaacgacgagcgtgacaccacgatgcctgtagcaatggcaacaacgttgcgcaaactattaactggcg
aactacttactctagcttcccggcaacaattaatagactggatggaggcggataaagttgcaggaccacttctgcgctcggcccttc
cggctggctggtttattgctgataaatctggagccggtgagcgtgggtctcgcggtatcattgcagcactggggccagatggtaag
ccctcccgtatcgtagttatctacacgacggggagtcaggcaactatggatgaacgaaatagacagatcgctgagataggtgcctc
actgattaagcattggtaactgtcagaccaagtttactcatatatactttagattgatttaaaacttcattttttaatttaaaaggatct
aggtgaagatcctttttgataatctcatgaccaaaatcccttaacgtgagttttcgttccactgagcgtcagaccccgtagaaaagatc
aaaggatcttcttgagatcctttttttctgcgcgtaatctgctgcttgcaaacaaaaaaaccaccgctaccagcggtggtttgtttgcc
ggatcaagagctaccaactctttttccgaaggtaactggcttcagcagagcgcagataccaaatactgttcttctagtgtagccgtagt
taggccaccacttcaagaactctgtagcaccgcctacatacctcgctctgctaatcctgttaccagtggctgctgccagtggcgataag
tcgtgtcttaccgggttggactcaagacgatagttaccggataaggcgcagcggtcgggctgaacggggggttcgtgcacacagcccag
cttggagcgaacgacctacaccgaactgagatacctacagcgtgatgtatgaaaagcgccacgcttcccgaagggagaaaggc
ggacaggtatccggtaagcggcagggtcggaacaggagagcgcacgagggagcttccaggggggaaacgcctggtatcttttata
gtcctgtcgggtttcgccacctctgacttgagcgtcgatttttgtgatgctcgtcaggggggcggagcctatggaaaaacgccagca
acgcggcctttttacggttcctggccttttgctggccttttgctcacatgttctttcctgcgttatcccctgattctgtggataaccgt
attaccgcc 209|tttgagtgagctgataccgctcgccgcagccgaacgaccgagcgcagcgagtcagtgagcgaggaagcggaagagcgc
ccaatacgcaaaccgcctctccccgcgcgttggccgattcattaatgcagctggcacgacaggtttcccgactggaaagcgggca
gtgagcgcaacgcaattaatgtgagttagctcactcattaggcaccccaggctttacactttatgcttccggctcgtatgttgtgtgga
attgtgagcggataacaatttcacacaggaaacagctatgaccatgattacgccaagctatttaggtgacactatagaatactcaagc
ggccgcctactccaagaatatcaaagatacagtctcagaagaccaaagggctattgagactttcaacaaagggtaatatcgggaa
acctcctcggattccattgcccagctatctgtcacttcatcaaaaggacagtagaaaaggaaggtggcacctacaaatgccatcatt
gcgataaaggaaaggctatcgttcaagatgcctctgccgacagtggtcccaaagatggaccccacccacgaggagcatcgtgg
aaaaagaagacgttccaaccacgtcttcaaagcaagtggattgatgatctactccagaataccaaagatacagtctcagaagac
caaagggctattgagactttcaacaaagggtaatatcgggaaacctcctcggattccattgcccagctatctgtcacttcatcaaaag
gacagtagaaaaggaaggtggcacctacaaatgccatcattgcgataaaggaaaggctatcgttcaagatgcctctgccgacagt
ggtcccaaagatggaccccacccacgaggagcatcgtggaaaaagaagacgttccaaccacgtcttcaaagcaagtggattga
tgtgatatctccactgacgtaagggatgacgcacaatcccactaatcctctatataaggaagttcattcattt
ggagaggtattaaaattttcataagatttgaaattttgataaaccgcgatcacaggttgccgcacccttaaaaccggaaacaaaagcaat
cgttacttgatttcaagaatcttccaatttcttcctacttcttggtgtacgatttcttaagagaaagaaaatcactctctgtgctggcc
acagacttcgtgaatcatttcttttccactcttagtttatttgctgaacactctccctatttgatataggacttcgtgtcagatttaaa
cttttttctgtttctttctcagttctctgcttaatttcaagtttaagctggtgaaatcttggattagtgctcccactctcctatctggta
taggacttcgtgg 209|gtagacattctatttctgtcttttctttcactctcttcttctcactgatccgcattgccgttcaaagtggtcttatttgaaaaac
acttgggcgttggtgcaaatgtttgcttcgttaatttctctggggacaacaggctcactgagaaaacaattttttacttgcagagattt
ggacatcttggttgtttattatacaatagcaactcaatttagaaaatttctaccgcattaccattaggtggcatctgtatacctgttga
tctacattctcccatcttttctcactgctgaaattaaatataagcggaatctgagtaatattcatatttctggcttattttacgacggc
agatataaattctggactaaacacgagaaaatcttgctttgacagaagaggaaaagatggaagtgattagaaacaaaggcattcctgc
tgatgttcttgcaaagcgagctcatgaatttgaaaaacatgttgctcatgaaagcctcaaggatcaaattcctgctgttgacaagttgt
attctactaaggttaataagtttgcaaaaattatgaacctagacaaagtgttgttggtgatcttaaacttcttactgatgggaagttg
tatgagggtaagcatattcctgtatctaatattagtgcaggggagaatcatgtagttcaaatacccctaatggcacaggaggaaattct
gtcttctagtgcaagtgatttcagaactgcaatggtgagtaaaaatagcaagcctcaagctactgcaatgcatgtaggagctatagaaa
ttatcattgatagtttcgcaagtcctgactgcaacatagttggtgcaatgattggttgatacttatcataccaatcctgaaaatgcag
ttcgtagtattatgttgcgcctttcagaggcggaaggcccattcgggtggtacatttccgaataccattgtgcagattgaaccagaca
tgaattcaaggtttcagcttttgagtaccactaccaatggtgattttgttcaaggaaaagatctcgcaatggttaaagttaatgtagca
tgtgctgctgttggcttgacatcaagttacactccaactccactgttggaatctgtttggaaaagacagagggttaattgtggaata
ttttggaaggatgtcttacgttgctcataacgttaatcagccccaagagaaagatttgttggagggaaattttttcctttgatattaaat
ctcgctctagattggaaaaagtttcttctactaaagcacaatttgttagtggaaaaaccttcaaatatgataattggtgctggttca
cattcttcagaagattttcctaaaaaagaagatcaagaaaaacccaaaaagattgatgccagattg 209|agacaaagaatagatcccccaatacaatgaggttcaggctcagatggaaacaaatttgtttaaattgtctcttgatgatgttgaaa
ctcctaaaggttccatgttggatcttaaaatttctcaatctaaaattgcacttcccaaaaacacagttggaggaaccattctgcgtagt
gatctattggcaaatttttttgacagagggcaattttagagcaagtgttgatttgcagcgcactcatcgtattaaaggaatgattaaaat
ggtggccacagttggtattcctgagaatacaggtatatcattggcctgtgctatgaatagttcttttagggggcgtgccagtctgata
tttacaccatctgctctcaagactgtgaattatgaatcctgcttgcacaaaagcaatgactatgtcatttaatccaaaccgtgttct
gatgcatggagttttgaattttgaagcgtaccggatttcattgtgatatcatttgtgtcactggatggactgccaccccaatgcagga
tgttcaggttacaattgattggtttattcctcctcaggaatgtgtttcccaggaccttattgtgtttttaaatccacaaattcctttttgtgt
taaataggtggatgggcaaactgacttttcccccagggcacttcccgaagtgtttaaaagaatgcctcctttctataggggagagctggt
gcaaagaatgctattctcatgaatatgccaaatgctgttcttcaatgtggagatattttgtggagatctcgtcttttgaagtttctaa
gatgacttctccctacattaaatgtacagtctcttttcttcatagcatttggaaatttggctgatgacaccattaattttgaggcttttc
cccacaagctggtgcagtttggagaaattcaggaaaagtgtattgaaattttcacaagaggaattcttacgcttggtcaactcag
gtgcgtcctgcaacaactctgttggctgatgggtgcatcatttgtatgcgtatgcatagttcagtgtctacaataccaggtga
ttttgtcattggtgttaagttggcaaccataaacaatatgtgtgcatatgggctcaatcctgtatttcaggtctcgtcttttgggca
ccattcctcagtccatttcacagcaaactgtttgaatcagatggcaacagtgagaacaccattgaattttgatcctagcaagcagagc
ttttgtcaatttctctattgaccttctcggtggaggaattttagtggacaaaactggagattggatcacacttatacaaaattctccaat
tagtaacttgttgagagttgctgcttggaagaaaggctgtttaatggttaagattgtgatgtctgggaa

TABLE II-continued

```
209|tgcagcagtcaaaaggagtgattgggcctcattggtacaagtgtattaacaaacagcaacagtacagagcattagatgcatg
taagtggacaaaatcggaaccacattcctgggaattgatcttcccaatagaggtgtgtggtcctaacaatggttttgaaatgtggagtt
ctgagtgggcaaatcaaacttcatggcatttgagtttccttattgacaatcccaaacagtctacagttttgacattctcctgggaatt
tcccaagattttgaaatgctggtaatactcttatgccagctttttctgttccacaggctactgccagatcttctgaaaatgcggaatc
ctctgcagcgcctgcaaaacagctcttaaactttgacctacttaagttagcaggtgacgttgagtccaaccctgggcccggatccatga
gtaaaggagaagaacttttcactggagttgtcccaattcttgttgaattagatggtgatgttaatgggcacaaattttctgtcagtgga
gagggtgaaggtgatgcaacatacggaaaacttacccttaaatttatttgcactactggaaaactacctgttccatggccaacacttgt
cactactttctcttatggtgttcaatgcattcaagatacccagatcatatgaagcggcacgacttcttcaagagcgccatgcctgaggg
atacgtgcaggagaggaccatctctttcaaggacgacgggaactacaagacacgtgctgaagtcaagtttgagggagacaccctcgtca
acaggatcgagcttaagggaatcgatttcaaggaggacggaaacatcctcggccacaagttggaatacaactacaactcccacaac
gtatacatcacggcagacaaacaaaagaatggaatcaaagctaacttcaaaattagacacaacattgaagatggaagcgttcaact
agcagaccattatcaacaaaatactccaattggcgatggccctgtccttttaccagacaaccattacctgtccacacaatctgccctt
cgaaagatcccaacgaaaagagagaccacatggtccttcttgagtttgtaacagctgctgggattacacatggcatggatgaactat
acaaaggatcctgatctggaatttgtgttttcttcgtttgttcgcttgtttaattcaataaaggaaattaggcatgaccctctcgttg
agtatgctctgtctatttgaaaatttccacacctcttttaattgtcgtaatgatgtgtgaagtgtgtgttatttaaaaaaaaaaaaaa
aaaatcgatagctcgaattccccgatcgttcaaacatttggcaataaagtttcttaagattgaatcctgttgccg
```

```
209|gtcttgcgatgattatcatataatttctgagaattacgttaagcatgtaataattaacatgtaatgcatgacgttatttatgaga
tgggttttatgattagagtcccgcaattatacatttaatacgcgatagaaaacaaaatatagcgcgcaaactaggataaattatcgcg
cgcggtgtcatctatgttactagatcgggaattccaattcgcc
```

210
212
25|pBPMV-GFP2 (pBPMV-V3)
27|1
222|3
33|8682
236|472234174
26|8561
28|0
219|0
220|1
221|1
29|0
30|0
217|0
31|0
32|1
255
224|Demo User
50
256
224|Demo User
50
1001|0
45
51|43
52|NOS Terminator
53|0
55|8398
56|8673
57|0
281|1
282|1
283|1
284|1
50
45
51|21
52|FMDV-2A
53|0
55|6427
56|6498
57|0
281|1
282|1
283|1
284|1
50
45
51|21
52|19 AA of CP-L
53|0
55|5644
56|5700
57|0
281|1
282|1
283|1
284|1

TABLE II-continued

```
50
45
51|21
52|GFP (between XhoI and SmaI)
53|0
55|5707
56|6420
57|0
281|1
282|1
283|1
284|1
50
205
37|0
38|0
39|0
40|0
24
```

209|tatagtgagtcgtattacaattcactggccgtcgttttacaacgtcgtgactgggaaaaccctggcgttacccaacttaatcgcc
ttgcagcacatccccctttcgccagctggcgtaatagcgaagaggcccgcaccgatcgcccttcccaacagttgcgcagcctgaat
ggcgaatggacgcgccctgtagcggcgcattaagcgcggcgggtgtggtggttacgcgcagcgtgaccgctacacttgccagc
gccctagcgcccgctcctttcgctttcttcccttcctttctcgccacgttcgccggctttccccgtcaagctctaaatcgggggctccc
tttagggttccgatttagtgctttacggcacctcgaccccaaaaaacttgattagggtgatggttcacgtagtgggccatcgccctgat
agacggttttcgccctttgacgttggagtccacgttctttaatagtggactcttgttccaaactggaacaacactcaaccctatctcg
gtctattcttttgatttataagggattttgccgatttcggcctattggttaaaaaatgagctgatttaacaaaaatttaacgcgaattt
taacaaaatattaacgcttacaatttcctgatgcggtattttctccttacgcatctgtgcggtatttcacaccgcatatggtgcactct
cagtacaatctgctctgatgccgcatagttaagccagccccgacacccgccaacacccgctgacgcgccctgacgggcttgtctgctcc
cggcatccgcttacagacaagctgtgaccgtctccgggagctgcatgtgtcagaggttttcaccgtcatcaccgaaacgcgcgagacga
aagggcctcgtgatacgcctatttttataggttaatgtcatgataataatggtttcttagacgtcaggtggcacttttcggggaaatgt
gcgcggaacccctatttgtttatttttctaaatacattcaaatatgtatccgctcatgagacaataaaccctgataaatgcttcaataat
attgaaaaaggaagagtatgagtattcaacatttccgtgtcgcccttattcccttttttgcggcattttgccttcctgtttttgctcac
ccagaaacgctggtgaaagtaaaagatgctgaagatcagttgggtgcacgagtgggttacatcgaactggatctcaacagcggtaagat
ccttgagagttttcgccccgaagaacgttttccaatgatgagcacttttaaagttctgctatgtggcgcggtattatcccgtattgacg
ccgggcaagagcaactcggtcgccgcatacactattctcagaatgacttggttgagtactcaccagtcacagaaaagc 209|atcttacggatggcatgacagtaagagaattatgcagtgctgccataaccatgagtgataacactgcggccaacttacttctga
caacgatcggaggaccgaaggagctaaccgcttttttgcacaacatgggggatcatgtaactcgccttgatcgttgggaaccggag
ctgaatgaagccataccaaacgacgagcgtgacaccacgatgcctgtagcaatggcaacaacgttgcgcaaactattaactggcg
aactacttactctagcttcccggcaacaattaatagactggatgaggcggataaagttgcaggaccacttctgcgctcggcccttc
cggctggctggtttattgctgataaatctggagccggtgagcgtgggtctcgcggtatcattgcagcactggggccagatggtaag
ccctcccgtatcgtagttatctacacgacggggagtcaggcaactatggatgaacgaaatagacagatcgctgagataggtgcctc
actgattaagcattggtaactgtcagaccaagtttactcatatatactttagattgatttaaaacttcatttttaatttaaaaggatct
aggtgaagatcctttttgataatctcatgaccaaaatcccttaacgtgagttttcgttccactgagcgtcagaccccgtagaaaagatc
aaaggatcttcttgagatcctttttttctgcgcgtaatctgctgcttgcaaacaaaaaaaccaccgctaccagcggtggtttgtttgcc
ggatcaagagctaccaactctttttccgaaggtaactggcttcagcagagcgcagataccaaatactgttcttctagtgtagccgtagt
taggccaccacttcaagaactctgtagcaccgcctacatacctcgctctgctaatcctgttaccagtggctgctgccagtggcgataag
tcgtgtcttaccgggttggactcaagacgatagttaccggataaggcgcagcggtcgggctgaacggggggttcgtgcacacagcccag
cttggagcgaacgacctacaccgaactgagatacctacagcgtgagctatgagaaagcgccacgcttcccgaagggagaaaggc
ggacaggtatccggtaagcggcagggtcggaacaggagagcgcacgagggagcttccaggggggaaacgcctggtatctttata
gtcctgtcgggtttcgccacctctgacttgagcgtcgatttttgtgatgctcgtcaggggggcggagcctatggaaaaacgccagca
acgcggcctttttacggttcctggccttttgctggccttttgctcacatgttctttcctgcgttatcccctgattctgtggataaccgt
attaccgcc 209|tttgagtgagctgataccgctcgccgcagccgaacgaccgagcgcagcgagtcagtgagcgaggaagcggaagagcgc
ccaatacgcaaaccgcctctccccgcgcgttggccgattcattaatgcagctggcacgacaggtttcccgactggaaagcgggca
gtgagcgcaacgcaattaatgtgagttagctcactcattaggcacccccaggctttacactttatgcttccggctcgtatgttgtgtgga
attgtgagcggataacaatttcacacaggaaacagctatgaccatgattacgccaagctatttaggtgacactatagaatactcaagc
tggccgcctactccaagaatatcaaagatacagtctcagaagaccaaaggctattgagacttttcaacaaagggtaatatcggga
aacctcctcggattccattgcccagctatctgtcacttcatcaaaaggacagtagaaaaggaaggtggcacctcaaatgccatcatt
gcgataaaggaaaggctatcgttcaagatgcctctgccgacagtggtcccaaagatggacccccacccacgaggagcatcgtgg
aaaaagaagacgttccaaccacgtcttcaaagcaagtggattggatgatctactccaagaatatcaaagatacagtctcagaagac
caaagggctattgagacttttcaacaaagggtaatatcgggaaacctcctcggattccattgcccagctatctgtcacttcatcaaaag
gacagtagaaaaggaaggtggcacctcaaatgccatcattgcgataaaggaaaggctatcgttcaagatgcctctgccgacagt
ggtcccaaagatggacccccacccacgaggagcatcgtggaaaaagaagacgaccaaccacgtcttcaaagcaagtggattga
tgtgatatctccactgacgtaagggtgacgcacaatcccactatccttgcagaaccctcctctatataaggaagttcatttcattt
gggagaggtattaaaattttcataagatttgaaattttgataaaccgcgatcacaggtgccgcaccttaaaaccggaaacaaaagcaat
cgttacttgatttcaagaatcttccaatttcttcctacttcttggtgtacgatttcttaagagaaagaaaatcactctctgtgctggcc
acagacttcgtgaatcatttttcttttccactcttagtttatttgctgaacactctccatttttgatataggacttcgtgtcagatttaaa
ctttttctgtttctttctcagttctctgcttaattttcaagtttaagctggtgaaatcttggattagtgctcccactctcctatctggta
taggacttcgtg 209|ggtagacttttctatttctgtcttttctttcactctatcttctcactgatccgcattgccgttcaaagtggtcttatttgaaaaa
cacttgggcgttggtgcaaatgtttgcttcgttaattttctctggggacaacaggctcactgagaaaacaattttttacttgcagagatt
tggacatcttggttgtttattacaatagcaactcaatttagaaaatttctaccgcattacattaggtggcatctgtataccttgttg
atctacattctcccatcttttctcactgctgaaattaaatataagcggaatctgagtaatattcatatttctggcttattttacgacgg
cagatataaattctggactaaacacgagaaaatcttgctttgacagaagaggaaaagatggaagtgattagaaacaaaggcattcctg
ctgatgttcttgcaaagcgagctcatgaatttgaaaaacatgttgctcatgaaagcctcaaggatcaaattcctgctgttgacaagttg
tattctactaaggttaataagtttgcaaaaattatgaaccttagacaaagtgttgaggtgatcttaaacttcttactgatgggaagttg

TABLE II-continued

209|tatgagggtaagcatattcctgtatctaatattagtgcaggggagaatcatgtagttcaaataccccttaatggcacaggaggaaattct
gtcttctagtgcaagtgatttcagaactgcaatggtgagtaaaaatagcaagcctcaagctactgcaatgcatgtaggagctatagaaa
ttatcattgatagtttcgcaagtcctgactgcaacatagttggtgcaatgcttttggttgatacttatcataccaatcctgaaaatgca
gttcgtagtattttttgttgcgcctttcagaggcggaaggcccattcgggtggttacatttccgaatacattgtgcagattgaaccaga
catgaattcaaggtttcagcttttgagtaccactaccaatggtgattttgttcaaggaaaagatctcgcaatggttaaagttaatgtag
catgtgctgctgttggcttgacatcaagttacactccaactccactgttggaatctggtttgcaaaaagacagagggttaattgtggaa
tattttggaaggatgtcttacgttgctcataacgttaatcagccccaagagaaagatttgttggagggaaattttttcctttgatattaa
atctcgctctagattggaaaaagtttcttctactaaagcacaatttgttagtggaaaaaccttcaaatatgatataattggtgctggtt
cacattcttcagaagattttcctaaaaaagaagatcaagaaaaacccaaaaagattgatgccagatt 209|gagacaaagaatagatcccaatacaatgaggttcaggctcagatggagaccaacctcttcaagctcagcttggacgacgt
agagacaccaaagggaagcctcgagatgagtaaaggagaagaacttttcactggagttgtcccaattcttgttgaattagatggtga
tgttaatgggcacaaattttctgtcagtggagagggtgaaggtgatgcaacatacggaaaacttaccccttaaatttatttgcactactg
gaaaactacctgttccatggccaacacttgtcactacttttctcttatggtgttcaatgcttttcaagatacccagatcatatgaagcgg
cacgacttcttcaagagcgccatgcctgagggatacgtgcaggagaggaccatctctttcaaggacgacgggaactacaagacacgt
gctgaagtcaagtttgagggagacaccctcgtcaacaggatcgagcttaagggaatcgatttcaaggaggacggaaacatcctcg
gccacaagttggaatacaactacaactcccacaacgtatacatcacggcagacaaacaaaagaatggaatcaaagctaacttcaa
aattagacacaacattgaagatggaagcgttcaactagcagaccattatcaacaaaatactccaattggcgatggccctgtcttta
ccagacaaccattacctgtccacacaatctgccctttcgaaagatcccaacgaaaagagagaccacatggtccttcttgagtttgtaa
cagctgctgggattacacatggcatggatgaactatacaaacccggggcccagctaagcaattgctgaatttcgatctcttgaaac
tggctggagatgtagaatcaaatccaggcccgatggaaacaaattttgtttaaattgtctcttgatgatgttgaaactcctaaaggttcc
atgttggatcttaaaattttctcaatctaaaattgcacttcccaaaaacacagttggaggaaccattctgcgtagtgatctattggcaaa
tttttttgacagagggcaatttagagcaagtgttgatttgcagcgcactcatcgtattaaaggaatgattaaaatggtggccacagttg
gtattcctgagaatacaggtatatcattggcctgtgctatgaatagttctttttaggggcgtgccagttctgatatttacaccatctgc
tctcaagactgtgaattatggaatcctgcttgcacaaaagcaatgactatgtcatttaatccaaacccgtgttctgatgcatggagttt
ggaatttttgaagcgtaccggatttcattgtgatatcatttgtgtcactggatggactgccaccccaatgcaggatgttcaggttacaa 209|ttgattggtttatttcctctcaggaatgtgttcccaggaccatattgtgttttaaatccacaaaatccttttgtgttaaataggtg
gatgggcaaactgactttcccccagggcacttcccgaagtgttaaaagaatgcctcttttctataggggaggagctggtgcaaagaatg
ctattctcatgaatatgccaaatgctgttcttttcaatgtggagatatttttgttggagatctcgtcttttgaagttttctaagatgacttct
ccctacattaaatgtacagtctctcttttcttcatagcatttggaaatttggctgatgacaccattaattttgaggcttttccccacaagct
ggtgcagtttggagaaattcaggaaaaagttgtattgaaattttcacaagaggaatttcttacagcttggtcaactcaggtgcgtcctg
caacaactctgttggctgatgggtgtccatatttgtatgctatggtgcatgatagttcagtgtctacaataccaggtgattttgtcatt
ggtgttaagttggcaaccataaacaatatgtgtgcatatgggctcaatcctggtatttcaggttctcgtctttttgggcaccattcctca
gtccattcacagcaaactgtttggaatcagatggcaacagtgagaacaccattgaattttgatcctagcaagcagagctttttgtcaat
tttctattgaccttctcggtgaggaattttagtggacaaaactggagattggatcacacttatacaaaattctccaattagtaacttg
ttgagagttgctgcttggaagaaaggctgtttaatggttaagattgtgatgtctgggaatgcagcagtcaaaaggagtgattgggcctc
attggtacaagtgttttaacaaacagcaacagtacagagcattttgatgcatgtaagtggacaaaatcggaaccacattcctgggaat
tgatcttcccaatagaggtgtgtggtcctaacaatggttttgaaatgtggagttctgagtgggcaaatcaaacttcatgcgatttgagt
ttcctattgacaatcccaaacagtctacagtttttgacattctcctgggaatttcccaagattttgaaattgctggtaatactcttat
gccagcttttctgttccacaggctactgccagatcttctgaaaatgcgaatcctctgcatgaggatcctctgaatttgtgttttct
ttcgtttgttcgcttgtttaattcaataaaggaaattaggcatgaccctctcgttgagtatgctctgtctatttgaaaatttccacacc
tcttttaattgtcgtaatgatgtgtgaagtgtgtgttattttaaaaaaaaaaaaaaaaaaatcgatagc 209|tcgaatttcccgatcgttcaaacatttggcaataaagtttcttaagattgaatcctgttgccggtcttgcgatgattatcatat
aatttctgttgaattacgttaagcatgtaataattaacatgtaatgcatgacgttatttatgagatgggttttttatgattagagtcccg
caattatacatttaatacgcgatagaaaacaaaatatagcgcgcaaactaggataaattatcgcgcgcggtgtcatctatgttactaga
tcgggaattccaattcgcc 210
212
25|pBPMV-M1
27|1
222|3
33|7898
236|470921559
26|8575
28|0
219|0
220|1
221|1
29|0
30|0
217|0
31|0
32|1
255
224|Demo User
50
256
224|Demo User
50
1001|0
45
51|4
52|BPMV-RNA2
53|0
55|3839
56|7607
57|0

TABLE II-continued

```
281|1
282|1
283|1
284|1
50
45
51|38
52|FMDV 2A
53|0
55|7359
56|7430
57|0
281|1
282|1
283|1
284|1
50
45
51|43
52|Nos terminator
53|0
55|7614
56|7889
57|0
281|1
282|1
283|1
284|1
50
45
51|21
52|BamHI for foreign gene insertion
53|0
55|7431
56|7436
57|0
281|1
282|1
283|1
284|1
50
45
51|21
52|CaMV 35S promoter
53|0
55|3147
56|3838
57|0
281|1
282|1
283|1
284|1
50
205
37|0
38|0
39|0
40|0
24
```

209|tatagtgagtcgtattacaattcactggccgtcgttttacaacgtcgtgactgggaaaaccctggcgttacccaacttaatcgcc
ttgcagcacatccccctttcgccagctggcgtaatagcgaagaggcccgcaccgatcgcccttcccaacagttgcgcagcctgaat
ggcgaatggacgcgccctgtagcggcgcattaagcgcggcgggtgtggtggttacgcgcagcgtgaccgctacacttgccagc
gccctagcgcccgctcctttcgctttcttcccttcctttctcgccacgttcgccggctttccccgtcaagctctaaatcggggggctccc
tttagggttccgatttagtgctttacggcacctcgaccccaaaaaacttgattagggtgatggttcacgtagtgggccatcgccctgat
agacggtttttcgccctttgacgttggagtccacgttctttaatagtggactcttgttccaaactggaacaacactcaaccctatctcg
gtctattcttttgatttataagggattttgccgatttcggcctattggttaaaaaatgagctgatttaacaaaaatttaacgcgaatttt
taacaaaatattaacgcttacaatttcctgatgcggtattttctccttacgcatctgtgcggtatttcacaccgcatatggtgcactct
cagtacaatctgctctgatgccgcatagttaagccagccccgacacccgccaacacccgctgacgcgccctgacgggcttgtctgctcc
cggcatccgcttacagacaagctgtgaccgtctccgggagctgcatgtgtcagaggttttcaccgtcatcaccgaaacgcgcgagacga
aagggcctcgtgatacgcctatttttataggttaatgtcatgataataatggtttcttagacgtcaggtggcacttttcggggaaatgt
gcgcggaacccctatttgtttatttttctaaatacattcaaatatgtatccgctcatgagacaataaccctgataaatgcttcaataat
attgaaaaaggaagagtatgagtattcaacatttccgtgtcgcccttattcccttttttgcggcattttgccttcctgtttttgctcac
ccagaaacgctggtgaaagtaaaagatgctgaagatcagttgggtgcacgagtgggttacatcgaactggatctcaacagcggtaagat
ccttgagagttttcgccccgaagaacgttttccaatgatgagcacttttaaagttctgctatgtggcgcggtattatcccgtattgacg
ccgggcaagagcaactcggtcgccgcatacactattctcagaatgacttggttgagtactcaccagtcacagaaaagc 209|atcttacggatggcatgacagtaagagaattatgcagtgctgccataaccatgagtgataacactgcggccaacttacttctga
caacgatcggaggaccgaaggagctaaccgcttttttgcacaacatgggggatcatgtaactcgccttgatcgttgggaaccggag
ctgaatgaagccataccaaacgacgagcgtgacaccacgatgcctgtagcaatggcaacaacgttgcgcaaactattaactggcg TABLE II-continued aactacttactctagcttcccggcaacaattaatagactggatggaggcggataaagttgcaggaccacttctgcgctcggcccttc
cggctggctggtttattgctgataaatctggagccggtgagcgtgggtctcgcggtatcattgcagcactggggccagatggtaag
ccctcccgtatcgtagttatctacacgacggggagtcaggcaactatggatgaacgaaatagacagatcgctgagataggtgcctc
actgattaagcattggtaactgtcagaccaagtttactcatatatactttagattgatttaaaacttcattttttaatttaaaaggatct
aggtgaagatccttttttgataatctcatgaccaaaatcccttaacgtgagtttccactgagcgtcagacccgtagaaaagatc
aaaggatcttcttgagatcctttttttctgcgcgtaatctgctgcttgcaaacaaaaaaaccaccgctaccagcggtggtttgtttgcc
ggatcaagagctaccaactcttttttccgaaggtaactggcttcagcagagcgcagataccaaatactgttcttctagtgtagccgtagt
taggccaccacttcaagaactctgtagcaccgcctacatacctcgctctgctaatcctgttaccagtggctgctgccagtggcgataag
tcgtgtcttaccgggttggactcaagacgatagttaccggataaggcgcagcggtcgggctgaacggggggttcgtgcacacagcccag
cttggagcgaacgacctacaccgaactgagatacctacagcgtgagctatgagaaagcgccacgcttcccgaaggggagaaaggc
ggacaggtatccggtaagcggcagggtcggaacaggagagcgcacgagggagcttccaggggggaaacgcctggtatctttata
gtcctgtcgggtttcgccacctctgacttgagcgtcgatttttgtgatgctcgtcaggggggcggagcctatggaaaaacgccagca
acgcggccttttacggttcctggccttttgctggccttttgctcacatgttctttcctgcgttatcccctgattctgtggataaccgt
attaccgcc 209|tttgagtgagctgataccgctcgccgcagccgaacgaccgagcgcagcgagtcagtgagcgaggaagcggaagagcgc
ccaatacgcaaaccgcctctccccgcgcgttggccgattcattaatgcagctggcacgacaggtttcccgactggaaagcgggca
gtgagcgcaacgcaattaatgtgagttagctcactcattaggcacccaggcttttacactttatgcttccggctcgtatgttgtgtgga
attgtgagcggataacaatttcacacaggaaacagctatgaccatgattacgccaagctatttaggtgacactatagaatactcaagc
ggccgcctactccaagaatatcaaagatacagtctcagaagaccaaagggctattgagacttttcaacaaagggtaatatcgggaa
acctcctcggattccattgcccagctatctgtcacttcatcaaaaggacagtagaaaaggggtggcacctacaaatgccatcatt
gcgataaaggaaaaggctatcgttcaagatgcctctgccgacagtggtcccaaagatggaccccccacccacgaggagcatcgtgg
aaaaagaagacgttccaaccacgtcttcaaagcaagtggattgatgtgatctactccaagaatatcaaagatacagtctcagaagac
caaagggctattgagacttttcaacaaagggtaatatcgggaaacctcctcggattccattgcccagctatctgtcacttcatcaaaag
gacagtagaaaaggaaggtggcacctacaaatgccatcattgcgataaaggaaaaggctatcgttcaagatgcctctgccgacagt
ggtcccaaagatggaccccccacccacgaggagcatcgtggaaaaagaagacgttccaaccacgtcttcaaagcaagtggattga
tgtgatatctccactgacgtaagggatgacgcacaatcccactatccttcgcaagacccttcctctatataaggaagttcatttcattt
ggagaggtattaaaattttcataagatttgaaattttgataaaccgcgatcacaggttgccgcacctttaaaaccggaaacaaaagcaat
cgttacttgatttcaagaatcttccaatttcttcctacttcttggtgtacgatttcttaagagaaagaaaatcactctctgtgctggcc
acagacttcgtgaatcattttcttttccactcttagtttatttgctgaacactctccctatttgatataggacttcgtgtcagatttaaa
cttttctgttctcttctcagttctctgcttaatttcaagtttaagctggtgaaatcttggattagtgctcccactctcctatctggta
taggacttcgtgg 209|gtagacttttctatttctgtctttttctttcactctcttcttctcactgatccgcattgccgttcaaagtggtcttatttgaaaaa
cacttgggcgttggtgcaaatgtttgcttcgttaattttctctggggacaacaggctcactgagaaaacaattttttacttgcagagatt
tggacatcttggttgtttattatacaatagcaactcaatttagaaaatttctaccgcattacattaggtggcatctgtataccttgttg
atctacattctcccatctttctcactgctgaaatttaaatataagcggaatctgagtaatattcatatttctggcttattttacgacgg
cagatataaattctggactaaacacgagaaaaatcttgctttgacagaagaggaaaaaagtgattagaaacaaaggcattcctg
ctgatgttcttgcaaagcgagctcatgaatttgaaaaacatgttgctcatgaaagcctcaaggatcaaattcctgctgttgacaagttg
tattctactaaggttaataagtttgcaaaaattatgaaccttagacaaagtgttgttggtgatcttaaacttcttactgatgggaagtt
gtatgagggtaagcatattcctgtatctaatattagtgcaggggagaatcatgtagttcaaataccccctaatggcacaggaggaaattc
tgtcttctagtgcaagtgatttcagaactgcaatggtggtgaaaatagcaagcctcaagctactgcaatgcatgtaggagctatagaa
attatcattgatagtttcgcaagtcctgactgcaacatagttggtgcaatgcttttggttgatacttatcataccaatcctgaaaatgc
agttcgtagtatttttgttgcgcctttcagaggcggaaggcccattcgggtggttacatttccgaataccattgtgcagattgaaccag
acatgaattcaaggtttcagcttttgagtaccactaccaatggtgattttgttcaaggaaaagatctcgcaatggttaaagttaatgta
gcatgtgctgctgttggcttgacatcaagttacactccaactccactgttggaatctggtttgcaaaaagacagagggttaattgtgga
atattttggaaggatgtcttacgttgctcataacgttaatcagccccaagagaaagatttgttggagggaaattttttcctttgatatta
aatctcgctctagattggaaaaagtttcttctactaaagcacaatttgttagtgaaaaaccttcaaatatgataattggtgctggt
tcacattcttcagaagattttcctaaaaaagaagatcaagaaaaaacccaaaaagattgatgccagatg 209|agacaaagaatagatccccaatacaatgaggttcaggctcagatggaaacaaatttgtttaaattgtctcttgatgatgttgaaa
ctcctaaaggttccatgttggatcttaaaatttctcaatctaaaattgcacttcccaaaaacacagttggaggaaccattctgcgtagt
gatctattggcaaatttttttgacagagggcaattttagagcaagtgttgatttgcagcgcactcatcgtattaaaggaatgattaaaat
ggtggccacagttggtattcctgagaatacaggtatatcattggcctgtgctgatgaatagttcttttaggggggcgtgccagttctgata
tttacaccatctgctctcaagactgtgaattatggaatcctgcttgcacaaaagcaatgactatgtcatttaatccaaaccccgtgttct
gatgcatggagtttggaatttttgaagcgtaccggatttcattgtgatatcatttgtgtcactggatggactgccaccccaatgcagga
tgttcaggttacaattgattggtttattcctctcaggaatgtgttcccaggaccctattgtgttttaaatccacaaaatccttttgtgt
taaataggtggatgggcaaactgactttcccccagggcacttcccgaagtgttaaaagaatgcctcttttctatagggggaggagctggt
gcaaagaatgctattctcatgaatatgccaaatgctgttcttttcaatgtggagatattttgttggagatctcgtcttttgaagtttctaa
gatgacttctccctacattaaatgtacagtctctttcttcatagcatttggaaatttggctgatgacaccattaattttgaggcttttc
cccacaagctggtgcagtttggagaaattcaggaaaaagttgtattgaaattttcacaagaggaattttcttacagcttggtcaactcag
gtgcgtcctgcaacacctctgttggctgatgggtgtccatatttgtatgctatggtgcatgatagttcagtgtctacaataccaggtga
ttttgtcattggtgttaagttggcaaccataaacaatatgtgtgcatatgggctcaatcctggtatttcaggttctcgtcttttgggca
ccattcctcagtccatttcacagcaaactgtttggaatcagatggcaacagtggaacaccattgaattttgatcctagcaagcagagc
ttttgtcaattttctattgaccttctcggtggaggaatttttagtggacaaaactggagattggatcacacttatacaaaattctccaat
tagtaacttgttgagagttgctgcttggaagaaaggctgtttaatggttaagattgtgatgtctgggaa 209|tgcagcagtcaaaaggagtgattgggcctcattggtacaagtgttttaacaaacagcaacagtacagagcattttgatgcatg
taagtggacaaaatcggaaccacattcctgggaattgatcttcccaatagaggtgtgtggtcctaacaatggttttgaaatgtggagtt
ctgagtgggcaaatcaaacttcatggcatttgagtttccttattgacaatcccaaacagtctacagtattgacattctcctgggaattt
cccaagattttgaaattgctggtaatactcttatgccagcttttttctgttccacaggctactgccagatcttctgaaaatgcggaatcc
tctgcagcgcctgcaaaacagctcttaaactttgacctacttaagttagcaggtgacgttgagtccaaccctgggccggatcctgatc
tggaatttgtgattattcgtttgttcgcttgtttaattcaataaaggaaattaggcatgaccctctcgttgagtatgctctgtctattt
gaaaatttccacacctcttttaattgtcgatgatgtgtggagtgtgttatttttaaaaaaaaaaaaaaaatgatagctcgaa
tttccccgatcgttcaaacattttggcaataaagttcttttaagattgaatcctgttgccggtcttgcgatgattatcatataatttctgt
tgaattacgttaagcatgtaataattaacatgtaatgcatgacgttatttatgagatggttttatgattagagtcccgcaattatac
atttaatacgcgatagaaaacaaaatatagcgcgcaaactaggataaaattatcgcgcgcggtgtcatctatgttactagatcggaatt
ccaattcgcc

TABLE II-continued

```
210
212
25|pBPMV-R1A
27|1
222|3
33|10169
236|471014100
26|8573
28|0
219|0
220|1
221|1
29|0
30|1
217|0
31|0
32|1
34|Complementary copy of IA-1D7H-01
255
224|Demo User
50
256
224|Demo User
50
1001|0
45
51|21
52|NESGHFN
53|0
55|6204
56|6224
57|0
281|1
282|1
283|1
284|1
50
45
51|21
52|BPMV RNA1
53|0
55|3839
56|9824
57|0
281|1
282|1
283|1
284|1
50
45
51|21
52|Nos Terminator
53|0
55|9885
56|10100
57|0
281|1
282|1
283|1
284|1
50
45
51|21
52|CaMV 35S Promoter
53|0
55|3147
56|3838
57|0
281|1
282|1
283|1
284|1
50
205
37|0
38|0
39|0
40|0
24
```

TABLE II-continued

209 | tatagtgagtcgtattacaattcactggccgtcgttttacaacgtcgtgactgggaaaaccctggcgttacccaacttaatcgcc
ttgcagcacatccccctttcgccagctggcgtaatagcgaagaggcccgcaccgatcgcccttcccaacagttgcgcagcctgaat
ggcgaatggacgcgccctgtagcggcgcattaagcgcggcgggtgtggtggttacgcgcagcgtgaccgctacacttgccagc
gccctagcgcccgctccttcgctttcttcccttcctttctcgccacgttcgccggctttccccgtcaagctctaaatcgggggctccc
tttagggttccgatttagtgctttacggcacctcgaccccaaaaaacttgattagggtgatggttcacgtagtgggccatcgccctgat
agacggttttcgccctttgacgttggagtccacgttctttaatagtggactcttgttccaaactggaacaacactcaaccctatctcg
gtctattcttttgatttataagggattttgccgatttcggcctattggttaaaaaatgagctgatttaacaaaaatttaacgcgaattt
taacaaaatattaacgcttacaatttcctgatgcggtattttctccttacgcatctgtgcggtatttcacaccgcatatggtgcactct
cagtacaatctgctctgatgccgcatagttaagccagccccgacacccgccaacacccgctgacgcgccctgacgggcttgtctgctcc
cggcatccgcttacagacaagctgtgaccgtctccgggagctgcatgtgtcagaggttttcaccgtcatcaccgaaacgcgcgagacga
aagggcctcgtgatacgcctatttttataggttaatgtcatgataataatggtttcttagacgtcaggtggcacttttcggggaaatgt
gcgcggaaccccctatttgtttatttttctaaatacattcaaatatgtatccgctcatgagacaataaaccctgataaatgcttcaataat
attgaaaaaggaagagtatgagtattcaacatttccgtgtcgcccttattccctttttttgcggcattttgccttcctgtttttgctcac
ccagaaacgctggtgaaagtaaaagatgctgaagatcagttgggtgcacgagtgggttacatcgaactggatctcaacagcggtaagat
ccttgagagttttcgccccgaagaacgttttccaatgatgagcacttttaaagttctgctatgtggcgcggtattatcccgtattgacg
ccgggcaagagcaactcggtcgccgcatacactattctcagaatgacttggttgagtactcaccagtcacagaaaagc 209 | atcttacggatggcatgacagtaagagaattatgcagtgctgccataaccatgagtgataacactgcggccaacttacttctga
caacgatcggaggaccgaaggagctaaccgcttttttgcacaacatgggggatcatgtaactcgccttgatcgttgggaaccggag
ctgaatgaagccataccaaacgacgagcgtgacaccacgatgcctgtagcaatggcaacaacgttgcgcaaactattaactggcg
aactacttactctagcttcccggcaacaattaatagactggatggaggcggataaagttgcaggaccacttctgcgctcggcccttc
cggctggctggtttattgctgataaatctggagccggtgagcgtgggtctcgcggtatcattgcagcactggggccagatggtaag
ccctcccgtatcgtagttatctacacgacggggagtcaggcaactatggatgaacgaaatagacagatcgctgagataggtgcctc
actgattaagcattggtaactgtcagaccaagtttactcatatactttagattgatttaaaacttcatttttaatttaaaaggatct
aggtgaagatccttttttgataatctcatgaccaaaatcccttaacgtgagttttcgttccactgagcgtcagaccccgtagaaaagatc
aaaggatcttcttgagatcctttttttctgcgcgtaatctgctgcttgcaaacaaaaaaaccaccgctaccagcggtggtttgtttgcc
ggatcaagagctaccaactctttttccgaaggtaactggcttcagcagagcgcagataccaaatactgttcttctagtgtagccgtagt
taggccaccacttcaagaactctgtagcaccgcctacatacctcgctctgctaatcctgttaccagtggctgctgccagtggcgataag
tcgtgtcttaccgggttggactcaagacgatagttaccggataaggcgcagcggtcgggctgaacggggggtcgtgcacacagcccag
cttgagcgaacgacctacaccgaactgagatacctacagcgtgagctatgagaaagcgccacgcttcccgaagggagaaaggc
ggacaggtatccggtaagcggcagggtcggaacaggagagcgcacgagggagcttccaggggaaacgcctggtatctttata
gtcctgtcgggtttcgccacctctgacttgagcgtcgatttttgtgatgctcgtcaggggggcggagcctatggaaaaacgccagca
acgcggcctttttacggttcctggccttttgctggccttttgctcacatgttctttcctgcgttatcccctgattctgtggataaccgt
attaccgcc 209 | tttgagtgagctgataccgctcgccgcagccgaacgaccgagcgcagcgagtcagtgagcgaggaagcggaagagcgc
ccaatacgcaaaccgcctctccccgcgcgttggccgattcattaatgcagctggcacgacaggtttcccgactggaaagcgggca
gtgagcgcaacgcaattaatgtgagttagctcactcattaggcaccccaggctttacacttatgcttccggctcgtatgttgtgtgga
attgtgagcggataacaatttcacacaggaaacagctatgaccatgattacgccaagctatttaggtgacactatagaatactcaagc
ggccgcctactccaagaatatcaaagatacagtctcagaagaccaaagggctattgaacttttcaacaaagggtaatatcgggaa
acctcctcggattccattgcccagctatctgtcacttcatcaaaaggacagtagaaaaggaaggtggcacctacaaatgccatcatt
gcgataaaggaaaggctatcgttcaagatgcctctgccgacagtggtcccaaagatggacccccaccacggaggagcatcgtgg
aaaaagaagacgttccaaccacgtcttcaaagcaagtggattgatgtgatctactccaagaataccaaagatacagtctcagaagac
caaagggctattgaacttttcaacaaagggtaatatcgggaaacctcctcggattccattgcccagctatctgtcacttcatcaaaag
gacagtagaaaaggaaggtggcacctacaaatgccatcattgcgataaaggaaaggctatcgttcaagatgcctctgccgacagt
ggtcccaaagatggacccccaccacggaggagcatcgtggaaaaagaagacgttccaaccacgtcttcaaagcaagtggattga
tgtgatatctccactgacgtaaggggatgacgcacaatcccactatccttcgcaagacccttcctctatataaggaagttcatttcattt
ggagaggtattaaaattttcataagatttgaaattttgataaaccgcgatcataggttgccgcaccttaaaaccggaaacaaaagcaat
cgttacttgatttcaaagacttctcaatttctttctacatttcttgtatacggctttcaaagtgaaagaaaatcactctctgtgctggt
cacagacttcgtgaatcattttcttttctgctctcagttcatttgctgaacactctccatttgatataggacttcgtgtcagatttgaa
cttctcctatctcttttttctcggttcttcatttgatttcaaacttttctgaaatttaaatctcttttgacatttttgaactttgtgttgg
ctccatttgaaaa 209 | acaacatgaagttctatcctggtcaaaatatttccgaaatttgtttaccactttcagagtaatgagacagccaataggttagatgc
atattttgcttgtggctgtgaggaggatactgaagtcctcgctcgtttgaagcagtgtaatcctcgtctgcttcatctgtcatatgctg
ccttttgtttggaaatgggcagtcattcaatagaggaaatggaatatgatgatggggaattaatttttttcctatttccaaaacttttta
ctttccatcgtttccaattcttctaaaacaaccaaattgagagcatacattcgttcagcatttgcatatcattttcagcatttttgttga
atttgatcaatatacaaatgattctctcaatactgtggatacaagtgtatcagcccaagggatagcagacttggctctctctatggtta
gatggataccactcagattaaaaaagttgttaatttggtgtgggatctgttatagatgtcttttttcagagcattttaataagctcttg
atgcaatattgtccaatagttttttcaagctacagctgggtcaacaatataggacaatggtcaaagagtggatagaagaagctgcgaaag
agatttcatgatttgcaaggatgcaaagagttgctagcctggggaatgtgtattttggctagctcctgtgctctaggattggttgaaa
aatgccttatctctttgggcatgatttccgaatcttttgatttggttggtttgtttgttcgatctgccattgtgggagctttctgtgtt
tccataaaaactgcaagttcatcacgaatagtgaattggtcacttgtgctaccattgcagttcgtaccacaatgagttaatgtctca
ggcttttaagccttctgaagagattaagggggcagttccaagcccttcagttctagaagggttggcaacacagctcacttcgttttgtg
acacgtctttagttgctatgggaaaaacctgcacagcttttaatcaaatttgcactgctggcaaaaatgttaaggtgattgcaggtagg
ttgctggaagttgtttctaattttgtcagaaaattattaggattggatagtgcttttctcagagatgctgcactcatttttttcccaaga
tgtggatggattggtgcgtaacatcagttggtgccaggaacagtttttgttgaaagcttacatgtcgcaagatgatcttattgtcctgc
gctctttagttgttaaaggtgaaagaatgagggaacagatgcgtgaaggagaagtttaaggtatctccaagtgtttgcaaccttattgtc
aaaggctgtgaagaagcaaataaattgatgcgtgagagcgcacttcattgttcaaaaacaattagg 209 | aagattccttttgttattttgctcacggtgaatcccgagagggaaatctctgttggttgataagctaatcacagatttctgtga
tcatttggaaattggagaagatgctgtgtactcaaggaatccatcagatcctttctggagtggatatagaaggcagccaattgttacta
ttgatgattttgctgctgttgtttcggagccatctgctgaagctcaattaattccattagtttcaagtgctccttatccattaaacatg
gctggttagaggagaagggaatgcactttgattcccagatcatgatgtgttcttcaaatttcttagagccgtcctgaagctaaaat
tagagatgatatggcttttagaaatcggagacatgtgctgatcacagttgaactcaaacctggggttgaatatgatgagagtgatttta
ctaaaaatcagcgatatttgctgaaaactggttttcatgatcattatgttgtagacaaactttgagtcctatgctgatctgctggca
cattgttttaccaagtgggagacatgttaaggagcaagagtcaaatctgtctcaaattaagggcaagaaaagtgaaagtggtcattt
ttataattttcaacaacttatggatttggctgtttcttggaatcttaatgcagatatcatgaaaaacaggatcaaggctgagagaagtg
acatggtttatgttttttctgcagggaggaaggataaaattttgcattgttttctgaacaaggaaggcgagtgcacggttcgtcctgat
tcaatagatgatcctgaagcgcaagctttgctcaaagcttcagagacaatgctcatgaaagcctatgccttccttaaatacaataatgc TABLE II-continued

```
aacaaatttgattgtcagaacccatttggcagaactagtgaatgaagatttttatgatgagaaattcaatttcattggaacaattggaa
caccggctatcatcgccaaatagctgcacatttggaaaagatgccattgtggcaaaaagcaattttgtgtggaatgggacattgtttgt
ctcggaaaagcaaagagacctggtatactggtatgaaggagaaatttgtgcagatgatgaaaagcatctatgaaactgaagtcacagac
tggccagtgccattgaaaatcatttctggtactattctagccaccattttgggaacaactttttggaagttattttccttttttaaggga
tgctggcaatggaggtgttttgttggtaatgttgcttcagcatttaccacatcaagtgtgcttgaggcgcaaagccgaaaacccaaca
gatatgaggtctctcaatataggtatcgcaatgtgccaataaagcgcagagcgtgggttgagggtca 209|aatgtcttttgatcaatcagtggtggcaattatgtcaaaatgtaaagccagtatgagaatgggaaacactgatgctcaaattttg
atggttccagggcgtagattcattgcacatggtcattttttttaagaatctcacccaaaaagttagagtccaaattgttacttctgagaa
aagctattggcatgtgtatgatcctgataaatttcaaatgtttgataacagtgaaatcgggttgtatacaaatccaactttggaggaca
tcccacattctgcttgggaccttttctgctgggacagtgagaaaactttgccaaacaattttttctgctgaactgctttcctgtaaattg
gacaccgttacgggacaatattacccagaatgggctccaataaattgtcgagtacatcggcaaccaattcacataactgaagggaatta
tgtcaggaaacaagatgtgagcattgaatatgatgcctgcacaattcctaatgattgtggatctctggtggttgctaaggtcggaaatc
acaagcaaattgttggtttccatgttgctggaagtaaaggaagattgggctatgcttcattgataccatatgttgagcctgtggtacaa
gcccaaagtgctgaagtctattttgatttctttcctgtggaagttgatagtcaaggggagttgctcatattggtgaactcaaatctgg
agtttatgtaccattgcccacaaaaactaatcttgtggaaactcccaaagaatggcagttggatttgccttgtgataagattccaagtg
tgttaaccactactgatgagagattggttggcacggagcatgaaggatatgaccatttcttggtggtattcaaaaatatgcaactccc
atgatgcctctagatgaggagattctttccaaagttgcacaagacatggttgaagaatggtttgattgtgttgatgaggaggatacatt
tgaagaagtttctttgagtgctgcactcaatggtgttgaaggtttggattacatggaacgcattcctcttgccacttcagagggttttc
ctcatgttctgtccaggaaaaatggtgaaaaaggcaagagaagatttgtcactggagatggtgaagaaatgtcactaattcctggtacc
agtgttgaagaagcatacaataaattgactgttgaactagaaaagtgtgttccaacattggttggcatagaatgtcccaaagatgaaaa
acttccccgtcgcaaaattttgataaacccaagacgcgctgcttcaccatacttcctatggaatttaatctggtggtgcgtcaaaaat
tcttgaattttgtgcgattcattatgaagaaaagggacaaattgagttgccaagttggaatcaatccat 209|attctatggagtggactggtttggcaaatagactgttgagcaagggaaatgacattttgtgttgtgattatgctagttttgatgg
tctgataactaagcaagtcatgagcaagatggcagaaaatgataaacagtctttgtggtggagatgagaaactgatgcgtgagagaacg
catcttctgttagcttgttgctccaggatggcaatctgtaaaaaagatgtttggagagttgagtgtggtatcccttctggatttccact
cactgttatctgcaatagcattttcaatgagatgcttatcagatatagttatgaaaagttgctgcgtcaagctaaggctcctagtatgt
ttctccagtcttttaaaaatttatttctagtgtgtttatggagatgataatttaattagtgttcatgagtatgttaagccatattta
gtggttctaaattgaaaagatcctagctagtcataactaccattactgatggaattgacaaaactagtgcaactttacagtttagaa
agttgtcagagtgtgattttcttaaaagaaatttaagcaaatgtccaatgttttgtgggtagctcctgaagacaaagctagtttgtgg
tcacaattacactatgtttcatgtaacaatttggaaatgcaagaagcttatcttgttaacttggttaatgtgttgcgtgagttgtacct
gcacagtccagaagaagctcgtcaattgagaagaaaggctctctctcgcattgagtggttgcaaaaagctgatgtgcccaccatagcac
aaattgaagaatttcattcaatgcagaggattatgaatgctcctgactcaaatgataatattgatctttttgttgagcattgacttgttg
ggtcttcagggtgcaggcaaggcctccccaaataagattgtgtagatgataaattggtattggcaaatacacaagaattttttgatgga
aattttccaacagattcttggttaccaatatttgtcaattgtctttacccctgtgagtcaattgcccgcagaggctgtcactgttaatgt
tgtttgtgggagtgggcgtggtggtttgcctactactgcttggattagttctgcagttaacaatcgctcctcagatatcaataagaaaa
ttcggacagcacttgggaaaggtaagaaaatttgtcttttgactagagttgatccttttcctgtggccttgttagctgttcttttttggt
gttaagaacgaaattctgagttctaatgccacaaatccaatgttgacaaggcacttgagaactgcagagagtcttaaatatttggttgat
gagtgtcctatgcatttgttaactagtttgtaatattttgctcacttaaataaagcgcattacta 209|tgtgcaataagtgtgataaatataaaaaaaaaaaaaaaaaatcgatgggcctggatcctaggttcacaaagtgtcatcgat
agctcgaatttccccgatcgttcaaacatttggcaataaagtttcttaagattgaatcctgttgccggtcttgcgatgattatcatata
atttctgttgaattacgttaagcatgtaataattaacatgtaatgcatgacgttatttatgagatgggatttatgattagagtcccgca
attatacatttaatacgcgatagaaaacaaaatatagcgcgcaaactaggataaattatcgcgcgcggtgtcatctatgttactagatc
gggaattccaattcgcc 210
212
25|pBPMV-R1B
27|1
222|3
33|10169
236|471014100
26|8577
28|0
219|0
220|1
221|1
29|0
30|1
217|0
31|0
32|1
34|Complementary copy of IA-1D7H-01
255
224|Demo User
50
256
224|Demo User
50
1001|0
45
51|21
52|BPMV RNA1
53|0
55|3839
56|9824
57|0
281|1
```

TABLE II-continued

```
282|1
283|1
284|1
50
45
51|21
52|Mutation site
53|0
55|6204
56|6224
57|0
281|1
282|1
283|1
284|1
50
45
51|21
52|Nos Terminator
53|0
55|9885
56|10100
57|0
281|1
282|1
283|1
284|1
50
45
51|21
52|CaMV 35S promoter
53|0
55|3147
56|3838
57|0
281|1
282|1
283|1
284|1
50
205
37|0
38|0
39|0
40|0
24
```

209|tatagtgagtcgtattacaattcactggccgtcgttttacaacgtcgtgactgggaaaaccctggcgttacccaacttaatcgcc
ttgcagcacatccccctttcgccagctggcgtaatagcgaagaggcccgcaccgatcgcccttcccaacagttgcgcagcctgaat
ggcgaatggacgcgccctgtagcggcgcattaagcgcggcgggtgtggtggttacgcgcagcgtgaccgctacacttgccagc
gccctagcgcccgctcctttcgctttcttcccttcctttctcgccacgttcgccggctttccccgtcaagctctaaatcggggctccc
tttagggttccgatttagtgctttacggcacctcgaccccaaaaaacttgattagggtgatggttcacgtagtgggccatcgccctgat
agacggttttcgccctttgacgttggagtccacgttctttaatagtggactcttgttccaaactggaacaacactcaaccctatctcg
gtctattcttttgatttataagggattttgccgatttcggcctattggttaaaaaatgagctgatttaacaaaaatttaacgcgaattt
taacaaaatattaacgcttacaatttcctgatgcggtattttctccttacgcatctgtgcggtatttcacaccgcatatggtgcactct
cagtacaatctgctctgatgccgcatagttaagccagccccgacacccgccaacacccgctgacgcgccctgacgggcttgtctgctcc
cggcatccgcttacagacaagctgtgaccgtctccgggagctgcatgtgtcagaggttttcaccgtcatcaccgaaacgcgcgagacga
aagggcctcgtgatacgcctatttttataggttaatgtcatgataataatggtttcttagacgtcaggtggcacttttcggggaaatgt
gcgcggaacccctatttgtttatttttctaaatacattcaaatatgtatccgctcatgagacaataaccctgataaatgcttcaataat
attgaaaaaggaagagtatgagtattcaacatttccgtgtcgcccttattcccttttttgcggcattttgccttcctgtttttgctcac
ccagaaacgctggtgaaagtaaaagatgctgaagatcagttgggtgcacgagtgggttacatcgaactggatctcaacagcggtaagat
ccttgagagttttcgccccgaagaacgttttccaatgatgagcactttttaaagttctgctatgtggcgcggtattatcccgtattgacg
ccgggcaagagcaactcggtcgccgcatacactattctcagaatgacttggttgagtactcaccagtcacagaaaagc 209|atcttacggatggcatgacagtaagagaattatgcagtgctgccataaccatgagtgataacactgcggccaacttacttctga
caacgatcggaggaccgaaggagctaaccgcttttttgcacaacatgggggatcatgtaactcgccttgatcgttgggaaccggag
ctgaatgaagccataccaaacgacgagcgtgacaccacgatgcctgtagcaatggcaacaacgttgcgcaaactattaactggcg
aactacttactctagatcccggcaacaattaatagactggatggaggcggataaagttgcaggaccacttctgcgctcggcccttc
cggctggctggtttattgctgataaatctggagccggtgagcgtgggtctcgcggtatcattgcagcactggggccagatggtaag
ccctcccgtatcgtagttatctacacgacggggagtcaggcaactatggatgaacgaaatagacagatcgctgagataggtgcctc
actgattaagcattggtaactgtcagaccaagtttactcatatatactttagattgatttaaaacttcattttttaatttaaaaggatct
aggtgaagatcctttttgataatctcatgaccaaaatcccttaacgtgagttttcgttccactgagcgtcagaccccgtagaaaagatc
aaaggatcttcttgagatcctttttttctgcgcgtaatctgctgcttgcaaacaaaaaaaccaccgctaccagcggtggtttgtttgcc
ggatcaagagctaccaactctttttccgaaggtaactggcttcagcagagcgcagataccaaatactgttcttctagtgtagccgtagt
taggccaccacttcaagaactctgtagcaccgcctacatacctcgctctgctaatcctgttaccagtggctgctgccagtggcgataag
tcgtgtcttaccgggttggactcaagacgatagttaccggataaggcgcagcggtcgggctgaacggggggttcgtgcacacagcccag TABLE II-continued cttggagcgaacgacctacaccgaactgagatacctacagcgtgagctatgagaaagcgccacgcttcccgaagggagaaaggc
ggacaggtatccggtaagcggcagggtcggaacaggagagcgcacgagggagcttccaggggaaacgcctggtatctttata
gtcctgtcgggtttcgccacctctgacttgagcgtcgattttttgtgatgctcgtcaggggggcggagcctatggaaaaacgccagca
acgcggccttttttacggttcctggccttttgctggccttttgctcacatgttctttcctgcgttatccctgattctgtggataaccgt
attaccgcc 209|tttgagtgagctgataccgctcgccgcagccgaacgaccgagcgcagcgagtcagtgagcgaggaagcggaagagcgc
ccaatacgcaaaccgcctctccccgcgcgttggccgattcattaatgcagctggcacgacaggtttcccgactggaaagcgggca
gtgagcgcaacgcaattaatgtgagttagctcactcattaggcaccccaggctttacactttatgcttccggctcgtatgttgtgtgga
attgtgagcggataacaatttcacacaggaaacagctatgaccatgattacgccaagctatttaggtgacactatagaatactcaagc
ggccgcctactccaagaatatcaaagatacagtctcagaagaccaaagggctattgacttttcaacaaagggtaatatcgggaa
acctcctcggattccattgcccagctatctgtcacttcatcaaaaggacagtagaaaaggaaggtggcacctacaaatgccatcatt
gcgataaaggaaaggctatcgttcaagatgcctctgccgacagtggtcccaaagatggaccccccacccacgaggagcatcgtgg
aaaaagaagacgttccaaccacgtcttcaaagcaagtggattgatgtgatctactccaagaatatcaaagatacagtctcagaagac
caaagggctattgacttttcaacaaagggtaatatcgggaaacctcctcggattccattgcccagctatctgtcacttcatcaaaag
gacagtagaaaaggaaggtggcacctacaaatgccatcattgcgataaaggaaaggctatcgttcaagatgcctctgccgacagt
ggtcccaaagatggaccccccacccacgaggagcatcgtggaaaaacaagacgttccaaccacgtcttcaaagcaagtggattga
tgtgatatctccactgacgtaagggatgacgcacaatcccactatccttcgcaagacccttcctctatataaggaagttcatttcattt
ggagaggtattaaaattttcataagatttgaaattttgataaaccgcgatcataggttgccgcaccttaaaaccggaaacaaaagcaat
cgttacttgatttcaaagacttctcaatttctttctacatttcttgtatacggctttcaaagtgaaagaaaatcactctctgtgctggt
cacagacttcgtgaatcattactttctgctctcagttcatttgctgaacactctcctatttgatataggacttcgtgtcagatttgaac
ttctcctatctcttttttctcggttcttcatttgatttcaaacttttctgaaattttaaatctcttttgacatttttgaactttgtgttggc
tccatttgaaaa 209|acaacatgaagttctatcctggtcaaaatatttccgaaattgtttaccactttcagagtaatgagacagccaataggttagatgc
atattttgcttgtggctgtgaggaggatactgaagtcctcgctcgtttgaagcagtgtaatcctcgtctgcttcatctgtcatatgctg
ccttttgtttggaaatgggcagtcattcaatagaggaaatggaatatgatgatggggaattaatttttttcctatttccaaaacttttta
ctttccatcgtttccaattcttctaaaacaaccaaattgagagcatacattcgttcagcatttgcatatcattttcagcatttttgttga
atttgatcaatatacaaatgattctctcaatactgtggatacaagtgtatcagcccaaggggatagcagacttggctctctctatggtta
gatggatacccactcagattaaaaaagttgttaattttggtgtgggatctgttatagagtcttttttcagagcatttttaataagctcttg
atgcaatattgtccaatagttttttcaagctttcagctgggtcaacaatatttggacaatggtcaaagagtggatagaagaagctgcgaa
agagatttcatggttttttgcaaggatgcaaagagttgctagcctgggggaatgtgtatttttggctagctcctgtgctctaggattggttg
aaaaaatgccttatctctttgggcatgatttccgaatcttttgatttggttggttttgtttgttcgatctgccattgtgggagctttctgt
gtttccataaaaactggcaagttcatcacgaatagtgaattggtcactgtgctaccattgcagttttctacaatagcaactgtaatgtc
tcaggcttttaagccttctgaagagattaaggggcagttccaagcccttctcagttctagaagggttggcaacacagctcacttcgtttt
gtgacacgtctttagttgctatgggaaaaacctgcacagcttttaatcaaatttgcactgctggcaaaaatgttaaggtgattgcaggt
aggttgctggaagttgtttctaatttttgtcagaaaattattaggattggatagtgctttttctcagagatgctgcactcatttttttccca
agatgtggatggatggttgcgtaacatcagttggtgccaggaacagttttttgttgaaagcttacatgtcgcaagatgatcttattgtcc
tgcgctctttagttgttaaaggtgaaagaatgagggaacagatgcttgaaggagaagttaaggtatctccaagtgtttgcaaccttatt
gtcaaaggctgtgaagaagcaaataaattgatgcgtgagagcgcacttcattgttcaaaaacaattagg 209|aagattccttttgttattatgctcacggtgaatcccgagagggaaatctctgttggttgataagctaatcacagatttctgtgat
catttggaaattggagaagatgctgtgtactcaaggaatccatcagatcctttctggagtggatatagaaggcagccaattgttactat
tgatgattttgctgctgttgtttcggagccatctgctgaagctcaattaattccattagtttcaagtgctccttatccattaaacatgg
ctggtttagaggagaagggaatgcactttgattcccagatcatgatgtgttcttcaaatttcttagagccgtctcctgaagctaaaatt
agagatgatatggcttttagaaatcggagacatgtgctgtcacagttgaactcaaacctgggggttgaatatgatgagagtgattttac
taaaaaatcagcgatatttgctgaaaacttggatcatgatcattatgagtagaccaaacttttgagtcctatgctgatctgctggacat
tgttttaccaagtggggagagacatgttaaggagcaagagtcaaatctgtctcaaattaagggcaagaaaaatgaaagtggtcatttaa
taatttttcaacaacttatggatttggctgtttcttggaatcttaatgcagatatcatgaaaaacaggatcaaggctgagagaagtgaca
tggtttatgtttttttctgcagggaggaaggataaaattttgcattgttttctgaacaagaaggcgagtgcacggttcgtcctgattca
atagatgatcctgaagcgcaagcttttgctcaaagcttcagagacaatgctcatgaaagcctatgccttccttaaatacaataatgcaac
aaatttgattgtcagaacccatttggcagaactagtgaatgaagattttatgatgagaaattcaatttcattggaacaattggaacac
cggcttttcatcgccaaatagctgcacatttggaaaagatgccattgtggcaaaaagcaattttgtgtggaatgggacattgtttgtct
cggaaaagcaaagagacctggtatactggtatgaaggagaaatttgtgcagatgatgaaaagcatctatgaaactgaagtcacagactg
gccagtgccattgaaaatcatttctggtactattctagccaccattttgggaacaacttttttggaagttatttttccttttttaagggatg
ctggcaatggaggtgttttttgttggtaatgttgcttcagcatttaccacatcaagtgtgcttgaggcgcaaagccgaaaacccaacaga
tatgaggtctctcaatataggtatcgcaatgtgccaataaagcgcagagcgtgggttgagggtca 209|aatgtcttttgatcaatcagtggtggcaattatgtcaaaatgtaaagccagtatgagaatgggaaacactgatgctcaaattttg
atggttccagggcgtagattcattgcacatggtcattttttaagaatctcacccaaaaagttagagtccaaattgttacttctgagaa
aagctattggcatgtgtatgatcctgataaatttcaaatgtttgataacagtgaaatcgggttgtatacaaatccaactttggaggaca
tcccacattctgcttgggacctttctctgctgggacagtgagaaaactttgccaaacaattttttctgctgaactgctttcctgtaaattg
gacaccgttacgggacaatattacccagaatgggctccaataaattgtcagatacatcggcaaccaattcacataactgaaggggaatta
tgtcaggaaacaagatgtgagcattgaatatgatgcctgcacaattcctaatgattgtggatctctggtggttgctgctaaggtcggaaatc
acaagcaaattgttggtttccatgttgctggaagtaaaggaagattgggctatgcttcattgataccatatgttgagcctgtggtacaa
gcccaaagtgctgaagtctattttgatttcttcctgtggaagttgatagtcaagagggagttgctcatattggtgaactcaaatctgg
agtttatgtaccattgcccacaaaaaactaatcttgtggaaactcccaaagaatgcgattttgcctttgtaagaattccaagtg
tgttaaccactactgatgagagattggttggcacggagcatgaaggatatgacccatttcttggtgtattcaaaaatatgcaactccc
atgatgcctctagatgaggagattcttccaaagttcacaagacatggttgaagatgttttgattgtgttgatgaggaggatacatt
tgaagaagtttcttgagtgctgcactcaatggtgttgaaggtttggattacatggaacgcattcctcttgccacttcagagggttttc
ctcatgactgtcaggaaaaatggtgaaaaaggcaagagaagatttgtcactggagatggtgaagaaatgtcactaattcctggtacca
gtgttgaagaagcatacaataaattgactgttgaactagaaaagtgtgttccaacattggttggcataaataatgtcccaaagatgaaaa
cttccccgtcgcaaaatttttgataaacccaagacgcgctgcttcaccatacttcctatggaatttaatctggtggtgcgtcaaaaatt
cttgaatttttgtgcgattcattatgaagaaaggacaaattgagttgccaagttggaatcaatccat 209|attctatggagtggactggtttggcaaatagactgttgagcaagggaaatgacattttgtgttgtgattatgctagtttttgatgg
tctgataactaagcaagtcatgagcaagatggcagaaatgataaacagtctttgtggtggagatgagaaactgatgcgtgagagaacg
catcttctgttagcttgttgctccaggatggcaatctgtaaaaagatgtttggagagttgagtgtggtatcccttctggatttccact
cactgttatctgcaatagcattttcaatgagatgcttatcagatatagttatgaaaagttgctgcgtcaagctaaggctcctagtatgt
ttctccagtcttttaaaaatttttatttcttgtgtgtttatggagatgataatttaattagtgttcatgagtatgttaagccatatttt

TABLE II-continued

```
agtggttctaaattgaaaagtttcctagctagtcataacatcaccattactgatggaattgacaaaactagtgcaactttacagtttag
aaagttgtcagagtgtgattacttaaaagaaattttaagcaaatgtccaatgttttgtgggtagctcctgaagacaaagctagtttgtg
gtcacaattacactatgtttcatgtaacaatttggaaatgcaagaagcttatcttgttaacttggttaatgtgttgcgtgagttgtacc
tgcacagtccagaagaagctcgtcaattgagaagaaaggctctctctcgcattgagtggttgcaaaaagctgatgtgcccaccatagca
caaattgaagaatttcattcaatgcagaggattatgaatgctcctgactcaaatgataatattgatcttttgttgagcattgacttgtt
gggtcttcagggtgcaggcaaggccttcccaaataagattgtgtttgatgataaattggtattggcaaatacacaagaattttttgatg
gaaattttccaacagattcttggttaccaatatttgtcaattgtctttaccctgtgagtcaattgcccgcagaggctgtcactgttaat
gttgtttgtgggagtgggcgtggtggtttgcctactactgcttggattagttctgcagttaacaatcgctcctcagatatcaataagaa
aattcggacagcacttgggaaaggtaagaaaattgtcttttttgactagagttgatccttttcctgtggccttgttagctgttctttttg
gtgttaagaacgaaattctgagttctaatgccacaaatccaatgttgacaaggcttcttgagaactgcaagagtcttaaatatttggtt
gatgagtgtcctttttgcatttgttaactagtttgtaatattttgctcacttaaataaagcgcattacta 209|tgtgcaataagtgtgtttaaatataaaaaaaaaaaaaaaaaatcgatgggcctggatcctaggttcacaaagtgtcatcgat
agctcgaatttccccgatcgttcaaacatttggcaataaagtttcttaagattgaatcctgttgccggtcttgcgatgattatcatata
atttctgttgaattacgttaagcatgtaataattaacatgtaatgcatgacgttatttatgagatgggttttatgattagagtcccgc
aattatacatttaatacgcgatagaaaacaaaatatagcgcgcaaactaggataaattatcgcgcgcggtgtcatctatgttactagat
cgggaattccaattcgcc 210
212
25|pBPMV-R2
27|1
222|3
33|8035
236|470921559
26|8579
28|0
219|0
220|1
221|1
29|0
30|0
217|0
31|0
32|1
255
224|Demo User
50
256
224|Demo User
50
1001|0
45
51|21
52|Nos Terminator
53|0
55|7536
56|7751
57|0
281|1
282|1
283|1
284|1
50
45
51|21
52|CaMV 35S promoter
53|0
55|3147
56|3838
57|0
281|1
282|1
283|1
284|1
50
45
51|21
52|BPMV RNA2
53|0
55|3839
56|7511
57|0
281|1
282|1
283|1
284|1
50
205
370
```

TABLE II-continued

```
38|0
39|0
40|0
24

209|tatagtgagtcgtattacaattcactggccgtcgtttttacaacgtcgtgactgggaaaaccctggcgttacccaacttaatcgcc
ttgcagcacatccccctttcgccagctggcgtaatagcgaagaggcccgcaccgatcgcccttcccaacagttgcgcagcctgaat
ggcgaatggacgcgccctgtagcggcgcattaagcgcggcgggtgtggtggttacgcgcagcgtgaccgctacacttgccagc
gccctagcgcccgctcctttcgctttcttcccttcctttctcgccacgttcgccggctttccccgtcaagctctaaatcggggctccc
tttaggggttccgatttagtgctttacggcacctcgaccccaaaaaacttgattagggtgatggttcacgtagtgggccatcgccctgat
agacggttttttcgcccctttgacgttggagtccacgttctttaatagtggactcttgttccaaactggaacaacactcaaccctatctcg
gtctattcttttgatttataagggattttgccgatttcggcctattggttaaaaaatgagctgatttaacaaaaatttaacgcgaattt
taacaaaatattaacgcttacaatttcctgatgcggtattttctccttacgcatctgtgcggtatttcacaccgcatatggtgcactct
cagtacaatctgctctgatgccgcatagttaagccagccccgacacccgccaacacccgctgacgcgccctgacgggcttgtctgctcc
cggcatccgcttacagacaagctgtgaccgtctccgggagctgcatgtgtcagaggttttcaccgtcatccgaaacgcgcgagacga
aagggcctcgtgatacgcctatttttataggttaatgtcatgataataatggtttcttagacgtcaggtggcacttttcggggaaatgt
gcgcggaacccctatttgtttatttttctaaatacattcaaatatgtatccgctcatgatgagacaataaaccctgataaatgcttcaataat
attgaaaaaggaagagtatgagtattcaacatttccgtgtcgcccttattccctttttgcggcattttgccttcctgttttttgctcac
ccagaaacgctggtgaaagtaaaagatgctgaagatcagttgggtgcacgagtgggttacatcgaactggatctcaacagcggtaagat
ccttgagagttttcgccccgaagaacgttttccaatgatgagcacttttaaagttctgctatgtggcgcggtattatcccgtattgacg
ccgggcaagagcaactcggtcgccgcatacactattctcagaatgacttggttgagtactcaccagtcacagaaaagc 209|atcttacggatggcatgacagtaagagaattatgcagtgctgccataaccatgagtgataacactgcggccaacttacttctga
caacgatcggaggaccgaaggagctaaccgcttttttgcacaacatgggggatcatgtaactcgccttgatcgttgggaaccggag
ctgaatgaagccataccaaacgacgagcgtgacaccacgatgcctgtagcaatggcaacaacgttgcgcaaactattaactggcg
aactacttactctagcttcccggcaacaattaatagactggatggaggcggataaagttgcaggaccacttctgcgctcggcccttc
cggctggctggtttattgctgataaatctggagccggtgagcgtgggtctcgcggtatcattgcagcactggggccagatggtaag
ccctcccgtatcgtagttatctacacgacggggagtcaggcaactatggatgaacgaaatagacagatcgctgagataggtgcctc
actgattaagcattggtaactgtcagaccaagtttactcatatatactttagattgatttaaaacttcattttttaatttaaaaggatct
aggtgaagatcctttttgataatctcatgaccaaaatcccttaacgtgagttttcgttccactgagcgtcagaccccgtagaaaagatc
aaaggatcttcttgagatcctttttttctgcgcgtaatctgctgcttgcaaacaaaaaaaccaccgctaccagcggtggtttgtttgcc
ggatcaagagctaccaactctttttccgaaggtaactggcttcagcagagcgcagataccaaatactgttcttctagtgtagccgtagt
taggccaccacttcaagaactctgtagcaccgcctacatacctcgctctgctaatcctgttaccagtggctgctgccagtggcgataag
tcgtgtcttaccgggttggactcaagacgatagttaccggataaggcgcagcggtcgggctgaacggggggttcgtgcacacagcccag
cttggagcgaacgacctacaccgaactgagatacctacagcgtgagctatgagaaagcgccacgcttcccgaagggagaaaggc
ggacaggtatccggtaagcggcagggtcggaacaggagagcgcacgagggagcttccagggggaaacgcctggtatctttata
gtcctgtcgggtttcgccacctctgacttgagcgtcgatttttgtgatgctcgtcaggggggcggagcctatggaaaaacgccagca
acgcggcctttttacggttcctggccttttgctggccttttgctcacatgttctttcctgcgttatcccctgattctgtggataaccgt
attaccgcc 209|tttgagtgagctgataccgctcgccgcagccgaacgaccgagcgcagcgagtcagtgagcgaggaagcggaagagcgc
ccaatacgcaaaccgcctctccccgcgcgttggccgattcattaatgcagctggcacgacaggtttcccgactggaaagcgggca
gtgagcgcaacgcaattaatgtgagttagctcactcattaggcaccccaggctttacactttatgcttccggctcgtatgttgtgtgga
attgtgagcggataacaatttcacacaggaaacagctatgaccatgattacgccaagctatttaggtgacactatagaatactcaagc
ggccgcctactccaagaatatcaaagatacagtctcagaagaccaaagggctattgagacttttcaacaaagggtaatatcgggaa
acctcctcggattccattgcccagctatctgtcacttcatcaaaaggacagtagaaaggaaggtggcacctacaaatggccatcatt
gcgataaaggaaaggctatcgttcaagatgcctctgccgacagtggtcccaaagatggacccccacccacggaggagcatcgtgg
aaaaagaagacgttccaaccacgtcttcaaagcaagtggattgatgtgatctactccaagaatatcaaagatacagtctcagaagac
caaagggctattgagacttttcaacaaagggtaatatcgggaaacctcctcggattccattgcccagctatctgtcacttcatcaaaag
gacagtagaaaggaaggtggcacctacaaatgccatcattgcgttcaagatgcctctgccgacagt
ggtcccaaagatggacccccacccacgaggagcatcgtggaaaaagaagacgttccaaccacgtcttcaaagcaagtggattga
tgtgatatctccactgacgtaagggatgacgcacaatcccactatccttcgcaagacccttcctctatataaggaagttcatttcattt
ggagaggtattaaaattttcataagatttgaaattttgataaaccgcgatcacaggttgccgcaccttaaaaccggaaacaaaagcaat
cgttacttgatttcaagaatcttccaatttcttcctacttcttggtgtacgatttcttaagagaaagaaaatcactctctgtgctggcc
acagacttcgtgaatcattttcttttccactcttagtttatttgctgaacactctccatttgatataggacttcgtgtcagatttaaa
cttttttctgttttctttctcagttctctgcttaatttcaagtttaagctggtgaaatcttggattagtgctcccactctcctatctggta
taggacttcgtgg 209|gtagacttactatttctgtatttctttcactctcttcttctcactgatccgcattgccgttcaaagtggtcttatttgaaaaacac
ttgggcgttggtgcaaatgtttgcttcgttaattttctctggggacaacaggctcactgagaaaacaatttttacttgcagagatttgg
acatcttggttgttttattatacaatagcaactcaatttagaaaatttctaccgcattacattaggtggcatctgtataccttgttgatc
tacattctcccatcttttctcactgctgaaattaaatataagcggaatctgagtaatattcatatttctggcttattttacgacggcag
atataaattctggactaaacacgagaaaatcttgctttgacagaagaggaaaaatgatggaagttgattagaaacaaaggcattcctgctg
atgttcttgcaaagcgagctcatgaatttgaaaaacatgttgctcatgaaagcctcaaggatcaaattcctgctgttgacaagttgtat
tctactaaggttaataagtttgcaaaaattatgaacctttagacaaagtgttgttggtgatcttaaacttcttactgatgggaagttgta
tgagggtaagcatattcctgtatctaatattagtgcagggagaatcatgtagttcaaatacccctaatggcacaggaggaaattctgt
cttctagtgcaagtgatttcagaactgcaatggtgagtaaaaatagcaagcctcaagctccaatgcatgtagagcctataggaatt
atcattgatagtttcgcaagtcctgactgcaacatagttggtgcaatgcttttggttgatacttatcataccaatcctgaaaatgcagt
tcgtagtattttgttgcgcctttcagaggcggaaggcccattcgggtggttacatttccgaataccattgtgcagattgaaccagaca
tgaattcaaggtttcagcttttgagtaccactaccaatggtgattttgttcaggaaaagatctcgcaatggttaaagttaatgtagca
tgtgctgctgttggcttgacatcaagttacactccaactccactgttggaatctgttttcagaaaagacagggttaattgtgaaata
ttttgaaggatgtcttacgttgctcataacgttaatcagcccaagagaaatttgttggagggaaatttttcctttgatattaaat
ctcgctctagattgaaaaagtttcttctactaaagcacaatttgttagtggaaaaaccttcaaatatgatataattggtgctggttca
cattcttcagaagatttcctaaaaaagaagatcaagaaaaacccaaaaagattgatgccagattg 209|agacaaagaataagatcccccaatacaatgaggttcaggctcagatggaaacaaatttgataaattgtctcttgatgatgttgaaa
ctcctaaaggttccatgttggatcttaaaatttctcaatctaaaattgcacttcccaaaaacacagttggaggaaccattctgcgtagt
gatctattggcaaattttttgacagagggcaattttagagcaagtgttgatttgcagcgcactcatcgtattaaaggaatgattaaaat
ggtggccacagttggtattcctgagaatacaggtatatcattggcctgtgctatgaatagttcttttaggggggcgtgccagttctgata
tttacaccatctgctctcaagactgtgaattatgaatcctgcttgcacaaaagcaatgactatgtcatttaatccaaacccgtgttct
```

TABLE II-continued

```
gatgcatggagtttggaattttttgaagcgtaccggatttcattgtgatatcatttgtgtcactggatggactgccaccccaatgcagga
tgttcaggttacaattgattggtttatttcctctcaggaatgtgttcccaggacctattgtgttttaaatccacaaaatccttttgtgt
taaataggtggatgggcaaactgactttcccccagggcacttcccgaagtgttaaaagaatgcctcttttctataggggaggagctggt
gcaaagaatgctattctcatgaatatgccaaatgctgttattcaatgtggagatattagaggagatctcgtctttgaagtttctaagat
gacttctccctacattaaatgtacagtctctttcttcatagcatttggaaatttggctgatgacaccattaattttgaggcttttcccc
acaagctggtgcagtttggagaaattcaggaaaaagttgtattgaaattttcacaagaggaatttcttacagcttggtcaactcaggtg
cgtcctgcaacaactctgttggctgatgggtgtccatatttgtatgctatggtgcatgatagttcagtgtctacaataccaggtgattt
tgtcattggtgttaagttggcaaccataaacaatatgtgtgcatatgggctcaatcctggtatttcaggttctcgtcttttgggcacca
ttcctcagtccatttcacagcaaactgtttggaatcagatggcaacagtgagaacaccattgaattttgatcctagcaagcagagcttt
tgtcaatttctcattgaccttctcggtggaggaattttagtggacaaaactggagattggatcacacttatacaaaattctccaattag
taacttgttgagagttgctgcttggaagaaaggctgtttaatggttaagattgtgatgtctgggaa 209|tgcagcagtcaaaaggagtgattgggcctcattggtacaagtgttttttaacaaacagcaacagtacagagcattttgatgcatg
taagtggacaaaatcggaaccacattcctgggaattgatcttcccaatagaggtgtgtggtcctaacaatggttttgaaatgtggagtt
ctgagtgggcaaatcaaacttcatggcatttgagtttccttattgacaatcccaaacagtctacagttttttgacattctcctgggaatt
tcccaagattttgaaattgctggtaatactcttatgccagcttttttctgttccacaggctactgccagatcttctgaaaatgcggaatc
ctctgcatgatctggaatttgtgttttctttcgtttgttcgcttgtttaattcaataaaggaaattaggcatgaccctctcgttgagta
tgctctgtctatttgaaaatttccacacctcttttaattgtcgtaatgatgtgtgaagtgtgtgttatttttaaaaaaaaaaaaaaaaaa
atcgatagctcgaatttccccgatcgttcaaacatttggcaataaagtttcttaagattgaatcctgttgccggtcttgcgatgattat
catataatttctgagaattacgttaagcatgtaataattaacatgtaatgcatgacgttatttatgagatgggttttttatgattagagt
cccgcaattatacatttaatacgcgatagaaaacaaaatatagcgcgcaaactaggataaattatcgcgcgggtgtcatcatgttac
tagatcgggaattccaattcgccctatagtgagtcgtattacaattcactggccgtcgttttacaacgtcgtgactgggaaaaccctgg
cgttacccaacttaatcgccttgcagcacatccccctttcgccagctggcgtaatagcgaagaggcccgcaccgatcgcccttcccaac
agttgcgcagcctgaatggcgaatggacgcgccctgtagcggcgcattaagcgcggcggg 210
212
25|pBPMV-V1
27
222|3
33|8041
236|470921559
26|8560
28|0
219|0
220|1
221|1
29|0
30|0
217|0
31|0
32|1
255
224|Demo User
50
256
224|Demo User
50
1001|0
45
51|21
52|Nos Terminator
53|0
55|7542
56|7757
57|0
281|1
282|1
283|1
284|1
50
45
51|21
52|CaMV 35S promoter
53|0
55|3147
56|3838
57|0
281|1
282|1
283|1
284|1
50
45
51|21
52|BamHI for foreign gene insertion
53|0
55|7362
56|7367
57|0
```

TABLE II-continued

281|1
282|1
283|1
284|1
50
205
37|0
38|0
39|0
40|0
24

209|tatagtgagtcgtattacaattcactggccgtcgttttacaacgtcgtgactgggaaaaccctggcgttacccaacttaatcgcc
ttgcagcacatcccctttcgccagctggcgtaatagcgaagaggcccgcaccgatcgcccttcccaacagttgcgcagcctgaat
ggcgaatggacgcgccctgtagcggcgcattaagcgcggcgggtgtggtggttacgcgcagcgtgaccgctacacttgccagc
gccctagcgcccgctccttcgctttcttcccttcctttctcgccacgttcgccggctttccccgtcaagctctaaatcggggctccc
tttagggttccgatttagtgctttacggcacctcgaccccaaaaaacttgattagggtgatggttcacgtagtgggccatcgccctgat
agacggttttcgccctttgacgttggagtccacgttctttaatagtggactcttgttccaaactggaacaacactcaaccctatctcg
gtctattcttttgatttataagggattttgccgatttcggcctattggttaaaaaatgagctgatttaacaaaaatttaacgcgaattt
taacaaaatattaacgcttacaatttcctgatgcggtattttctccttacgcatctgtgcggtatttcacaccgcatatggtgcactct
cagtacaatctgctctgatgccgcatagttaagccagccccgacacccgccaacacccgctgacgcgccctgacgggcttgtctgctcc
cggcatccgcttacagacaagctgtgaccgtctccgggagctgcatgtgtcagaggttttcaccgtcatcaccgaaacgcgcgagacga
aagggcctcgtgatacgcctatattataggttaatgtcatgataataatggatcttagacgtcaggtggcactatcggggaaatgtgcg
cggaaccccctatttgttattttctaaatacattcaaatatgtatccgctcatgagacaataaccctgataaatgcttcaataatatt
gaaaaaggaagagtatgagtattcaacatttccgtgtcgcccttattccatttttcgcggcattttgccttcctgttttttgctcaccca
gaaacgctggtgaaagtaaaagatgctgaagatcagttgggtgcacgagtgggttacatcgaactggatctcaacagcggtaagatcct
tgagagttttcgccccgaagaacgttttccaatgatgagcacttttaaagttctgctatgtggcgcggtattatcccgtattgacgccg
ggcaagagcaactcggtcgccgcatacactattctcagaatgacttggttgagtactcaccagtcacagaaaagc 209|atcttacggatggcatgacagtaagagaattatgcagtgctgccataaccatgagtgataacactgcggccaacttacttctga
caacgatcggaggaccgaaggagctaaccgcttttttgcacaacatgggggatcatgtaactcgccttgatcgttgggaaccggag
ctgaatgaagccataccaaacgacgagcgtgacaccacgatgcctgtagcaatggcaacaacgttgcgcaaactattaactggcg
aactacttactctagcttcccggcaacaattaatagactggatggaggcggataaagttgcaggaccacttctgcgctcggcccttc
cggctggctggtttattgctgataaatctggagccggtgagcgtgggtctcgcggtatcattgcagcactggggccagatggtaag
ccctcccgtatcgtagttatctacacgacggggagtcaggcaactatggatgaacgaaatagacagatcgctgagataggtgcctc
actgattaagcattggtaactgtcagaccaagtttactcatatatactttagattgatttaaaacttcattttttaatttaaaaggatct
aggtgaagatcctttttgataatctcatgaccaaaatcccttaacgtgagttttcgttccactgagcgtcagaccccgtagaaaagatc
aaaggatcttcttgagatcctttttttctgcgcgtaatctgctgcttgcaaacaaaaaaaccaccgctaccagcggtggtttgtttgcc
ggatcaagagctaccaactctttttccgaaggtaactggcttcagcagagcgcagataccaaatactgttcttctagtgtagccgtagt
taggccaccacttcaagaactctgtagcaccgcctacatacctcgctctgctaatcctgttaccagtggctgctgccagtggcgataag
tcgtgtcttaccgggttggactcaagacgatagttaccggataaggcgcagcggtcgggctgaacggggggttcgtgcacacagcccag
cttggagcgaacgacctacaccgaactgagatacctacagcgtgagctatgagaaagcgccacgcttcccgaagggagaaaggc
ggacaggtatccggtaagcggcagggtcggaacaggagagcgcacgagggagcttccaggggaaacgcctggtatctttata
gtcctgtcgggtttcgccacctctgacttgagcgtcgatttttgtgatgctcgtcaggggggcggagcctatggaaaaacgccagca
acgcggcctttttacggttcctggccttttgctggccttttgctcacatgttctttcctgcgttatcccctgattctgtggataaccgt
attaccgcc 209|tttgagtgagctgataccgctcgccgcagccgaacgaccgagcgcagcgagtcagtgagcgaggaagcggaagagcgc
ccaatacgcaaaccgcctctccccgcgcgttggccgattcattaatgcagctggcacgacaggtttcccgactggaaagcgggca
gtgagcgcaacgcaattaatgtgagttagctcactcattaggcaccccaggctttacactttatgcttccggctcgtatgttgtggga
attgtgagcggataacaatttcacacaggaaacagctatgaccatgattacgccaagctatttaggtgacactatagaatactcaagc
ggccgcctactccaagaatatcaaagatacagtctcagaagaccaaaggggctattgagacttttcaacaaagggtaatatcgggaa
acctcctcggattccattgcccagctatctgtcacttcatcaaaaggacagtagaaaaggaaggtggcacctacaaatgccatcatt
gcgataaaggaaaggctatcgttcaagatgcctctgccgacagtggtcccaaagatggacccccacccacgaggagcatcgtgg
aaaaagaagacgttccaaccacgtcttcaaagcaagtggattgatgctgatctccagaatatcaaagatacagtctcagaagac
caaagggctattgagacttttcaacaaagggtaatatcgggaaacctcctcggattccattgcccagctatctgtcacttcatcaaaag
gacagtagaaaaggaaggtggcacctacaaatgccatcattgcgataaaggaaaggctatcgttcaagatgcctctgccgacagt
ggtcccaaagatggacccccacccacgaggagcatcgtggaaaaagaagacgttccaaccacgtcttcaaagcaagtggattga
tgtgatatctccactgacgtaagggatgacgcacaatcccactatccttcgcaagacccttcctctatataaggaagttcatttcattt
ggagaggtattaaaattacataagatttgaaattttgataaaccgcgatcacaggttgccgcaccttaaaaccggaaacaaaagcaat
cgttacttgatttcaagaatcttccaatttcttcctacttcttggtgtacgatttcttaagagaaagaaaatcactcctctgtgctggcc
acagacttcgtgaatcatttcttttccactcttagtttatttgctgaacactctcctatttgatataggacttcgtgtcagatttaaa
cttttttctgtttctttctcagttctctgcttaatttcaagtttaagctggtgaaatcttggattagtgctcccactctcctatctggta
taggacttcgtgg 209|gtagacttttctatttctgtcttactttcactctcttcttctcactgatccgcattgccgttcaaagtggtcttatttgaaaaac
acttgggcgttggtgcaaatgtttgcttcgttaatttttctctggggacaacaggctcactgagaaaacaatttttacttgcagagattt
ggacatcttggttgtttattatacaatagcaactcaatttagaaaatttctaccgcattacattaggtggcatctgtataccttgttga
tctacattctcccatctttctcactgctgaaattaaatataagcggaatctgagtaatattcatatttctggcttattttacgacggc
agatataaattctggactaaaacacgagaaaaatcttgctttgacagaagaggaaaagatggaagtgattagaaacaaaggcattcctgc
tgatgttcttgcaaagcgagctcatgaatttgaaatttgaaaaacatgttgctcatgaaagcctcaaggatcaaattcctgctgttgcaagttgt
attctactaaggttaataagtttgtcaaaaattatgaacctttagacaaagtgttgttggtgatcttaaacttcttactgatgggaagttg
tatgagggtaagtattcctgtatctaatattagtgcagggagaatcatgtagttcaaatacccctaatggcacaggaggaaattct
gtcttctagtgcaagtgatttcagaactgcaatggtgagtaaaaatagcaagcctcaagctactgcaatgcatgtaggagctatagaaa
ttatcattgatagtttcgcaagtcctgactgcaacatagttggtgcaatgcttttggttgatacttatcataccaatcctgaaaatgca
gttcgtagtattttttgttgcgcctttcagaggcggaaggcccattcgggtggttacatttccgaataccattgtgcagattgaaccaga

TABLE II-continued

```
catgaattcaaggtttcagcttttgagtaccactaccaatggtgattttgttcaaggaaaagatctcgcaatggttaaagttaatgtag
catgtgctgctgttggcttgacatcaagttacactccaactccactgttggaatctggtttgcaaaaagacagagggttaattgtggaa
tattttggaaggatgtcttacgttgctcataacgttaatcagccccaagagaaagatttgttggagggaaattttttcctttgatattaa
atctcgctctagattggaaaaagtttcttctactaaagcacaatttgttagtggaaaaaccttcaaatatgatataattggtgctggtt
cacattcttcagaagattttcctaaaaaagaagatcaagaaaaacccaaaaagattgatgccagattg 209|agacaaagaatagatccccaatacaatgaggttcaggctcagatggaaacaaatttgtttaaattgtctcttgatgatgttgaaa
ctcctaaaggttccatgttggatcttaaaatttctcaatctaaaattgcacttcccaaaaacacagttggaggaaccattctgcgtagt
gatctattggcaaattttttgacagagggcaattttagagcaagtgttgatttgcagcgcactcatcgtattaaaggaatgattaaaat
ggtggccacagttggtattcctgagaatacaggtatatcattggcctgtgctatgaatagttcttttaggggcgtgccagttctgata
tttacaccatctgctctcaagactgtgaattatggaatcctgcttgcacaaaagcaatgactatgtcatttaatccaaacccgtgttct
gatgcatggagtttggaatttttgaagcgtaccggatttcattgtgatatcatttgtgtcactggatggactgccacccaatgcagga
tgttcaggttacaattgattggtttatttcctctcaggaatgtgttcccaggacctattgtgttttaaatccacaaaatccttttgtgt
taaataggtggatgggcaaactgacttttcccccagggcacttcccgaagtgttaaaagaatgcctctttctatagggggaggagctggt
gcaaagaatgctattctcatgaatatgccaaatgctgactttcaatgtggagatattttgttggagatctcgtctttgaagtttctaag
atgacttctccctacattaaatgtacagtctctttcttcatagcatttggaaatttggctgatgacaccattaattttgaggcttttcc
ccacaagctggtgcagtttggagaaattcaggaaaaagttgtattgaaattttcacaagaggaattcttacagcttggtcaactcagg
tgcgtcctgcaacaactctgttggctgatgggtgtccatatttgtatgctatggtgcatgatagttcagtgtctacaataccaggtgat
tttgtcattggtgttaagttggcaaccataaacaatatgtgtgcatatgggctcaatcctggtatttcaggttctcgtcttttgggcac
aaactgtttggaatcagatggcaacagtgagaacaccattgaattttgatcctagcaagcagagcttttgtcaattttctattgacctt
ctcattcctcagtccatttcacagccggtggaggaattttagtggacaaaactggagattggatcacacttatacaaaattctccaatt
agtaacttgttgagagttgctgcttggaagaaaggctgtttaatggttaagattgtgatgtctgggaa 209|tgcagcagtcaaaaggagtgattgggcctcattggtacaagtgtttttaacaaacagcaacagtacagagcattttgatgcatg
taagtggacaaaatcggaaccacattcctgggaatttgatcttcccaatagaggtgtggtcctaacaatggttttgaaatgtggagtt
ctgagtgggcaaatcaaacttcatggcatttgagtttccttattgacaatcccaaacagtctacagttttttgacattctcctgggaatt
tcccaagatttttgaaattgctggtaatactcttatgccagcttttctgttccacaggctactgccagatcttctgaaaatgcggaatc
ctctgcatgaggatcctctggaatttgtgttttctttcgtttgttcgcttgtttaattcaataaaggaaattaggcatgaccctctcgt
tgagtatgctctgtctatttgaaaattccacacctcttttaattgtcgtaatgatgtgtgaagtgtgtgttattttaaaaaaaaaaaa
aaaaaaatcgatagctcgaatttccccgatcgttcaaacatttggcaataaagtttcttaagattgaatcctgttgccggtcttgcgat
gattatcatataatttctgttgaattacgttaagcatgtaataattaacatgtaatgcatgacgttatttatgagatgggttttatga
ttagagtcccgcaattatacatttaatacgcgatagaaaacaaaatatagcgcgcaaactaggataaattatcgcgcgcggtgtcatct
atgttactagatcgggaattccaattcgccctatagtgagtcgtattacaattcactggccgtcgttttacaacgtcgtgactgggaaa
accctggcgttacccaacttaatcgccttgcagcacatcccccttcgccagctggcgtaatagcgaagaggcccgcaccgatcgccct
tcccaacagttgcgcagcctgaatggcgaatggacgcgccctgtagcggcgcattaagcgcggcggg 210
212
25|pBPMV-V2
27|1
222|3
33|8067
236|470921559
26|8563
28|0
219|0
220|1
221|1
29|0
30|0
217|0
31|0
32|1
255
224|Demo User
50
256
224|Demo User
50
1001|0
45
51|21
52|MCS (BamHI SalI StuI XhoI)
53|0
55|7362
56|7389
57|0
281|1
282|1
283|1
284|1
50
45
51|21
52|Nos Terminator
53|0
55|7568
56|7783
57|0
281|1
```

TABLE II-continued

```
282|1
283|1
284|1
50
45
51|21
52|CaMV 35S promoter
53|0
55|3147
56|3838
57|0
281|1
282|1
283|1
284|1
50
205
37|0
38|0
39|0
40|0
24

209|tatagtgagtcgtattacaattcactggccgtcgttttacaacgtcgtgactgggaaaaccctggcgttacccaacttaatcgcc
ttgcagcacatccccctttcgccagctggcgtaatagcgaagaggcccgcaccgatcgcccttcccaacagttgcgcagcctgaat
ggcgaatggacgcgccctgtagcggcgcattaagcgcggcgggtgtggtggttacgcgcagcgtgaccgctacacttgccagc
gccctagcgcccgctcctttcgctttcttcccttcctttctcgccacgttcgccggctttccccgtcaagctctaaatcgggggctccc
tttagggttccgatttagtgctttacggcacctcgaccccaaaaaacttgattagggtgatggttcacgtagtgggccatcgccctgat
agacggttttcgccctttgacgttggagtccacgttctttaatagtggactcttgttccaaactggaacaacactcaaccctatctcg
gtctattctttgatttataagggattttgccgatttcggcctattggttaaaaaatgagctgatttaacaaaaatttaacgcgaatata
acaaaatattaacgcttacaatttcctgatgcggtattttctccttacgcatctgtgcggtatttcacaccgcatatggtgcactctca
gtacaatctgctctgatgccgcatagttaagccagccccgacacccgccaacacccgctgacgcgccctgacgggcttgtctgctcccg
gcatccgcttacagacaagctgtgaccgtctccgggagctgcatgtgtcagaggttttcaccgtcatcaccgaaacgcgcgagacgaaa
gggcctcgtgatacgcctatttttataggttaatgtcatgataataatggtttcttagacgtcaggtggcacttttcggggaaatgtgc
gcggaacccctatttgtttatttttctaaatacattcaaatatgtatccgctcatgagacaataaccctgataaatgcttcaataatat
tgaaaaaggaagagtatgagtattcaacatttccgtgtcgcccttattcccttttttgcggcattttgccttcctgtttttgctcaccc
agaaacgctggtgaaagtaaaagatgctgaagatcagttgggtgcacgagtgggttacatcgaactggatctcaacagcggtaagatcc
ttgagagttttcgccccgaagaacgttttccaatgatgagcacttttaaagttctgctatgtggcgcggtattatcccgtattgacgcc
gggcaagagcaactcggtcgccgcatacactattctcagaatgacttggttgagtactcaccagtcacagaaaagc 209|atcttacggatggcatgacagtaagagaattatgcagtgctgccataaccatgagtgataacactgcggccaacttacttctga
caacgatcggaggaccgaaggagctaaccgcttttttgcacaacatgggggatcatgtaactcgccttgatcgttgggaaccggag
ctgaatgaagccataccaaacgacgagcgtgacaccacgatgcctgtagcaatggcaacaacgttgcgcaaactattaactggcg
aactacttactctagcttcccggcaacaattaatagactggatggaggcggataaagttgcaggaccacttctgcgctcggcccttc
cggctggctggtttattgctgataaatctggagccggtgagcgtgggtctcgcggtatcattgcagcactggggccagatggtaag
ccctcccgtatcgtagttatctacacgacgggggagtcaggcaactatggatgaacgaaatagacagatcgctgagataggtgcctc
actgattaagcattggtaactgtcagaccaagtttactcatatatactttagattgatttaaaacttcatttttaatttaaaaggatct
aggtgaagatcctttttgataatctcatgaccaaaatcccttaacgtgagttttcgttccactgagcgtcagaccccgtagaaaagatc
aaaggatcttcttgagatcctttttttctgcgcgtaatctgctgcttgcaaacaaaaaaaccaccgctaccagcggtggtttgtttgcc
ggatcaagagctaccaactctttttccgaaggtaactggcttcagcagagcgcagataccaaatactgttcttctagtgtagccgtagt
taggccaccacttcaagaactctgtagcaccgcctacatacctcgctctgctaatcctgttaccagtggctgctgccagtggcgataag
tcgtgtcttaccgggttggactcaagacgatagttaccggataaggcgcagcggtcgggctgaacggggggttcgtgcacacagcccag
cttggagcgaacgacctacaccgaactgagataccagcgtgagctatgagaaagcgccacgcttcccgaagggagaaaggc
ggacaggtatccggtaagcggcagggtcggaacaggagagcgcacgagggagcttccaggggaaacgcctggtatctttata
gtcctgtcgggtttcgccacctctgacttgagcgtcgatttttgtgatgctcgtcaggggggcggagcctatggaaaaacgccagca
acgcggcctttttacggttcctggccttttgctggccttttgctcacatgttcttcctgcgttatcccctgattctgtggataaccgt
attaccgcc 209|tttgagtgagctgataccgctcgccgcagccgaacgaccgagcgcagcgagtcagtgagcgaggaagcggaagagcgc
ccaatacgcaaaccgcctctccccgcgcgttggccgattcattaatgcagctggcacgacaggtttcccgactggaaagcgggca
gtgagcgcaacgcaattaatgtgagttagctcactcattaggcaccccaggctttacactttatgcttccggctcgtatgttgtgtgga
attgtgagcggataacaatttcacacaggaaacagctatgaccatgattacgccaagctatttaggtgacactatagaatactcaagc
ggccgcctactccaagaatatcaaagatacagtctcagaagaccaaaagggctattgagactttcaacaaagggtaatatgcggacttcctttgcccagctatctgtcacttcatcaaagg
acctcctcggattccattgcccagctatctgtcacttcatcaaaggacagtagaaaaggaaggtggcacctacaaatgccatcatt
gcgataaaggaaaggctatcgttcaagatgcctctgccgacagtggtcccaaagatggaccccacccacgaggagcatcgtgg
aaaagaagacgttccaaccacgtcttcaaagcaagtggattgatgtgatctactccaagaatatcaaagatacagtctcagaagac
caaagggctattgagactttcaacaaagggtaatatcgggacttcctttgcccagctatctgtcacttcatcaaag
gacagtagaaaaggaaggtggcacctacaaatgccatcattgcgataaaggaaaggctatcgttcaagatgcctctgccgacagt
ggtcccaaagatggaccccacccacgaggagcatcgtggaaaagaagacgttccaaccacgtcttcaaagcaagtggattga
tgtgatatctccactgacgtaagggatgacgcacaatcccactatccttcgcaagacccttcctctatataaggaagttcatttcattt
ggagaggtattaaaattttcataagattttgaaattttgataaaccggatcacaggttgccgcaccttaaaaccggaaacaaaagcaat
cgttacttgatttcaagaatcttccaatttcttcctacttcttggtgtacgatttcttaagagaaagaaaatcactctctgtgctggcc
acagacttcgtgaatcattttctttccactcttagtttatttgctgaacactctcctatttgatataggacttcgtgtcagatttaaa
ctttttctgtttctttctcagttctctgcttaatttcaagtttaagctggtgaaatcttggattagtgctcccactctcctatctggta
taggacttcgtgg 209|gtagacttactatactgtcattcttttcactctcttcttctcactgatccgcattgccgttcaaagtggtcttatttgaaaaacac
ttgggcgttggtgcaaatgtttgcttcgttaattttctctggggacaacaggctcactgagaaaacaattttttacttgcagagatttgg
acatcttggttgtttattatacaatagcaactcaattagaaaatttctaccgcattacattaggtggcatctgtataccttgttgatc
tacattctcccatctttttctcactgctgaaattaaatataagcggaatctgagtaatattcatatttctggcttattttacgacggcag
```

TABLE II-continued

```
atataaattctggactaaacacgagaaaaatcttgctttgacagaagaggaaaagatggaagtgattagaaacaaaggcattcctgctg
atgttcttgcaaagcgagctcatgaatttgaaaaacatgttgctcatgaaagcctcaaggatcaaattcctgctgttgacaagttgtat
tctactaaggttaataagtttgcaaaaattatgaaccttagacaaagtgttgttggtgatcttaaacttcttactgatgggaagttgta
tgagggtaagcatattcctgtatctaatattagtgcaggggagaatcatgtagttcaaataccccctaatggcacaggaggaaattctgt
cttctagtgcaagtgatttcagaactgcaatggtgagtaaaaatagcaagcctcaagctactgcaatgcatgtaggagagctataagaaatt
atcattgatagtttcgcaagtcctgactgcaacatagttggtgcaatgcttaggttgatacttatcataccaatcctgaaaatgcagtt
cgtagtatttagagcgcctttcagaggcggaaggcccattcgggtggttacatttccgaataccattgtgcagattgaaccagacatga
attcaaggtttcagcttttgagtaccactaccaatggtgattttgttcaaggaaaagatctcgcaatggttaaagttaatgtagcatgt
gctgctgttggcttgacatcaagttacactccaactccactgttggaatctggtttgcaaaagacagagggttaattgtggaatattt
tggaaggatgtcttacgttgctcataacgttaatcagccccaagagaaagatttgttggagggaaatttttcctttgatattaaatctc
gctctagattggaaaaagtttcttctactaaagcacaatttgttagtggaaaaaccttcaaatatgatataattggtgctggttcacat
tcttcagaagattttcctaaaaaagaagatcaagaaaaacccaaaaagattgatgccagattg
```

```
209|agacaaagaatagatccccaatacaatgaggttcaggctcagatgaaacaaatttgtttaaattgtctcttgatgatgttgaaa
ctcctaaaggttccatgttggatcttaaaatttctcaatctaaaattgcacttcccaaaaacacagttggaggaaccattctgcgtagt
gatctattggcaaatttttgacagagggcaattttagagcaagtgttgatttgcagcgcactcatcgtattaaaggaatgattaaaat
ggtggccacagttggtattcctgagaatacaggtatatcattggcctgtgctatgaatagttcttttaggggggcgtgccagttctgata
tttacaccatctgctctcaagactgtgaattatggaatcctgcttgcacaaaagcaatgactatgtcatttaatccaaaccgtgttct
gatgcatggagtttggaattttgaagcgtaccggatttcattgtgatatcatttgtgtcactggatggactgccacccaatgcagga
tgttcaggttacaattgattggttatttcctctcaggaatgtgttcccaggaccattgtgttttaaatccacaaaatcctttttgtgt
taaataggtggatgggcaaactgactttccccccgagggcacttcccgaagtgttaaaagaatgcctcttttctataggggggaggagctggt
gcaaagaatgctattctcatgaatatgccaaatgctgttctttcaatgtggagatattttgttggagatctcgtcttttgaagtttctaa
gatgacttctccctacattaaatgtacagtctctttcttcatagcatttggaaatttggctgatgacaccattaattttgaggcttttc
cccacaagctggtgcagtttggagaaattcaggaaaaagttgtattgaaattttcacaagaggaatttcttacagcttggtcaactcag
gtgcgtcctgcaacaactctgttggctgatgggtgtccatatttgtatgctatggtgcatgatagttcagtgtctacaataccaggtga
ttttgtcattggtgttaagttggcaaccataaacaatatgtgtgcatatgggctcaatcctggtatttcaggttctcgtcttttgggca
ccattcctcagtccatttcacagcaaactgtttggaatcagatggcaacagtgagaacaccattgaattttgatcctagcaagcagagc
ttttgtcaattttctattgaccttctcggtggaggaattttagtggacaaaactggagattggatcacacttatacaaaattctccaat
tagtaacttgttgagagttgctgcttggaagaaaggctgtttaatggttaagattgtgatgtctgggaa
```

```
209|tgcagcagtcaaaaggagtgattgggcctcattggtacaagtgttttaacaaacagcaacagtacagagcattttgatgcatg
taagtggacaaaatcggaaccacattcctgggaattgatcttcccaatagaggtgtgtggtcctaacaatggttttgaaatgtggagtt
ctgagtgggcaaatcaaacttcatggcatttgagtttccttattgacaatcccaaacagtctacagttttgacattctcctgggaatt
tcccaagattttgaaattgctggtaatactcttatgccagctttttctgttccacaggctactgccagatcttctgaaaatgcggaatc
ctctgcatgaggatccgcgtcgactccaggcctgagagatctctggaatttgtgttttcttcgtttgttcgcttgtttaattcaata
aaggaaattaggcatgaccctctcgttgagtatgctctgtctatttgaaaatttccacacctcttttaattgtcgtaatgatgtgtgaa
gtgtgtgttattttaaaaaaaaaaaaaaaaatcgatagctcgaatttccccgatcgttcaaacatttggcaataaagtttcttaaga
ttgaatcctgttgccggtcttgcgatgattatcatataatttctgttgaattacgttaagcatgtaataattaacatgtaatgcatgac
gttatttatgagatggggttttttatgattagagtcccgcaattatacatttaatacgcgatagaaaacaaaatatagcgcgcaaactagg
ataaaattatcgcgcgcggtgtcatctatgttactagatcgggaattccaattcgccctatagtgagtcgtattacaattcactggccgt
cgttttacaacgtcgtgactgggaaaaccctggcgttacccaacttaatcgccttgcagcacatccccctttcgccagctggcgtaata
gcgaagaggcccgcaccgatcgcccttcccaacagttgcgcagcctgaatggcgaatggacgcgccctgtagcggcgcattaagcgcgg
cggg
```

```
210
207
19
```

---

What is claimed is:

1. A Bean Pod mottle virus (BPMV) helper sequence for a BPMV vector inoculation in a recipient plant, comprising a BPMV I-Di1 isolate RNA1 sequence that has been modified so that said inoculation produces enhanced symptoms in a recipient plant as compared to a wild type BPMV I-Di1 RNA1, and less severe symptoms as compared to a wild type BPMV K-Ho1 RNA1, and wherein said BPMV I-Di1 isolate RNA1 sequence encodes a polypeptide comprising a BPMV RNA1 helicase having modifications consisting of modifications to the amino acids at position 359 and 365 of the BPMV RNA1 helicase, wherein said amino acid positions are determined by alignment with SEQ ID NO:2 and wherein said BPMV I-Di1 isolate RNA1 sequence encodes a polypeptide having at least 90% identity to SEQ ID NO:8.

2. The helper sequence of claim 1 wherein said modifications modify a serine at position 359 and a tyrosine at position 365 of a wild type BPMV I-Di1 isolate RNA1, wherein said amino acid positions are determined by alignment with SEQ ID NO:2.

3. The helper sequence of claim 1 wherein said sequence comprises a modification to a serine at position 359 and a tyrosine at position 365, wherein said amino acid positions are determined by alignment with SEQ ID NO:2, and further comprises:

(a) a polynucleotide that encodes a polypeptide having at least 90% sequence identity to a polypeptide of SEQ ID NO: 2 or 8;

(b) a polynucleotide of SEQ ID NO:1; or (c) a polynucleotide which is a full length compliment of a polynucleotide of (a) or (b).

4. A method for expressing a heterologous polypeptide in a soybean plant, comprising inoculating a soybean plant with the modified BPMV helper sequence of claim 1, and a recombinant BPMV RNA2 comprising a heterologous sequence encoding the heterologous polypeptide.

* * * * *